(12) United States Patent
Weiss et al.

(10) Patent No.: US 11,300,567 B2
(45) Date of Patent: Apr. 12, 2022

(54) METHODS AND COMPOSITIONS FOR PROTEIN PURIFICATION AND ENZYME REACTION

(71) Applicants: THE REGENTS OF THE UNIVERSITY OF CALIFORNIA, Oakland, CA (US); THE FLINDERS UNIVERSITY OF SOUTH AUSTRALIA, Bedford Park (AU)

(72) Inventors: Gregory A. Weiss, Irvine, CA (US); Joshua Britton, Irvine, CA (US); Colin L. Raston, South Australia (AU)

(73) Assignees: The Regents of the University of California, Oakland, CA (US); The Flinders University of South Australia

( * ) Notice: Subject to any disclaimer, the term of this patent is extended or adjusted under 35 U.S.C. 154(b) by 313 days.

(21) Appl. No.: 15/754,797

(22) PCT Filed: Aug. 24, 2016

(86) PCT No.: PCT/US2016/048437
§ 371 (c)(1),
(2) Date: Feb. 23, 2018

(87) PCT Pub. No.: WO2017/035253
PCT Pub. Date: Mar. 2, 2017

(65) Prior Publication Data
US 2018/0252713 A1    Sep. 6, 2018

Related U.S. Application Data

(60) Provisional application No. 62/209,107, filed on Aug. 24, 2015.

(51) Int. Cl.
*G01N 33/573* (2006.01)
*C12N 13/00* (2006.01)
(Continued)

(52) U.S. Cl.
CPC ............. *G01N 33/573* (2013.01); *C07K 1/22* (2013.01); *C12N 9/14* (2013.01); *C12N 9/96* (2013.01);
(Continued)

(58) Field of Classification Search
CPC ................. G01N 33/573; G01N 31/10; G01N 2203/0055; G01N 2400/00; C12N 13/00;
(Continued)

(56) References Cited

U.S. PATENT DOCUMENTS 5,057,421 A    10/1991  Hofman et al.
5,462,861 A    10/1995  Spencer et al.
(Continued)

FOREIGN PATENT DOCUMENTS

CN    102 199 632 A    9/2011
JP    H-05 268961 A    10/1993
(Continued)

OTHER PUBLICATIONS

Babicz, Ivelize et al., Lipase-Catalyzed Diacylglycerol Production Under Sonochemical Irradiation, Ultrasonics Sonochemistry, vol. 17, No. 1, 2010, pp. 4-6. (Year: 2010).*
(Continued)

*Primary Examiner* — Olivia M. Wise
*Assistant Examiner* — Anjali Ajit Hirani
(74) *Attorney, Agent, or Firm* — Mintz, Levin, Cohn, Ferris, Glovsky and Popeo, P.C.

(57) ABSTRACT

There are provided, inter alia, methods for reacting an enzyme and its substrate, methods for purifying a protein and an enzyme reactor and its use thereof.

11 Claims, 72 Drawing Sheets

Specification includes a Sequence Listing.

(51) Int. Cl.
    C12N 11/00     (2006.01)
    G01N 31/10     (2006.01)
    C12N 9/96      (2006.01)
    C07K 1/22      (2006.01)
    C12N 9/14      (2006.01)
(52) U.S. Cl.
    CPC .............. *C12N 11/00* (2013.01); *C12N 13/00* (2013.01); *G01N 31/10* (2013.01); *C12Y 301/03001* (2013.01); *C12Y 301/04001* (2013.01); *C12Y 302/01023* (2013.01); *G01N 2203/0055* (2013.01); *G01N 2400/00* (2013.01)
(58) Field of Classification Search
    CPC . C12N 11/00; C12N 9/96; C12N 9/14; C07K 1/22; C12Y 301/03001; C12Y 301/04001; C12Y 302/01023
    See application file for complete search history.

(56) References Cited

U.S. PATENT DOCUMENTS

| | | |
|---|---|---|
| 7,312,056 B2 | 12/2007 | Saville et al. |
| 8,241,880 B2 | 8/2012 | Diner et al. |
| 8,715,982 B2 | 5/2014 | Ying et al. |

FOREIGN PATENT DOCUMENTS

| | | |
|---|---|---|
| WO | WO-94/12621 A1 | 6/1994 |
| WO | WO-2004/081207 A1 | 9/2004 |
| WO | WO-2010/080434 A1 | 7/2010 |
| WO | WO-2010/080461 A1 | 7/2010 |
| WO | WO-2013/027053 A2 | 2/2013 |
| WO | WO-2013/027053 A3 | 2/2013 |
| WO | WO-2013/151757 A1 | 10/2013 |

OTHER PUBLICATIONS

Britton, Joshua et al., Continuous Flow Fischer Esterifications Harnessing Vibrational-Coupled Thin Film Fluidics, RSC Advances, vol. 5, No. 3, 2014, pp. 1655-1660. (Year: 2014).*
Thermofisher et al., Thermo Scientific Pierce Protein Purification Technical Handbook, Nov. 2010, Version 2, pp. 1-81. (Year: 2010).*
Hyatt et al., Use of Silica Nanosprings in an Enzyme-Based Continuous Flow Reactor, Nano Science and technology Institute, vol. 2, 2011, pp. 462-465. (Year: 2011).*
Bolivar et al., Smart enzyme immobilization in microstructured reactors, 2013, Microreactors, vol. 31, No. 3, pp. 50-54 (Year: 2013).*
Protein Purification, 2014, European Molecular Biology Laboratory: https://www.embl.de/pepcore/pepcore_services/protein_purification/extraction_clarification/centrifugation/ (Year: 2014).*
Scientific Industries, The Multi-Task Genie Family Product Information, 2014, pp. 1-2 (Year: 2014).*
Britton, J. et al., Continuous Flow Fischer esterifications harnessing vibrational-coupled thin film fluidics, 2014, RSC Advances, 5(3), 1655-1660 (Year: 2014).*
Thermo Scientific Pierce Protein Purification Technical Handbook, Version 2, Nov. 2010 (Year: 2010).*
Godoy, L. C., Lipase-catalyzed purification and functionalization of Omega-3 polyunsaturated fatty acids and production of structured lipids, 2012, INSA de Toulouse; Universidade técnica (Lisbonne), 1-276 (Year: 2012).*
Yasmin, L. et al., Optimising a Vortex Fluidic Device for Controlling Cehmical Reactivity and Selectivity, 2013, Scientific Reports, 3(2282), 1-6 (Year: 2013).*
Britton, J. et al., Continuous Flow Fischer esterifications harnessing vibrational-coupled thin film fluidics, 2014, RSC Advances, 5(3), 1655-1660 (Year: 2015).*

Kuznetsova, I. et al., Beyond the Excluded Volume Effects: Mechanistic Complexity of the Crowded Milieu, 2015, Molecules, 20(1), 1377-1409 (Year: 2015).*
Adamo, A. et al. (Apr. 1, 2016). "On-demand continuous-flow production of pharmaceuticals in a compact, reconfigurable system," Science 352(6281):61-67.
Ali, M. et al. (2007). "Capillary Phenomena on a Liquid Surface," Journal of Mechanical Engineering ME38, 45-51.
Andrade, L.H. et al. (2014). "Continuous flow synthesis of chiral amines in organic solvents: immobilization of *E. coli* cells containing both ω-transaminase and PLP," Org Lett 16(23):6092-6095.
Arcus, V.L. et al. (Aug. 4, 2015, e-published Jul. 11, 2015). "Change in heat capacity accurately predicts vibrational coupling in enzyme catalyzed reactions," FEBS Lett 589(17):2200-2206.
Babicz, I. et al. (Jan. 2010, e-published Jul. 30, 2009). "Lipase-catalyzed diacylglycerol production under sonochemical irradiation," Ultrason Sonochem 17(1):4-6.
Barbosa, O. et al. (2014). "Glutaraldehyde in bio-catalysts design: a useful crosslinker and a versatile tool in enzyme immobilization," RSC Adv. 4:1583-1600.
Barbosa, O. et al. (Sep.-Oct. 2015, e-published Mar. 14, 2015). "Strategies for the one-step immobilization-purification of enzymes as industrial biocatalysts," Biotechnol. Adv. 33(5):435-456.
Bloom, J.D. et al. (2005). "Evolving strategies for enzyme engineering," Current Opinion in Structural Biology 15, 447-452.
Bogdan, A.R. et al. (2009). "The Continuous-Flow Synthesis of Ibuprofen," Angew. Chem. Int. Edit. 2009, 48, 8547-8550.
Bolon, D.N. et al. (2002). "De novo design of biocatalysts," Current Opinion in Chemical Biology 6, 125-129.
Boonyaratanakornkit, B. et al. (2002). "Pressure effects on intra- and intermolecular interactions within proteins," Biochimica et Biophysica Acta (BBA)—Protein Structure and Molecular Enzymology 1595, 235-249.
Braginskaya, F.I. et al. (1990). "Low Intensity Ultrasonic Effects on Yeast Hexokinase," Radiat. Environ. Bioph. 29:47-56.
Britton, J. et al. (Aug. 2016). Accelerating Enzymatic Catalysis Using Vortex Fluidics, Angewandte Chemie International Edition 55(38):11387-11391.
Britton, J. et al. (2015). "Rapid high conversion of high free fatty acid feedstock into biodiesel using continuous flow vortex fluidics," RSC Advances 5:2276-2280.
Britton, J. et al. (2016). "The synthesis of di-carboxylate esters using continuous flow vortex fluidics," Green Chem 18:2193-2200.
Britton, J. et al. (Aug. 9, 2016). "Rapid protein immobilization for thin film continuous flow biocatalysis," Chem Commun (Camb) 52(66):10159-10162.
Britton, J. et al. (Jun. 19, 2015). "Rapid Vortex Fluidics: Continuous Flow Synthesis of Amides and Local Anesthetic Lidocaine," Chemistry A European Journal 21 (30:10660-10665.
Britton, J. et al. (Nov. 2014). "Continuous Flow Fischer Esterifications Harnessing Vibrational-Coupled Thin Film Fluidics," RSC Advances 5:1655-1660.
Cassimjee, K.E. et al. (Feb. 15, 2008). "Silica-immobilized His6-tagged enzyme: alanine racemase in hydrophobic solvent," Biotechnol Bioeng 99(3):712-716.
Chen, S. et al. (2004). Structural and functional characterization of a novel phosphodiesterase from Methanococcus jannaschii, J. Bio. Chem. 279(30):31854-31862.
Choi, J-M et al. (Nov. 15, 2015, e-published Mar. 6, 2015). "Industrial applications of enzyme biocatalysis: Current status and future aspects," Biotechnol. Adv. 33:1443-1454.
Coleman, J.E. (1992). "Structure and Mechanism of Alkaline Phosphatase," Annual Review of Biophysics and Biomolecular Structure 21:441-483.
Correia, C.A. et al. (2015). "A Concise Flow Synthesis of Efavirenz," Chem. Int. Edit. 54:4945-4948.
Dale, M.P. et al. (1985). "Reversible Inhibitors of β-Glucosidase," Biochemistry 24:3530-3539.
Database Accession No. NLM6361013 (Nov. 1983), 1 page.
Desouza, R.O.M.A. et al. (Jan. 2010). "Lipase-Catalyzed Diacylglycerol Production Under Sonochemical Irradiation," Ultrasonics Sonochemistry, 1 page.

(56) References Cited

OTHER PUBLICATIONS

Diaz, J.E. et al. (Sep. 2011, e-published Aug. 2, 2011). "Computational design and selections for an engineered, thermostable terpene synthase," Protein Sci 20(9):1597-1606.
Dicosimo, R. et al. (2013). Industrial Use of Immobilized Enzymes, Chem. Soc. Rev. 42:6437-6474.
Dodani, S.C. et al. (May 2016, e-published Mar. 21, 2016). "Discovery of a regioselectivity switch in nitrating P450s guided by molecular dynamics simulations and Markov models," Nat. Chem. 8(5):419-425.
Farwell, C.C. et al. (May 27, 2015, e-published Apr. 22, 2015). "Enantioselective Enzyme-Catalyzed Aziridination Enabled by Active-Site Evolution of a Cytochrome P450," ACS Central Sci. 1(2):89-93.
Fischbach, M.A. et al. (2006). "Assembly-line enzymology for polyketide and nonribosomal Peptide antibiotics: logic, machinery, and mechanisms," Chem. Rev. 106:3468-3496.
Fu, J. et al. (2014, e-published May 25, 2014). "Multi-enzyme complexes on DNA scaffolds capable of substrate channelling with an artificial swinging arm," Nat. Nano 9(7):531-536.
Garcia-Galan, C. et al. (2011). "Potential of Different Enzyme Immobilization Strategies to Improve Enzyme Performance," Adv. Synth. Catal. 353:2885-2904.
Greenberg, W.A. et al. (Apr. 20, 2004, e-published Apr. 6, 2004). "Development of an efficient, scalable, aldolase-catalyzed process for enantioselective synthesis of statin intermediates," PNAS USA 101(16):5788-5793.
Gutmann, B. et al. (Jun. 2015, e-published May 18, 2015). "Continuous-flow technology—a tool for the safe manufacturing of active pharmaceutical ingredients," Angew. Chem. Int. Edit. 54(23):6688-6728.
Guzik, U. et al. (Jun. 27, 2014). "Immobilization as a strategy for improving enzyme properties-application to oxidoreductases," Molecules 19:8995-9018.
Han, X. et al. (Jul. 30, 2014, e-published Jul. 18, 2014). "Reactions in elastomeric nanoreactors reveal the role of force on the kinetics of the Huisgen reaction on surfaces," Journal of the American Chemical Society 136(30):10553-10556.
Harsha, S.P. et al. (2004). "Non-linear dynamic behaviors of rolling element bearings due to surface waviness," Journal of Sound and Vibration 272:557-580.
Hay, S. et al. (Jan. 29, 2012). "Good vibrations in enzyme-catalysed reactions," Nat Chem 4(3):161-168.
Heider, P.L. et al. (2014). "Development of a Multi-Step Synthesis and Workup Sequence for an Integrated, Continuous Manufacturing Process of a Pharmaceutical," Org. Process Res. Dev. 18:402-409.
Henzler-Wildman, K.A. et al. (Dec. 2007, e-published Nov. 18, 2007). "A hierarchy of timescales in protein dynamics is linked to enzyme catalysis" Nature 2007, 450: 913-916.
Herath, A. et al. (Feb. 5, 2010). "Fully automated continuous flow synthesis of highly functionalized imidazo[1,2-a] heterocycles," Org. Lett 12:412-415.
Hillson, N. et al. (Dec. 21, 1999). Pressure-induced protein-folding/unfolding kinetics, PNAS USA 96(26):4848-14853.
Hyatt, D.C. et al. (2011). "Use of Silica Nanosprings in an Enzyme-Based Continous Flow Reactor," NSTI-Nanotech 2:462-465.
Hytonen, V.P. et al. (Mar. 7, 2007). "Structure and characterization of a novel chicken biotin-binding protein A (BBP-A)," BMC Structural Biology 7:8.
Ilie, A. et al. (2015). "P450-catalyzed region- and stereoselective oxidative hydroxylation of disubstituted cyclohexanes:creation of three centers of chirality in a single CH-activation event," Tetrahedron, 71:470-475.
International Search Report dated Jan. 13, 2017, for PCT Application No. PCT/US2016/048437, filed Aug. 24, 2016, 6 pages.
Jennewein, S. et al. (May 2006). "Directed evolution of an industrial biocatalyst: 2-deoxy-D-ribose 5-phosphate aldolase," Biotechnology Journal 1(5):537-548.
Jung, H-S. et al. (2012). "Quantitative Analysis and Efficient Surface Modification of Silica Nanparticles," J. Nanomaterials, 8 pages.
Keatinge-Clay, A.T. et al. (Feb. 2016). "Stereocontrol within polyketide assembly lines," Nat. Prod. Rep., 33:141-149.
Koeller, K.M. et al. (Jan. 11, 2001). "Enzymes for chemical synthesis," Nature 409(6817):232-240.
Kovalenko, G.A. et al. (May 19, 2008, e-published Feb. 13, 2008). "Immobilization of glucoamylase by adsorption on carbon supports and its application for heterogeneous hydrolysis of dextrin," Carbohydr Res 343(7):1202-1211.
Kuchner, O. et al. (1997). "Directed evolution of enzyme catalysts," Trends in Biotechnology 15:523-530.
Ladner, C.C. et al. (Mar. 2016, e-published Nov. 2, 2015). "Harnessing natural product assembly lines: structure, promiscuity, and engineering," J Ind Microbiol Biotechnol. 43(2-3):371-387.
Landowski, C.P. et al. (Feb. 2006). "Nucleoside ester prodrug substrate specificity of liver carboxylesterase," J Pharmacol Exp Ther 316(2):572-580.
Lerin, L.A. et al. (Dec. 2014, e-published Jun. 7, 2014). "A review on lipase-catalyzed reactions in ultrasound-assisted systems," Bioproc. Biosyst. Eng 37:2381-2394.
Levesque, F. et al. (Feb. 2012, e-published Jan. 16, 2012). "Continuous-flow synthesis of the anti-malaria drug artemisinin," Angew Chem Int Ed Engl 51(7):1706-1709.
Ley, S.V. et al. (Mar. 9, 2015, e-published Jan. 13, 2015). "Organic synthesis: march of the machines," Angew Chem Int Ed Engl 54(11):3449-3464.
Mateo, M. et al. (2007). "Improvement of Enzyme Activity, Stability and Selectivity via Immobilization Techniques," Enzyme Microb. Tech. 40:1451-1463.
McQuade, D.T. et al. (Jul. 5, 2013, e-published Jun. 20, 2013). "Applying flow chemistry: methods, materials, and multistep synthesis," 78(13):6384-6389.
Meier, J.L. et al. (Jul. 2009, e-published Mar. 27, 2009). "The chemical biology of modular biosynthetic enzymes," Chem Soc Rev 38(7):2012-2045.
Menger, F.M. et al. (1987). "Origin of Rate Accelerations in an Enzyme Model: The p-Nitrophenyl Ester Syndrome," J. Am. Chem. Soc. 109:3145-3146.
Meyer, L.D. et al. (1980). An Analytic Model for Ball Bearing Vibrations to Predict Vibration Response to Distributed Defects. Journal of Mechanical Design 102, 205-210.
Migneault, I. et al. (Nov. 2004). "Glutaraldehyde: behavior in aqueous solution, reaction with proteins, and application to enzyme crosslinking," BioTechniques, 2004, 37(5):790-802.
Miller A.W. et al. (1983). "Sodium Cyanoborohydride in the Immobilization of Proteins to Glutaraldehyde-Activated Aminoalkyl Silica," Biotechnology and Bioengineering 25:2795-2800.
Min, K. et al. (2014). "Recent Progress in Nanobiocatalysis for Enzyme Immobilization and Its Application," Biotechnology and Bioprocess Engineering 19:553-567.
Moriyama, A. et al. (Nov. 1983). "Porcine liver succinyltrialanine p-nitroanilide hydrolytic enzyme. Its purification and characterization as a post-proline cleaving enzyme," J Biochem 94(5):1387-1397.
Nestl, B.M. et al. (Apr. 2011, e-published Dec. 30, 2010). "Recent progress in industrial biocatalysis," Curr. Opin. Chem. Biol. 15(2):187-193.
Newton, S. et al. (May 5, 2014, e-published Apr. 11, 2014). "Accelerating spirocyclic polyketide synthesis using flow chemistry," Angew. Chem. Int. Edit. 53:4915-4920.
Nguyen, G.K. et al. (Dec. 7, 2015, e-published Dec. 7, 2015). "Butelase 1: A Versatile Ligase for Peptide and Protein Macrocyclization," J. Am. Chem. Soc.137(49):15398-15401.
Obermayer, D. et al. (Aug. 2011, e-published Jul. 13, 2011). "Microwave-assisted and continuous flow multistep synthesis of 4-(pyrazol-1-yl)carboxanilides,". J. Org. Chem. 76(16):6657-6669.
Oueis, E. et al. (2016). "Enzymatic Macrocyclization of 1,2,3,-Triazole Peptide Mimetics," Angew Chem 128:5936-5939.
P. C. Sims, I. S. Moody, Y. Choi, C. Dong, M. Iftikhar, B. L. Corso, 0. T. Gul, P. G. Collins, G. A. Weiss, J. Am. Chem. Soc. 2013, 135, 7861-7868.

(56) References Cited

OTHER PUBLICATIONS

Partial European Search Report dated Feb. 5, 2019, for EP Patent Application No. 16840049.7, 13 pages.
Perham, R.N. et al. (2000). "Swinging arms and swinging domains in multifunctional enzymes: catalytic machines for multistep reactions," Annu. Rev. Biochem. 69:961-1004.
Pessela, B.C.C. et al. (2006). "Purification and very strong reversible immobilization of large proteins on anionic exchanges by controlling the support and the immobilization conditions," Enzyme Microb. Tech. 39:909-915.
Pollard, D.J. et al. (Feb. 2007). "Biocatalysis for pharmaceutical intermediates: the future is now," Trends Biotechnol. 25(2):66-73.
Porcar, R. et al. (2012). "Stereoselective Chemoenzymatic Synthesis of Enantiopure 2-(1H-imidazol-yl) cycloalkanols under Continuous Flow Conditions," ACS Catal. 2:1976-1983.
Renata, h. et al. (Mar. 9, 2015, e-published Feb. 3, 2015). "Expanding the enzyme universe: accessing non-natural reactions by mechanism-guided directed evolution," Angew. Chem. Int. Edit. 54(11):3351-3367.
Rodrigues, R.C. et al. (Aug. 7, 2013). "Modifying enzyme activity and selectivity by immobilization," Chem. Soc. Rev, 2013, 42(15):6290-6307.
Romero, P.A. et al. (Dec. 2009). "Exploring protein fitness landscapes by directed evolution," Nat. Rev. Mol. Cell. Biol 10:866-876.
Rusmini, F. et al. (Jun. 2007, e-published Apr. 20, 2007). "Protein immobilization strategies for protein biochips," Biomarcomolecules 8(6):1775-1789.
Sato, H. et al. (Apr. 7, 2015,—published Feb. 20, 2015). "Cooperative catalysis of noncompatible catalysts through compartmentalization: wacker oxidation and enzymatic reduction in a one-pot process in aqueous media," Angew Chem. Int. Edit.54:4488-4492.
Schramm, V.L. et al. (1998). "Enzymatic transition states and transition state analog design," Annu. Rev. Biochem. 67:693-720.
Secundo, F. (Aug. 7, 2013). "Conformational changes of enzymes upon immobilisation," Chem. Soc. Rev. 42: 6250-6261.
Sheldon, R.A. et al. (Aug. 7, 2013). "Enzyme immobilisation in biocatalysis: why, what and how." Chem. Soc. Rev. 42(15):6223-6235.
Shrestha, U.R. et al. (Nov. 10, 2015, e-published Oct. 26, 2015). "Effects of pressure on the dynamics of an oligomeric protein from deep-sea hyperthermophile," PNAS USA 112(45):13886-13891.
Siegel, J.B. et al. (Mar. 24, 2015). "Computational protein design enables a novel one-carbon assimilation pathway," PNAS USA 112(12):3704-3709.
Sims, P.C. et al. (May 29, 2013, e-published May 14, 2013). "Electronic measurements of single-molecule catalysis by cAMP-dependent protein kinase A," J Am Chem Soc 135(21):7861-7868.
Sirajuddin, S. et al. (Apr. 14, 2015, e-published Apr. 1, 2015). "Enzymatic oxidation of methane," 54(14):2283-2294.
Srivastava, P. et al. (Jul. 24, 2015). "Engineering a dirhodium artificial metalloenzyme for selective olefin cyclopropanation," Nat. Commun. 6:7789.
Staunton, J. et al. (Aug. 2001). "Polyketide biosynthesis: a millennium review," Nat. Prod. Rep. 18(4):380-416.
Stepankova, V. et al. (2013). "Strategies for Stabilization of Enzymes in Organic Solvents," ACS Catal. 3:2823-2836.
Stroppolo, M. E. et al. (Sep. 2001). "Superefficient enzymes," Cell. Mol. Life Sci. 58:1451-1460.
Subrizi, F. et al. (2014). "Versatile and Efficient Immobilization of 2-Deoxyribose-5-Phosphate Aldolase (DERA) on Multiwalled Carbon Nanotubes," ACS Catalysis 4:3059-3068.
Tinberg, C.E. et al. (Sep. 12, 2013, e-published Sep. 4, 2013). "Computational design of ligand-binding proteins with high affinity and selectivity," Nature 501(7466):212-216.
Tsubogo, T. et al. (Apr. 16, 2015). "Multistep continuous-flow synthesis of (R)- and (S)-rolipram using heterogeneous catalysts," Nature 520(7547):329-332.
Turner, N.J. (Aug. 2009). "Directed evolution drives the next generation of biocatalysts," Nat. Chem. Biol 5(8):567-573.
Turrini, N.G. et al. (2015). "Enzymatic Synthesis of Optically Active Lactones via Asymmetric Bioreduction using Ene-Reductases from the Old Yellow Enzyme Family," Adv. Synth. Catal. 357:1861-1871.
Vaghari, H. et al. (Feb. 2016, e-published Oct. 15, 2015). Application of magnetic nanoparticles in smart enzyme immobilization, Biotechnol. Lett. 38(2):223-233.
Vedadi, M. et al.(2007). "Genome-scale protein expression and structural biology of Plasmodium falciparum and related Apicomplexan organisms," Mol. Biochem Parasit. 151:100-110.
Vimalanathan, K. et al. (Oct. 2014). "Shear induced fabrication of intertwined single walled carbon nanotube rings," Chem Commun (Camb) 50(77):11295-11298.
Wallace, S. et al. (Jun. 8, 2015, e-published Apr. 29, 2015). "Interfacing microbial styrene production with a biocompatible cyclopropanation reaction," Angew Chem Int Ed Engl. 54(24):7106-7109.
Walsh, C.T. (Jan. 2008, e-published May 17, 2007). "The chemical versatility of natural-product assembly lines," Accounts Chem. Res 41(1):4-10.
Wang, D. et al. (Sep. 14, 2007, e-published Aug. 9, 2007). "2-deoxyribose as a rich source of chiral 5-carbon building blocks," J. Org. Chem 72(19):7307-7312.
Wang, Z.J. et al. (2014). "Improved Cyclopropanation Activity of Histidine-Litigated Cytochrome P450 Enables the Enantioselective Formal Synthesis of Levomilnacipran," Angew. Chem. Int. Edit. 126:6928-6931.
Weissman, K.J. (Mar. 2015). "Uncovering the structures of modular polyketide synthases," Nat. Prod. Rep. 32(3):436-453.
Wenzel, S.C. et al. (Dec. 2007, e-published Jun. 11, 2007). "Myxobacterial natural product assembly lines: fascinating examples of curious biochemistry," Nat. Prod. Rep. 24(6):1211-1224.
Wheeldon, I. et al. (Apr. 2016). "Substrate channelling as an approach to cascade reactions," Nat Chem 8(4):299-309.
Wolfenden, R. et al. (Dec. 2001). "The depth of chemical time and the power of enzymes as catalysts," Accounts Chem. Res. 34(12):938-945.
Written Opinion dated Jan. 13, 2017, for PCT Application No. PCT/US2016/048437, filed Aug. 24, 2016, 6 pages.
Xie, S. (2001). "Single-Molecule Approach to Enzymology," Single Mol. 2(4):229-236.
Yadav, G.D. et al. (2012). "Microwave assistated lipase caralyzed synthesis of isoamyl myristate in solvent-free system," Journal of Molceular Catalysis B:Enzymatic 83:16-22.
Yasmin, L. et al. (Dec. 4, 2013). "Stereospecific synthesis of resorcin[4]arenes and pyrogallol[4]arenes in dynamic thin films," Chem Commun (Camb) 49(93):10932-10934.
Yasmin, L. et al. (Jul. 2013). "Optimising a cortex fluid device for controlling chemical reactivity and selectivity," Scientific Reports 3(2282):6 pages.
Yuan, T.Z. et al. (Feb. 9, 2015, e-published Jan. 23, 2015). "Shear-stress-mediated refolding of proteins from aggregates and inclusion bodies," ChemBioChem 16(3):393-396.
Zhang, P. et al. (2014). "Continuous Flow Total Synthesis of Rufinamide," Org. Process Res. Dev. 18:1567-1570.
Zhao, D. et al. (2013). "Recent Advances in Asymmetric Catalysis in Flow," ACS Catal 3:928-944.
Zhu, K. et al. (2010). "Study of ultrasound-promoted, lipase-catalyzed synthesis of fructose ester," Front Chem Eng China 4(3):367-371.
Britton, J et al. (2016, e-published Jun. 22, 2016). "Harnessing Thin-Film Continuous-Flow Assembly Lines," *Chemistry* 22(31):10773-10776.
Britton, J. et al. (Sep. 27, 2017, e-published Aug. 16, 2017). "Vortex Fluidic Chemical Transformations," *Chemistry* 23(54):13270-13278.
Kovalenko, G.A. et al. (2006). "Vortex Reactors for Heterogeneous Biocatalytical Processes," Chapter 6 in *Industrial Application of Biotechnology*, Nova Science Publishers, Inc., pp. 45-53.

* cited by examiner

Flow rate: 1.00 mL min$^{-1}$
Total reaction time: 320 min
Waste: 120 mL
Residence time of protein: 1500 s Flow rate: 13.30 mL min$^{-1}$
Total reaction time: 10 min
Waste: 33 mL
Residence time of protein: 60 s

Kinetic values derived

$V_{max}$ - $1.74 \times 10^{-8} \pm 1.86 \times 10^{-9}$ Ms$^{-1}$
$k_M$ – 64 ± 0 mM
Enzyme concentration - 3.481 nM
$k_{cat}$ - 5.01 ± 0.53 s$^{-1}$
$k_{cat}/k_M$ - 0.078 ± 0.0083 mM$^{-1}$s$^{-1}$

Kinetic values derived

$V_{max}$ – $1.21 \times 10^{-7} \pm 1.51 \times 10^{-8}$ Ms$^{-1}$
$k_M$ – $0.267 \pm 0.02$ mM
Enzyme concentration - 3.481 nM
$k_{cat}$ – $31.31 \pm 4.34$ s$^{-1}$
$k_{cat}/k_M$ – $113.43 \pm 14.91$ mM$^{-1}$s$^{-1}$

SEQUENCE LISTING

```
<160> NUMBER OF SEQ ID NOS: 27

<210> SEQ ID NO 1
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 1
gacgacgaca agatggctaa ttatacagaa aaattcgcag cgtggtcag          49

<210> SEQ ID NO 2
<211> LENGTH: 72
<212> TYPE: DNA
<213> ORGANISM: Artificial Sequence
<220> FEATURE:
<223> OTHER INFORMATION: Synthetic polynucleotide

<400> SEQUENCE: 2
gaggagaagc ccggttcatc acaatggaca ttgagaaata acttttctca attttatcac     60
taatgatgat ga                                                         72

<210> SEQ ID NO 3
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 3
gacgacgaca aggtagtagt agtagtagta atggtgagca agggcgagga ggacaacatg     60
gccatc                                                                66

<210> SEQ ID NO 4
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 4
gaggagaagc ccggttcact tgtacagctc gtccatgccg ccggtggagt ggcggccctc     60

<210> SEQ ID NO 5
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 5
```

```
gacgacgaca agatggtgaa acaaagcact attgcactgg cactcttacc g        51

<210> SEQ ID NO 6
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 6
gaggagaagc ccggttcatc agtggtggtg gtggtggtgt tcagccccca gggc     54

<210> SEQ ID NO 7
<211> LENGTH: 45
<212> TYPE: DNA
<213> ORGANISM: Artificial Sequencer
<220> FEATURE:
<223> OTHER INFORMATION: Synthetic polynucleotide

<400> SEQUENCE: 7
gacgacgaca agatgaaaat tgggataatg agcgataccc atgac              45

<210> SEQ ID NO 8
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 8
gaggagaagc ccggttcatc ataacactat ctccctatac tcctt              45

<210> SEQ ID NO 9
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 9
gacgacgaca agatgccaac aattaattcg attcaaacaa ccgtc              45

<210> SEQ ID NO 10
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 10
gaggagaagc ccggttcatc actaaattaa cgcggccgcc atcac              45

<210> SEQ ID NO 11
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 11

Gly Leu Asn Asp Ile Phe Glu Ala Gln Lys Ile Glu Trp His Glu
1               5                   10                  15

<210> SEQ ID NO 12
<211> LENGTH: 26
<212> TYPE: PRT
```

```
<213> ORGANISM: Artificial Sequence
<220> FEATURE:
<223> OTHER INFORMATION: Synthetic polypeptide

<400> SEQUENCE: 12

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 13
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 13

Glu Glu Glu Glu Glu Glu
1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic polypeptidfe

<400> SEQUENCE: 14

Gly Ala Pro Val Pro Tyr Pro Asp Pro Leu Glu Pro Arg
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 15

Asp Tyr Lys Asp Asp Asp Asp Lys
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 16

Tyr Pro Tyr Asp Val Pro Asp Tyr Ala
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 17

His His His His His His
1               5

<210> SEQ ID NO 18
```

```
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 18

Glu Gln Lys Leu Ile Ser Glu Glu Asp Leu
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 19

Lys Glu Thr Ala Ala Ala Lys Phe Glu Arg Gln His Met Asp Ser
1               5                   10                  15

<210> SEQ ID NO 20
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 20

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 21
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 21

Ser Leu Ala Glu Leu Leu Asn Ala Gly Leu Gly Gly Ser
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 22

Thr Gln Asp Pro Ser Arg Val Gly
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 23
```

```
Trp Ser His Pro Gln Phe Glu Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 24

Cys Cys Pro Gly Cys Cys
1               5

<210> SEQ ID NO 25
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 25

Gly Lys Pro Ile Pro Asn Pro Leu Leu Gly Leu Asp Ser Thr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 26

Tyr Thr Asp Ile Glu Met Asn Arg Leu Gly Lys
1               5                   10

<210> SEQ ID NO 27
<211> LENGTH: 8
<212> TYPE: PRT
<213> ORGANISM: Artificial Sequencer
<220> FEATURE:
<223> OTHER INFORMATION: Synthetic polypeptide

<400> SEQUENCE: 27

Asp Leu Tyr Asp Asp Asp Asp Lys
1               5
```

METHODS AND COMPOSITIONS FOR PROTEIN PURIFICATION AND ENZYME REACTION

CROSS-REFERENCES TO RELATED APPLICATIONS

This application is the national stage filing under USC 371 of international application PCT/US2016/048437, filed Aug. 24, 2016, which claims the benefit and the priority of U.S. Provisional Application No. 62/209,107, filed Aug. 24, 2015, the content of each of which is incorporated hereby by reference in its entirety and for all purposes.

STATEMENT AS TO RIGHTS TO INVENTIONS MADE UNDER FEDERALLY SPONSORED RESEARCH AND DEVELOPMENT

This invention was made with Government support under grant number 1RO1 GM100700-01 awarded by the National Institutes of Health. The Government has certain rights in this invention.

INCORPORATION BY REFERENCE OF SEQUENCE LISTING

The Sequence Listing written in file 048538-523N01US_ST25.TXT, created Feb. 21, 2018, 6,374 bytes, machine format IBM-PC, MS-Windows operating system, is hereby incorporated herein by reference in its entirety and for all purposes.

BACKGROUND

Enzymes catalyze chemical transformations and are used extensively in industrial, food, and research applications. Accelerating such catalysis could lower the costs for such processes. Current methods to enhance the activity of enzymes largely focus on engineering the enzyme for improved activity; this approach is slow and cumbersome. There is additionally a need for more efficient and cost effective protein purification methods.

Solutions to these and other problems in the art of enzyme reacting and protein purification are provided herein.

SUMMARY

In a first aspect, there is provided a method for reacting an enzyme and a substrate. The method includes combining an enzyme and a substrate of the enzyme to form an enzyme-substrate mixture. The method further includes mechanically mixing the enzyme-substrate mixture. The method further includes applying a vibrational energy to the enzyme-substrate mixture, thereby reacting the enzyme and the substrate.

In another aspect, there is provided a method for purifying a protein. The method includes contacting a protein mixture that includes the protein with a protein binding film, where the protein binding film is immobilized to a solid support, thereby forming a protein binding film complex. The method further includes separating the protein from the protein binding film complex, thereby obtaining a purified protein.

In another aspect, there is provided an enzyme reactor including a first enzyme, a protein binding film and a solid support, wherein the first enzyme is immobilized to the protein binding film in a first zone, and where the protein binding film is immobilized to the solid support.

In another aspect, there is provided a method for reacting an enzyme and a substrate. The method includes contacting the protein binding film of the enzyme reactor as disclosed herein with a substrate of the first enzyme. The method further includes allowing the substrate to react with the first enzyme.

BRIEF DESCRIPTION OF THE DRAWINGS

FIG. 3A depicts the fold enhancement of alkaline phosphatase in the VFD when testing at a range of rotational speeds over set periods of time. The fold enhancement refers to the relative activity compared to the same reaction left at room temperature (not VFD-processed); typically, the VFD enhanced enzyme activity, and was >1. Bar graph bins: processing time (min); within each bar graph bin, rotational speed (left to right): 4, 5, 6, 7, 8, and 9 krpm, respectively. FIG. 3N depicts how the rotational speed of the device effects the enzyme enhancement at with different volumes of enzyme to substrate. It can be seen that there is very little difference when using different enzyme/substrate volumes. Bar graph bins (left to right): 0.700 mL of lipase and 0.600 mL of substrate; 0.200 mL of lipase and 1.100 mL of substrate.

FIG. 4A depicts the concentration of APTES used in the coatings. See Example 2. Bar graph bins (left to right): 1% APTES, 2% APTES, 5% APTES, 10% APTES, 15% APTES, 20% APTES. FIG. 4B depicts the APTES reaction time. Bar graph bins (left to right): 1, 2, 3, 4, 5, and 6 hrs. FIG. 4C depicts the APTES reaction temperature. Bar graph bins (left to right): 298 K, 303 K, 313 K and 323 K. FIG. 4D depicts the annealing time. Bar graph bins (left to right): 1.0, 1.5, 2.0 and 2.5 hours annealing.

FIG. 6A: Schematic of the chemical transformation occurring and the fold enhancement of activity using (FIG. 6B) different processing time at different rotational speeds, (FIG. 6C) a dynamic substrate-enzyme change in concentration to scan the processing space efficiently, (FIG. 6D) an in depth rotational speed scan to monitor fold enhancement, (FIG. 6E) different inclination angles of the rotating tube, (FIG. 6F) variation in the concentration of PEG at variable speeds, (FIG. 6G) variation in 4-nitrophenol concentration to mimic product inhibition in the VFD and (FIG. 6H) variation in the dibasic phosphate concentration to mimic product inhibition in the VFD. Legend: FIG. 6B: Bar graph bins (left to right): 4, 5, 6, 7, 8, and 9 krpm; FIG. 6C: 6.65, 7.30, and 8.00 kprm VFD; FIG. 6E: 8000 rpm (diamonds), 7300 rpm (squares), 6550 rpm (triangles); FIG. 6F: Bar graph bins (left to right): 6550 rpm PEG 8000, 7300 rpm PEG 3350, 7300 rpm PEG 8000, 8000 rpm PEG 3350, 8000 rpm PEG 8000, 6550 rpm PEG 3350; FIG. 6G: 8.00, 7.30, and 6.55 krpm, respectively in turn; FIG. 6H: 8.00, 7.30 and 6.55 krpm, respectively.

FIG. 7A depicts the acceleration in enzyme activity vs. time. Bar graph bins (left to right): esterase, lipase, beta-glucosidase, respectively. FIGS. 7B-7E: The concerted substrate-enzyme concentrations scans for the four enzymes: DERA (FIG. 7B); esterase (FIG. 7C); lipase (FIG. 7D), and beta-glucosidase (FIG. 7E). These scans were conducted at a 8000-rpm rotational speed, at a 45-degree tilt angle using a 17.7 mm internal diameter NMR tube. FIG. 7F: fold acceleration (over non-VFD conditions) as a function of rotation speed. Bar graph bins (left to right): beta-glucosidase, lipase, esterase, respectively at each time point.

FIG. 8A: A schematic of the VFD. FIG. 8B: A VFD sample tube containing 5 mL solution rotating at 3.50 krpm at a tilt angle, θ, of 45°, shows Faraday waves formed within the thin film. Overlaid schematically, such pressure waves can affect the enzyme-substrate complex. FIG. 8C: This enlargement focuses on VFD-generated Faraday waves.

FIG. 9A: A time dependent study at a fixed rotational speed (8.00 krpm) reveals processing times for further optimization. As indicated with a star character, DERA required longer reaction times of 60, 80, 100, 120, 140, 160 and 180 min. Bar graph bin order (left to right): esterase, DERA, β-glucosidase, alkaline phosphatase. FIG. 9B: Simultaneous changes to the substrate and enzyme concentrations at a 8.00 krpm rotational speed mapped the reaction landscape (Tables 4A-4D). Bar graph bin order (left to right): as set forth for FIG. 9A. FIG. 9C: Rotational speed scans in 50 rpm increments identify harmonic oscillations associated with Faraday wave-promoted biocatalysis. Error bars are larger for DERA than any other enzyme due to the product's non-linear, fluorescence calibration curve. Bar graph bin order (left to right): esterase, β-glucosidase, alkaline phosphatase; overlaid line (DERA). FIG. 9D: Varying the tilt angle of the sample tube identifies 45° as optimal. Thus, a 45° tilt angle was used throughout this example. Legend at peak at 45-deg (bottom to top): 6.55 krpm, 7.30 krpm, 8.00 kprm. FIG. 9E: The addition of PEG dramatically slowed the non-VFD control, but the VFD processed solution demonstrated significant catalytic activity. Error bars indicate the standard deviation around the mean (n=3 with three independent measurements on three different VFDs). With the exception of a single data point requiring 90% confidence limits, all data reported here have no overlapping errors within 95% confidence limits. The concentrations of enzymes and substrates are as follows: alkaline phosphatase (6.77 nM) and its substrate p-nitrophenol phosphate (0.17 mM), β-glucosidase (19.3 nM) and its substrate 4-nitrophenyl β-D-glucopyranoside (7.5 mM), esterase (0.12 nM) and its substrate p-nitrophenol acetate (44 µM) and DERA (7.69 µM) and its fluorogenic substrate (0.52 mM) unless otherwise indicated, and as described in Table 4A-4D. Bar graph bin order (left to right): 6.55 krpm PEG 3350; 6.55 krpm PEG 8000; 7.30 krpm PEG 3350; 7.30 krpm PEG 8000; 8.00 krpm PEG 3350; 8.00 krpm PEG 8000.

FIG. 11A: A thermal IR (FLIR) image of the device operating at a 8 krpm rotational speed after 1 h of processing. The heat generated is localized to the upper and lower bearing, and the sample tube remains at roughly ambient temperature (23° C.). FIG. 11B: The lower bearing contains two O-rings that stop direct contact of the bearing to the sample tube. This design modification limits heat transfer to the sample tube and allows the sample tube to remain at ambient temperature for sustained periods of time. FIG. 11C: In this experiment, 1.30 mL of blue food coloring, an identical volume to reactions reported here, was rotated at 8 krpm and the distance the fluid travelled was monitored. This chosen volume ensures processed solutions do not enter into the upper bearing region and become exposed to slightly elevated temperatures.

FIG. 17A: Estimating the MW of commercial FAsTAP™ alkaline phosphatase. In this 12% Tris-glycine SDS-PAGE, each lane was loaded with 12 µL of protein solution as follows. L1 PageRuler Plus pre-stained protein ladder; L2 0.45 µM BSA (99% purity); L3 0.75 µM BSA; L4 1.51 µM BSA; L5 3.01 µM BSA; L6 4.52 µM BSA; L7 6.02 µM BSA; and L8 and L9 Identical samples of FAsTAP™ Alkaline Phosphatase solution. The BSA standards provided an estimation of the enzyme concentration as further confirmed by BCA assay (below). From this experiment, FAsTAP™ alkaline phosphatase has an estimated MW of 36 KDa. FIG. 17B: Determining the concentration of FAsTAP™ alkaline phosphatase as provided by the supplier. For this experiment a BCA assay kit was used (Thermo Scientific). The FAsTAP™ alkaline phosphatase stock solution was diluted 1:100 solution into PBS to dilute glycerol. The concentration of the stock solution was 0.11 mM.

FIG. 18A: Alkaline phosphatase; FIG. 18B: β-glucosidase; FIG. 18C: esterase; and FIG. 18D: DERA. The enzymes were processed as previously described, and the fold acceleration calculated through comparison to identical enzyme-substrate solutions that were not VFD-processed. Error is indicated as standard deviation around the mean (n=3). The concentration of enzyme and substrate used in the above experiment are as follows (1.30 mL total volume): Alkaline phosphatase (6.77 nM) and its substrate p-nitrophenol phosphate (0.167 mM), β-glucosidase (19.3 nM) and its substrate 4-nitrophenyl β-D-glucopyranoside (7.5 mM), esterase (0.12 nM) and its substrate p-nitrophenol acetate (44 µM) and DERA (7.69 µM) and its fluorogenic substrate (0.52 mM).

FIG. 20A: alkaline phosphatase; FIG. 20B: β-glucosidase; FIG. 20C: esterase; and FIG. 20D: DERA. Error is indicated as standard deviation around the mean (n=3). The rotational speed used for analyzing the effect of substrate concentration on DERA was non-optimized here, hence why little difference is observed. However, variation of the rotational speed (FIG. 20C) gives high levels of enhancement. Legend symbols are as indicated in FIGS. 20A-20D.

FIG. 22A: The addition of dibasic phosphate decreases catalytic activity for both VFD-processed and non-VFD-processed enzyme-substrate solutions. FIG. 22B: Similarly, the addition of 4-nitrophenol results in decreased substrate conversion for both VFD and non-VFD conditions. Error is indicated as standard deviation around the mean (n=3). The concentrations of alkaline phosphatase used was 6.77 nM and its substrate p-nitrophenol phosphate 0.167 mM. The total volume used in this experiment was 1.30 mL.

FIGS. 24A-24B: These are enlarged versions of the photographs in FIGS. 8A-8C and depict a Faraday wave generated in the VFD at 3.50 krpm rotational speed with 5.0 mL of water. FIG. 24A is in black and white for higher levels of contrast. FIGS. 24C-24D: Photographs of the Faraday waves generated in the VFD at a 8.00 krpm rotational speed with 3.00 mL of water. Shown in both black and white for high levels of contrast (FIG. 24C) as well as original photograph (FIG. 24D). Photography conditions taken using a Pentax-Kr camera with a 18-55 mm lens, shutter speed; 1/60, exposure; 0.7 EV, focal length; 28.13 mm, with LED lighting. At higher rotational speeds the Faraday waves have much shorter wavelengths.

FIG. 27A: The graph compares the observed data to calculated data using the LSF approach. The model was then fitted to provide the lowest value for the sum of squared residuals (SSR) whilst maintaining a good visual fit. Both Km (FIG. 27B) and Vmax (FIG. 27C) were varied independently of each other in finding global minima SSR.

FIG. 28A: The graph compares the observed data to calculated data using the LSF approach. The model was then fitted to provide the lowest value for the sum of squared residuals (SSR) whilst maintaining a good visual fit. Both Km (FIG. 28B) and Vmax (FIG. 28C) were varied independently of each other in finding global minima SSR.

FIGS. 29A-29B. FIGS. 29A-29B depict photographs at different angles of 3D printed VFD collar with the interchangeable plastic sleeve (center feature). This approach ensured that the vibrations were maintained. After about 4 h, a new sleeve can be inserted, and the enzyme enhancement maintained.

FIG. 30A: For thin film protein purification and immobilization, all reagents and protein solutions can be fed into the reactor via pumps, e.g., peristaltic or syringe pumps. The protein of interest (e.g., mCherry or eGFP) binds to the IMAC resin attached to the reactor surface as shown. FIG. 30B: This immobilization technique allows a range of protein zones to be created, illustrated here with mCherry and eGFP coatings. Possible reactor configurations include catalysis by a single enzyme [features (1) and (2)], half enzyme-coated plus half non-coated reactor [features (3) and (4)], and then finally multistep transformations with 18 or 28 stripes of enzymes [features (5) and (6)]. FIG. 30C: Cell lysate can be fed directly into the IMAC-coated VFD reactor. The approach provides both a biosynthetic reactor for continuous flow applications, and also an effective method for protein purification. As shown by SDS-PAGE (12% acrylamide), the eluted protein is >90% homogeneous; *indicates a protein that co-elutes with mCherry by both conventional and VFD purification. FIG. 30D: As shown by contour plot, the efficiency of mCherry immobilization can reach nearly quantitative levels; almost all protein is removed from the applied solution, and complexes to the resin. FIG. 30E: Furthermore, a wide range of protein concentrations can be immobilized, as illustrated in the contour plots. Such flexibility can adjust for different enzyme-catalyzed, reaction speeds.

FIG. 31A: A two-step biosynthetic pathway was used to model the effects of enzyme zones for enabling multistep reactivity. Here, phosphodiesterase transforms the bis(p-nitrophenol)phosphate monosodium salt into p-nitrophenoxoide (absorbance at 405 nm) and p-nitrophenol phosphate. The next enzyme in the pathway, alkaline phosphatase transforms the p-nitrophenol phosphate to another molecule of p-nitrophenoxoide and inorganic phosphate ($P_i$). Monitoring the concentration of p-nitrophenoxoide liberated by the reaction determines the pathway efficiency. FIG. 31B: Photographs depict that in this experiment, the reactor is divided into distinct zones, with each zone containing either phosphodiesterase or alkaline phosphatase. FIG. 31C: Bar graph depicting results after each reactor is then tested under continuous flow conditions (0.5 mL min$^{-1}$) for quantification of p-nitrophenoxoide concentration. Error is indicated as standard deviation around the mean (n=10). Bar graph order (left to right): IMAC alone, phosphodiesterase, phosphodiesterase and alkaline phosphatase, mixture.

FIG. 38A: Following coating the sample tube surface with the IMAC resin, NiSO$_4$.6H$_2$O solution (100 mM) was flowed through the reactor at a flow rate of 1.00 mL min$^{-1}$ and a sample collected every five min. From this sample, 100 µL was added to a 96-well plate and the absorbance read at 391 nm ($\lambda_{max}$ for NiSO$_4$.6H$_2$O solution, c—3.80 M cm$^{-1}$). FIG. 38B: Following IMAC activation, the residual Ni$^{2+}$ is washed out from the system. PBS buffer was flowed through the reactor at a flow rate of 1.00 mL min$^{-1}$ and a sample collected every five min From this sample, 100 µL is added to a 96-well plate and the absorbance read at 391 nm. FIG. 38C: Once the reactor has been charged with Ni$^{2+}$, and the residual metal removed from the reactor, mCherry is then flowed through the reactor and is concentration in the flow through solution monitored. The starting concentration of mCherry was 10 µM, and optimal immobilization was observed after ten cycles. A 100 µL sample of the flow through was taken every five cycles and the concentration of mCherry determined by its absorbance value at 584 nm ($\lambda_{max}$ for mCherry, ε—72,000 M$^{-1}$ cm$^{-1}$). FIG. 38D: In order to monitor the concentration of mCherry, the $\lambda_{max}$ was determined by a wavelength scan, the $\lambda_{max}$ was found to be 584 nm. FIG. 38E: In order to monitor the concentration of NiSO$_4$.6H$_2$O, the $\lambda_{max}$ was determined by a wavelength scan, the $\lambda_{max}$ was found to be 391 nm. FIG. 38F: A Beer-Lambert plot was constructed to determine the molar extinction co-efficient of the NiSO$_4$.6H$_2$O solution.

FIG. 40A: This photograph shows the charging of the IMAC resin with the NiSO$_4$.6H$_2$O solution. FIG. 40B: This photograph shows how the jet feed is held in place for positioning down the center of the rotating tube. FIG. 40C: In this photograph, mCherry is being cycled around the VFD in performing the immobilization step. FIG. 40D: As mCherry and eGFP are susceptible to photo bleaching, the reactor is protected from light by an aluminum cover. FIG. 40E: The jet feed is positioned directly down the center of the reactor when performing continuous flow experiments.

FIG. 41A: In this 12% tris-glycine SDS-PAGE a total purification time of 320 min gave pure TEAS from cell lysate. Optimization of the results of FIG. 41A provides the results set forth in FIG. 41B. FIG. 41B: Decreasing this reaction time to ten min via a series of optimizations affords protein of similar purity, but with dramatically less waste and residence time.

FIG. 44A: First, the zones can be marked with a marker pen onto the surface of the reactor. FIG. 44B: The sample tube can be brought to 8 krpm, and then the protein bound IMAC solution can be added to the correct position in the reactor. FIG. 44C: The stripes at the bottom of the sample tube first are created, and then work up to the top of the reactor.

µL 4 M NaOH and immediately analyzed as described previously. Error is reported as standard deviation around the mean (n=3).

Figure 46:
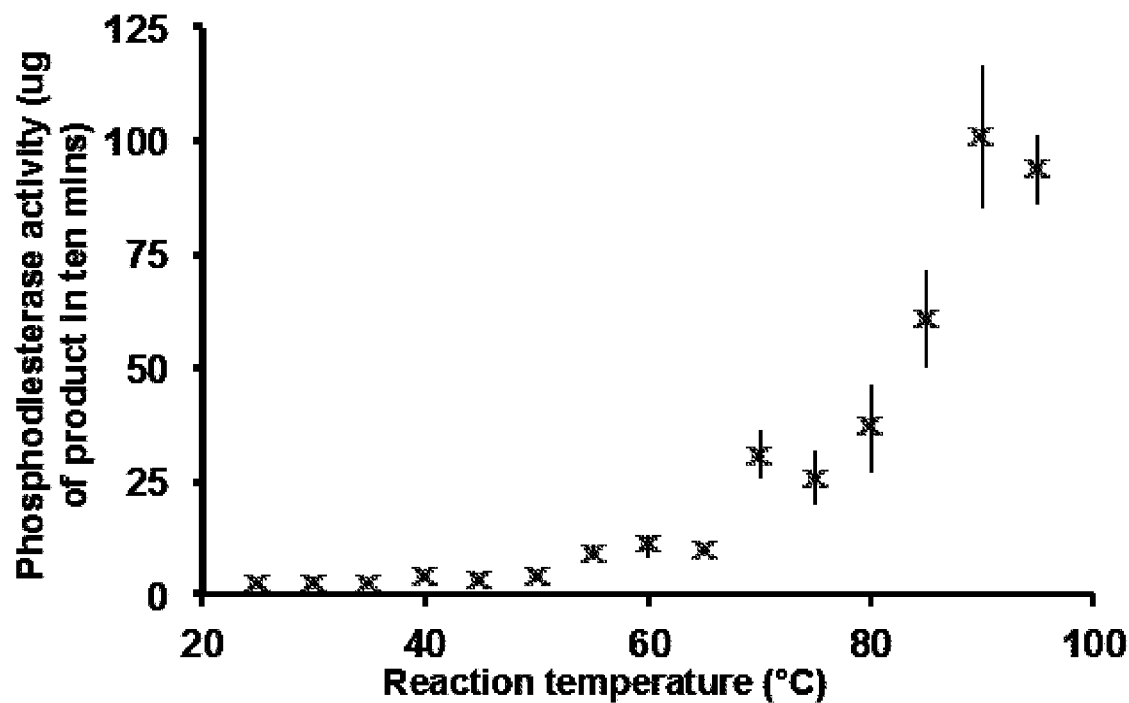

FIG. 46. Monitoring the effect of reaction temperature on the liberation of p-nitrophenol. For this experiment, 1000 µL of substrate solution (0.7 mM bis(p-nitrophenyl) phosphate sodium salt) was added to a 2 mL sinter vial and allowed to heated to the required temperature over five min. Once the temperature had been reached, phosphodiesterase (4.96 nMoles) was added to the solution. After ten min, the reaction was quenched with 300 µL 4 M NaOH and analyzed as previously described. Error is reported as standard deviation around the mean (n=3).

Figure 47:
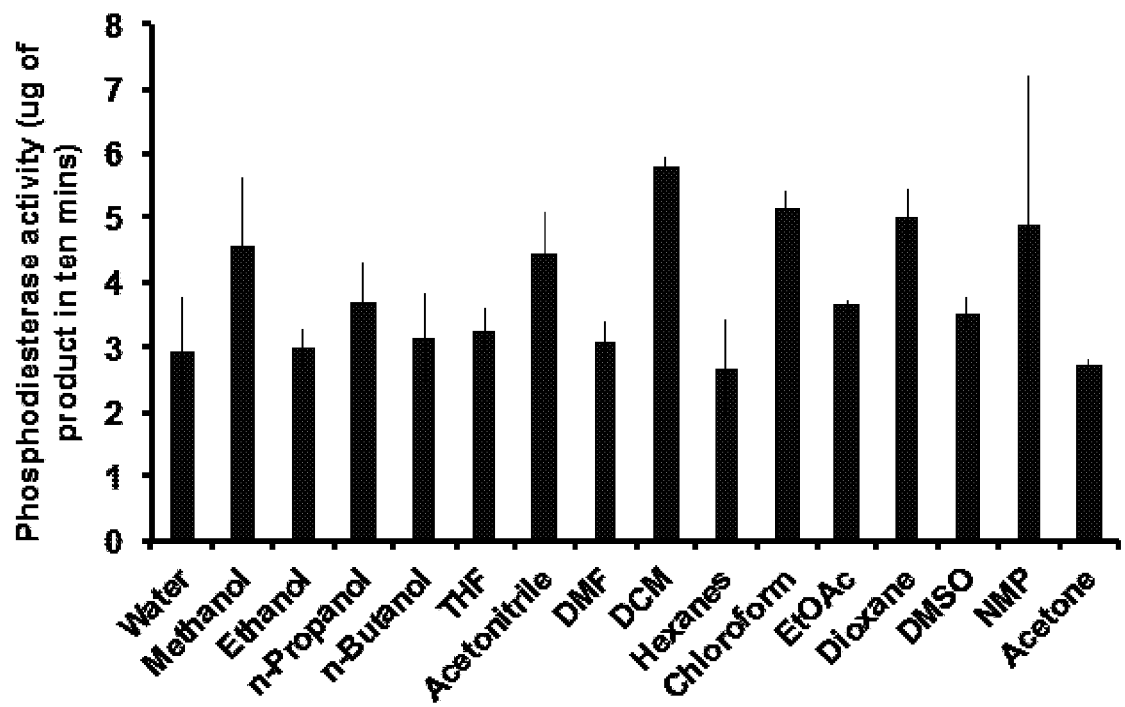

FIG. 47. Bar graph depicting the effect of reaction temperature on the liberation of p-nitrophenol. For this experiment, 1000 µL of substrate solution (0.7 mM bis(p-nitrophenyl) phosphate sodium salt and 5% of the desired organic solvent) was added to a 2.00 mL sinter vial and was heated to the 70° C. for five min. Once the temperature had been reached, phosphodiesterase (4.96 nMoles) was added to the solution. After ten min, the reaction was quenched with 300 µL 4 M NaOH and immediately analyzed as described previously. Error is reported as standard deviation around the mean (n=3).

Figure 48:
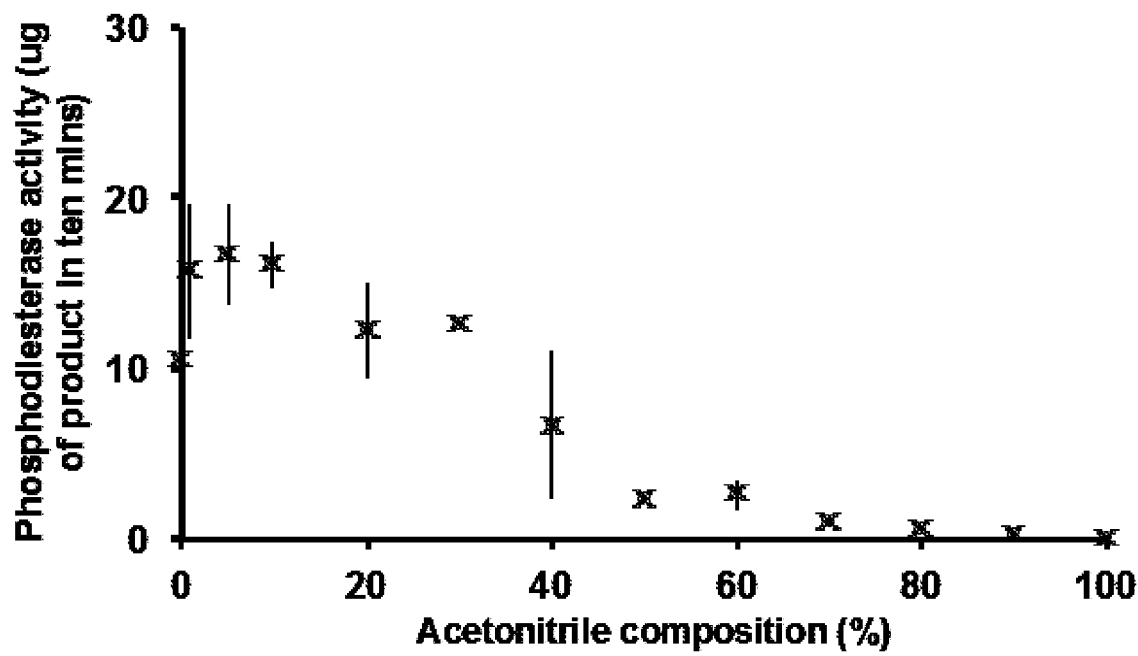

FIG. 48. Monitoring the effects acetonitrile composition on the liberation of p-nitrophenol. For this experiment, 1000 µL of substrate solution (0.7 mM bis(p-nitrophenyl) phosphate sodium salt and varying levels of acetonitrile) was added to a 2.00 mL sinter vial and allowed to warm to 70° C. over five min. Once the temperature had been reached, phosphodiesterase (4.96 nMoles) was added to the solution. After ten min, the reaction was quenched with 300 µL 4 M NaOH and immediately analyzed as described previously. Error is reported as standard deviation around the mean (n=3).

Figure 49:
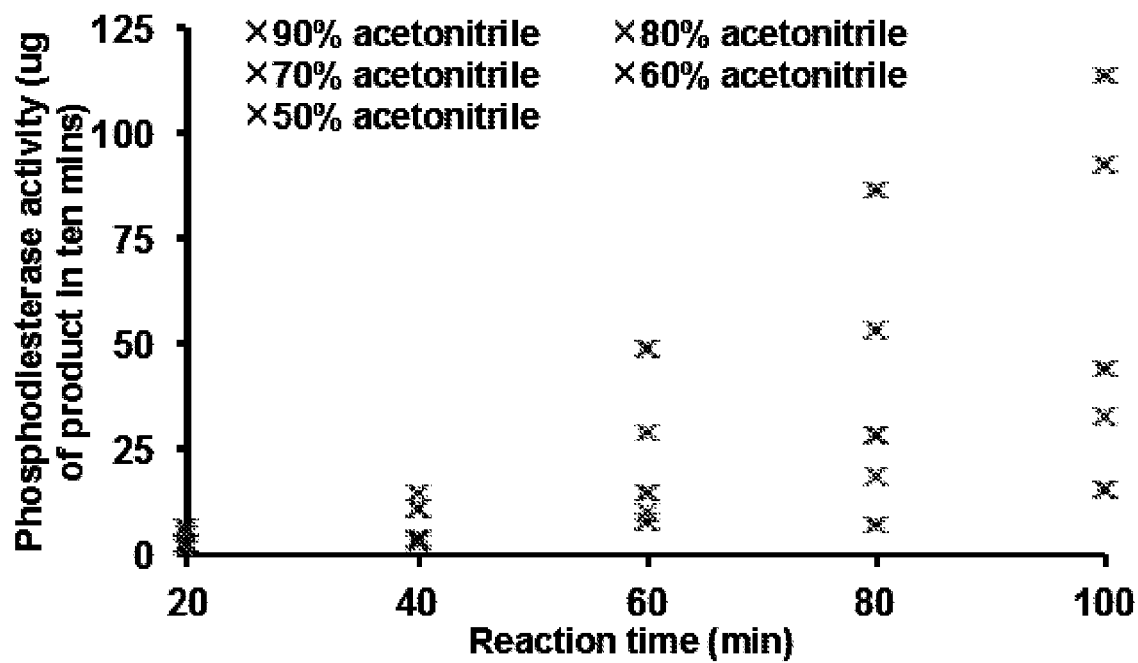

FIG. 49. Monitoring the reaction profile for phosphodiesterase in varying higher acetonitrile compositions. For this experiment, 1000 µL of substrate solution (0.7 mM bis(p-nitrophenyl) phosphate sodium salt, and varying levels of acetonitrile) was added to a 2.00 mL sinter vial and allowed to warm to 70° C. over five min. Once the temperature had been reached, phosphodiesterase (4.96 nMoles) was added to the solution. After ten min, the reaction was quenched with 300 µL 4 M NaOH and immediately analyzed as described previously. Error is reported as standard deviation around the mean (n=3).

Figure 50:
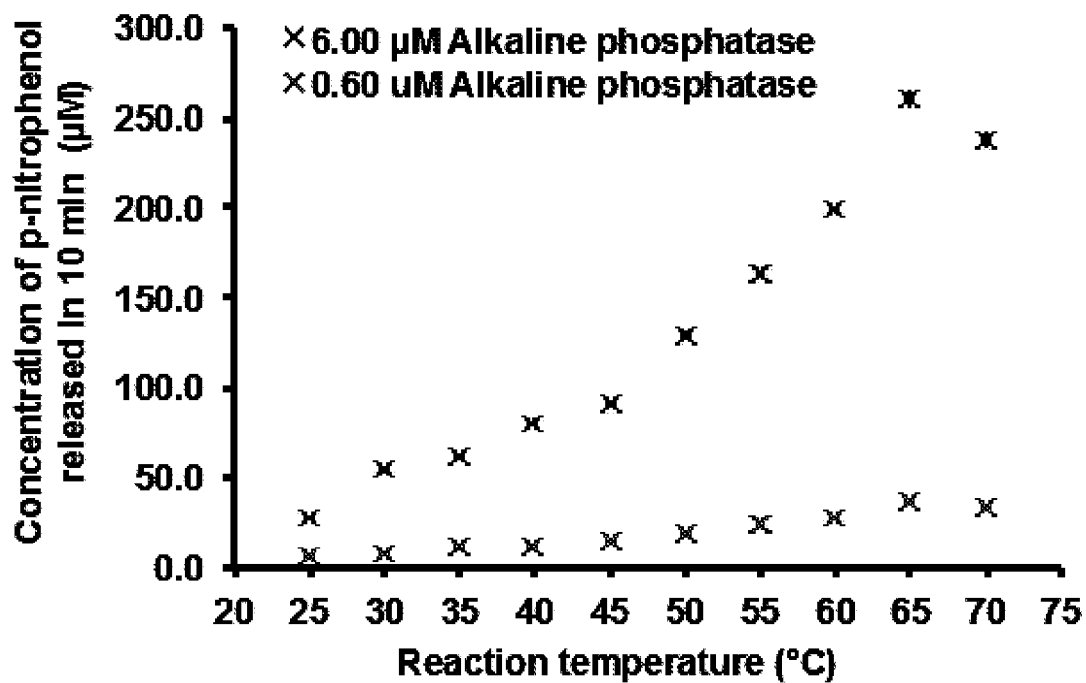

FIG. 50. Monitoring the effect of reaction temperature on the reactivity of alkaline phosphatase. For this experiment, 1000 µL of substrate solution (0.7 mM p-nitrophenyl phosphate sodium salt) was added to a 2.00 mL sinter vial and allowed to warm to the required temperature over five min. At this point 50 µL of either 6.00 µM or 0.60 µM of alkaline phosphatase was added to the substrate solution and left to react for five min. After the reaction time had ended, the reaction was quenched with 200 µL of 4 M NaOH, and the sample analyzed as described above. Error is reported as standard deviation around the mean (n=3). Data points (crosses) for 6.00 µM alkaline phosphatase generally lie above those for 0.60 µM alkaline phosphatase.

Figure 51:
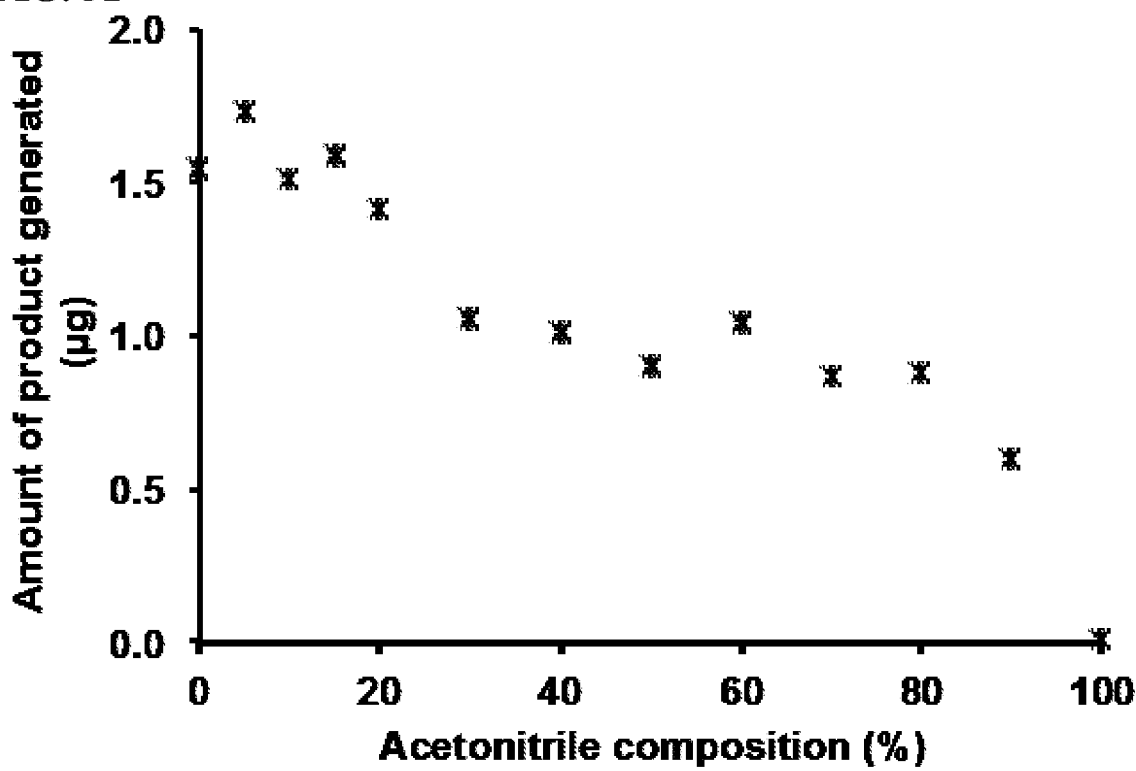

FIG. 51. Monitoring the effect of buffer acetonitrile composition on the reactivity of alkaline phosphatase. For this experiment, 1000 µL of substrate solution p-nitrophenyl phosphate sodium salt and 0-100% acetonitrile) was added to a 2.00 mL sinter vial and warmed to 65° C. over three min. At this point, 50 µL of 6.0 µM alkaline phosphatase was added, and the reaction proceeded for five min. A control reaction devoid of enzyme was performed under identical conditions to serve as a bank measurement. The reaction and blank were then quenched with 200 µL of 4 M NaOH, and the sample as previously described. Error is reported as standard deviation around the mean (n=3).

Figure 52:
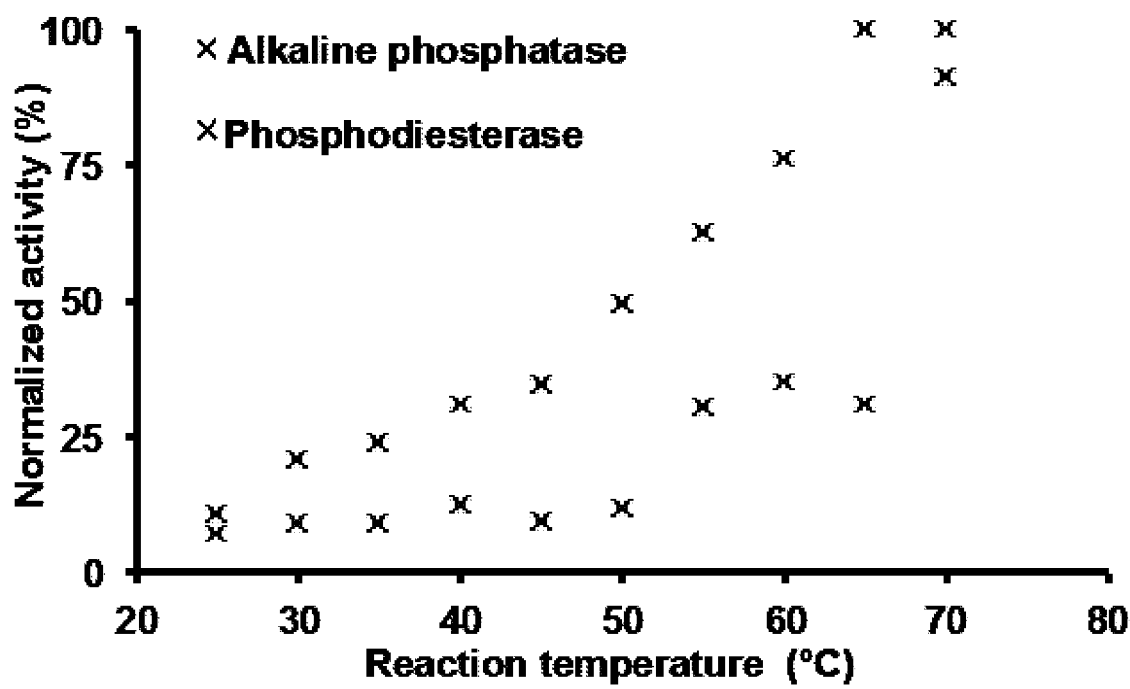

FIG. 52. The effect of reaction temperature on phosphodiesterase and alkaline phosphatase. This graph concludes that both enzymes function more efficiently at higher temperatures. For the experiments discussed in the manuscript, a reaction temperature of 65° C. was used. Even though a reaction temperature of 70° C. provides superior activity for phosphodiesterase, the rate limiting enzyme in this process is alkaline phosphatase, thus, ensuring that alkaline phosphatase has its most preferential reaction conditions is of prime importance. Data points for alkaline phosphtase (crosses) generally lie above those for phosphodiesterase.

Figure 53:
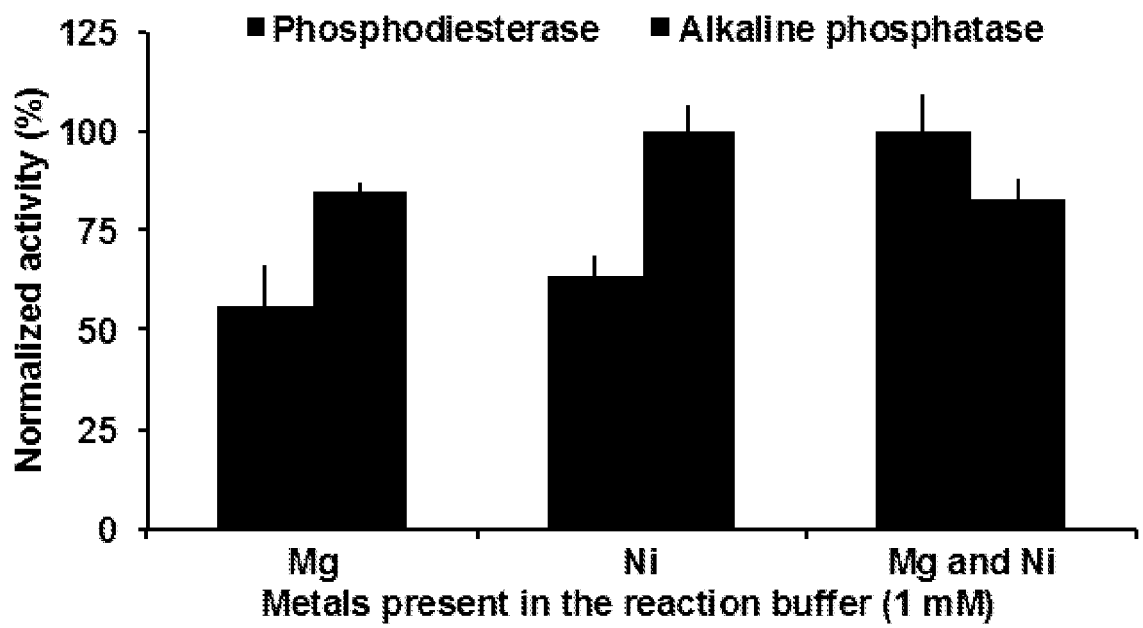

FIG. 53. Bar graph depicting the effect of different metal ions present in the reaction buffer on the activity of phosphodiesterase and alkaline phosphatase. This graph concludes that a mixture of both the metals is beneficial for reactivity (1 mM $Ni^{2+}$ and 1 mM $Mg^{2+}$). This was a surprising result as we expected similar activity. The increase in activity could be due to a higher salt concentration providing optimal activity, all though no additional experimentation was performed. Bar graph bin ordering (left to right); phosphodiesterase, alkaline phosphatase.

Figure 54A:
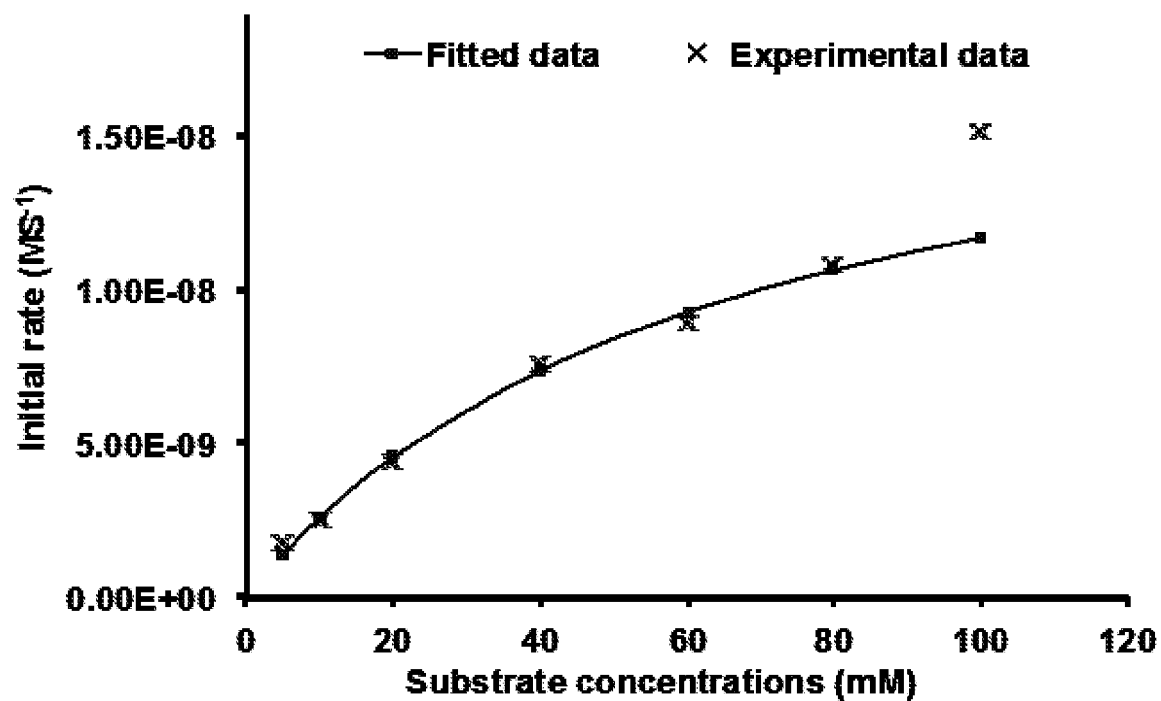
Figure 54B:
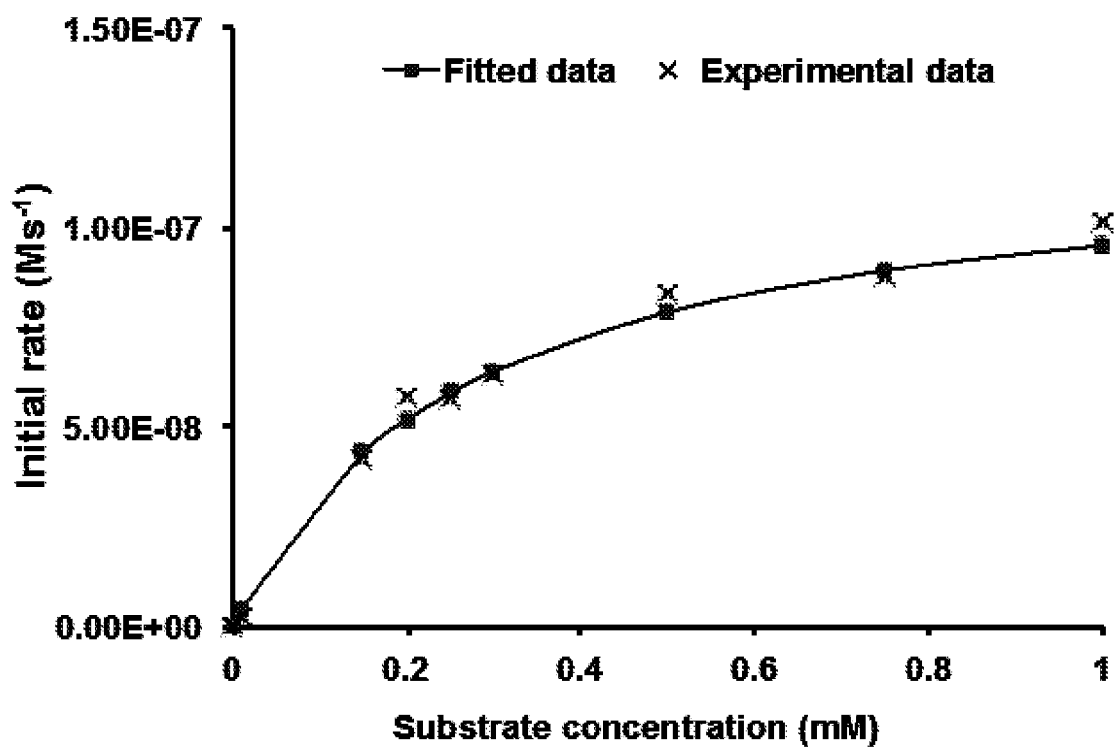

FIGS. 54A-54B. Michaelis-Menten plots for alkaline phosphatase and phosphodiesterase. FIG. 54A: The Michaelis-Menten values for recombinantly expressed alkaline phosphatase displayed that this enzyme is dramatically impacted by p-nitrophenol inhibition. The most important value this methodology is the $k_{cat}/k_M$ value, which in this case is 0.0078 mM $s^{-1}$. FIG. 54B: The Michaelis-Menten values for recombinantly expressed phosphodiesterase elucidated a $k_{cat}/k_M$ value of 113.43 mM $s^{-1}$. Thus, at the same concentration, phosphodiesterase performs 1450 faster than alkaline phosphatase. To create an efficient multistep reaction, alkaline phosphatase must be at 1450 greater concentration than phosphodiesterase. The assay conditions were as follows: 65° C. for five min, with 100 µL of enzyme solution at the indicated concentrations, and 900 µL of the substrate solution. Both reactions were immediately added to an ice bath after the reaction time had ended with 100 µL immediately added to a 96 well plate and analyzed as previously described. A non-linear regression analysis fitted the experimental data directly to a Michaelis-Menten curve. Error is reported as maximum and minimum around the mean. (n=3).

Figure 55:
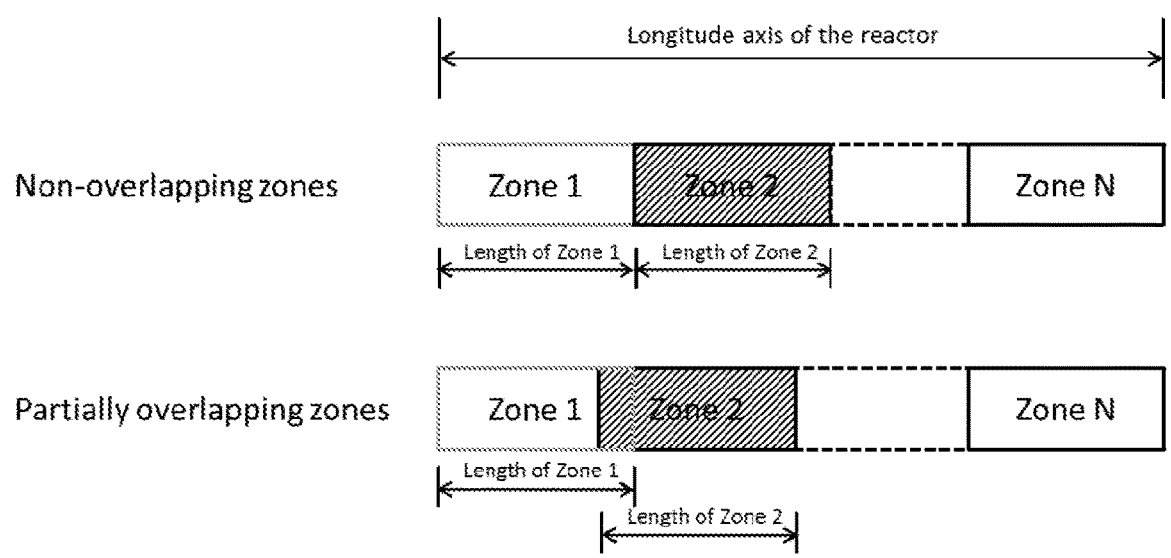

FIG. 55. Side view of a reactor (e.g., an enzyme reactor) depicting multiple zones. In embodiments, the zones are non-overlapping. In embodiments, the zones partially overlap.

Figure 56:
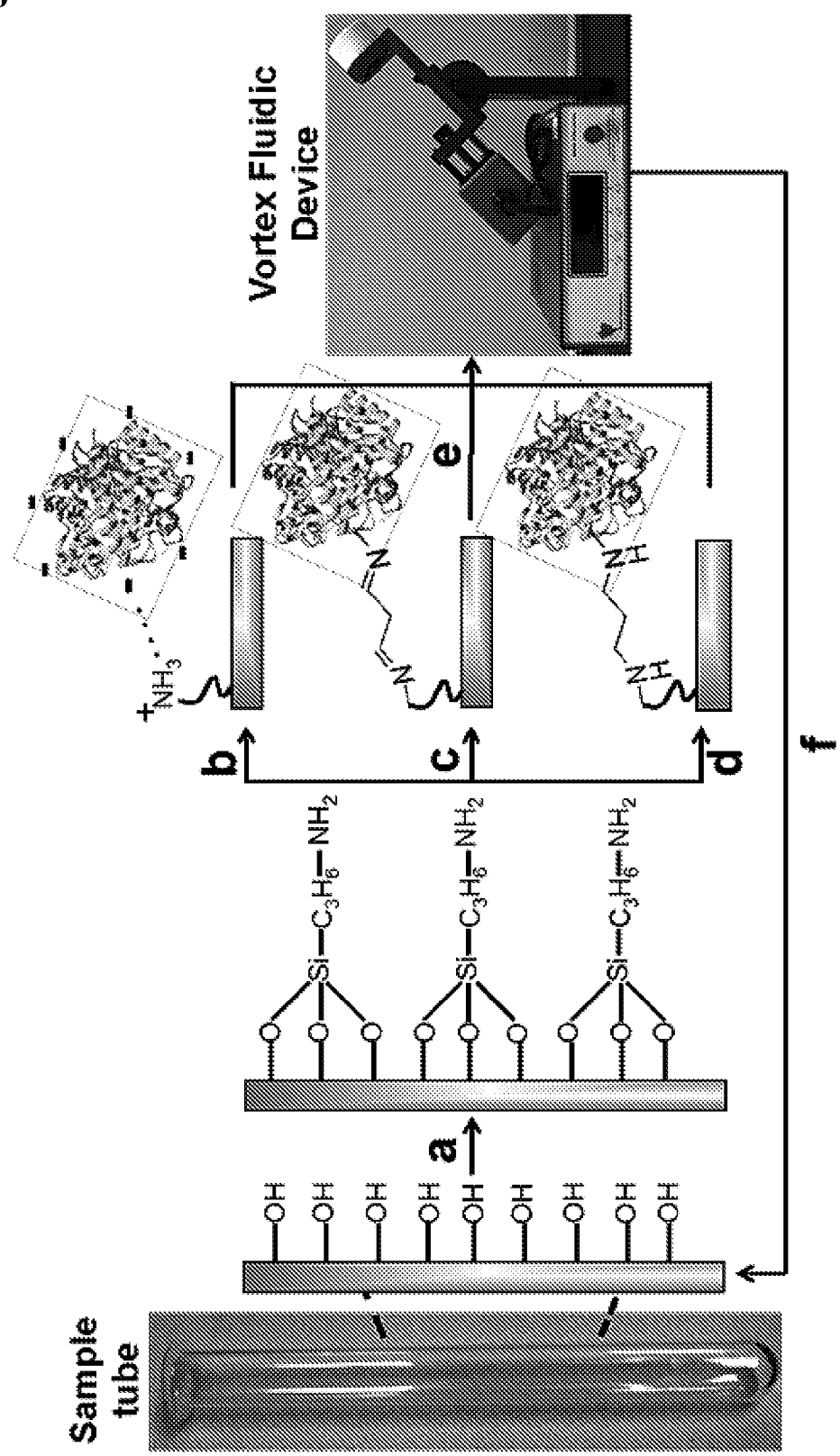

FIG. 56. Enzyme immobilization onto the surface of the VFD reactor. (Step a): First, the surface of the sample tube is coated with APTES (3-aminopropyl triethoxysilane) to generate a high concentration of surface-bound amines; a simplified depiction of this surface coating is shown here. (Step b): β-glucosidase is added directly to the APTES-coated sample tube for non-covalent immobilization. (Step c): After derivatization of the APTES layer with glutaraldehyde, β-glucosidase is attached in this simplified structure of the linker and cross-link. (Step d): The imine-glutaraldehyde is reduced with $NaBH_3CN$. (Step e): The immobilization efficiency was tested by VFD processing in the presence of the β-glucosidase substrate, 4-nitrophenyl β-D-glucopyranoside. (Step f): The sample tube can be regenerated through rapid treatment with a thin film of piranha solution. The reactions disclosed herein can be performed in continuous flow [Example 6, reference 39].

FIGS. 57A-57D. Non-covalent immobilization using β-glucosidase and 4-nitrophenyl β-D-glucopyranoside for optimization. (FIG. 57A): The enzyme and buffer salt concentration were varied during the immobilization step. The contour plot reveals that a 0.3 mg mL$^{-1}$ enzyme concentration in a 60 mM NaCl PBS buffer is optimal for high substrate conversion. (FIG. 57B): Decreased catalytic activity due to enzyme leaching is depicted in this contour plot. Thus, higher salt concentrations are revealed as beneficial for immobilization longevity. (FIG. 57C): Varying the pH of the attachment buffer established optimal immobilization in PBS at pH 8.0. The deviation from the trend at pH 5.0 is due to the isoelectric point of β-glucosidase. (FIG. 57D): For all optimization experiments, a β-glucosidase-4-nitrophenyl β-D-glucopyranoside (10 mM, 1.50 mL) system was used. β-glucosidase hydrolyses the substrate, releasing p-nitrophenol ($\lambda_{max}$ 405 nm) and β-D-glucopyranoside. Each assay was performed in the VFD for five min, and each reactor was assayed six times. Two separate reactors were used per data point, and the error is a standard deviation around the mean (n=12).

FIGS. 58A-58D. The conditions optimized here are general for a range of proteins. The protein solutions used in the immobilization step can be recycled to coat more than ten sample tubes, with the coated sample tubes still maintaining catalytic activity for weeks. (FIG. 58A): Switching from non-covalent to covalent attachments increased substrate conversion levels dramatically. (FIG. 58B): Applying the symmetrical amine-glutaraldehyde cross linker optimized for β-glucosidase to alkaline phosphatase and phosphodiesterase establishes the generality of the method, with all three proteins having good stability over 10 h of processing. (FIG. 58C): The β-glucosidase solution (3 mL, 0.3 mg mL$^{-1}$) used in the immobilization step can be recycled to coat more than ten sample tubes, with the first sample tube having the same substrate transformation rate as the last. It is believed that this solution can coat tens of sample tubes given the small amount of protein used in each immobilization. (FIG. 58D): Storing the enzyme-immobilized tubes devoid of buffer allowed >20% catalytic activity after one month. The rates displayed above are the average rates as described in FIG. 2 (n=12). The data in FIGS. 58A-58B were from continuous flow experiments with a flow rate of 1.0 mL min$^{-1}$.

Figure 59:
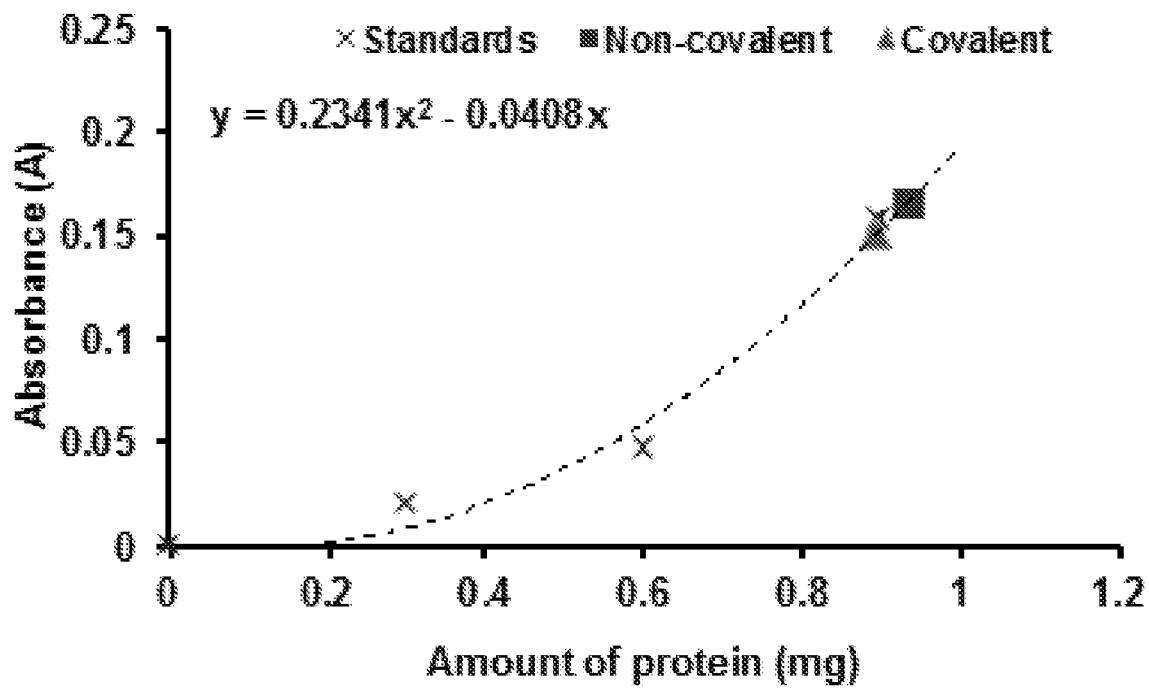

FIG. 59. Determining the amount of enzyme removed from the stock solution during non-covalent and covalent immobilization. The results demonstrate that very low quantities of β-glucosidase are removed from the stock solution for both the non-covalent and the imine-glutaraldehyde cross-linking immobilizations (<1% in each case). To ascertain the amount of protein for the tested solution, the quadratic equation shown was solved for each absorption value. The error is reported as standard deviation around the mean (n=3).

Figure 60:
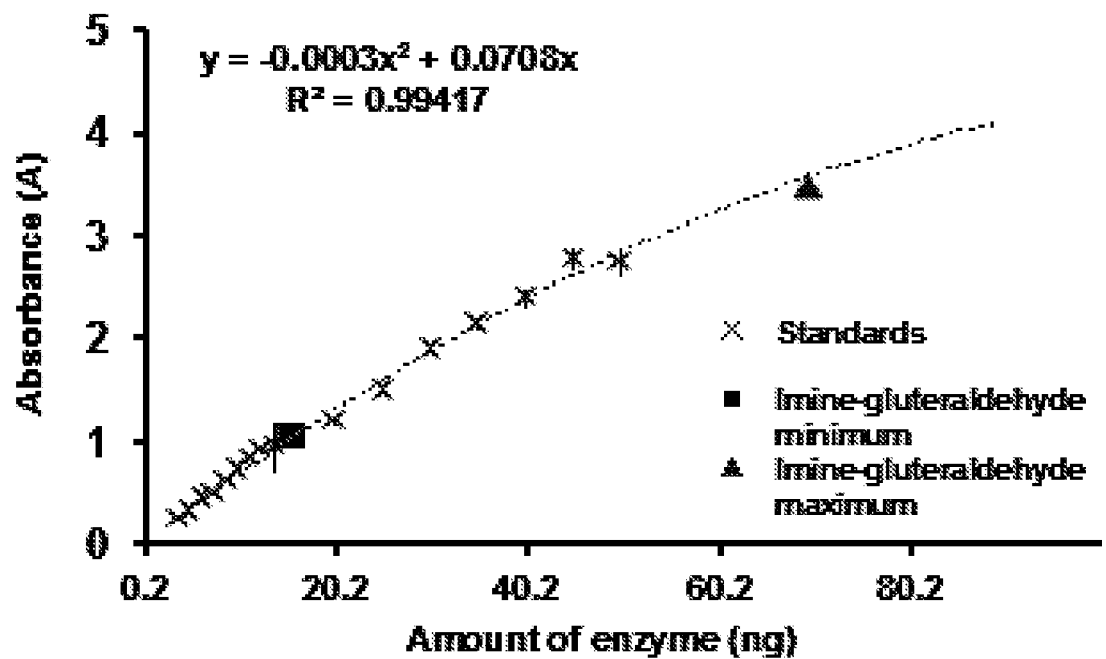

FIG. 60. Determining the amount of enzyme by substrate transformation levels. The results demonstrate that very low quantities of β-glucosidase are attached to the reactor, agreeing with the results in FIG. 59. For this analysis, the imine-glutaraldehyde cross linker immobilization method was used. The quadratic equation (shown) was solved for the minimum and maximum absorption values obtained in the experiments reported in this manuscript. The minimum value yielded a mass of 15.4 ng, and the maximum value obtained yielded 69.8 ng β-glucosidase on the reactor surface. The error is reported as a standard deviation around the mean (n=3).

Figure 61:
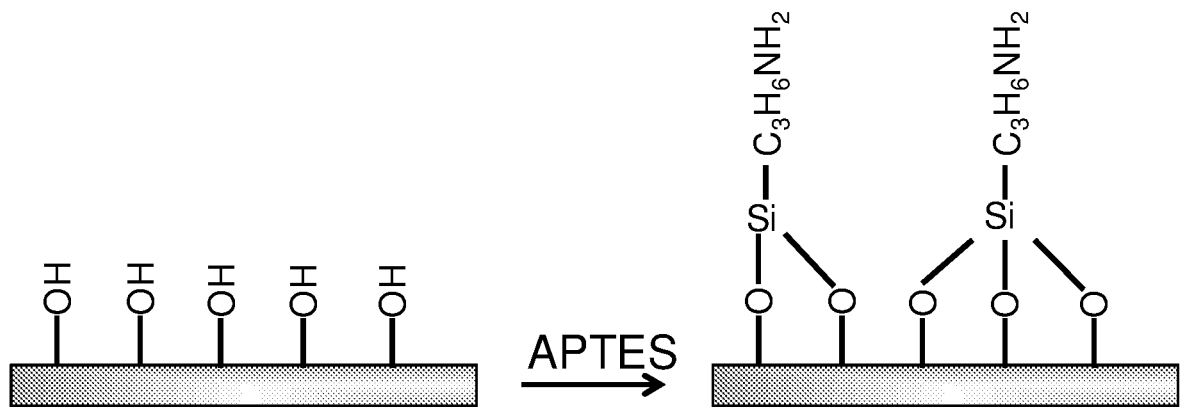

FIG. 61. Cartoon depicting preparation of APTES coated sample tube. See Example 6.

Figure 62:
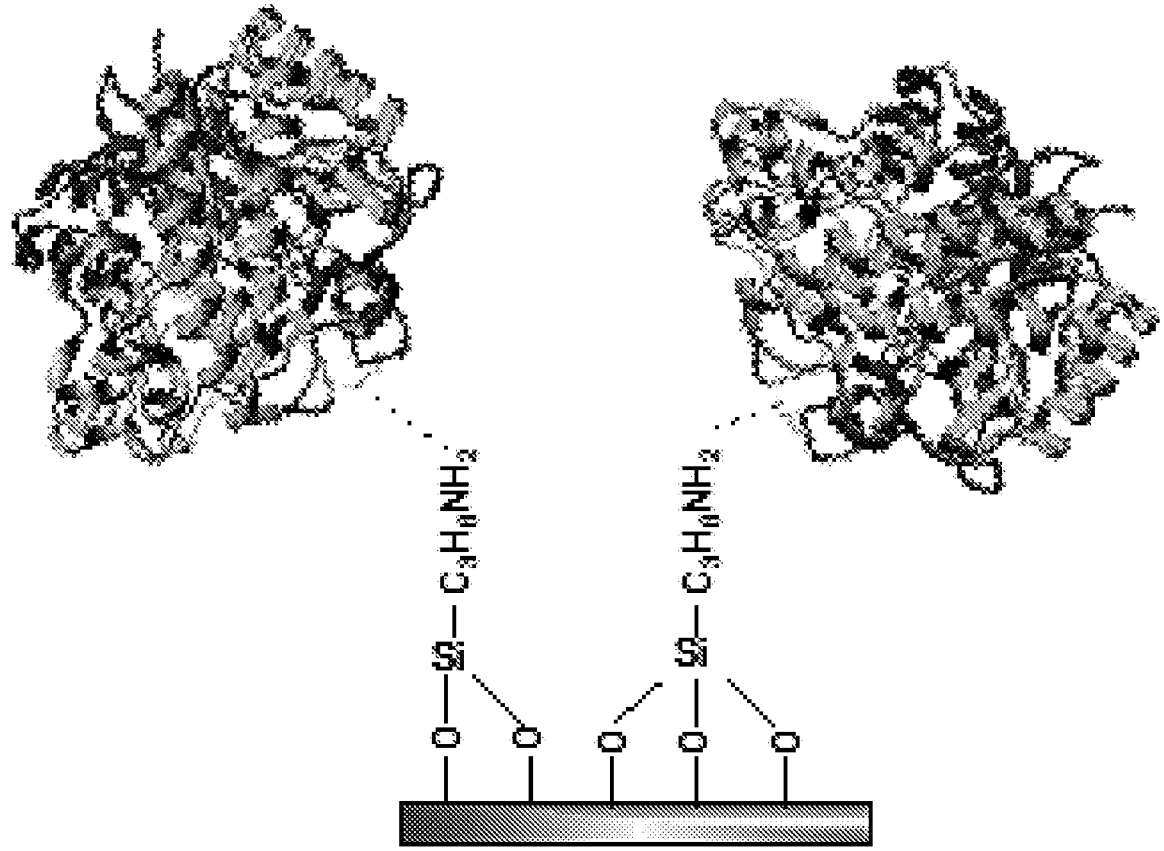

FIG. 62. Cartoon depicting non-covalent immobilization of proteins (shown in ribbon diagram at left and right) on APTES coated sample tube. See Example 6.

Figure 63:
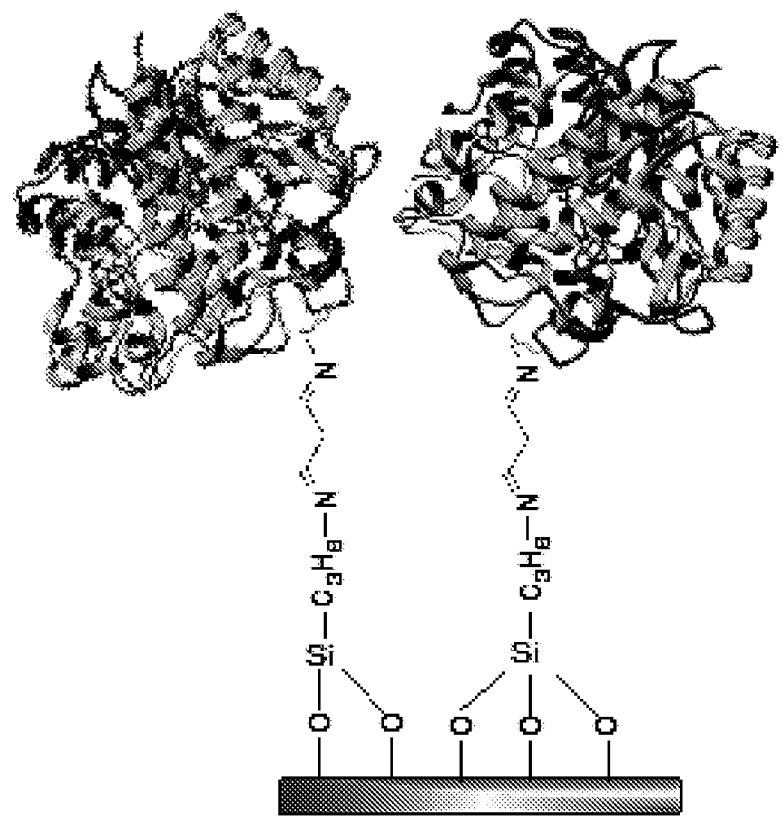

FIG. 63. Cartoon depicting imine-glutaraldehyde cross-linker immobilization. See Example 6.

Figure 64:
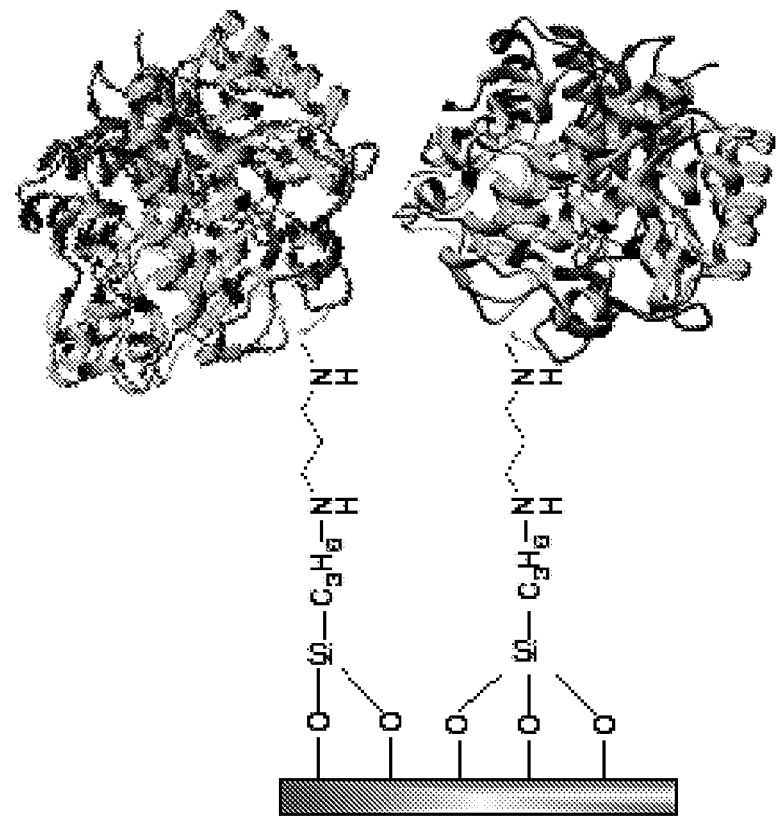

FIG. 64. Cartoon depicting amine-glutaraldehyde cross-linker immobilization. See Example 6.

DETAILED DESCRIPTION

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

The term "combining" or "contacting" is used in accordance with its plain ordinary meaning and refers to the process of allowing at least two distinct species (e.g. chemical compounds including enzymes and their substrates) to become sufficiently proximal to react, interact or physically touch. It should be appreciated, however, that the resulting reaction product can be produced directly from a reaction between the added reagents or from an intermediate from one or more of the added reagents which can be produced in the reaction mixture.

The term "covalently" or "covalent" means directly or through a covalently bonded intermediary via one or more chemical bonds that involve the sharing of electron pairs between atoms. The term "non-covalently" or "non-covalent" means interactions through ionic bond(s), van der Waal's bond(s)/interactions, hydrogen bond(s), polar bond(s), or combinations or mixtures thereof.

The term "enzyme" refers to macromolecular biological catalysts. Enzymes accelerate, or catalyze, chemical reactions. The molecules at the beginning of the process upon which enzymes may act are called substrates and the enzyme converts these into different molecules, called products. Enzymes must bind their substrates before they can catalyze any chemical reaction. Enzymes are usually very specific as to what substrates they bind and then the chemical reaction catalyzed. Specificity is achieved by binding pockets with complementary shape, charge and hydrophilic/hydrophobic characteristics to the substrates. The composition (e.g., liquid composition) that includes an enzyme and its substrate is called an "enzyme-substrate mixture" used herein. In embodiments, the enzyme-substrate mixture is in a liquid form (e.g., a solution) and referred as a "liquid enzyme-substrate mixture." In embodiments, the enzyme-substrate mixture is in a form of a gel, a hydrogel, or a paste. In embodiments, the enzyme is a water soluble enzyme. A "water soluble enzyme" is an enzyme that is able to be dissolved in a water-based liquid (an aqueous solvent or aqueous liquid).

The term "mechanically mixing" refers to combining two or more substances to form one substance or mass by mechanical forces (such as rotating or spinning) The term "rotationally mixing" or "rotating" or "rotational mixing" means an action of spinning around an axis or center.

The term "vibrational energy" as used herein refers to energy derived from a vibration (e.g. a mechanical vibration). In embodiments, the vibrational energy is a mechanical vibrational energy whereby oscillation occurs. In embodiments, the oscillations occur about an equilibrium point. In embodiments, the oscillations are periodic. Thus, the vibrational energy may be in the form of a wave that is generated by repetitive mechanical motions transmitted to the container/reactor (reaction vessel) used for the enzymatic reaction. The source of the vibration may be a machine, or components thereof, used to facilitate the enzymatic reaction. For example, the machine may be used to rotate the reaction vessel or to mechanically stir the contents of the reaction vessel.

In embodiments, the mechanical mixing (e.g., rotation or spinning) of the container (reaction vessel) that is used for the enzymatic reaction forces the mixture of the enzyme and the substrate (e.g., a solution, a gel, a hydrogel or a paste) into a thin layer upon such mechanical mixing (e.g., rapid mechanical mixing). This thin layer is referred herein as a "thin film." In embodiments, the thin film is about 50-500 μm in thickness (e.g., about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500 μm). In embodiments, the thin film is about 200-400 μm in thickness (e.g., about 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400 μm). In embodiments, the thin film is about 200-300 μm in thickness (e.g., about 200, 205, 210, 215, 220, 225, 230, 235, 240, 245, 250, 255, 260, 265, 270, 275, 280, 285, 290, 295, 300 μm). Accordingly, an "enzyme-substrate mixture thin film" used herein refers to a thin film that includes the enzyme-substrate mixture described herein. The thin film may be a liquid, gel or paste. In embodiments, the thin film is a liquid.

Faraday waves, also known as Faraday ripples, are non-linear standing waves that appear on liquids enclosed by a vibrating receptacle (e.g., vibrating reaction vessel).

"Harmonic vibrational frequency," as used herein, refers to a frequency of vibrational energy (e.g. a vibrational wave) that is harmonic in nature. In embodiments, a given harmonic vibrational energy generates a vibrational response within the enzyme-substrate mixture (e.g. enzyme-substrate mixture thin film).

The term "vibrational response" as used herein refers to an effect on the enzyme-substrate mixture caused by vibrational energy that results in a Faraday wave and/or an increase in enzyme functionality. In embodiments, the vibrational response is an increase in enzymatic activity of the enzyme, increase in turnover rate of the enzyme, increase in rate constant ($k_{cat}$), increase in enzymatic efficiency ($K_{cat}/K_m$), and/or decrease in the reaction time relative to an enzymatic reaction conducted in the absence of the vibrational energy. Enzyme activity or enzymatic activity may be calculated as moles of substrate converted per unit time or is calculated as rate×reaction volume. Enzyme activity may be a measure of the quantity of active enzyme present and is thus dependent on conditions. The apparent unimolecular rate constant $k_{cat}$ is also called turnover number and denotes the maximum number of enzymatic reactions catalyzed per second. The term "reaction time" refers to the duration of a complete enzymatic reaction. Michaelis-Menten equation is the basis for most single-substrate enzyme kinetics. The Michaelis constant $K_M$ is experimentally defined as the concentration at which the rate of the enzyme reaction is half $V_{max}$, which can be verified by substituting [S]=$K_m$, into the Michaelis-Menten equation and can also be seen graphically. If the rate-determining enzymatic step is slow compared to substrate dissociation ($k_2 \ll k\_1$), the Michaelis constant $K_M$ is roughly the dissociation constant KD of the enzyme-substrate complex.

Figure 8A:
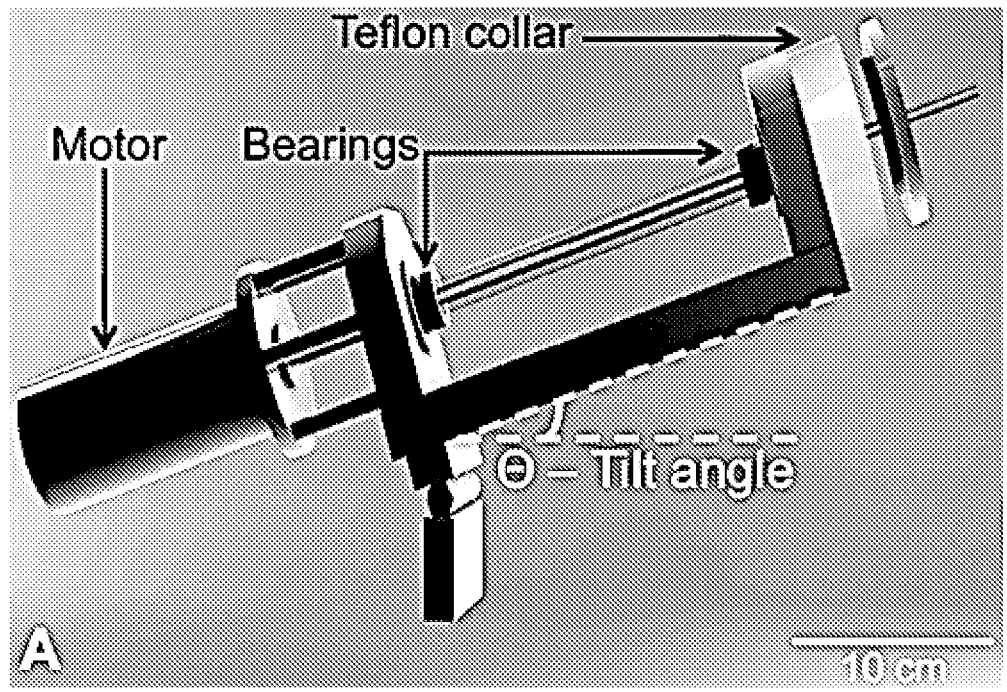
FIGS. 8A-8C. The VFD and its Faraday waves.

The "tilt angle (θ)" used herein refers to the angle of the longitudinal axis relative to the horizontal axis of the container (or reactor or enzyme reactor) for enzymatic reactions (see, e.g., FIG. 8A).

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers.

In embodiments, the mechanical mixing (e.g., rotation or spinning), such as rapid mechanical mixing of the reactor or enzyme reactor forces the protein binding material (e.g., materials that can covalently or non-covalently bind to the protein of interest) into a thin layer upon such mechanical mixing. This thin layer is referred herein as "protein binding film." In embodiments, the film is about 50-500 μm in thickness (e.g., about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500 µm). In embodiments, the thin film is about 200-400 µm in thickness (e.g., about 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400 µm). In embodiments, the thin film is about 200-300 µm in thickness (e.g., about 200, 205, 210, 215, 220, 225, 230, 235, 240, 245, 250, 255, 260, 265, 270, 275, 280, 285, 290, 295, 300 µm). Accordingly, a "protein binding film complex" used herein refers to a complex of protein of interest and the protein binding film, where the protein of interest is either covalently or non-covalently linked (bound) to the protein binding film.

A "binding moiety" refers to a functional group that is covalently attached to the molecule. In embodiments, the binding moiety attached to the protein recognizes and binds to the binding partner attached to the protein binding film. In embodiments, the binding moiety used herein is a reactive moiety. As used herein, the term reactive moiety includes any group capable of reacting with another molecule, e.g., a nucleic acid or polypeptide through covalent, non-covalent or other interactions. By way of example, a polypeptide or a protein of interest can include an amino acid reactive moiety that reacts with a funtional group on another molecule through a covalent, non-covalent or other interaction (e.g., to form a disulfide bond, amide bond or click chemistry bond). In embodiments, the binding moiety used herein is an expression tag. The term "expression tag" is further defined below.

A His-tag is a peptide moiety composed of 5-10 (e.g., 5, 6, 7, 8, 9 or 10) histidines capable of being used as a binding moiety. In embodiments, the His-tag is capable of binding to divalent nickel or divalent cobalt ligands.

The term "reactor" as used herein refers to a device for containing a chemical reaction (e.g., an enzymatic reaction) or process (e.g., purifying a protein) (e.g. a reaction vessel). The term "enzyme reactor" refers to a reactor for containing an enzymatic reaction (e.g. enzyme reaction vessel). In embodiments, the reactor is a VFD or the like. In embodiments, an enzyme reactor is a VFD or the like.

Methods

Enzymes make life possible by catalyzing diverse and challenging chemical transformations with exquisite specificity. Applications in both industry and academia rely on the selectivity and power of enzymes to catalyze otherwise challenging transformations. Biocatalysts offer remarkable rate accelerations compared to uncatalyzed reactions, with typical rate accelerations ($k_{cat}/k_{uncat}$) of $10^5$- to $10^{15}$-fold faster. Though some enzymes are diffusion-limited, the catalytic rates of enzymes are often more typically limited by their catalytic efficiency ($k_{cat}/K_m$); additionally, molecular crowding, along with product and substrate inhibition, can reduce enzyme efficiency. Though some enzymes catalyze transformations with rapid rates (e.g., laccases, fumarases and alcohol dehydrogenases), other enzymes operate at only modest reaction rates, requiring long reaction times and carefully optimized conditions; for example, DERA requires long processing times (hours to days), and is substrate-inhibited. The methods described herein solve these and other problems in the field of accelerating enzymatic catalytic reactions. In embodiments, methods are provided that utilize the combination of mechanically mixing of the enzyme-substrate mixture and applying a vibrational energy to the mixture, therefore generating a vibrational response within the mixture and accelerating the enzymatic reactions.

In a first aspect, there is provided a method for reacting an enzyme and a substrate. The method includes combining an enzyme and a substrate of the enzyme to form an enzyme-substrate mixture. The method further includes mechanically mixing the enzyme-substrate mixture. The method further includes applying a vibrational energy to the enzyme-substrate mixture, thereby reacting the enzyme and the substrate.

In embodiments, the method includes combining an enzyme and a substrate of the enzyme to form an enzyme-substrate mixture; mechanically mixing the enzyme-substrate mixture; generating an enzyme-substrate mixture thin film; and applying a vibrational energy to the enzyme-substrate mixture thin film, thereby reacting the enzyme and the substrate.

Enzymes are macromolecular biological catalysts. Enzymes accelerate, or catalyze, chemical reactions. The molecules at the beginning of the process upon which enzymes may act are called substrates and the enzyme converts these into different molecules, called products. Any enzymes can be used in the methods described herein, particularly water soluble enzymes. In embodiments, the enzyme is a water soluble enzyme. In embodiments, the water soluble enzyme is an esterase, a lipase, deoxyribose-5-phosphate aldolase (DERA), β-glucosidase, or an alkaline phosphatase.

In embodiments, the enzyme-substrate mixture is a liquid, a gel, a hydrogel, or a paste. In embodiments, the enzyme-substrate mixture is a liquid. In embodiments, the enzyme-substrate mixture is a gel. In embodiments, the enzyme-substrate mixture is a hydrogel. In embodiments, the enzyme-substrate mixture is a paste.

In embodiments, mechanically mixing the enzyme mixture forms an enzyme-substrate mixture thin film, where the vibrational energy is sufficient to produce a vibrational response within the enzyme-substrate mixture thin film. In embodiments, the thin film is about 50-500 in thickness (e.g., about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500 µm). In embodiments, the thin film is about 200-400 µm (e.g., about 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400 µm). In embodiments, the thin film is about 200-300 µm (e.g., about 200, 205, 210, 215, 220, 225, 230, 235, 240, 245, 250, 255, 260, 265, 270, 275, 280, 285, 290, 295, 300 µm).

In embodiments, a vibrational response within the enzyme-substrate mixture thin film is a Faraday wave. Faraday waves, also known as Faraday ripples, are nonlinear standing waves that appear on liquids enclosed by a vibrating receptacle. In embodiments, a vibrational response within the enzyme-substrate mixture thin film is to increase the enzymatic activity of the enzyme, increase the turnover rate of the enzyme, increase the rate constant ($K_{cat}$), increase the enzymatic efficiency ($K_{cat}/K_m$), and/or decrease the reaction time relative to an enzymatic reaction conducted in the absence of the vibrational energy.

In embodiments, the vibrational energy is sufficient to increase the enzymatic activity of the enzyme, increase the turnover rate of the enzyme, increase the rate constant ($K_{cat}$), increase the enzymatic efficiency ($K_{cat}/K_m$), and/or decrease the reaction time relative to an enzymatic reaction conducted in the absence of the vibrational energy. Examples of methods for quantifying the enzymatic activity, the turnover rate of the enzyme, the rate constant, the enzymatic efficiency and the reaction time are provided in Examples 1-4.

In embodiments, the vibrational energy is sufficient to increase the enzymatic activity of the enzyme relative to an enzymatic reaction conducted in the absence of the vibrational energy. In embodiments, the vibrational energy is sufficient to increase the enzymatic activity of the enzyme at least 2-fold (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100-fold or more) relative to the enzymatic activity in the absence of the vibrational energy. In embodiments, the enzymatic activity is increased from 2-fold to 100-fold. In embodiments, the enzymatic activity is increased from 2-fold to 50-fold. In embodiments, the enzymatic activity is increased from 2-fold to 15-fold. In embodiments, the enzymatic activity is increased from 5-fold to 20-fold.

In embodiments, the vibrational energy is sufficient to increase the turnover rate of the enzyme relative to an enzymatic reaction conducted in the absence of the vibrational energy. In embodiments, the vibrational energy is sufficient to increase the turnover rate of the enzyme at least 2-fold (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100-fold or more) relative to the turnover rate of the enzyme in the absence of the vibrational energy. In embodiments, the turnover rate is increased from 2-fold to 100-fold. In embodiments, the turnover rate is increased from 2-fold to 50-fold. In embodiments, the turnover rate is increased from 2-fold to 15-fold. In embodiments, the turnover rate is increased from 5-fold to 20-fold.

In embodiments, the vibrational energy is sufficient to increase the rate constant ($K_{cat}$) relative to an enzymatic reaction conducted in the absence of the vibrational energy. In embodiments, the vibrational energy is sufficient to increase the rate constant of the enzyme at least 2-fold (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100-fold or more) relative to the rate constant of the enzyme in the absence of the vibrational energy. In embodiments, the rate constant is increased from 2-fold to 100-fold. In embodiments, the rate constant is increased from 2-fold to 50-fold. In embodiments, the rate constant is increased from 2-fold to 15-fold. In embodiments, the rate constant is increased from 5-fold to 20-fold.

In embodiments, the vibrational energy is sufficient to increase the enzymatic efficiency ($K_{cat}/K_m$) relative to an enzymatic reaction conducted in the absence of the vibrational energy. In embodiments, the vibrational energy is sufficient to increase the enzymatic efficiency of the enzyme at least 2-fold (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100-fold or more) relative to the enzymatic efficiency of the enzyme in the absence of the vibrational energy. In embodiments, the enzymatic efficiency increased from 2-fold to 100-fold. In embodiments, the enzymatic efficiency is increased from 2-fold to 50-fold. In embodiments, the enzymatic efficiency is increased from 2-fold to 15-fold. In embodiments, the enzymatic efficiency is increased from 5-fold to 20-fold.

In embodiments, the vibrational energy is sufficient to decrease the reaction time relative to an enzymatic reaction conducted in the absence of the vibrational energy. In embodiments, the vibrational energy is sufficient to reduce reaction time of the enzyme at least 2-fold (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100-fold or more) relative to reaction time of the enzyme in the absence of the vibrational energy. In embodiments, the reaction time is reduced from 2-fold to 100-fold. In embodiments, the reaction time is reduced from 2-fold to 50-fold. In embodiments, the reaction time is reduced from 2-fold to 15-fold. In embodiments, the reaction time is reduced from 5-fold to 20-fold.

In embodiments, the vibrational energy produces a harmonic vibrational frequency. In embodiments, vibrational energy produces a non-harmonic (anharmonic) vibrational frequency. In embodiments, the vibrational energy produces a mix of harmonic vibrational frequency and non-harmonic vibrational frequency.

In embodiments, the mechanically mixing is rotationally mixing. In embodiments, the rotational speed of the rotationally mixing is about 3 krpm to about 10 krpm. In embodiments, the rotational speed is about 3 krpm, 3.5 krmp, 4 krmp, 4.5 krmp, 5 krmp, 5.5 krmp, 6 krmp, 6.5 krmp, 7 krmp, 7.5 krmp, 8 krmp, 8.5 krmp, 9 krmp, 9.5 krmp, or even 10 krmp. In embodiments, the rotational speed exceeds 10 krpm, e.g., 10.5 krpm, 11 krmp, 11.5 krmp, 12 krmp, 12.5 krmp, 13 krmp, 13.5 krmp, 14 krmp, 14.5 krmp, or even 15 krmp or greater. In embodiments, the maximum rotational speed depends on the type of motor used to impart rotational mixing. In embodiments, the rotational speed required for the enzymatic reaction depends on the type of enzyme.

In embodiments, the rotationally mixing is generated by a vortex fluid device (VFD). In embodiments, the VFD includes a tube reactor, which reactor includes a tube having a longitudinal axis, an inner cylindrical surface, and a closed and an open end. In embodiments, the tube is rotatable about the longitudinal axis. In embodiments, the tilt angle of the longitudinal axis relative to the horizontal is variable between about 0 degrees and about 90 degrees. In embodiments, the thin film tube reactor is substantially cylindrical or comprises at least a portion that is tapered. In embodiments, the thin film tube reactor is substantially cylindrical. In embodiments, the thin film tube reactor includes at least a portion that is tapered. In embodiments, the thin film tube includes a lip adjacent to the open end.

In embodiments, the enzyme-substrate mixture is within a confined container (i.e., the enzymatic reaction is conducted in a confined mode). In embodiments, the enzyme-substrate mixture is within a glass container. In embodiments, the mixture is within a metal or a plastic container. In embodiments, the container has a tilt angle of about 20 degree to about 90 degree. In embodiments, the glass container has a tilt angle of about 20 degree to about 90 degree (e.g., about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 degree).

In embodiments, the enzymatic reaction is conducted in a continuous flow mode, where the reagents (e.g., enzymes, substrates and other necessary reagents) are introduced into the rotating container in a continuous flow manner.

In embodiments, the vibrational energy is imparted to the enzyme-substrate mixture by acoustic energy, e.g., sound waves, from a sound source. In embodiments, the vibrational energy is imparted to the enzyme-substrate mixture by mechanical impingement; e.g., mechanical tapping. In embodiments, the vibrational energy is imparted to the enzyme-substrate mixture by fluidic manipulation. The term "fluidic manipulation" in this context includes mechanically induced manipulation of the fluid due to features in the sample tube holding the enzyme-substrate mixture, e.g., constrictions, expansions, knobs, paddles, and like formed into the walls of the sample tube. In embodiments, the vibrational energy is imparted to the enzyme-substrate mixture due to asymmetric rotation of the sample tube holding the enzyme-substrate mixture.

In embodiments, the container is subjected to acoustic energy. In embodiments, the tilt angle of the container can be any angle, if the container is subjected to acoustic energy. In embodiments, the container is subjected to mechanical impingement. In embodiments, the tilt angle of the container can be any angle, if the container is subjected to mechanical impingement. In embodiments, the container is subjected to fluidic manipulation. In embodiments, the tilt angle of the container can be any angle, if the container is subjected to fluidic manipulation. In embodiments, the container is subjected to asymmetric rotation. In embodiments, the tilt angle of the container can be any angle, if the container is subjected to asymmetric rotation.

In embodiments, the methods described herein include a plurality of enzymes. In embodiments, the methods described herein include a plurality of substrates.

In embodiments, the methods described herein include combining at least one enzyme, at least one substrate and at least one steric crowding reagent (e.g., polyethylene glycol (PEG) molecules, such as PEG 3350, PEG 8000).

In another aspect, there is provided a method for purifying a protein. The method includes contacting a protein mixture includes the protein with a protein binding film, where the protein binding film is immobilized to a solid support, thereby forming a protein binding film complex. The method further includes separating the protein from the protein binding film complex, thereby obtaining a purified protein. "Purified" protein is substantially free of other unwanted nucleotides and polypeptides (i.e., any nucleotides or polypeptides without a specific expression tag). Purified protein is also free of cellular material. For example, a purified protein is one that is at least about 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 80%, 81%, 82%, 83%, 84%, 85%, 86%, 87%, 88%, 89%, 90%, 91%, 92%, 93%, 94%, 95%, 96%, 97%, 98%, or even 99%, or 100% (w/w) of the desired protein by weight. Purity is measured by any appropriate standard method, for example, by SDS-PAGE analysis, column chromatography, thin layer chromatography, or high-performance liquid chromatography (HPLC) analysis.

The method for purifying a protein described herein provides great yield of the protein. In embodiments, the method provides at least about 80% (e.g., about 80%, 81%, 82%, 83%, 84%, 85%, 86%, 87%, 88%, 89%, 90%, 91%, 92%, 93%, 94%, 95%, 96%, 97%, 98%, or even 99%) yield rate of the protein. The yield rate is measured by weight percentage of the purified protein out of the initial total weight of this protein in the protein mixture. In embodiments, the method provides at least about 85% yield rate.

The method for purifying a protein described herein provides great efficiency. In embodiments, the purified protein prepared according to the method described herein is substantially pure. By "substantially pure" is meant a polypeptide or a protein that has been separated from the components that naturally accompany it. Typically, the polypeptide or the protein is substantially pure when they are at least about 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or even 99% or 99.5%, by weight, free from the unwanted nucleic acids, proteins and naturally-occurring organic molecules with they are naturally associated. In embodiments, the purified protein prepared according to the method described herein has at least about 76% purity.

The method for purifying a protein described herein is very rapid. In embodiments, the total time for purifying a protein is less than about 5 hours, 4 hours, 3 hours, 2 hours, 1 hour, 50 min, 40 min, 30 min, 20 min, 10 min or even 5 min. In embodiments, the total time for purifying a protein according to the method described herein is about 10 min. In embodiments, the method described herein does not include any dialysis step.

In embodiments, the contacting includes mechanically mixing. In embodiments, the mechanically mixing is rotationally mixing. In embodiments, the rotationally mixing has a rotational speed of about 3 krpm to 10 krpm. In embodiments, the rotational speed is about 3 krpm, 3.5 krmp, 4 krmp, 4.5 krmp, 5 krmp, 5.5 krmp, 6 krmp, 6.5 krmp, 7 krmp, 7.5 krmp, 8 krmp, 8.5 krmp, 9 krmp, 9.5 krmp, or even 10 krmp. In embodiments, the rotational speed exceeds 10 krpm, e.g., 10.5 krpm, 11 krmp, 11.5 krmp, 12 krmp, 12.5 krmp, 13 krmp, 13.5 krmp, 14 krmp, 14.5 krmp, or even 15 krmp or greater.

In embodiments, the protein mixture is within a cell lysate. In embodiments, the cell lysate can be centrifuged. In embodiments, the cell lysate is not centrifuged unlike other known conventional methods for purifying a protein (such as FPLC) where a slurry of cell lysate will immediately block the conventional protein purification apparatus with cell debris.

In another aspect, there is provided an enzyme reactor including a first enzyme, a protein binding film and a solid support, where the first enzyme is immobilized to the protein binding film in a first zone, and where the protein binding film is immobilized to the solid support.

In embodiments, the enzyme reactor includes one or more additional enzymes. In embodiments, one or more additional enzymes are different from the first enzyme. In embodiments, one or more additional enzymes are the same as the first enzyme. In embodiments one or more additional enzymes are immobilized in the first zone. In embodiments one or more additional enzymes are not immobilized in the first zone. In embodiments, one or more additional enzymes are the same as the first enzyme and are immobilized in the first zone. In embodiments, one or more additional enzymes are different from the first enzyme and are immobilized in the first zone.

In embodiments, the enzyme reactor includes one or more additional enzymes, each being different enzymes. In embodiments, the one or more additional enzymes are immobilized to the protein binding film in the first zone. In embodiments, at least one of the one or more additional enzymes are immobilized to the protein binding film in one or more zones that are different from the first zone.

In embodiments, the reactor can include a plurality types of different enzymes (including the first enzyme), e.g., including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or even greater than 50 types of enzymes in the reactor. In embodiments, each type of enzyme is a plurality of that type of enzymes.

In embodiments, a plurality types of different enzymes can be immobilized in the same zone. In embodiments, a plurality types of different enzymes can be immobilized in 2 or more zones (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or even more than 50 zones). In embodiments, some of the plurality types of different enzymes are in the same zone(s). In embodiments, some of the plurality types of different enzymes are in different zone(s).

In embodiments, the enzyme reactor includes one or more additional zones. In embodiments, the reactor includes a plurality of zones (including the first zone), e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or even greater than 50 zones in the reactor. In embodiments, each of the plurality of zones can be non-overlapping (see FIG. 55). In embodiments, the zones of the plurality of zones can be partially overlapping (see FIG. 55). In embodiments, some of the zones of the plurality of zones can be non-overlapping, and some of the zones of the plurality of zones can be overlapping. In embodiments, the first and the one or more additional zones are along the longitude axis of the solid support. In embodiments, the one or more zones of the enzyme reactor are continuously distributed along the longitude axis of the solid support. In embodiments, the one or more zones of the enzyme reactor are disconnected along the longitude axis of the solid support.

In embodiment, each zone may contain a plurality (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or even greater) types of enzymes. In embodiments, each zone may contain a plurality (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or even greater) types of enzymes where each type of enzyme is a plurality of that type of enzymes. In embodiments, each zone has a unique plurality types of enzymes (i.e., the enzymes among different zones are all different). In embodiments, the 2 or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or even more) zones contain same type or types of enzymes.

In embodiments, the enzyme is immobilized within discrete zones. In embodiments, there is a plurality of discrete zones within which one enzyme is immobilized. In embodiments, the plurality of discrete zones of enzyme immobilization is not contiguous.

In embodiments, the width of the first zone and any additional zones is from about 1 mm to the full length of the diameter of the solid support (i.e., the inner surface of the reactor). In embodiments, the width of one zone is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mm or greater or to the full length of the diameter of the solid support.

In embodiments, the length of the first zone and any additional zones is from about 1 mm to the full length (i.e., the full length of the longitude axis) of the solid support (see FIG. 55). In embodiments, the length of one zone is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mm. In embodiments, the length of one zone is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mm or even greater to the full length of the solid support (i.e., an inner surface of the enzyme reactor).

In embodiments, the solid support is an inner surface of the enzyme reactor.

In embodiments, each zone can have a singularity or a plurality of enzymes, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or even greater than 50 different enzymes. In embodiments, the enzyme(s) within each zone can be different. In embodiments, the enzyme(s) within each zone can be present in multiple zones. In other words, some zones can share the same enzyme(s).

In embodiments, the protein binding film used in any method or of any enzyme reactor described herein is covalently immobilized (e.g., bound) to the solid support. In embodiments, the protein binding film can be covalently immobilized to the solid support via siloxane bonds via e.g., APTES or other linker. In embodiments, the protein binding film can be covalently immobilized to the solid support through imine and/or amine linkages (e.g., the protein binding film including glutaraldehyde and the like).

In embodiments, the protein binding film used in any method or of any enzyme reactor described herein is non-covalently immobilized to the solid support. In embodiments, the protein binding film is non-covalently immobilized to the solid support through, e.g., specific adsorption or non-specific adsorption. In embodiments, the protein binding film is non-covalently immobilized to the solid support through, e.g., hydrophilic interactions or specific absorption (e.g., the protein binding film including IMAC resin). In embodiments, the protein binding film is non-covalently immobilized to the solid support through IMAC resin attachment(s). In embodiments, non-covalent linkage can be through a bifunctional reagent, e.g., glutaraldehyde and the like via non-specific adsorption.

In embodiments, the protein binding film used in any method or of any enzyme reactor described herein is non-covalently and covalently immobilized to the solid support. In embodiments, the protein binding film can be non-covalently immobilized to the solid support via, e.g., specific adsorption or non-specific adsorption and the protein binding film can be immobilized to the solid support covalently through imine and/or amine linkages.

In embodiments, the rotation of the sample tube (i.e., reactor or enzyme reactor) forces the protein binding film into a thin layer upon such rotation. In further embodiments, solvent (e.g., water) can evaporate leaving the protein binding film immobilized to the solid support.

In embodiments, the protein of interest (e.g., the protein to be purified or the one or more enzymes of the enzyme reactor) is covalently bound to the protein binding film. In embodiments, the protein of interest (e.g., the protein to be purified or the one or more enzymes of the enzyme reactor) is non-covalently bound to the protein binding film.

In embodiments, the binding of the protein of interest (e.g., the protein to be purified or the one or more enzymes of the enzyme reactor) to the protein binding film is stable. In embodiments, less than about 10%, 9%, 8%, 7%, 6%, 5%, 4%, 3%, 2%, 1% or lower percentage of the protein bound to the protein binding film is leached away from the protein binding film/the reactor over a period of time (e.g., at least about 30 min, 1, 2, 3, 4, 5, 6, 7, 8, 9, 10, 11, 12, 13, 14, 15, 16, 17, 18, 19, 20, 21, 22, 23, 24 hours, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 days or even longer time).

Further to any embodiment of the method or an embodiment of the enzyme reactor, in embodiments the protein of interest includes a binding moiety. In embodiments, the binding moiety is an expression tag. In embodiments, the expression tag is biotin-modified tag (e.g., a BirA encoding peptide), a streptavidin binding peptide, or an affinity chromatography epitope (e.g., polyArg, polyHis, or the like). In embodiments, the expression tag is a His tag.

An amino acid tag sequence, also called protein tag or expression tag, is peptide sequence genetically grafted onto a recombinant protein. These tags are often removable by chemical agents or by enzymatic means, such as proteolysis or intein splicing. Tags are attached to proteins for various purposes. Affinity tags are appended to proteins so that they can be purified from their crude biological source using an affinity technique. These include chitin binding protein (CBP), maltose binding protein (MBP), and glutathione-S-transferase (GST). The poly(His) tag is a widely used protein tag; it binds to metal matrices. Solubilization tags are used, especially for recombinant proteins expressed in chaperone-deficient species such as E. coli, to assist in the proper folding in proteins and keep them from precipitating. These include thioredoxin (TRX) and poly(NANP). Some affinity tags have a dual role as a solubilization agent, such as MBP, and GST. Chromatography tags are used to alter chromatographic properties of the protein to afford different resolution across a particular separation technique. Often, these consist of polyanionic amino acids, such as FLAG® tag.

Exemplary expression tags that can be used in the protein or enzyme described herein include, but are not limited to:

TABLE 6

Expression tags

| Name of Tags | Description | SEQ ID NO |
|---|---|---|
| AviTag ™ | a peptide allowing biotinylation by the enzyme BirA and so the protein can be isolated by streptavidin (GLNDIFEAQKIEWHE) | 11 |
| Calmodulin-tag | a peptide bound by the protein calmodulin (KRRWKKNFIAVSAANRFKKISSSGAL) | 12 |
| polyglutamate tag | a peptide binding efficiently to anion-exchange resin such as MONO Q ® (EEEEEE) | 13 |
| E-tag | a peptide recognized by an antibody (GAPVPYPDPLEPR) | 14 |
| FLAG ® tag | a peptide recognized by an antibody (DYKDDDDK) | 15 |
| HA-tag | a peptide from hemagglutinin recognized by an antibody (YPYDVPDYA) | 16 |
| His-tag | 5-10 (e.g., 5, 6, 7, 8, 9 or 10) histidines bound by a nickel or cobalt chelate (HHHHHH) | 17 |
| Myc-tag | a peptide derived from c-myc recognized by an antibody (EQKLISEEDL) | 18 |
| S-tag | a peptide derived from Ribonuclease A (KETAAAKFERQHMDS) | 19 |
| SBP-tag | a peptide which binds to streptavidin (MDEKTTGWRGGHVVEGLAGELEQLRARLEHHPQGQREP) | 20 |
| SOFTAG ™ 1 | for mammalian expression (SLAELLNAGLGGS) | 21 |
| SOFTAG ™ 3 | for prokaryotic expression (TQDPSRVG) | 22 |
| STREP TAG ® | a peptide which binds to streptavidin or the modified streptavidin called streptactin (STREP TAG ® II: WSHPQFEK) | 23 |
| TC tag | a tetracysteine tag that is recognized by FlAsH and ReAsH biarsenical compounds (CCPGCC) | 24 |
| V5 tag | a peptide recognized by an antibody (GKPIPNPLLGLDST) | 25 |
| VSV-tag | a peptide recognized by an antibody (YTDIEMNRLGK) | 26 |
| Xpress tag | (DLYDDDDK) | 27 |
| Glutathione-S-transferase-tag | a protein which binds to immobilized glutathione | |

In embodiments, the protein binding film used in any method or of any enzyme reactor described herein includes a binding partner of the binding moiety. In embodiments, the binding partner is a metal. In embodiments, the binding partner is nickel, cobalt or copper.

As used herein, the term "binding partners" includes two molecules, or portions thereof, which have a specific binding affinity for one another and typically will bind to each other in preference to binding to other molecules. Typically but not necessarily some or all of the structure of one member of a specific binding pair is complementary to some or all of the structure possessed by the other member, with the two members being able to bind together specifically by way of a bond between the complementary structures, optionally by virtue of multiple noncovalent attractions.

In embodiments, molecules that function as binding partners include: biotin (and its derivatives) and their binding partner avidin moieties, streptavidin moieties (and their derivatives); His-tags which bind with nickel, cobalt or copper; cysteine, histidine, or histidine patch which binds Ni-NTA; maltose which binds with maltose binding protein (MBP); lectin-carbohydrate binding partners; calcium-calcium binding protein (CBP); acetylcholine and receptor-acetylcholine; protein A and binding partner anti-FLAG antibody; GST and binding partner glutathione; uracil DNA glycosylase (UDG) and ugi (uracil-DNA glycosylase inhibitor) protein; antigen or epitope tags which bind to antibody or antibody fragments, particularly antigens such as digoxigenin, fluorescein, dinitrophenol or bromodeoxyuridine and their respective antibodies; mouse immunoglobulin and goat anti-mouse immunoglobulin; IgG bound and protein A; receptor-receptor agonist or receptor antagonist; enzyme-enzyme cofactors; enzyme-enzyme inhibitors; and thyroxine-cortisol. Another binding partner for biotin can be a biotin-binding protein from chicken (Hytonen, et al., BMC Structural Biology 7:8).

An avidin moiety can include an avidin protein, as well as any derivatives, analogs and other non-native forms of avidin that can bind to biotin moieties. Other forms of avidin moieties include native and recombinant avidin and streptavidin as well as derivatized molecules, e.g. nonglycosylated avidins, N-acyl avidins and truncated streptavidins. For example, avidin moiety includes deglycosylated forms of avidin, bacterial streptavidins produced by *Streptomyces* (e.g., *Streptomyces avidinii*), truncated streptavidins, recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin™, Captavidin™, Neutravidin™ and Neutralite Avidin™.

Further to any embodiment of the method or any embodiment of the enzyme reactor, in embodiments the solid support is an inner surface of a reactor. The term "reactor" used herein refers to a device for containing and controlling a chemical reaction (e.g., an enzymatic reaction) or process (e.g., purifying a protein). The term "enzyme reactor" refers to a reactor for containing and controlling an enzymatic reaction.

Further to any embodiment of the method or any embodiment of the enzyme reactor, in embodiments the reactor includes a closed end and an open end. In embodiments, the reactor can be in any shape. In embodiments, the reactor is cylindrical. In embodiments, the reactor is cuboidal. In embodiments, the reactor is a glass reactor. In embodiments, the reactor is a metal reactor. In embodiments, the reactor is a plastic reactor. In embodiments, the reactor is made of any material that is suitable for protein purification and/or enzymatic reactions.

Further to any embodiment of the method or any embodiment of the enzyme reactor, in embodiments the protein mixture is contacted with the protein binding film by continuous flow. In embodiments, the protein mixture is contacted with the protein binding film by bolus contact. In embodiments, the protein mixture is contacted with the protein binding film in a confined mode.

In another aspect, there is provided a method for reacting an enzyme and a substrate. The method includes contacting the protein binding film of the enzyme reactor as disclosed herein with a substrate of the first enzyme. The method further includes allowing the substrate to react with the first enzyme.

In embodiments, the substrate is contacted with the protein binding film by continuous flow. In embodiments, method and embodiments thereof include applying a vibrational energy described herein to the enzyme reactor.

In embodiments, the substrate is a plurality of substrates, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or even greater than 50. In embodiments, the substrate is a plurality of substrates, each corresponding to one enzyme of the enzyme reactor described herein.

In embodiments, any methods or enzyme reactors described herein may include one or more additional reagents besides enzyme and substrate.

In embodiments, the enzyme reactor described herein is a vortex fluid devise (VFD). In embodiments, the VFD provides shear stress, dynamic and standing pressure waves and micro-mixing of enzyme/substrate/reagents while rotating. In embodiments, the VFD is operated at constant volume of solution, where enzyme and substrate reagents do not flow into or out of the VFD during the reaction. In embodiments, the VFD is operated under continuous flow conditions of solution, where enzyme or substrate reagents flow into or out of the VFD during the reaction. In embodiments, the enzyme is immobilized within the VFD and substrate reagents flow into or out of the VFD during the reaction.

In embodiments, any method described herein is conducted at room temperature (25° C.). In embodiments, any method described herein is conducted at elevated temperature. In embodiments, any method described herein is conducted at reduced temperatures. In embodiments, any method described herein is conducted at atmospheric pressure. In embodiments, any method described herein is conducted at elevated pressure. In embodiments, any method described herein is conducted at reduced pressure.

EXAMPLES

Example 1. A General Approach to Accelerating Enzymatic Catalysis Using Vortex Fluidic Processing Summary.

We describe a general method to accelerate catalysis by enzymes. Specifically, a vortex fluidic device can drive enzyme activity without requiring enzyme mutagenesis, altered temperatures, or added chemicals, pressure, or microwaves. The enzyme and its substrate are spun rapidly in a tube (up to 10,000 rpm) whereby the mechanical energy of the device rotating the solution leads to a dramatic enzyme enhancement.

The Vortex Fluidic Device (VFD) can be operated with a constant volume of solution (confined mode) or continuous flow for higher volumes of solution. The enzyme and the substrate are introduced into a rotating glass tube (which is held between two bearings), and the tube spun rapidly for a set period of time. The degree of chemical conversion is then established through the use of a colorimetric assay. Enzyme activity for fast thermosensitive alkaline phosphatase (Thermo-fisher), lipase from wheat germ, Type 1 (Sigma and Aldrich) and β-glucosidase from almonds (Sigma and Aldrich) were enhanced with up to a 12-fold enhancement in catalytic productivity.

This technology could be readily applied to other enzymes important to both academia and industry. The industrial enzyme market is forecasted to be worth S6 billion by 2018. General processes to accelerate enzymatic catalysis could have a major impact. As this process can be used for smaller processes or a continuous flow system to enable processing of very large volumes, this technology will be competitive on both academic and industrial scales.

Introduction.

Enzymes catalyze chemical transformations and are used extensively in industrial, food, and research applications. Accelerating such catalysis could lower the costs for such processes. Current methods to enhance the activity of enzymes largely focus on engineering the enzyme for improved activity; this approach is slow and cumbersome. More general approaches to accelerating enzymatic catalysis apply (i) the use of forcing conditions such as high pressure and precise temperature control, (ii) acceptance of the limitation that enzymes can be inherently slow for some processes (giving the process longer time periods), (iii) increased enzyme loading, which costs more money and (iv) increased substrate loading, which eventually shuts down the enzyme due to substrate inhibition.

There have been numerous ways to increase enzyme activity including (i) Enzyme modification and design, which is specific only to the enzyme under consideration, (ii) Chemical additions to the reaction mixture, which increases the waste stream and adds to the purification challenges, (iii) High energy microwave radiation, (iv) Immobilization onto a solid support, (v) High pressure treatment, (vi) Polymer attachment (vii) Noble gas doping and (viii) Pretreatments. All of these processes, disclosed following, involve expensive, complex techniques and/or involve the addition of other chemicals to the process.

(i) Enzyme modification for individual enzymes—Engineering enzymes is a timely, costly, complex and idiosyncratic art. Many approaches have been made in this area, but none solve the problem of necessitating the synthesis and testing of large numbers of enzyme variants.

(ii) Chemical addition—Specific to the reaction and add expense and waste to synthesis. See e.g., WO1194012621.

(iii) High energy microwave radiation (general solution)—This high-energy process requires expensive infrastructure, and incurs safety implications. See e.g., WO2013027053.

(iv) Immobilization onto a solid support—This potentially complex path to enzyme enhancement raises questions about scalability. See e.g., U.S. Pat. No. 8,715,982.

(v) Purification agents—These are mainly related to (i) Specific washes to increase the purity of enzymes located on immobilization surfaces (see e.g., U.S. Pat. No. 7,312,056) and washing raw enzyme solutions with species like activated carbon to increase activity (see; e.g., CA2421832 C). These are specific to the reaction and adds expense to pathways.

(vi) Attachment to solid support—This approach requires optimization to achieve enzyme enhancement. See e.g., EP2834355, (vii) Noble gas doping—A is a complex approach to enzyme enhancement, which is difficult to scale, and noble gases have large added expense. See e.g., U.S. Pat. No. 5,462,861.

(viii) Pretreatment of enzyme solutions—Pretreatment of substrates with organic solvents, salts and other chemical species can be useful to increase enzyme activity. See e.g., EP2384364, U.S. Pat. No. 8,241,880 and WO2010080434. This is a time consuming step requiring the addition of chemicals.

Results and Discussion.

This disclosure reports an exciting new application for the previously disclosed vortex fluidic device (VFD). Here, we apply the approach to accelerate enzymatic catalysis using the following two modes of vortex fluidic processing. (1) Confined mode—whereby a fixed volume of liquid is rotated within the confinements of the glass tube and (2) Continuous flow mode—whereby reagents are introduced into the rotating tube in a continuous manner. The reagents are processed as they flow up the rotating glass tube and exit through the top of the unit, where they are collected. The resultant solutions are then subjected to a pH treatment or rapid dilution to quench enzymatic activity before analysis.

An enzyme is a protein-based catalyst that operates by decreasing the activation energy of a chemical reaction to result in an increased reaction rate. Enzymes exert exquisite control over reaction starting materials, transition states, intermediates and product; for example, enzymes can favor formation of specific stereochemistry from complex reactions. Due to such specificity, enzymes are employed extensively in industrial and academic processes. The VFD approach disclosed here can dramatically speed up enzymatic catalysis.

Figure 1:
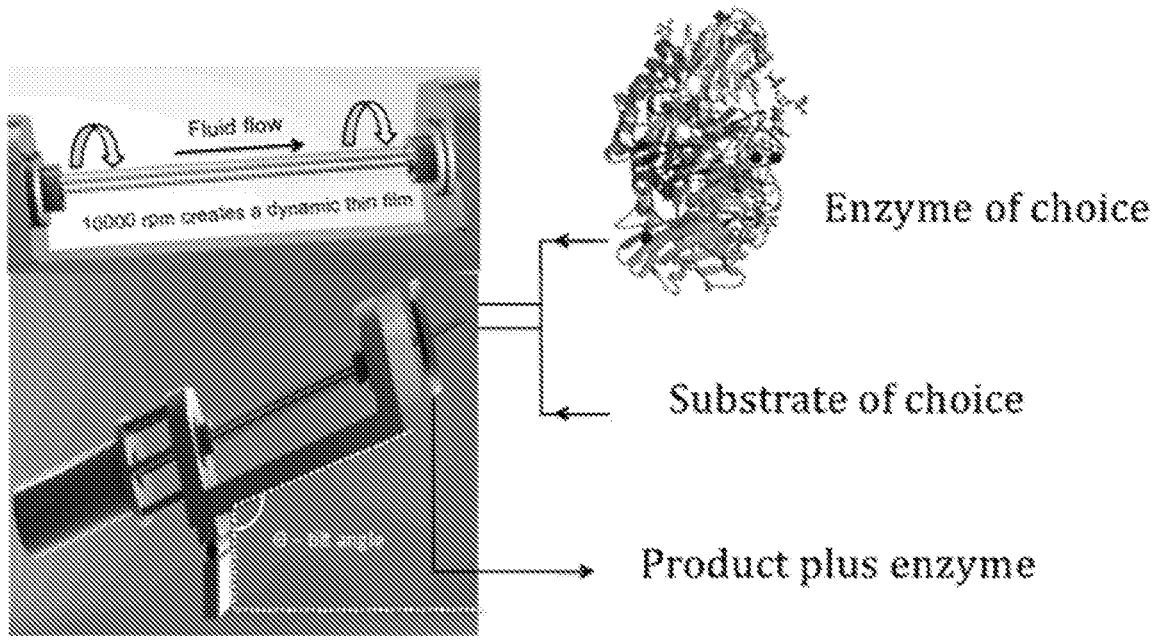
FIG. 1. The figure depicts an embodiment of the vortex fluidic device (VFD). At the top is depicted a rotating tube held between an upper and a lower bearing, At the bottom is depicted the VFD at a specific tilt angle. The arrows indicate that the solution can be passed into the VFD, the solution is then processed and the product mixture collected.

After introducing the enzyme and substrate into the VFD sample tube (FIG. 1), the solution experiences high levels of shear stress and micromixing. The enzyme and the substrate are rapidly mixed and as a result, the reaction occurs at a greater reaction rate than in traditional techniques. This increase in observed reaction rate arises from an increase in $k_{cat}$, the rate constants that drives certain aspects of enzyme activity. Without wishing to be bound by any theory, it is believed that at specific rotational speeds the rotating tube (now containing the liquid) falls into a harmonic vibration. This vibration is a primary mechanical response that results from the rotation of the tube within the bearings at specific rotational speeds. This leads to a secondary fluid dynamical response that results in a Faraday wave. A Faraday wave, as known in the art, is a non-linear standing wave. This study has demonstrated, for the first time, the use of a Faraday wave to promote enzyme activity and the dramatic enhancement of enzyme activity by the Faraday wave.

In a typical experiment, fast thermosensitive alkaline phosphatase (1 μL, 1 unit, Thermo-Fisher) was added to 10 mL of diethanolamine buffer (1.0 M diethanolamine buffer with 0.50 mM magnesium chloride at pH 9.8 at 25° C.) in creating an enzyme stock solution. This solution was stored on ice and not stored for more than two hours. p-nitrophenyl phosphate liquid substrate solution (500 μL, Sigma-Aldrich) was added to a 20 mm external diameter VFD tube. To this was added alkaline phosphatase enzyme solution (800 μL) and the tube was inserted into the VFD and immediately spun to the required rotational speed. The VFD tube was rotated about its axis for 10 minutes at a 45-degree tilt angle relative to the horizontal position. At the end of this time 4

Figure 3A:
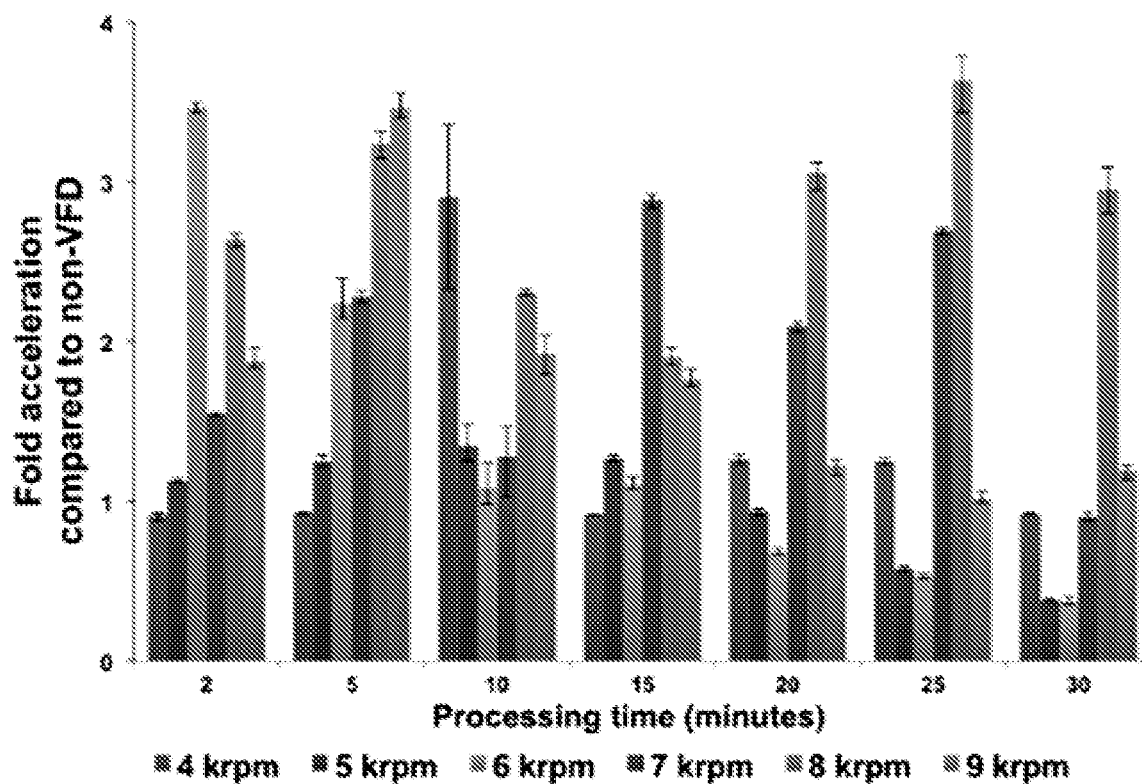
FIGS. 3A-3N.
Figure 3B:
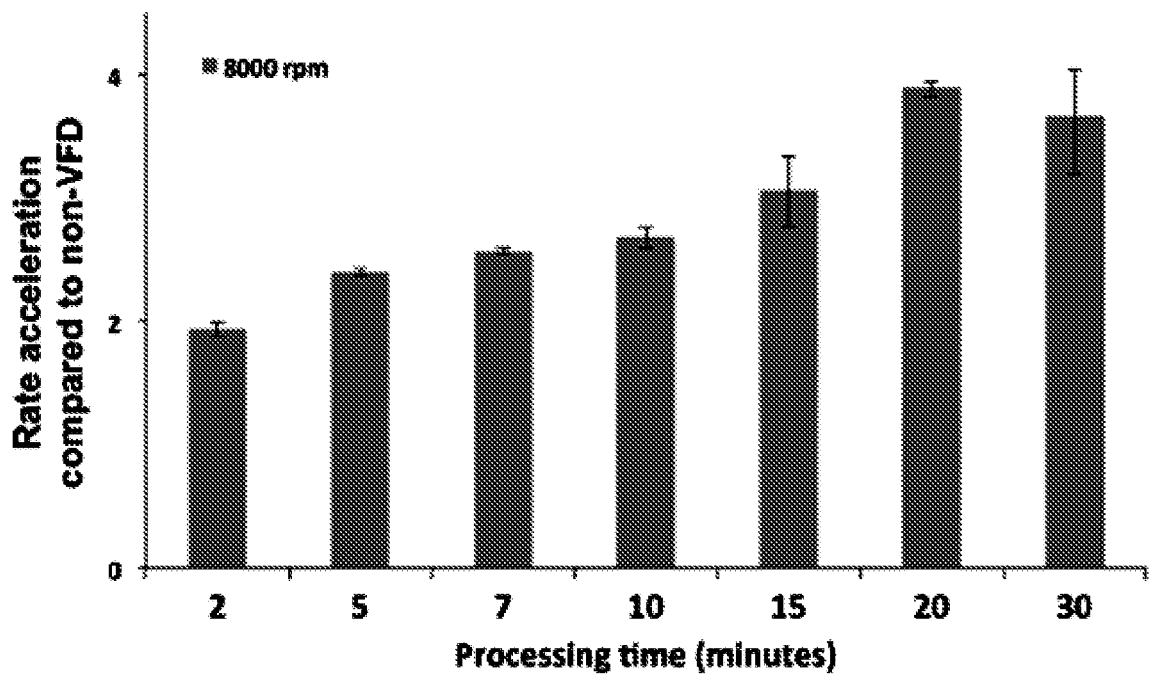
FIG. 3B depicts the fold enhancement of β-glucosidase in the VFD at a 8000 rpm rotational speed over set periods of time (min).
Figure 3C:
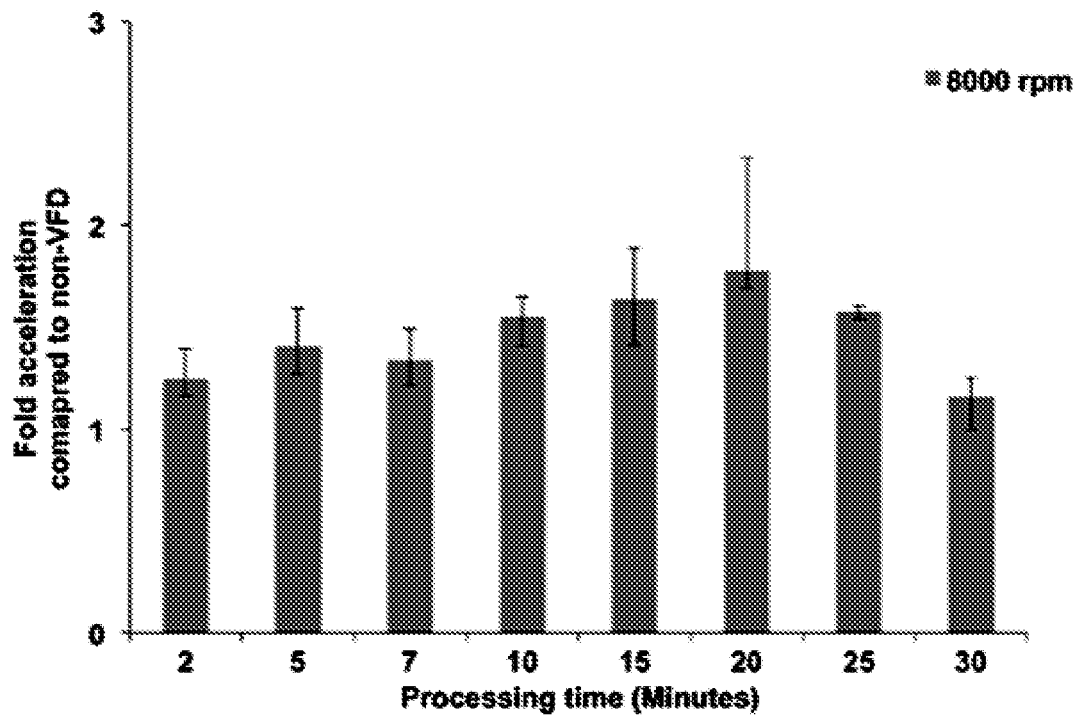
FIG. 3C depicts the fold enhancement of lipase in the VFD at a 8000 rpm rotational speed over set periods of time. Y-axis: fold acceleration compared to no n-VFD assay.
Figure 3D:
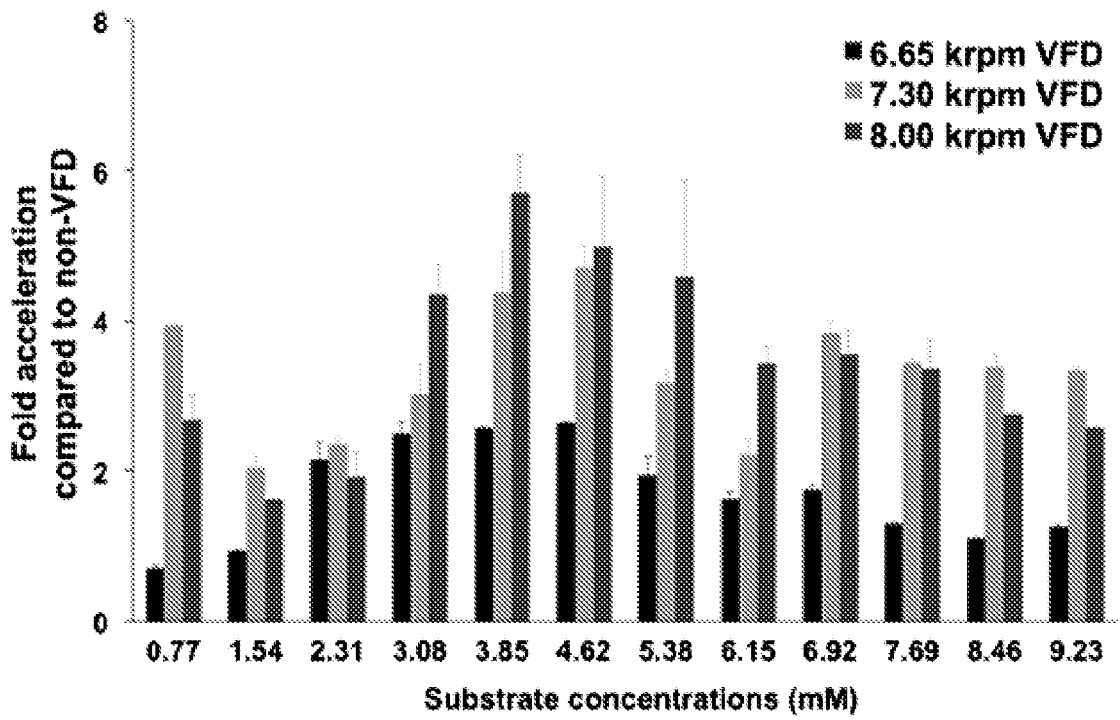
FIG. 3D depicts fold enhancement of alkaline phosphatase at different rotational speeds with a variation in the substrate concentration. Bar graph bins: substrate concentration as indicated; within each bar graph bin (left to right): 6.65, 7.30 and 8.00 krpm VFD, respectively.
Figure 3E:
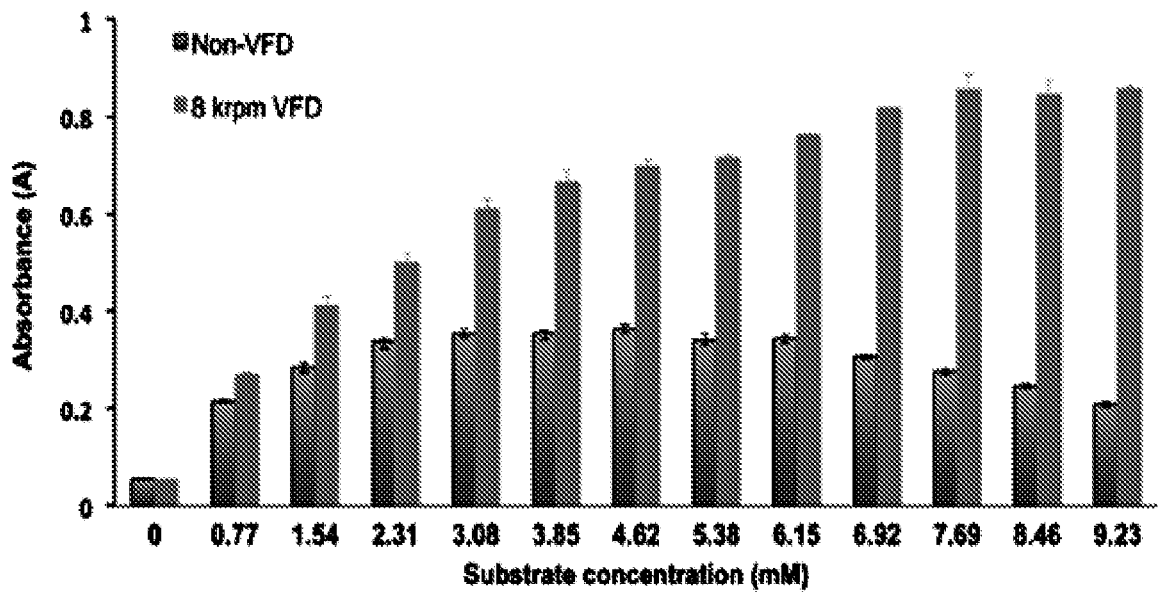
FIG. 3E depicts the absorbance values obtained when comparing VFD to batch for β-glucosidase with variation in the substrate concentration. Bar graph bins (left to right): non-VFD, 8 kprm VFD.
Figure 3F:
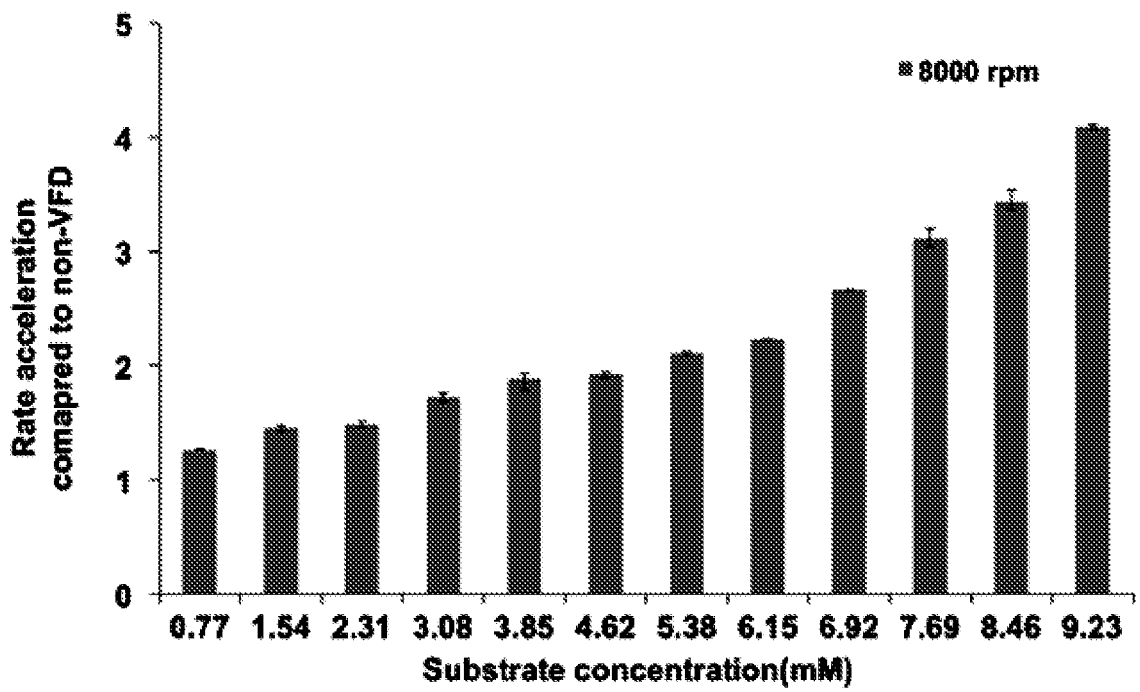
FIG. 3F depicts fold enhancement of β-glucosidase with variation in the substrate concentration.
Figure 3G:
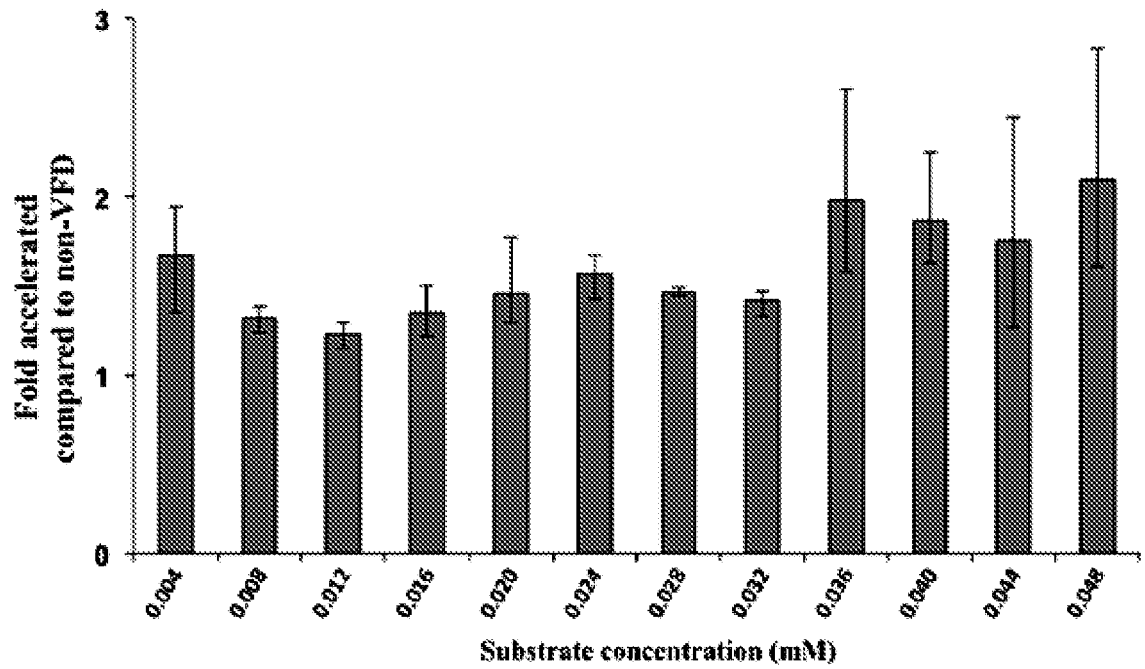
FIG. 3G depicts fold enhancement of lipase with variation in the substrate concentration.
Figure 3H:
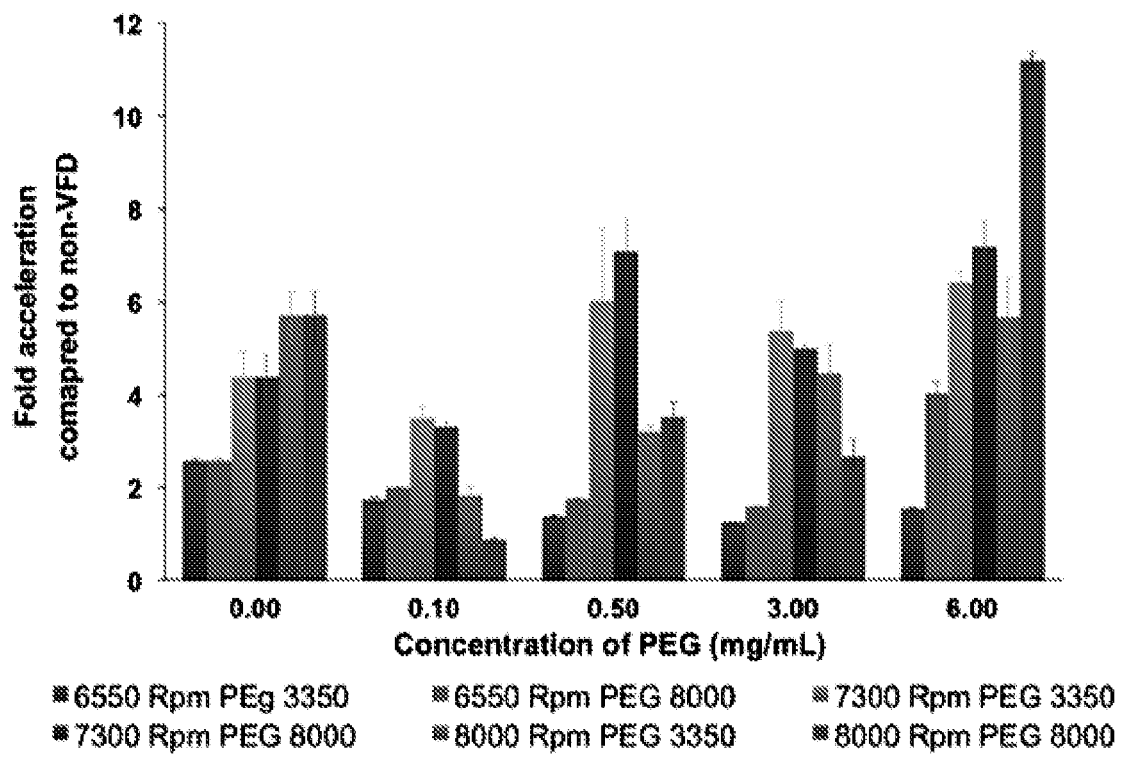
FIG. 3H depicts fold enhancement of alkaline phosphatase with variation in the PEG concentration (steric crowding reagent). Bar graph bins (left to right): 6550 rpm PEG 3350, 6550 rpm PEG 8000, 7300 rpm PEG 3350, 7300 rpm PEG 8000, 8000 rpm PEG 3350, 8000 rpm PEG 8000.
Figure 3I:
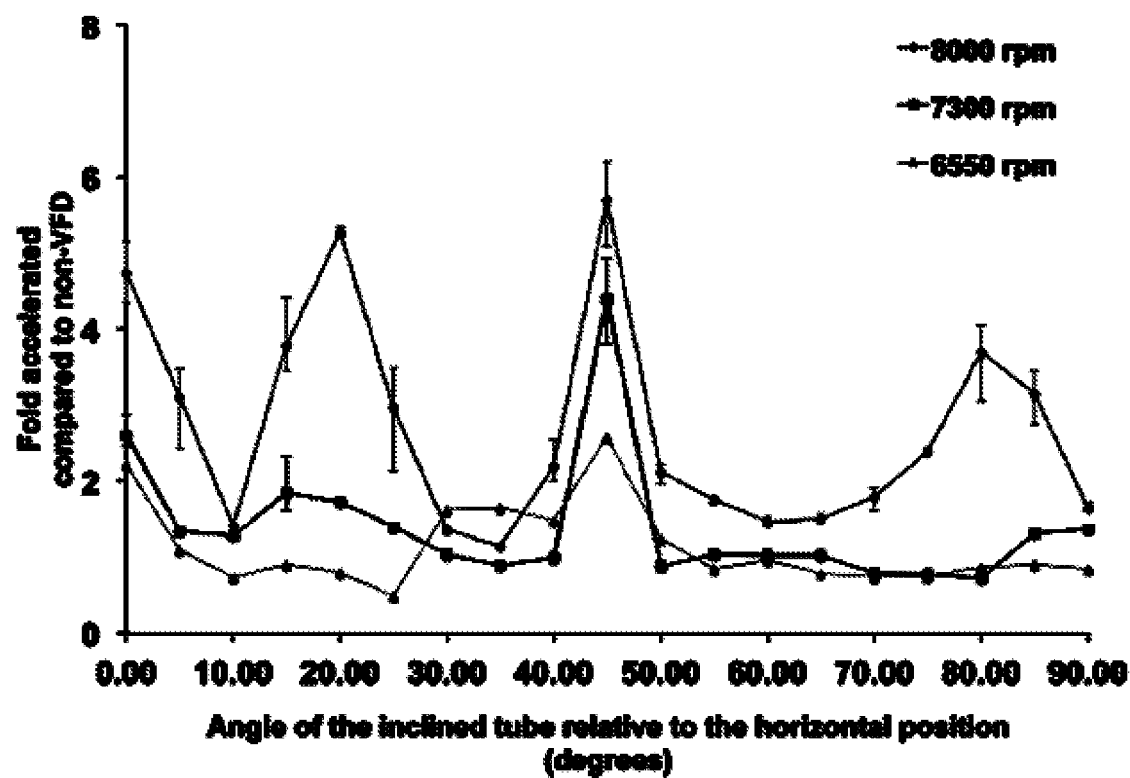
FIG. 3I depicts that the angle of the inclined tube affects the VFD enhancement of enzyme activity. Legend: 8000 rpm (diamonds), 7300 (squares), 6550 rpm (triangles).
Figure 3J:
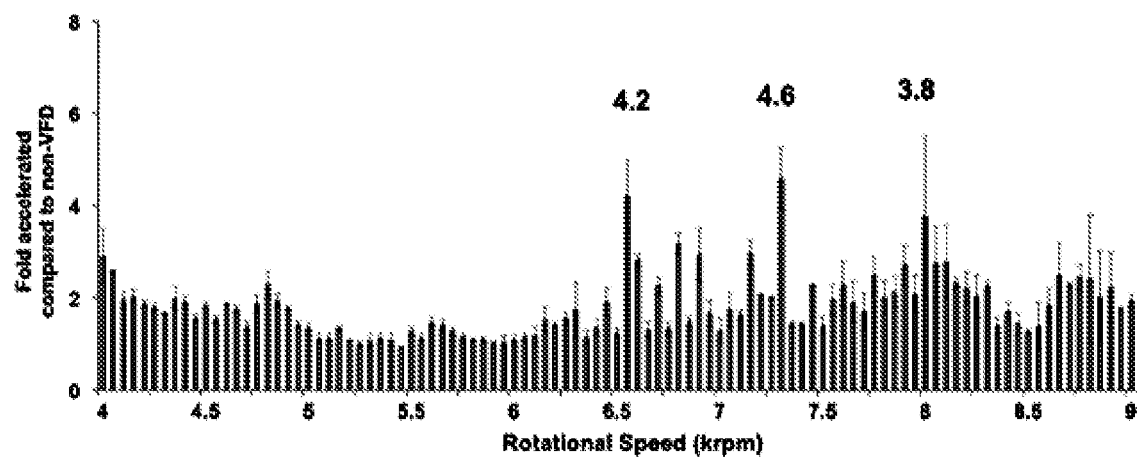
FIG. 3J depicts how the rotational speed of the device effects the enzyme enhancement. Experiment performed with alkaline phosphatase at a 45-degree tilt angle relative to the horizontal position.
Figure 3K:
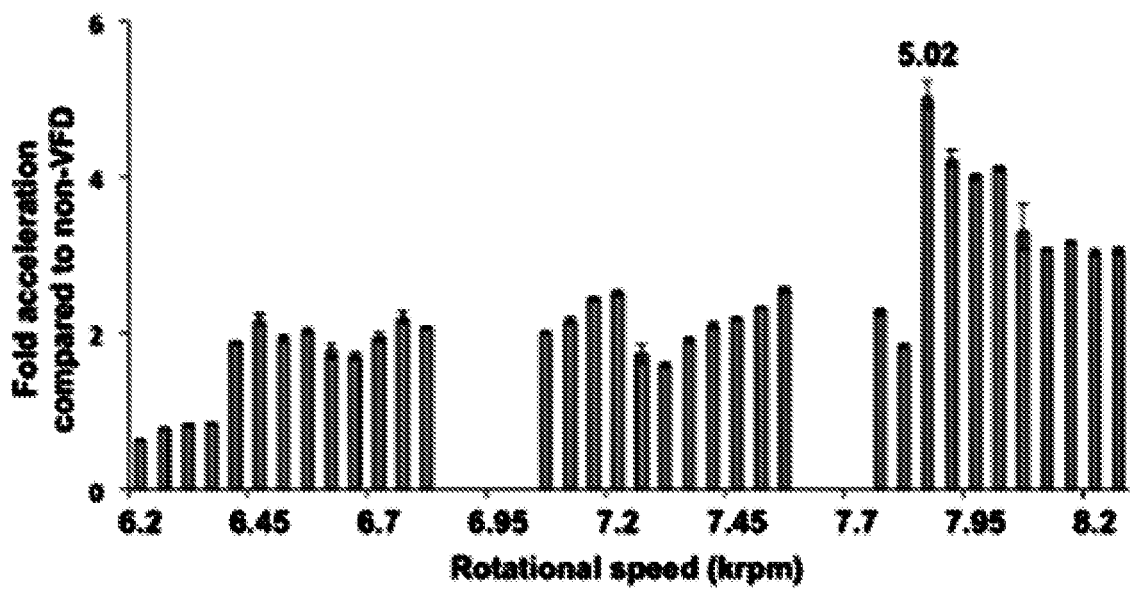
FIG. 3K depicts how the rotational speeds of the device effects the enzyme enhancement. Experiment performed with β-glucosidase at a 45-degree tilt angle relative to the horizontal position.
Figure 3L:
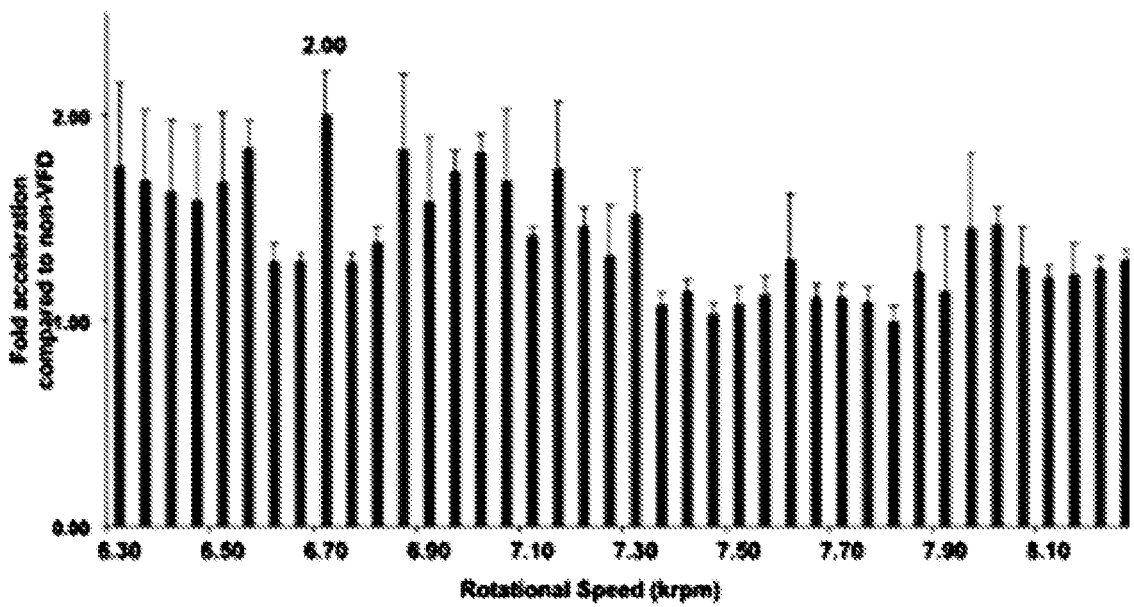
FIG. 3L depicts how the rotational speed of the device effects the enzyme enhancement. Experiment performed with lipase at a 45-degree tilt angle relative to the horizontal position. A volume of 0.700 mL of enzyme (0.5 mg/mL) and 0.600 mL of substrate (2.41×10−2 mM) was used in this experiment.
Figure 3M:
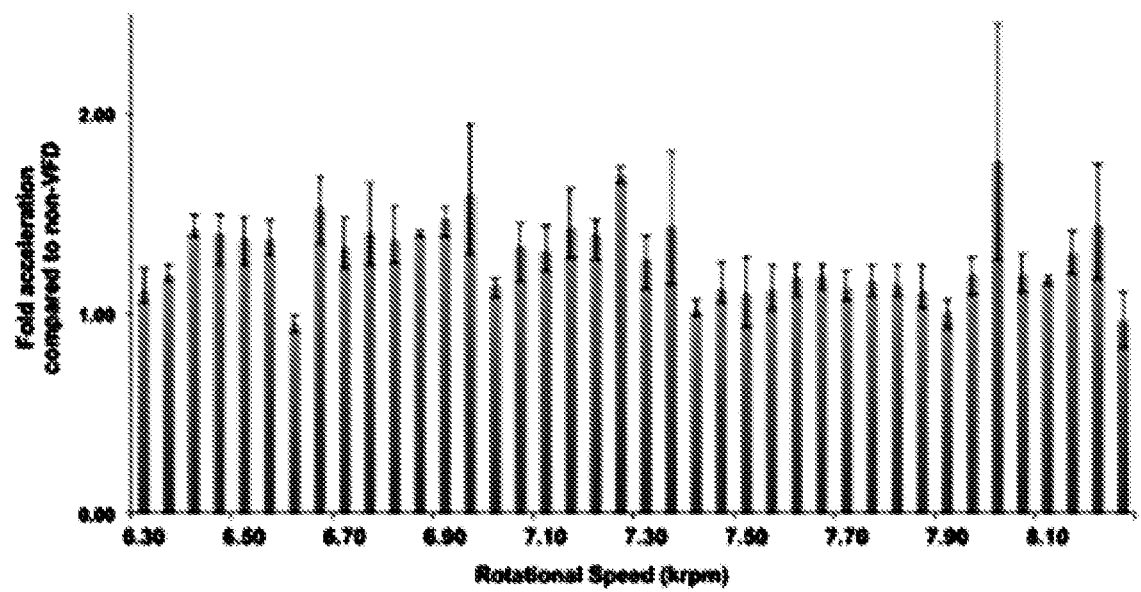
FIG. 3M depicts how the rotational speeds of the device effects the enzyme enhancement. Experiment performed with lipase at a 45-degree tilt angle relative to the horizontal position. A volume of 0.200 mL of enzyme (0.5 mg/mL) and 1.100 mL of substrate (4.42×10−2 mM) was used in this experiment.
Figure 3N:
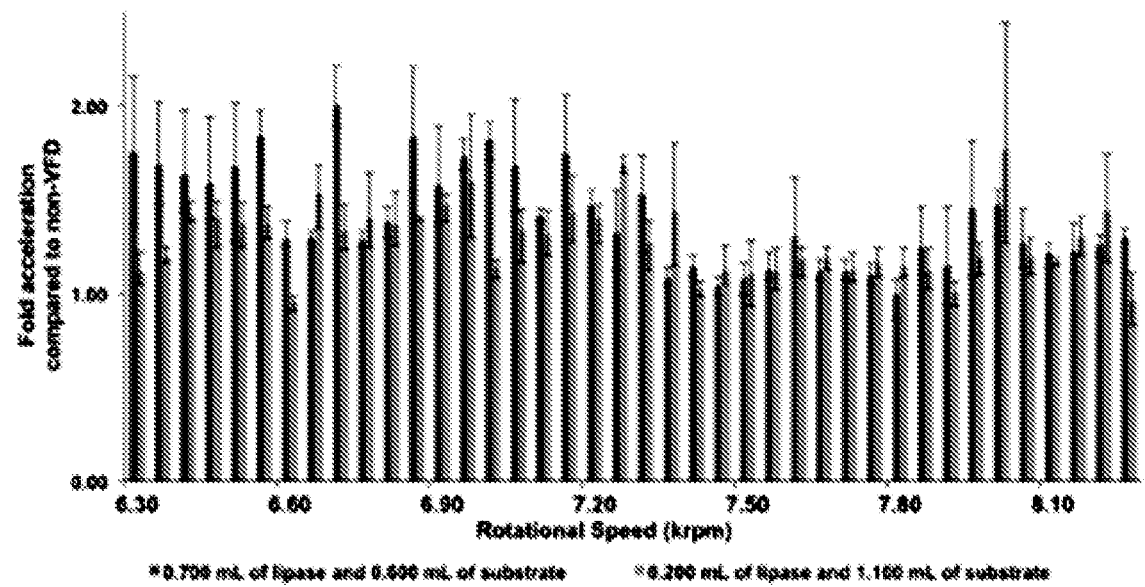

M NaOH (150 µL) was added in quenching the reaction. The sample was then added to a 96-well reader plate and the absorbance read at 401 nM (being the $\lambda_{max}$ for this system with 150 µL NaOH quench). The higher the enzyme activity the more P-nitrophenol is liberated, thus the stronger the absorption at 401 nM. The results obtained in this manner can be directly compared to a batch type experiment where by the enzyme and substrates are not introduced into the VFD, but allowed to reaction without mechanical involvement. From a comparison of the absorption values of the VFD vs. batch an enhancement factor can be determined (FIGS. 3A-3N). It was found that almost a 6× enhancement was observed in activity compared to a non-VFD sample.

For the steric crowding studies the following method was performed. Fast thermosensitive alkaline phosphatase (1 µL, 1 unit, Thermo-Fisher) was added to a 15 mL Eppendorf tube containing 10 mL of diethanolamine buffer (1.0 M diethanolamine buffer with 0.50 mM Magnesium Chloride at pH 9.8 at 25° C.) with the correct mass of $PEG_{3350}$ or $PEG_{8000}$ (0.5, 1, 2, 3 or 6 mg/mL) pre-dissolved. This created enzyme stock solutions with the correct level of PEG-doping. This solution was stored on ice and not stored for more than two hours. p-nitrophenyl phosphate liquid substrate solution (500 µL, Sigma-Aldrich) was added to a 20 mm external diameter VFD tube. To this was added alkaline phosphatase enzyme solution (800 µL) and the tube was inserted into the VFD and immediately spun to the required rotational speed. The VFD tube was rotated about its axis for 10 minutes at a 45-degree tilt angle relative to the horizontal position. At the end of this time 4 M NaOH (150 µL) was added in quenching the reaction. The sample was then added to a 96-well reader plate and the absorbance read at 401 nM (being the $\lambda_{max}$ for this system with 150 µL NaOH quench). The results obtained in this manner can be directly compared to a batch type experiment where by the enzyme and substrates are not introduced into the VFD, but allowed to reaction without mechanical involvement. From a comparison of the absorption values of the VFD vs. batch an enhancement factor can be determined (FIGS. 3A-3N). It was found that almost a 12× enhancement could be observed compared to a non-VFD sample when the solution was crowded with a 6 mg/mL $PEG_{8000}$ dopant.

For the concentration of substrate studies the following method was performed.

Example: β-Glucosidase. To a 15 mL centrifuge tube was added lyophilized β-glucosidase enzyme (5.0 mg). The enzyme was taken up in sodium acetate buffer (50 mM, pH 5.0, 10 mL) and vortexed for two minutes. From this solution a 100 µL aliquot was taken and added to 100 mL of sodium acetate (50 mM, pH 5.0) in creating a 0.005 mg/mL concentration of enzyme. The substrate solution constituted of 4-nitrophenyl β-D-glucopyranoside (31.25 mg) in 10 mL of sodium acetate buffer (50 mM, pH 5.0) in creating a 0.01 M substrate solution. For all concentration experiments the volume of the system was maintained at 1.300 mL and to scan the enzymatic enhancement space at a rapid rate the following was achieved.

For example; 100 µL of substrate was added to 1200 µL of enzyme solution and placed in a 20 mm external diameter VFD tube, in creating a 0.77 mM substrate concentration. The tube was rotated about its axis at a 45-degree tilt angle for 10 minutes. After this time the processed solution was added to 200 µL of sodium hydroxide-glycine buffer (pH 10.80) and quenched. An aliquot of 100 µL was then added to a 96 well plate and the absorbance tested at 405 nm. The level of absorption can be directly related to the level of enzymatic activity, with the absorption at 405 nm corresponding to the absorption of light due to the presence of 4-nitrophenol. The range of typical experiments follows: 100 µL of substrate solution and 1200 µL of enzyme solution in creating a 0.77 mM substrate concentration; 200 µL of substrate solution and 1100 µL of enzyme solution in creating a 1.54 mM substrate concentration; 300 µL of substrate solution and 1000 µL of enzyme solution in creating a 2.31 mM substrate concentration; 400 µL of substrate solution and 900 µL of enzyme solution in creating a 3.08 mM substrate concentration; 500 µL of substrate solution and 800 µL of enzyme solution in creating a 3.85 mM substrate concentration; 600 µL of substrate solution and 700 µL of enzyme solution in creating a 4.62 mM substrate concentration; 700 µL of substrate solution and 600 µL of enzyme solution in creating a 5.38 mM substrate concentration; 800 µL of substrate solution and 500 µL of enzyme solution in creating a 6.15 mM substrate concentration; 900 µL of substrate solution and 400 µL of enzyme solution in creating a 6.92 mM substrate concentration; 1000 µL of substrate solution and 300 µL of enzyme solution in creating a 7.69 mM substrate concentration; 1100 µL of substrate solution and 200 µL of enzyme solution in creating a 8.46 mM substrate concentration; or 1200 µL of substrate solution and 100 µL of enzyme solution in creating a 9.23 mM substrate concentration.

This methodology allows rapid determination of an optimum concentration in the system.

Figure 2:
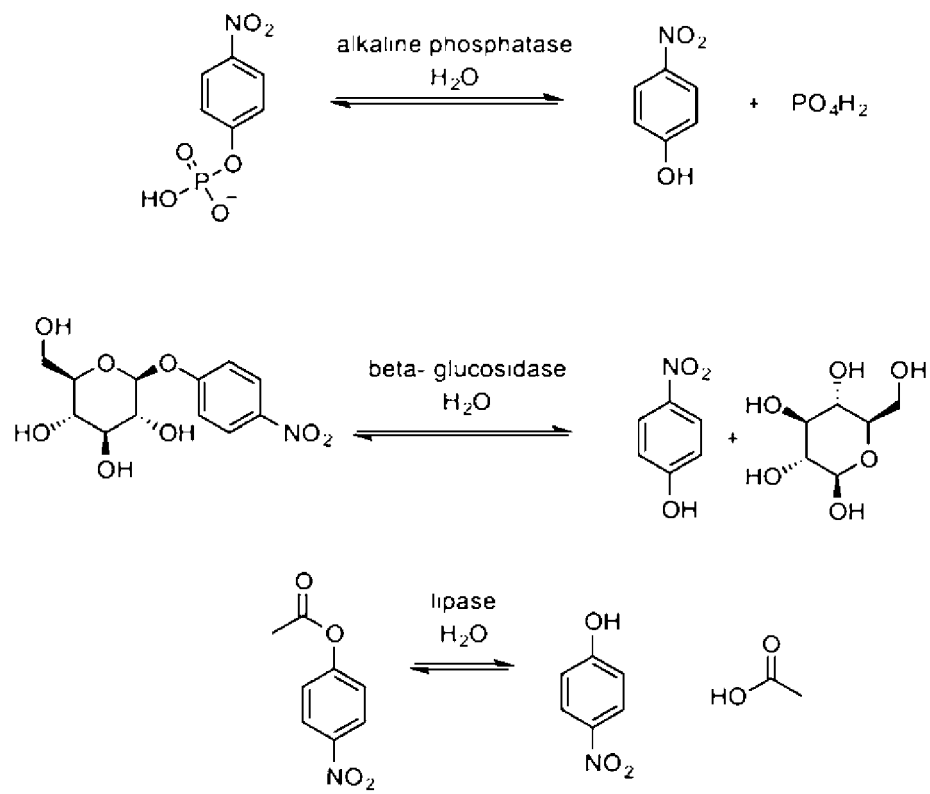
FIG. 2. The figure depicts a chemical reaction scheme disclosing enzymatic processes that were optimized for this disclosure; Top scheme: The chemical transformation using alkaline phosphatase; middle scheme: the enzymatic processing using β-glucosidase; bottom scheme: the enzymatic process using lipase.

As mentioned above, at specific rotational speeds the rotating tube can fall into a harmonic vibration, leading to a secondary fluid dynamical response. Thus, at specific rotational speeds we see a greater enhancement compared to other speeds. This has been investigated in detail and has been optimized for the three enzymes mentioned above. It is theorized that the increase in enzyme activity is a direct result from this harmonic vibration set up at specific rotational speeds. Through optimization of (i) enzyme concentration, (ii) substrate concentration, (iii) rotational speed of the tube, (iv) inclination angle of the rotating tube, (v) steric crowding reagents and (vi) reaction length the enzyme of choice can be optimized in short order to produce a dramatic enhancement. This was achieved for three enzymes studied to date, alkaline phosphatase, β-glucosidase and a lipase (FIG. 2).

This process occurs at room temperature and pressure. Thus, the VFD is a less expensive, safer operation compared to a high pressure or temperature systems. As there are no chemical additives required, this process is more efficient and more cost effective than other techniques.

This technology allows enzyme activity optimization on a small scale before going to continuous flow for industrial scale-up. Using the enzyme with its substrate in batch first allows quick optimization thus saving time and money. Once the enzyme has been optimized the parameters can be directly applied to the scaled-up continuous flow system, which again saves time and re-optimization, a caveat associated with most other approaches to this area of chemistry.

Other, less general approaches to enzyme optimization focus on making changes to the amino acid composition of the enzyme. Such enzyme engineering approaches take a long time, and are only applicable to the enzyme under study.

Other benefits include: (i) ease of operation, (ii) simplicity of the invention and (iii) most importantly, the invention is not specific to one enzyme, it can be used to enhance numerous enzymes, unlike other technologies patented in this area.

Example 2. Immobilization of Enzymes onto a Thin Film Reactor Tube for Rapid Enzymatic Synthesis in Continuous Flow Abstract.

Covalent attachment of enzymes to a rapidly rotating boro-silicate glass tube has been achieved within the confinements of a vortex fluidic device (VFD). The optimization process yielded enzyme attachment in less than four hours under mild conditions. These attachments now allow continuous flow enzymatic synthesis to occur within a VFD. The large surface area and high mass transfer within the tube ensures high levels of contact between reagents and immobilized enzymes. Utilizing dynamic thin films created within the device is a quality that no other flow chemistry device possesses. Conventionally, flow chemistry units pass liquids through well-defined channels and paths, and as a result have low levels of contact and mass transfer between the enzyme and substrate.

Methodology.

Enzyme attachment was optimized with β-glucosidase from almonds (Sigma). β-glucosidase is a commercial available enzyme that has a rapid colorimetric assay utilizing p-nitrophenol production from 4-nitrophenyl-β-D-glucopyranoside. Covalent attachment was carried out using the following method.

Preparing the enzyme coating; A 17.7 mm-internal diameter VFD tube was filled with piranha solution (33% $H_2O_2$ and 77% $H_2SO_4$) and left for one-hour at room temperature. The tube was then rinsed with copious amounts of deionized water (30×50 mL) to remove any remaining acidic solution and then placed in an oven at 160° C. for two hours to remove all remaining water. All residual water must be removed to achieve an efficient APTES coating. Following this, APTES (49 mL, 2% v/v in methanol) was added, and the tube sealed. The tube was then submerged in a water bath at 40° C. for one hour. After this time, the APTES solution was removed and the tube washed with copious amounts of methanol (10×50 mL), then placed in the oven at 160° C. for another two hours to anneal the newly formed APTES layer. After this period, the tube was removed from the oven, purged with $N_2$ for 5 minutes and then sealed.

The enzyme solution (0.30 mg/mL) composed of β-glucosidase (3 mg) added to 10 mL of PBS (3.00 mL) was immediately used for immobilization. This solution was bench vortexed for 1 minute and then left to stand for 14 minutes. After this time, 2.0 mL of this enzyme solution and an additional 1.0 mL of PBS buffer (pH 7.2) were added to the APTES coated VFD tube. The VFD was rotated about its axis at 8000 rpm, at a 45-degree tilt angle for 30 minutes to afford covalent attachment. The tube was then removed from the VFD and washed with PBS (10×50 mL).

Testing the enzyme coating; The substrate, 4-nitrophenyl-β-D-glucopyranoside (1.30 mL, 0.1 M in phosphate buffer pH 4.2, Sigma) was added to the VFD tube and rotated at a 45-degree tilt angles for 5 minutes at 8000 rpm. The solution was then removed from the tube and added to a quench of NaOH-Glycine buffer (0.200 mL, pH 10.8). From this quenched solution a 0.100 mL sample was removed and tested for its absorptivity at 405 nM. The product from the enzymatic reaction absorbs at 405 nM, thus providing direct analysis of enzyme activity. The same tube was tested three sequential times. These sequential tests ensure that the coating is covalent in nature and not intermolecular associations.

Results.

Figure 4A:
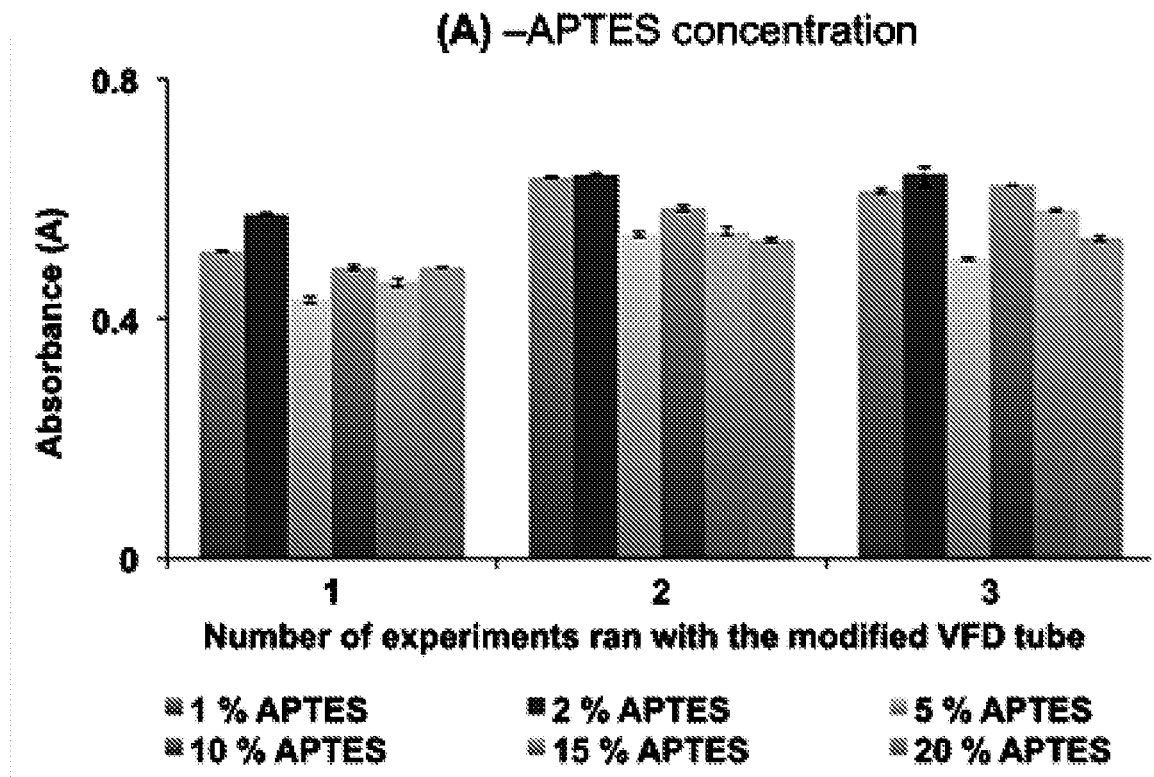
FIGS. 4A-4D.
Figure 4B:
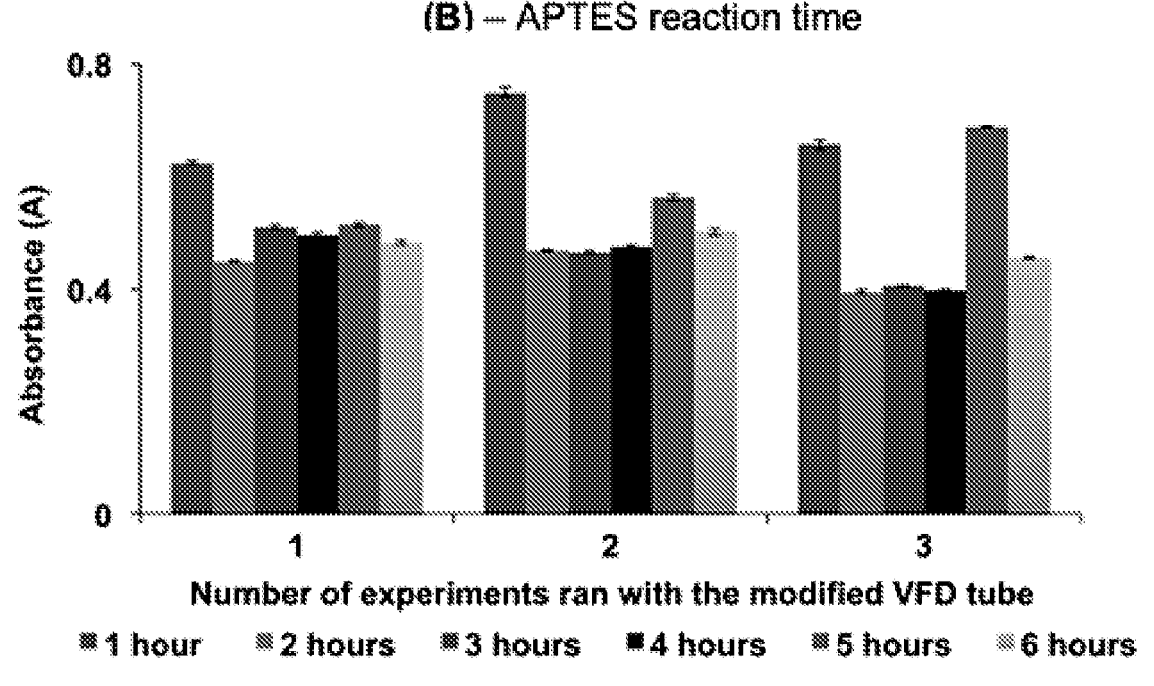
Figure 4C:
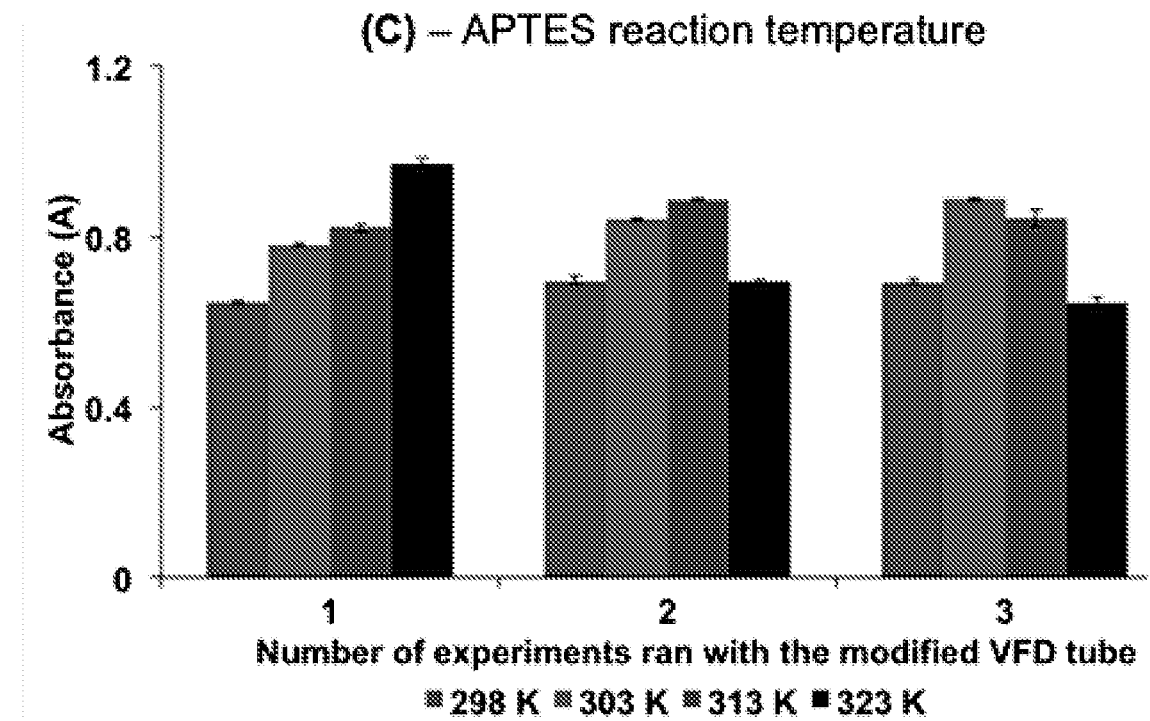
Figure 4D:
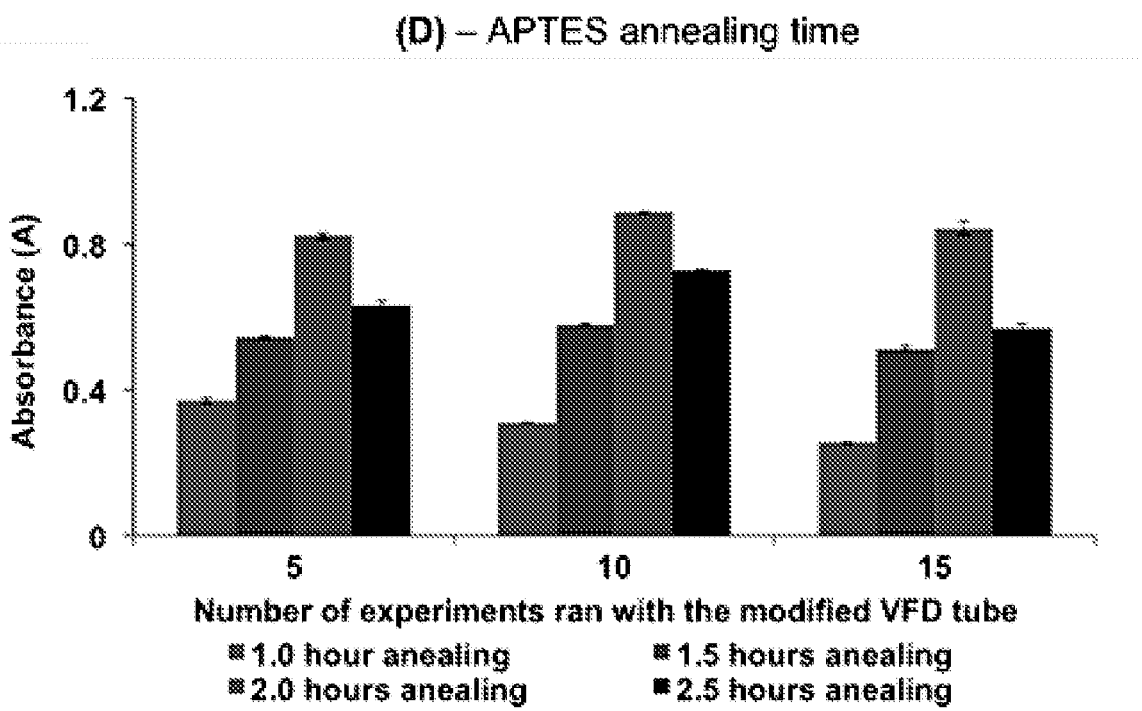

We report optimization of the APTES coating. FIG. 4A depicts the concentration of APTES used in the coatings. Each tube was filled with 49 mL of the appropriate concentration (v/v) of APTES in methanol and left overnight in a 40° C. water bath. Alternatively, the sample tube was rinsed with MeOH (6×5 mL), and heated (1 h, 160° C.) in an oven. The sample tube was then cooled to ambient temperature before usage. The tubes were then further modified and tested as specified in the general experimental. FIG. 4B depicts the APTES reaction time. Each tube was filled with 49 mL of 2% v/v APTES in methanol then added to a water bath at 40° C. for the specified amounts of time. The tubes were then further modified and tested as specified in the general experimental. FIG. 4C depicts the APTES reaction temperature. Each tube was filled with 49 mL of 2% v/v APTES in methanol. The tubes were then left for one-hour in a water bath at the specified reaction temperature. The tubes were then further modified and tested as specified in the general experimental. FIG. 4D depicts the time. Each tube was filled with 49 mL of 2% v/v APTES in methanol then added to a water bath at 40° C. for one hour. The tubes were then washed with methanol and added to an oven at 160° C. for the specified amount of time. The tubes were then further modified and tested as specified in the general experimental.

Example 3. A General Method for Enzyme Acceleration Using Vortex Fluidics

Abstract.

Enzymes provide outstanding stereo- and region-specificity when catalyzing diverse organic transformations under mild conditions. These biocatalysts are however typically slow. We describe a general method using a thin film vortex fluidic device (VFD) to accelerate enzymatic catalysis under standard conditions. The mechanical vibrations of the VFD at specific rotational frequencies generate Faraday waves within the thin film. These pressure waves can accelerate enzymatic catalysis by a reduction in the reaction and activation volumes. Five different enzymes, alkaline phosphatase, β-glucosidase, lipase, esterase and deoxyribose-5-phosphate aldolase (DERA) displayed increased activity through this approach, and essentially any soluble enzyme should be amenable to VFD-mediated rate acceleration.

Introduction.

Enzymes catalyze diverse and challenging chemical transformations with exquisite stereo- and regiospecificity. These biocatalysts offer remarkable rate accelerations compared to the uncatalyzed reaction—often $10^5$ to $10^8$-fold faster. However, despite such abilities, many enzymes run at only modest reaction rates. For their selectivity and abilities to catalyze other inaccessible reactions, enzymes find diverse applications in industrial, food, and laboratory processes.

Applications of enzymatic catalysts in synthetic chemistry have expanded driven by pressure to incorporate sustainable methods. Most enzymes operate at room temperature, can be used in conjunction with non-natural catalysts, and sometimes tolerate organic solvents [1]. Enzymes have contributed to key steps in the syntheses of atorvastatin, indinavirsulphate, and aprepitant [2,3]. Conventional methods to improve enzymatic catalysis explore directed evolution [4,5], computational design [6], and other methods. After laborious, expensive and time-consuming efforts, such methods typically uncover specific solutions to the challenges facing each enzyme. More general methods to accelerate enzyme activity include tinkering with the reaction temperature or small increases in pressure. However, too high a pressure can lead to denatured enzymes, a process used in the food industry.[7]

We have described applying the VFD to protein folding, another challenge requiring new generally applicable technologies. The VFD demonstrated effective folding of four different proteins within minutes at room temperature and pressures (standard conditions). Such abilities were ascribed to the shear forces and Faraday waves generated by the VFD. The VFD has also been successful in a number of chemical and materials transformations such as the assembly line synthesis of local anesthetic lidocaine,[8] the refolding of proteins [9] and several other organic transformations. [10,11] Since such forces also affect enzymatic catalysis, we were interested to explore biocatalysis by the VFD.

Figure 5:
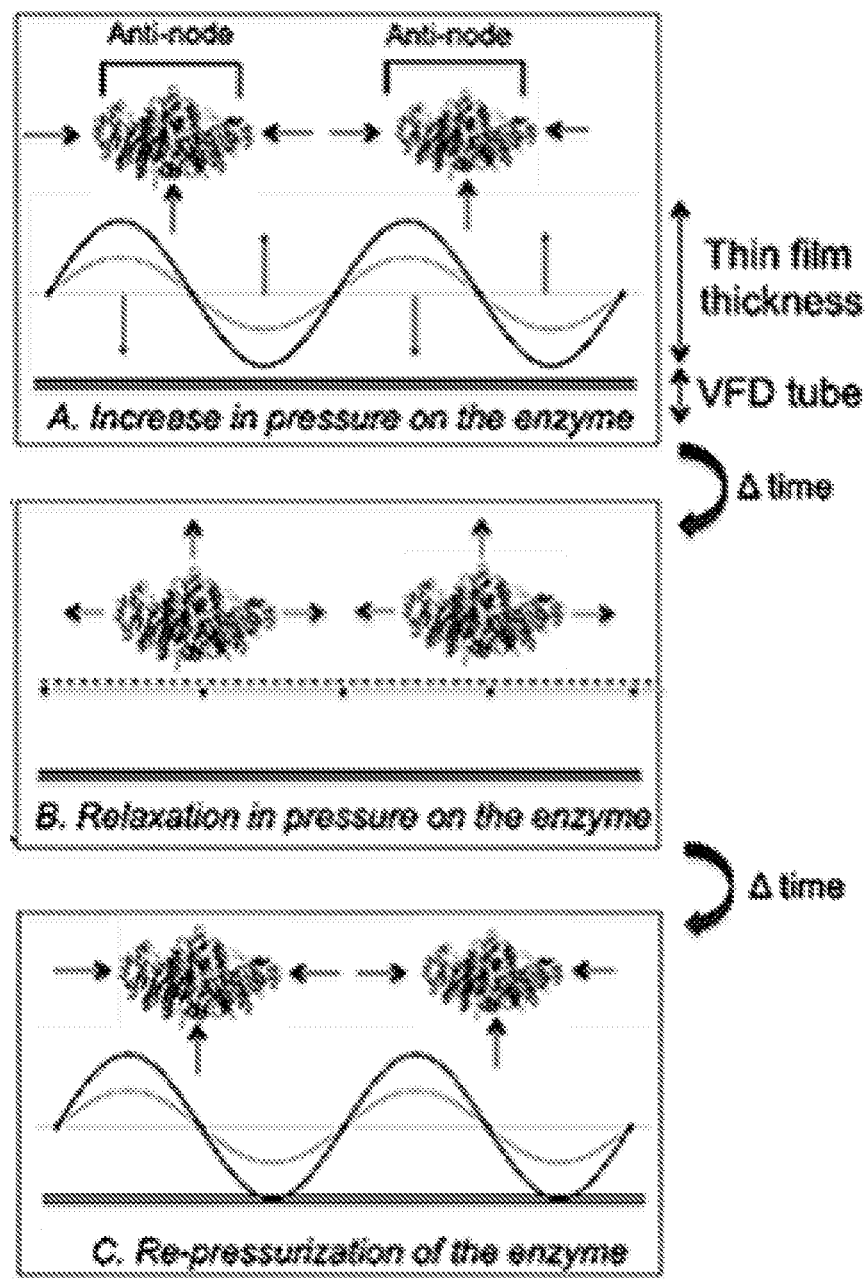
FIG. 5. The figure depicts the fluid dynamical response that induces a Faraday wave within the thin film. Shown is the sequence (A to C) of events that lead to the pressurizing of the enzyme in the thin film. At the anti-nodes of a standing wave the pressure is high, thus contracting the reaction/activation volume (A). With rapid modulation in the fluids pressure the wave passes through a point of equilibrium, (B) whereby the pressure on the enzyme is released and the reaction/activation volume increases. The anti-node then reforms and the pressure is once again increased (C). This sequence is recycled whilst the Faraday exists. Full schematics of the VFD have been previously reported.[11] See Example 3.

The VFD generates thin film of ≈200 μm through rotation of a tube at specific speeds. Held between two, multi-ball bearings, the tube rotates at a variable tilt angle, θ, relative to the horizontal (FIG. 5). The VFD can operate in either confined with a set volume of liquid or continuous flow operation whereby liquid is fed through jet feeds into the base of the sample tube. The vibrational landscape of a rotating shaft is controlled by its ball bearings.[12] At high rotational speeds, bearings produce noise, vibration and friction. At specific rotational speeds these vibrations fall into a harmonic oscillation. The speed in which these oscillations present themselves depend on radial loading, rotational speed and the order of the harmonics.[13] We previously confirmed the presence of Faraday waves within the thin film resulting from bearing vibrations, but the high throughout, enzymatic assays reported here could characterize the resultant rotational speed requirements to induce Faraday waves. Thus, we demonstrate that the VFD bearings impart a mechanical response into the thin film. This mechanical response allows the acceleration of five enzymes at standard temperature and pressure. Essentially any enzyme could be accelerated by this approach after an efficient and simple optimization process.

Experimental Section

At specific rotational speeds, the rotating sample tube fall into harmonic vibrations. This primary mechanical response induces a secondary fluid dynamical response into the thin film in the form of a Faraday wave. This has been linked to the many surprising transformations that occur within the VFD.[14-16] and this work is no exception. Faraday waves create rapid modulation in the thin film pressure. An increase in pressure at the rapidly fluctuating anti-nodes of the Faraday wave (FIG. 5, right (A)) lead to a contraction of reaction volume [17]. Once the reaction proceeds through an area of neutral pressure the reaction volume expands (FIG. 5, right B). The anti-node then reforms and the pressure again increases (FIG. 5, right C). This model of activation and reaction volume is supported by Braunschweig et al., whom reported that organic reactions can be accelerated by using AFM tips for increased activation volumes [18].

Results and Discussion

The rates and position of equilibrium with catalysis can be explained to varying degrees of vigor known in the art using the Van't Hoff equation;

$$\text{A kinetic consideration} - \left(\frac{d \ln k}{dP}\right)_T = \frac{-V^T}{RT}$$

-continued $$\text{A thermodynamic consideration} - \left(\frac{d \ln K}{dP}\right)_T = \frac{V}{RT}$$

Here the rate constant (k), equilibrium constant (K), pressure in the system (P), temperature of the system (T), the volume change from the initial state to the final state (V), the activation volume (V*) and the ideal gas constant (R). To consider the thermodynamics; if a ΔV is positive then the reaction favors the initial state and vice versa. However, given the complexity enzyme pathways, each chemical transformation has multiple steps associated. Conformational changes, unfolding and folding, ionization, hydration and the association and dissociation of subunits all have a thermodynamic consideration. High pressure processing on these variables has been thoroughly investigated but no study on rapid modulations of lower pressures systems exist to our knowledge. Kinetically, ΔV* is the difference between the activation volumes of the initial reactants and the activation volume of the transition state. If the activation volume is negative, an increase in pressure will accelerate the reaction and vice versa. Much like the thermodynamic, kinetically, enzymes encompass a multitude of steps such as; substrate binding and release, chemical transformation(s) of the substrate and eventual product release. These kinetic steps have been well studied and arise from Michaelis-Menton models. We now investigate how Faraday wave pressure modulation drives enzyme enhancement and if this effect is thermodynamic or kinetic in nature.

First to be ascertained was the ability of enzymes to withstand levels of high shear stress within the thin film. We previously disclosed that proteins can be refolded within the confinements of a VFD.[9] This process was driven by the high levels of shear stress mediating the folding process into a thermodynamic sink, much like a protein chaperone. In testing enzyme behavior in the VFD, shear stress has no effect. More impressive, is that the VFD accelerates the rate of biocatalysis.

Alkaline phosphatase is a well understood, commercially available hydrolase enzyme that is responsible for the removal of phosphate groups from a variety of nucleotides, proteins, and alkaloids.[19] This enzyme was used to explore the variables for accelerated enzyme activity within the VFD. For every VFD experiment, the corresponding control experiment was carried out. This ensures that any enhancement is directly from the VFD. Control reactions were ran from the same stock solution using the same volume (1.30 mL), concentration, temperature and reaction time for all enzymes tested. The substrate was also rotated at high speed in its buffer to demonstrate that the enhancement was not due to substrate hydrolysis. A quencher was used in order to immediately halt reactivity in both VFD and non-VFD samples. The use of colorimetric or fluorogenic assays was employed to allow high throughput testing so that optimization occurs in short order, vida infra.

Further control experiments provided an insight into the mechanism behind the observed acceleration. Centrifuging samples to 14,000 rpm to simulate high shear stress levels displayed no increase in enzymatic activity. A temperature-controlled experiment demonstrated that if any increase in temperature occurred during processing, it would be detrimental to enzyme activity. Rapid micromixing has increased the yield of several organic reactions in the VFD. However, many of the rotational speeds of the VFD tested in this work (often up to 9,000 rpm) afforded no acceleration (FIGS. 7A-7F). Thus, micro-mixing is not the drive for the acceleration. These vital experiments indicated that the observed enhancement is a direct effect of the rapidly rotating VFD tube. Further to this, a mechanical response from the bearings is most likely responsible, much like the Faraday wave driven esterifications previously reported.[11] This was further corroborated when the bearings were replaced with different bearing models. With a different number of ball bearings, the acceleration in enzyme activity changed. From the control experiments above, the bearings are believed to be the direct cause for accelerated enzyme activity in the VFD.

In order to fully quantify this system, the variables of; reaction time, simultaneous changes in enzyme and substrate concentration, tube inclination angle, rotational speed, product inhibition, substrate loading levels and the use steric crowding reagents were explored (FIGS. 6A-6H). The rotational speed of the device clearly controls the level of enzymatic enhancement. This is no surprise given that the rotating tube is directly in contact with the bearings. At specific rotational speeds the bearings fall into a harmonic vibration as previously discussed. Scanning across the rotational landscape identifies rotational speeds that are dramatically more effective in accelerating activity. For example, all rotational speeds below 6400 rpm had very little impact on enzyme activity. However, rotating at 6550, 7300 and 8000 rpm lead to a dramatic enhancement in activity. At these rotational speeds we suspect the ball bearings enter a harmonic vibration that set up a Faraday wave within the thin film. We predict that this leads to a rapid modulation in the thin films pressure and a change in the reaction volume and/or transition state volume. This is depicted in FIG. 5 sequences A-C.

Figure 6A:
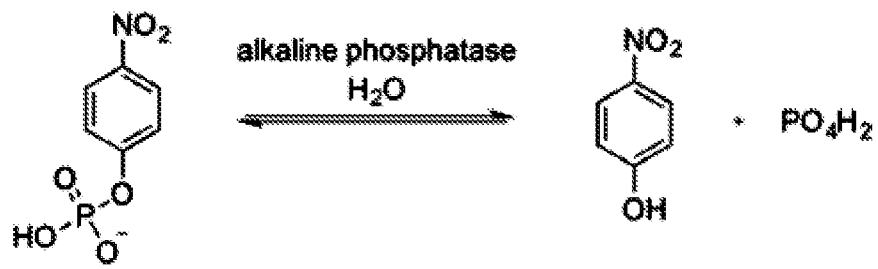
FIGS. 6A-6H. Optimization of alkaline phosphatase in the VFD.
Figure 6B:
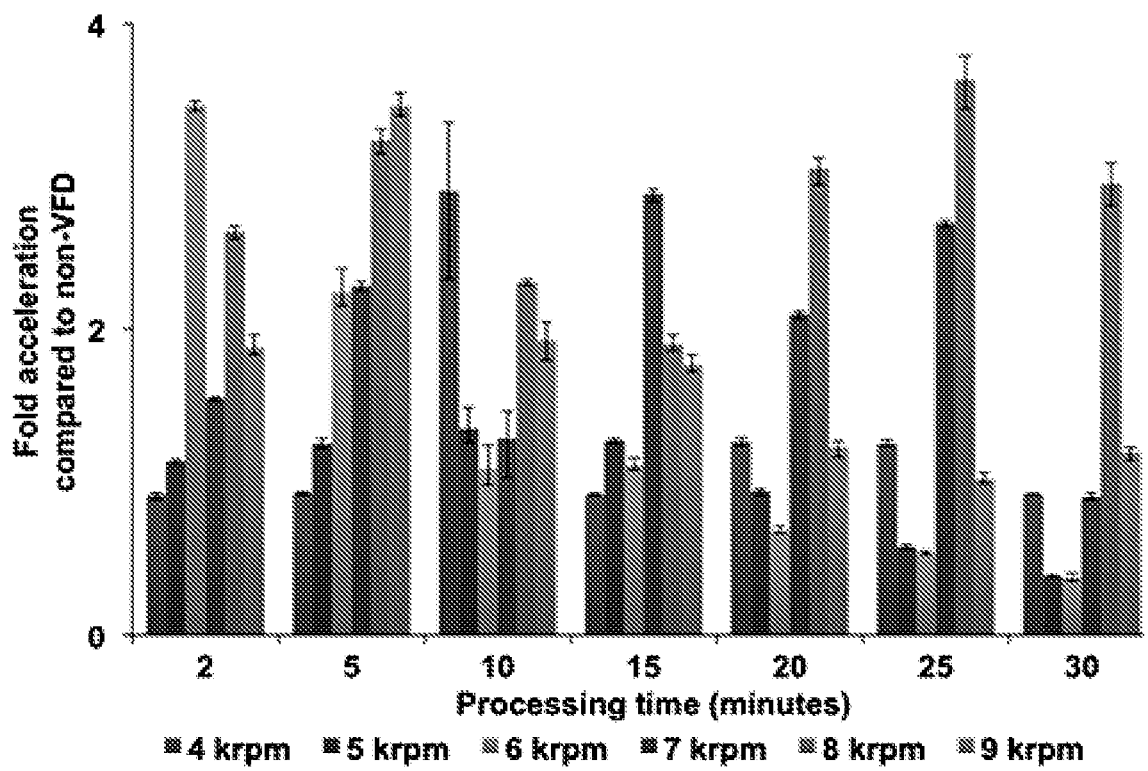
Figure 6C:
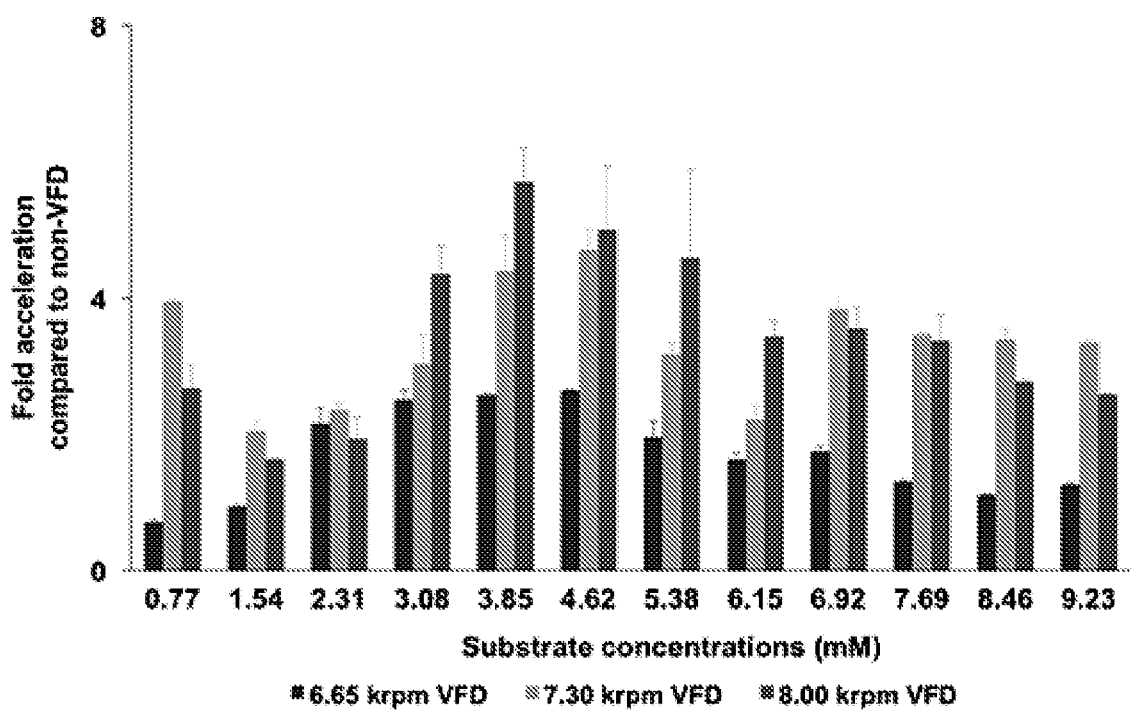
Figure 6D:
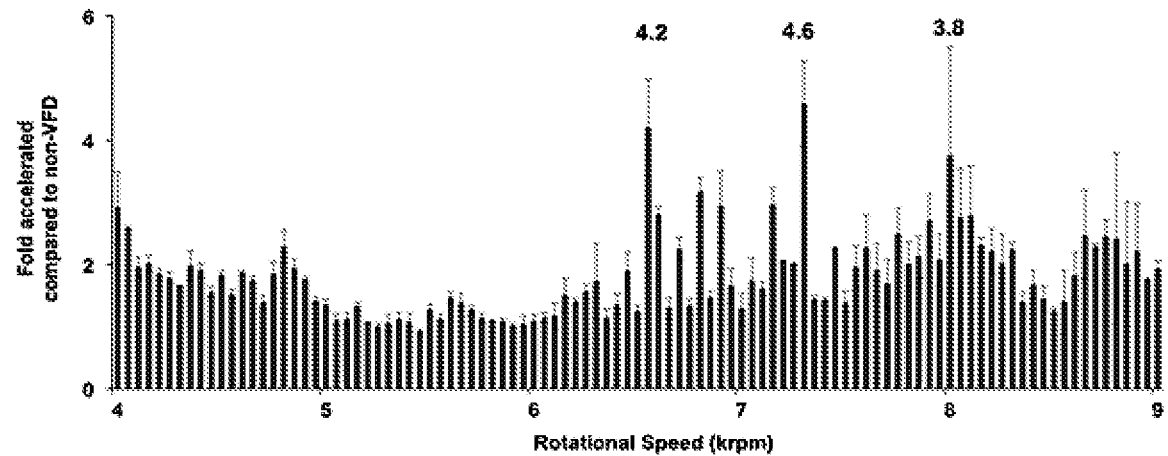
Figure 6E:
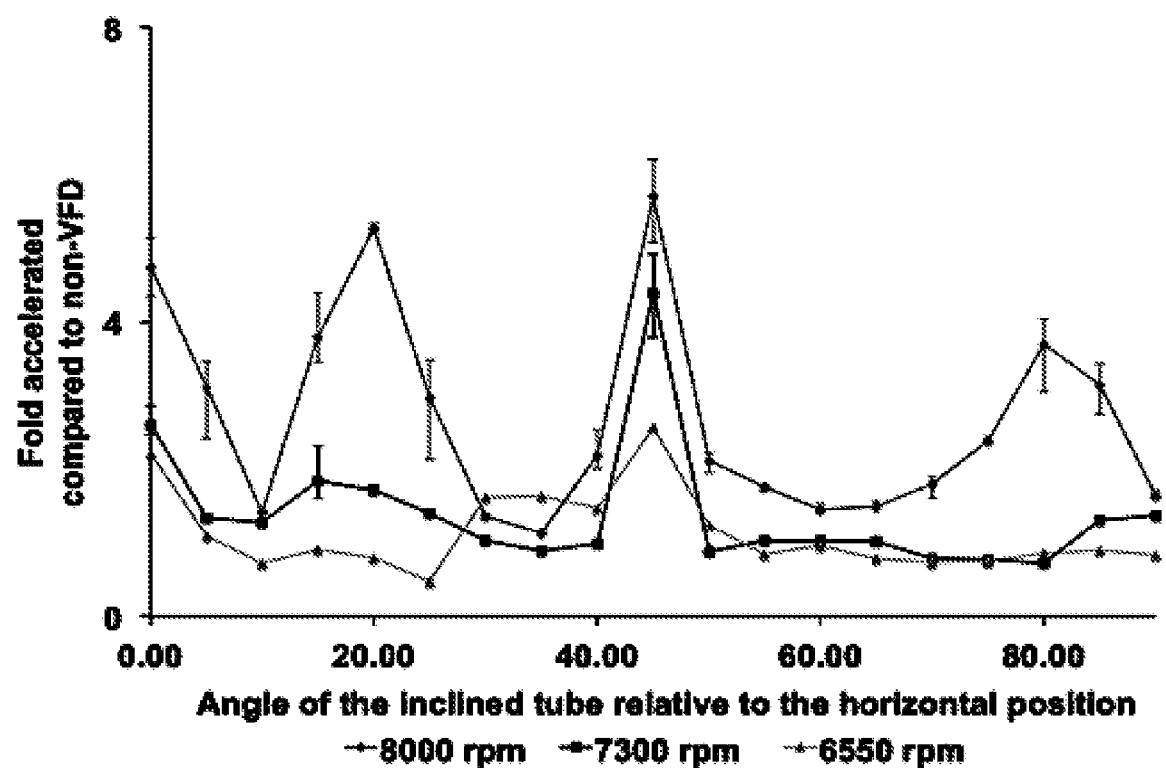
Figure 6F:
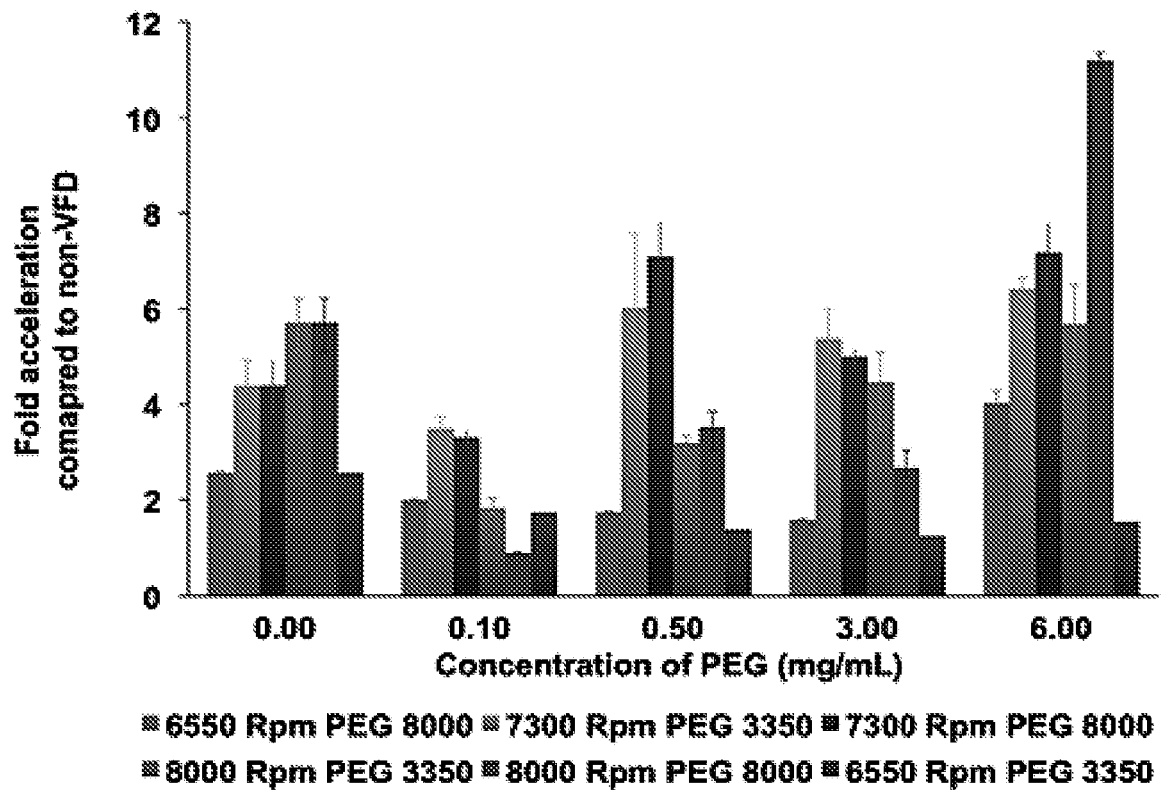
Figure 6G:
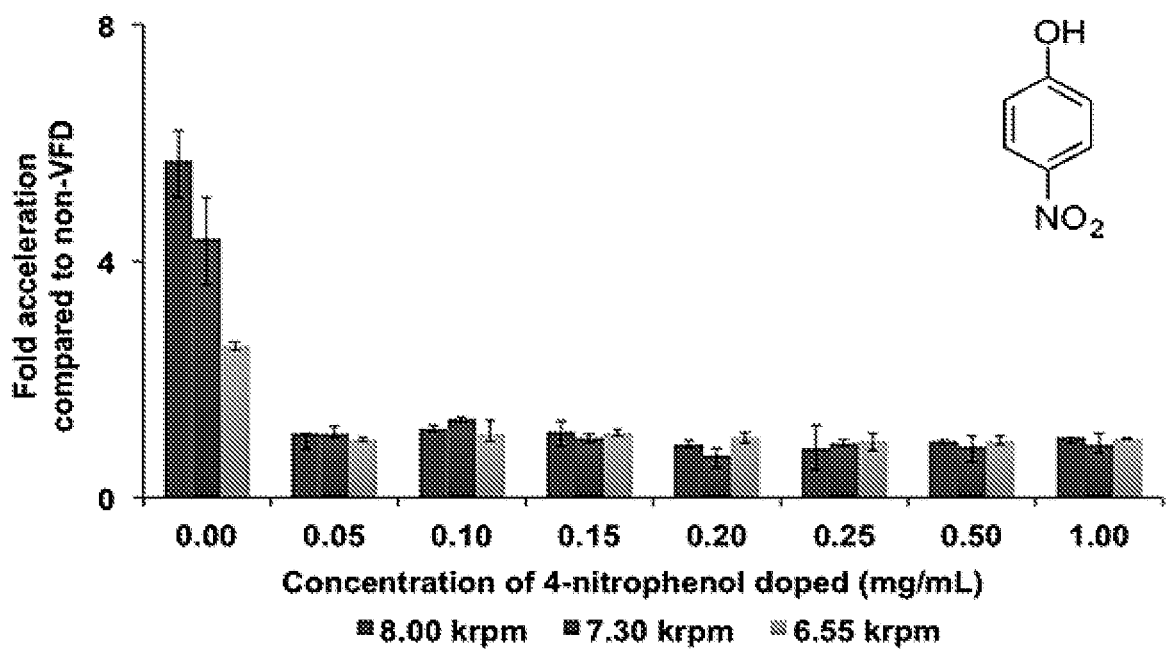
Figure 6H:
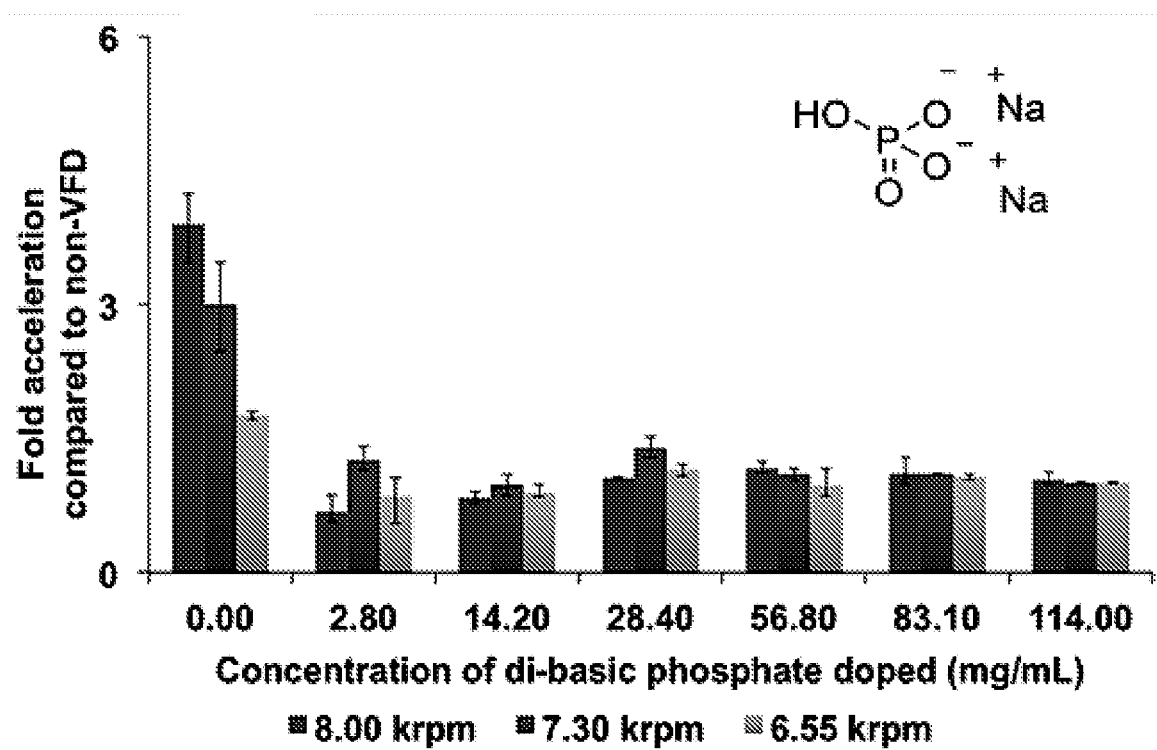
Figure 7A:
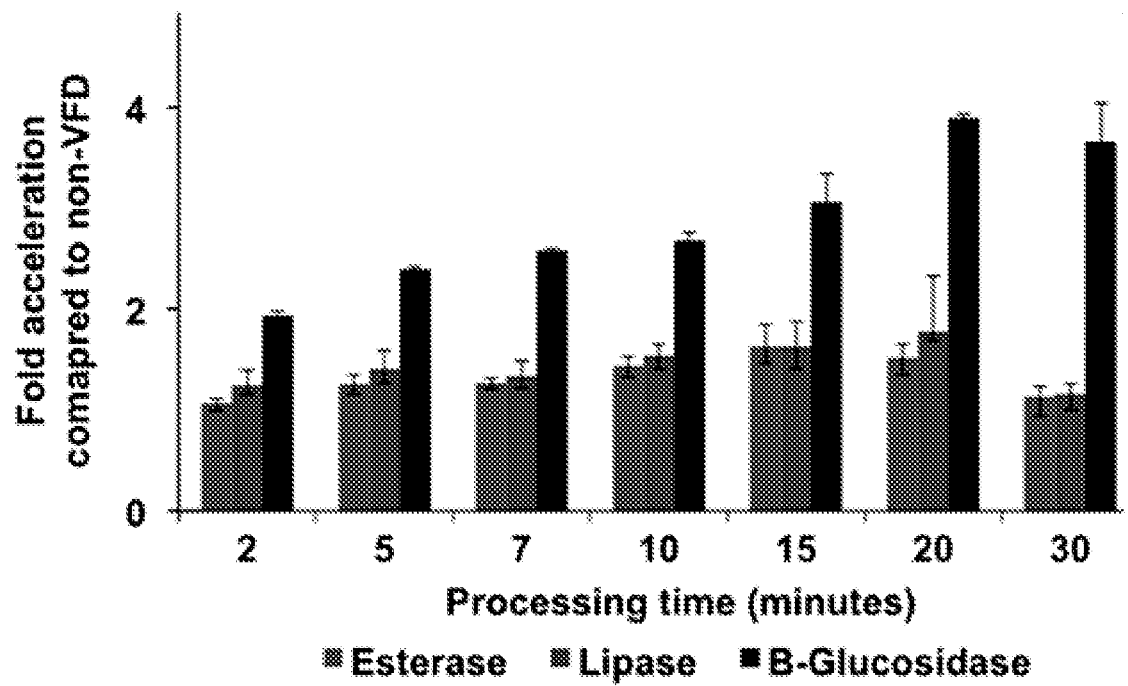
FIGS. 7A-7F. The three-step optimization process to enhance accelerated activity.
Figure 7B:
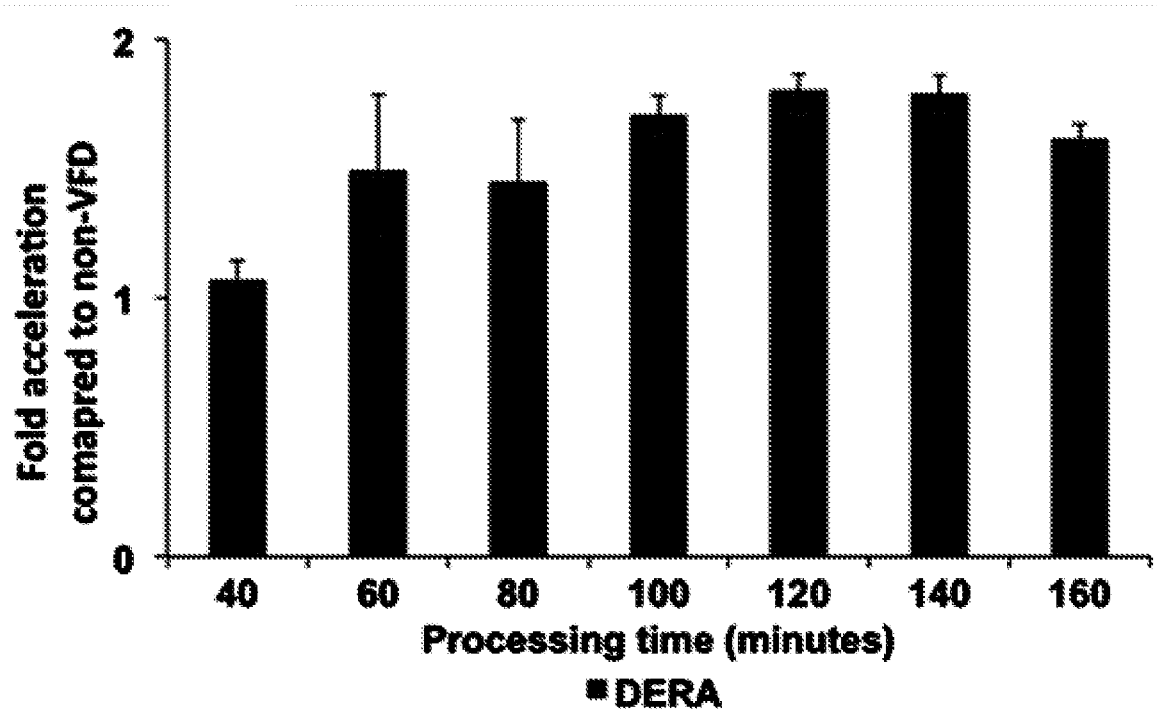
Figure 7C:
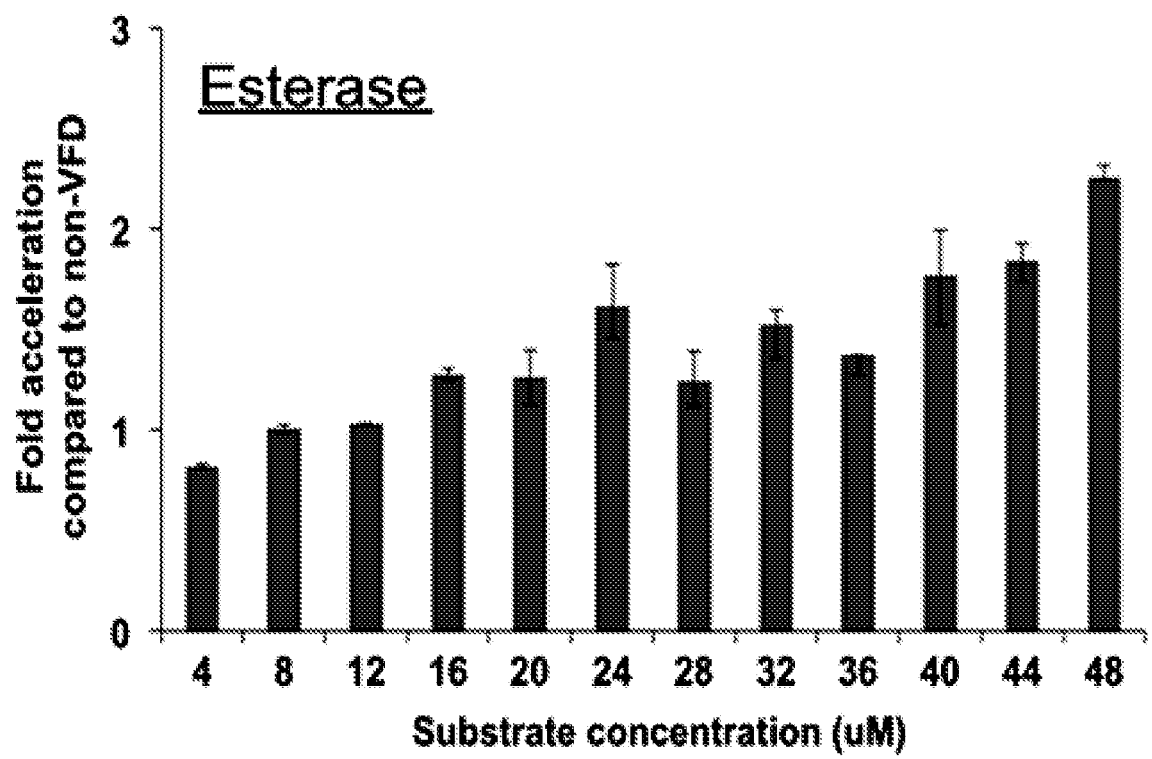
Figure 7D:
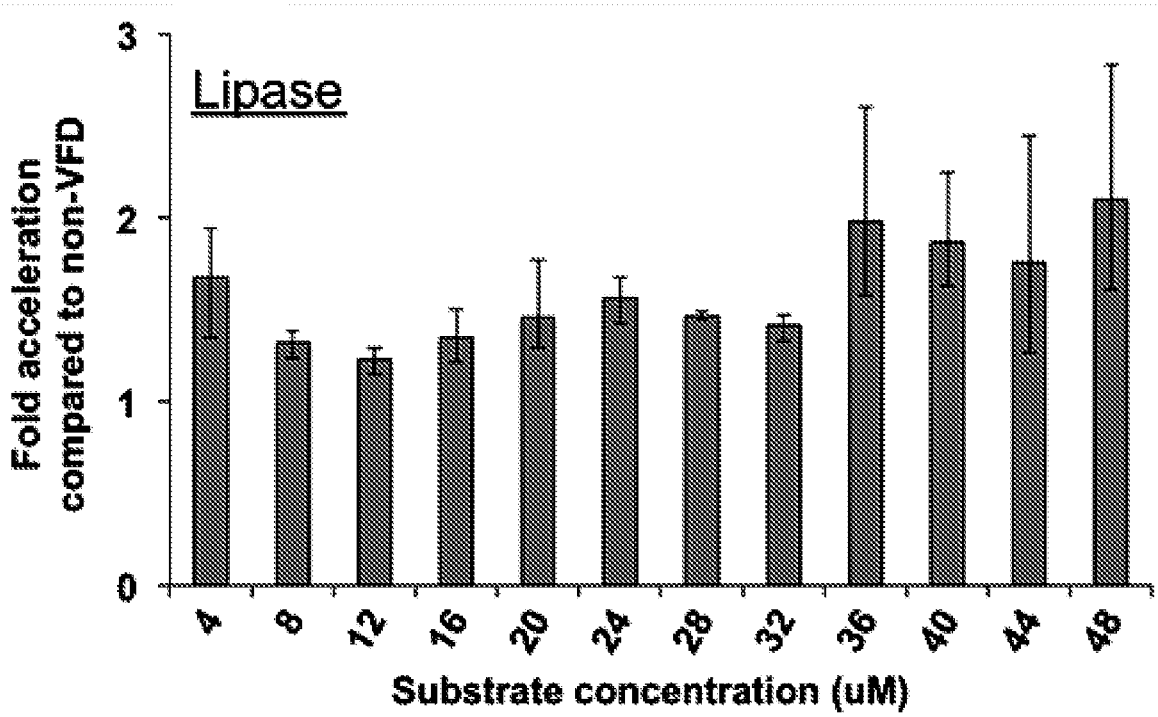
Figure 7E:
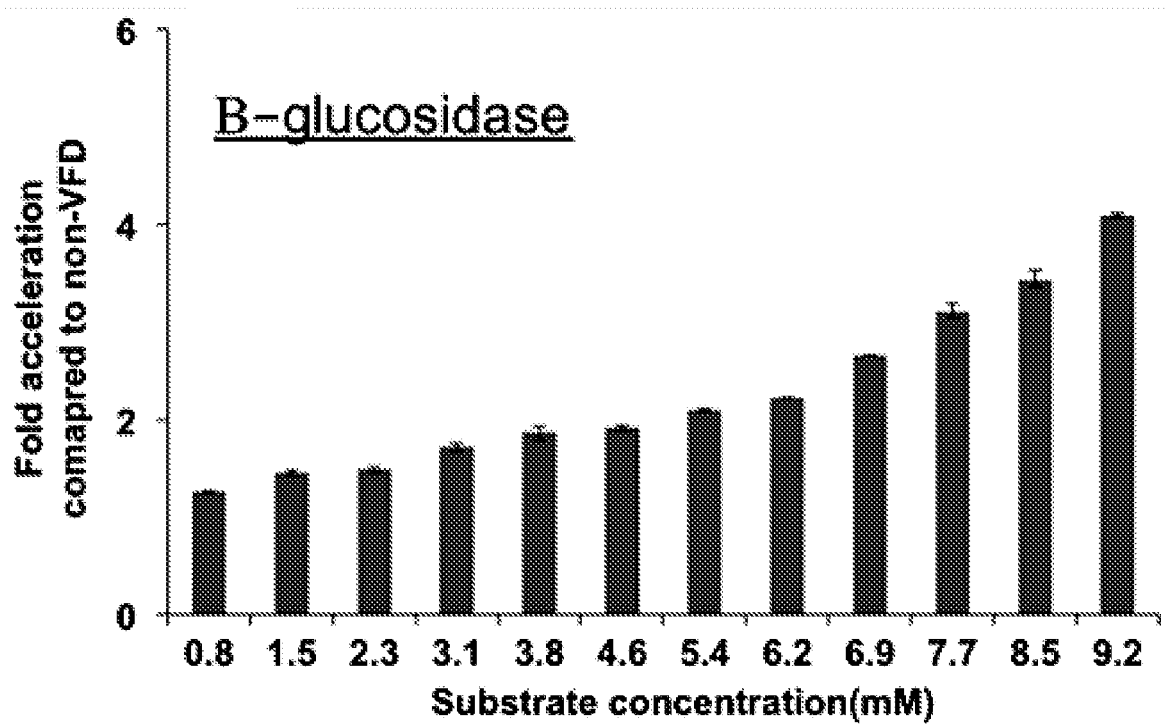
Figure 7F:
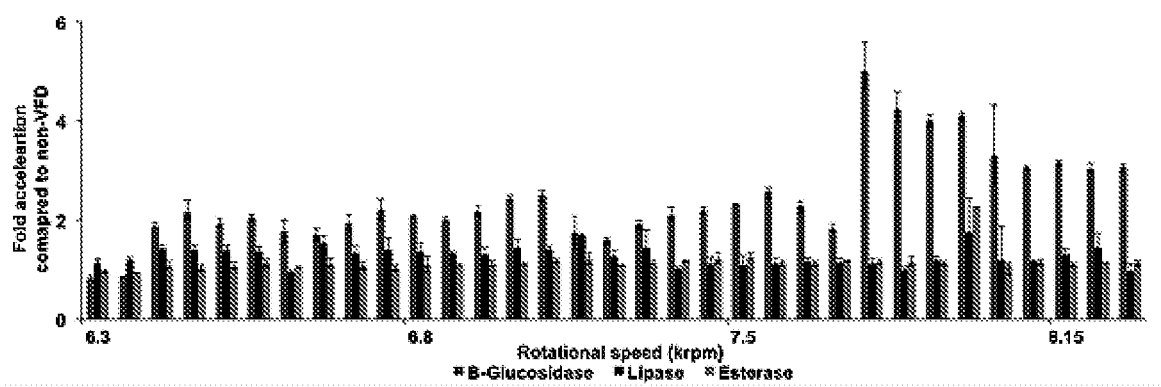

The angle of the inclined tube is also a key factor in the ability of the VFD to accelerate enzymes (FIG. 6E). The angle of the inclined tube has previously shown to be optimal at a 45-degree tilt angle, and this work is no exception. Without wishing to be bound by any theory, it is reasoned that this critical angle stems from the complex fluid dynamics of the system which we have previously discussed.[20]

Doping the reaction with set concentrations of both products (FIGS. 6G-6H) demonstrated that this process cannot overcome product inhibition. However, increasing substrate loading allowed continued enhancement compared to traditional techniques. This has significant relevance for industrial processes and leads to increased reaction efficiency. For the efficient scanning of reaction space, the substrate and enzyme concentration were varied simultaneously from very high concentration of enzyme compared to substrate to effectively a 1:1 volumetric ratio. For the rotational speeds tested, the optimum substrate concentration was 3.85 mmol. Interestingly, for the same substrate concentration in a non-VFD sample, a decrease in activity is observed, and this pattern is seen among all enzymes tested. This indicates that the VFD may be having a direct effect on $k_{cat}$ and $k_{on}$. As this is a kinetic effect, this may be determined from Michaelis-Menton models and this is tested vide infra.

The optimal conditions for alkaline phosphatase was used to explore four other enzymes; β-glucosidase, esterase, lipase and DERA. Three sets of crucial experiments are undertaken to allow rapid optimization of enzyme activity. Exploring reaction time, simultaneously changing enzyme and substrate concentration and variation in rotational speeds leads to rapid optimization. All enzymes were tested using these three experiments, and all enzymes demonstrated enhancement compared to non-VFD samples (FIGS. 7A-7F).

Forecasting that high usage of the bearings, the closed bearings (where additional lubricant cannot be added) were changed to open bearings so that additional lubricant can be added to allow maintenance. The closed bearings have a lifetime of around 200 hours before they need to be replaced. Using open bearings, with the same exact specification allows a much longer lifetime, given correct maintenance is undertaken. The switch to open bearings was made and a high-resolution, rotational speeds scan at 5.00-rpm increments was achieved. It was found that the activity landscape of these bearings is very fine and intricate. This further justifies the importance of the devices bearings.

In determining if the observed acceleration is due to a kinetic or thermodynamic effect, the initial rates of each reaction were explored. All five enzymes were subjected typical kinetic experiments using the Michaelis-Menton model. The intrinsic values of the enzymes in a batch type and VFD system could be ascertained (Table 1).

TABLE 1

The Michaelis-Menton parameters that were generated through initial rates experiments both in the VFD and non-VFD.

| Enzyme | $V_{max}$ (Mol/sec) | | $K_M$ (M) | | $k_{cat}$ (sec$^{-1}$) | | $k_{cat}/K_M$ (M$^{-1}$S$^{-1}$) | |
| --- | --- | --- | --- | --- | --- | --- | --- | --- |
| | Batch | VFD | Batch | VFD | Batch | VFD | Batch | VFD |
| Phosphatase | 2.271 × 10$^{-8}$ | — | 4.836 × 10$^{-4}$ | — | 1 | — | 1 | — |
| β-glucosidase | 1.489 × 10$^{-7}$ | — | 1.068 × 10$^{-2}$ | — | 4 | — | 375 | — |
| Lipase | 2.205 × 10$^{-8}$ | — | 1.452 × 10$^{-3}$ | — | 0.024 | — | 17 | — |
| Esterase | 1.439 × 10$^{-8}$ | — | 2.083 × 10$^{-3}$ | — | 337 | — | 1.56 × 10$^{-5}$ | — |
| DERA | | | | | | | | |

General Protocol.

To a 17.7 mm internal diameter VFD tube was added the substrate and enzyme in buffer at the appropriate concentration. The VFD tube was rotated about its axis at a specific rotational speed at an inclination angle of 45-degrees. After a set amount of time had elapsed, the rotation was immediately halted and the quenching reagent added. The exact same reaction was run alongside the VFD in mimicking a non-VFD process. From both the VFD processed and non-VFD processed sample an aliquot of 0.100 mL was removed and added to a 96 well plate and read at 405 nM to detect the production of p-nitrophenoxide. These measurements were carried out in triplicate and allow an accurate comparison to be drawn between VFD and non-VFD processing. For all alterations to this general protocol, assay and further experimental design, see supporting information.

References

Example 3

[1]. Koeller, C.-H. Wong, Enzymes for chemical synthesis. Nature 409, 232-240 (2001); [2]. D. J. Pollard, J. M. Woodley, Biocatalysis for pharmaceutical intermediates: the future is now. Trends in Biotechnology 25, 66-73 (2007); [3]. R. N. Patel, Microbial/enzymatic synthesis of chiral pharmaceutical intermediates. Curr. Opin. Drug. Discov. Devel 6, 902-920 (2003); [4]. O. Kuchner, F. H. Arnold, Directed evolution of enzyme catalysts. Trends in Biotechnology 15, 523-530 (1997); [5]. D. Bloom, M. M. Meyer, P. Meinhold, C. R. Otey, D. MacMillan, F. H. Arnold, Evolving strategies for enzyme engineering. Current Opinion in Structural Biology 15, 447-452 (2005); [6]. N. Bolon, C. A. Voigt, S. L. Mayo, De novo design of biocatalysts. Current Opinion in Chemical Biology 6, 125-129 (2002); [7]. B. Boonyaratanakornkit, C. B. Park, D. S. Clark, Pressure effects on intra- and intermolecular interactions within proteins. Biochimica et Biophysica Acta (BBA)—Protein Structure and Molecular Enzymology 1595, 235-249 (2002); [8]. J. Britton, J. M. Chalker, C. L. Raston, Rapid Vortex Fluidics: Continuous Flow Synthesis of Amides and Local Anesthetic Lidocaine. Chemistry—A European Journal 21, 10660-10665 (2015)10.1002); [9]. T. Z. Yuan, C. F. G. Ormonde, S. T. Kudlacek, S. Kunche, J. N. Smith, W. A. Brown, K. M. Pugliese, T. J. Olsen, M. Iftikhar, C. L. Raston, G. A. Weiss, Shear-Stress-Mediated Refolding of Proteins from Aggregates and Inclusion Bodies. ChemBioChem 16, 393-396 (2015)10; [10]. J. Britton, C. L. Raston, Continuous flow vortex fluidic production of biodiesel. RSC Advances 4, 49850-49854 (2014)10.1039; [11]. J. Britton, S. B. Dalziel, C. L. Raston, Continuous flow Fischer esterifications harnessing vibrational-coupled thin film fluidics. RSC Advances 5, 1655-1660 (2015); [12]. S. P. Harsha, K. Sandeep, R. Prakash, Non-linear dynamic behaviors of rolling element bearings due to surface waviness. Journal of Sound and Vibration 272, 557-580 (2004); [13]. L. D. Meyer, F. F. Ahlgren, B. Weichbrodt, An Analytic Model for Ball Bearing Vibrations to Predict Vibration Response to Distributed Defects. Journal of Mechanical Design 102, 205-210 (1980); [14]. J. Britton, C. L. Raston, Rapid high conversion of high free fatty acid feedstock into biodiesel using continuous flow vortex fluidics. RSC Advances 5, 2276-2280 (2015); [15]. K. Vimalanathan, X. Chen, C. L. Raston, Shear induced fabrication of intertwined single walled carbon nanotube rings. Chemical Communications 50, 11295-11298 (2014); [16]. L. Yasmin, X. Chen, K. A. Stubbs, C. L. Raston, Optimising a vortex fluidic device for controlling chemical reactivity and selectivity. Sci. Rep. 3, (2013); [17]. M. Ali, A. Umemura, Capillary Phenomena On A Liquid Surface. Journal of Mechanical Engineering ME38, 45-51 (2007); [18]. X. Han, S. Bian, Y. Liang, K. N. Houk, A. B. Braunschweig, Reactions in Elastomeric Nanoreactors Reveal the Role of Force on the Kinetics of the Huisgen Reaction on Surfaces. Journal of the American Chemical Society 136, 10553-10556 (2014); [19]. J. E. Coleman, Structure and Mechanism of Alkaline Phosphatase. Annual Review of Biophysics and Biomolecular Structure 21, 441-483 (1992); [20]. J. Britton, S. B. Dalziel, C. L. Raston, Enhancing the kinetics and thermodynamics of SN2 substitution reactions using vortex fluidic flow chemistry. Submitted (2015).

Example 4—Accelerating Enzymatic Catalysis Using Vortex Fluidics

Abstract:

Enzymes catalyze chemical transformations with outstanding stereo- and regio-specificities, but many enzymes are limited by their long reaction times. There is provided herein a general method to accelerate enzymes using pressure waves contained within thin films. Each enzyme responds best to specific frequencies of pressure waves, and we report acceleration landscapes for each protein. A vortex fluidic device introduces pressure waves that drive increased rate constants ($k_{cat}$) and enzymatic efficiency ($k_{cat}/K_m$). Four enzymes displayed an average seven-fold acceleration with deoxyribose-5-phosphate aldolase (DERA) achieving an average 15-fold enhancement through this approach. In solving a common problem in enzyme catalysis, we have uncovered a powerful, generalizable tool for enzyme acceleration. This research provides new insights into previously uncontrolled factors affecting enzyme function.

Introduction.

Enzymes make life possible by catalyzing diverse and challenging chemical transformations with exquisite specificity. Applications in both industry [1] and academia [2] rely on the selectivity and power of enzymes to catalyze otherwise challenging transformations. Biocatalysts offer remarkable rate accelerations compared to uncatalyzed reactions, with typical rate accelerations ($k_{cat}/k_{uncat}$) of $10^5$- to $10^{15}$-fold faster [3]. Though some enzymes are diffusion-limited [4], the catalytic rates of enzymes are often more typically limited by their catalytic efficiency ($k_{cat}/K_m$); additionally, molecular crowding, along with product and substrate inhibition, can reduce enzyme efficiency [5]. Though some enzymes catalyse transformations with rapid rates (e.g., laccases, fumarases and alcohol dehydrogenases) [6], other enzymes operate at only modest reaction rates, requiring long reaction times and carefully optimized conditions; for example, DERA requires long processing times (hours to days), and is substrate-inhibited [7]. There is provided a process that accelerates four different enzymes at standard temperature and pressure. Without wishing to be bound by theory, it is believed that many water-soluble enzymes could be accelerated.

Results and Discussion.

Figure 8B:
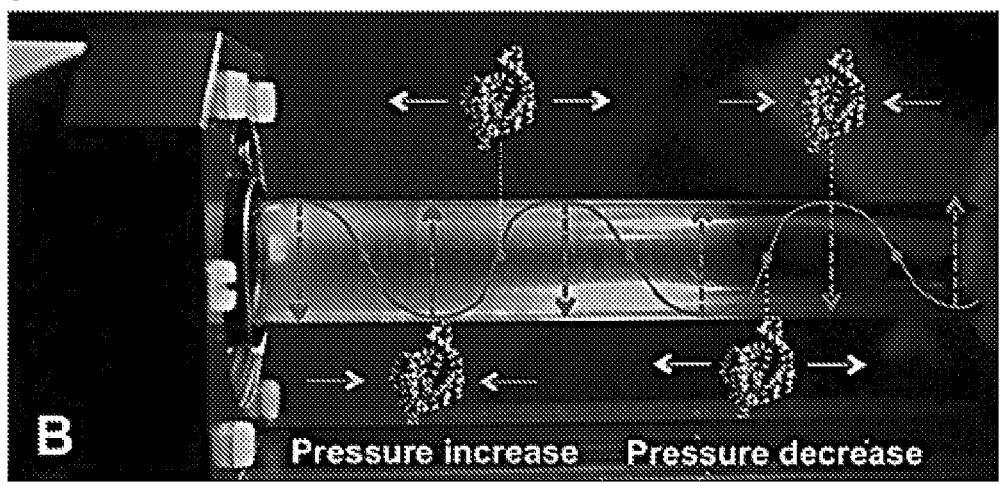
Figure 8C:
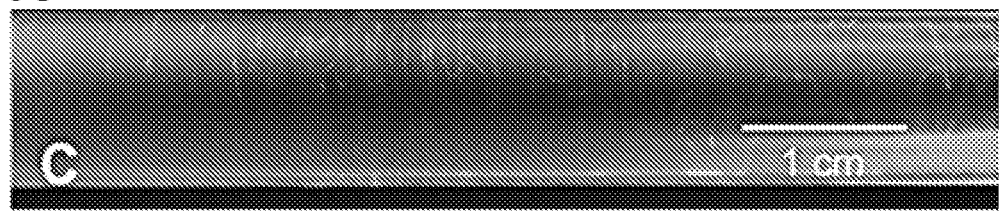

Recently, vortex fluidic devices (VFDs) have been used to accelerate covalent and non-covalent bond formation. VFDs process solutions in thin films by the rapid rotation of a sample tube (FIGS. 8A-8B) [8]. Within the thin film, species are subjected to high levels of shear stress, mass transfer, and vibrational energy input at specific rotational speeds. For example, the VFD demonstrated the effective folding of four different proteins within minutes at standard temperature and pressure [9]. The VFD has also been used to improve the synthesis of lidocaine [10] and other organic transformations [11]. In a continuous flow regime, flow rates of up to 20 mL/min can be achieved to process up to 30 L per day in the current, benchtop configuration. Since VFD processing increased the rates of organic reactions and protein folding, it is believed that biocatalysis, which requires both reactivity and correct protein fold, can benefit from the methods disclosed herein.

Figure 9A:
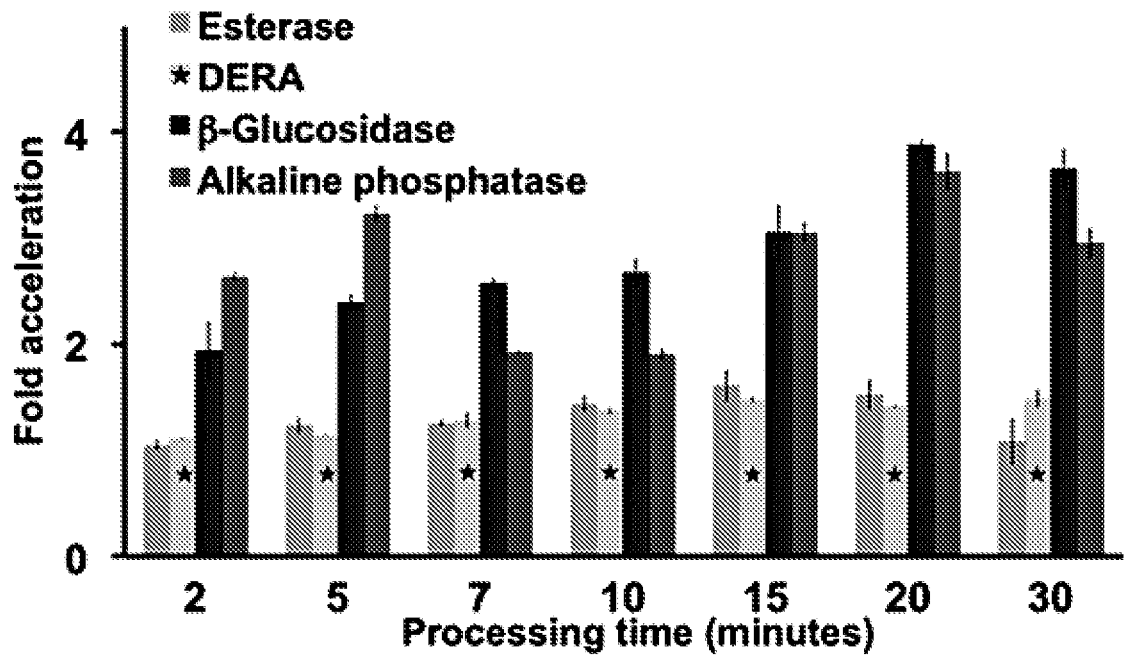
FIGS. 9A-9E. Parameters for accelerated biocatalysis of the four enzymes. Fold acceleration was determined by the ratio of the VFD-mediated substrate conversion to an identical enzyme-substrate solution not treated by the VFD.
Figure 12:
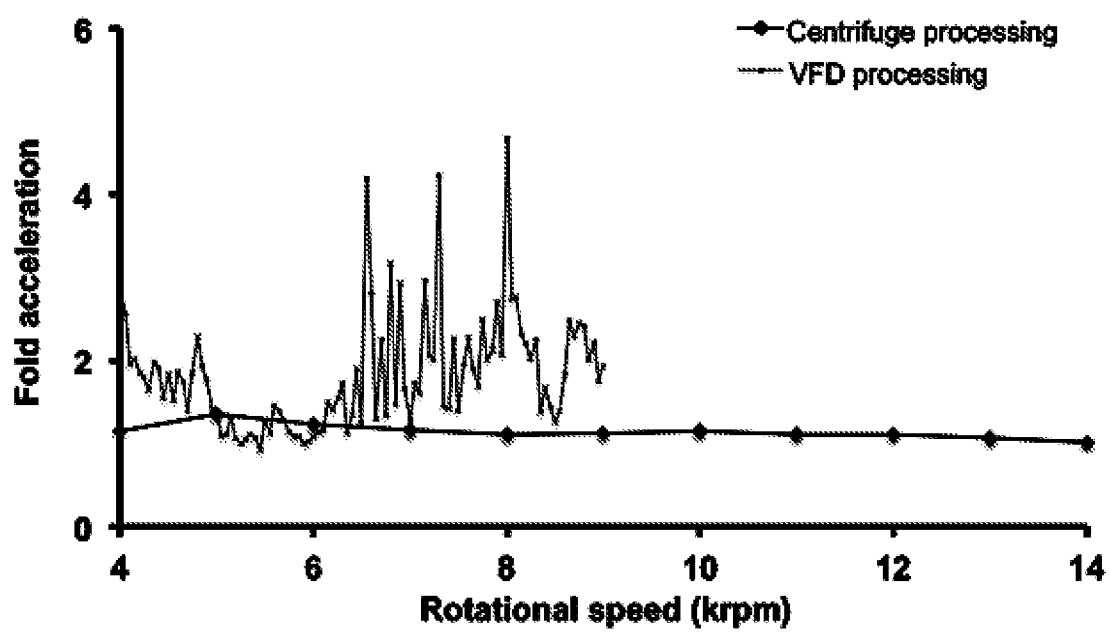
FIG. 12. Centrifugation compared to VFD-mediated processing. The centrifuged sample has no observed rate acceleration at any rotational speed. X-axis: fold acceleration; y-axis: Rotational speed (krpm). Legend: Centrifuge processing (diamonds); VFD processing (connected dots).
Figure 13:
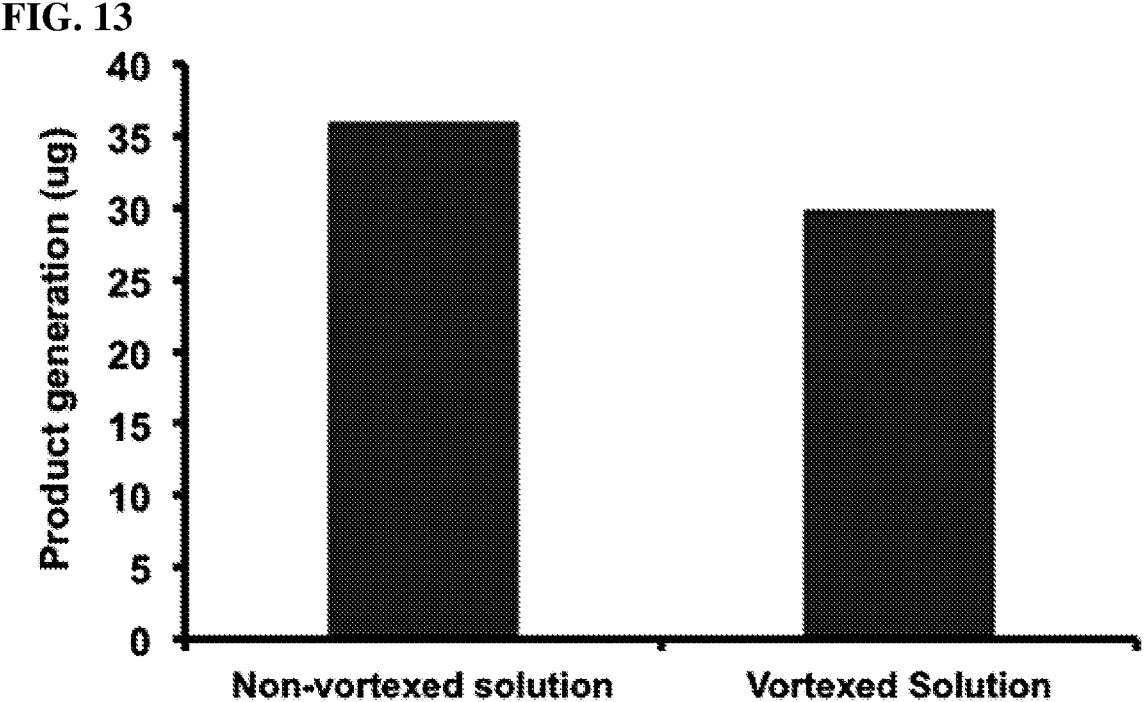
FIG. 13. Bar graph depicting non-vortexed (left) and vortexed (right) enzyme-substrate solution in a conventional bench top vortex. In this experiment, β-glucosidase (77 nM solution, 325 µL) and 4-nitrophenyl β-D-glucopyranoside (0.01 M solution, 975 µL) were used to examine the effects of vortexing on enzyme activity. In this example, the fold acceleration was not calculated, as the conventional vortexer decreases enzyme activity.
Figure 14:
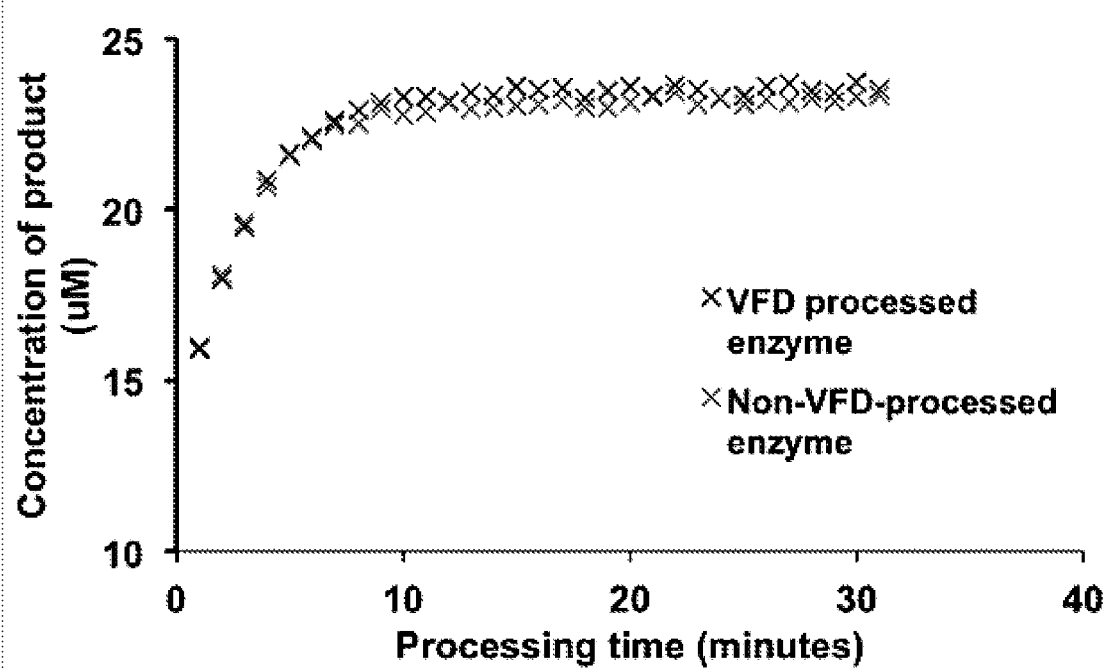
FIG. 14. The effect of VFD-processing on the enzyme before the enzymatic catalysis. After 10 mM of VFD processing, the conversion of 4-nitrophenyl β-D-glucopyranoside to 4-nitrophenol catalyzed by β-glucosidase was monitored at 351 nm. At this wavelength, the unquenched reaction can be monitored. The concentration of β-glucosidase was 19.3 nM and its substrate 4-nitrophenyl β-D-glucopyranoside was 7.5 mM. Legend: VFD processed enzyme (generally upper crosses beyond 10-mM); Non-VFD processed enzyme (generally lower crosses beyond 10-mM).

Control reactions with alkaline phosphatase can demonstrate the requirements for high, specific rotational speeds of the VFD to generate a thin film containing the enzyme for accelerated catalysis (FIGS. 12-14). VFD-mediated acceleration of four biocatalysts was compared to identical unprocessed enzyme-substrate solutions for efficient reaction optimization (FIGS. 9A-9E). First, VFD processing times were varied to identify short time periods (10 min to 2 h) suitable for further optimization (FIG. 9A). Esterase produced a lower VFD-based enhancement (two-fold) compared to the other three enzymes; esterase also needed longer reactions times due to the enzyme's requirements for low substrate concentrations [12]. In general, after long time periods, the substrate is expended, and the unprocessed solution can attain similar levels of substrate conversion. Furthermore, VFD-processed solutions display parallel activities to the non-VFD counterparts for the first few minutes before rapid acceleration (e.g., alkaline phosphatase in FIG. 19). A similar lag period before rate acceleration has been described previously for ultrasound-accelerated enzyme acceleration [13].

Figure 9B:
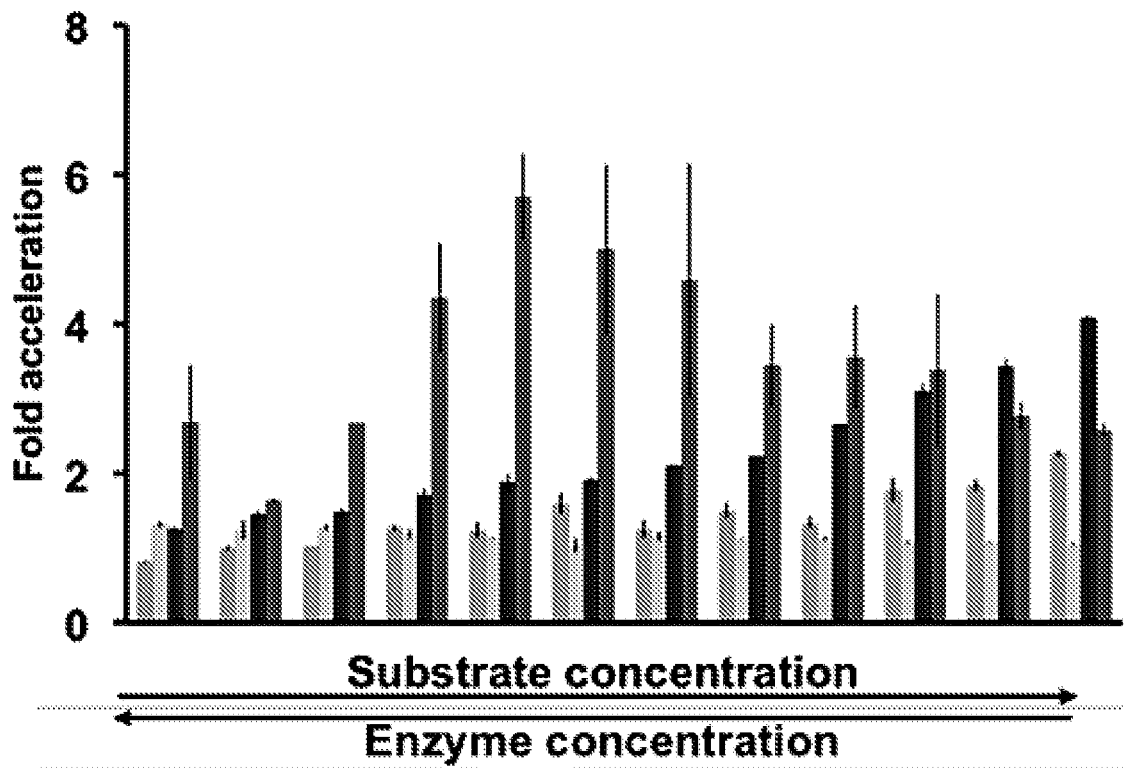
Figure 9C:
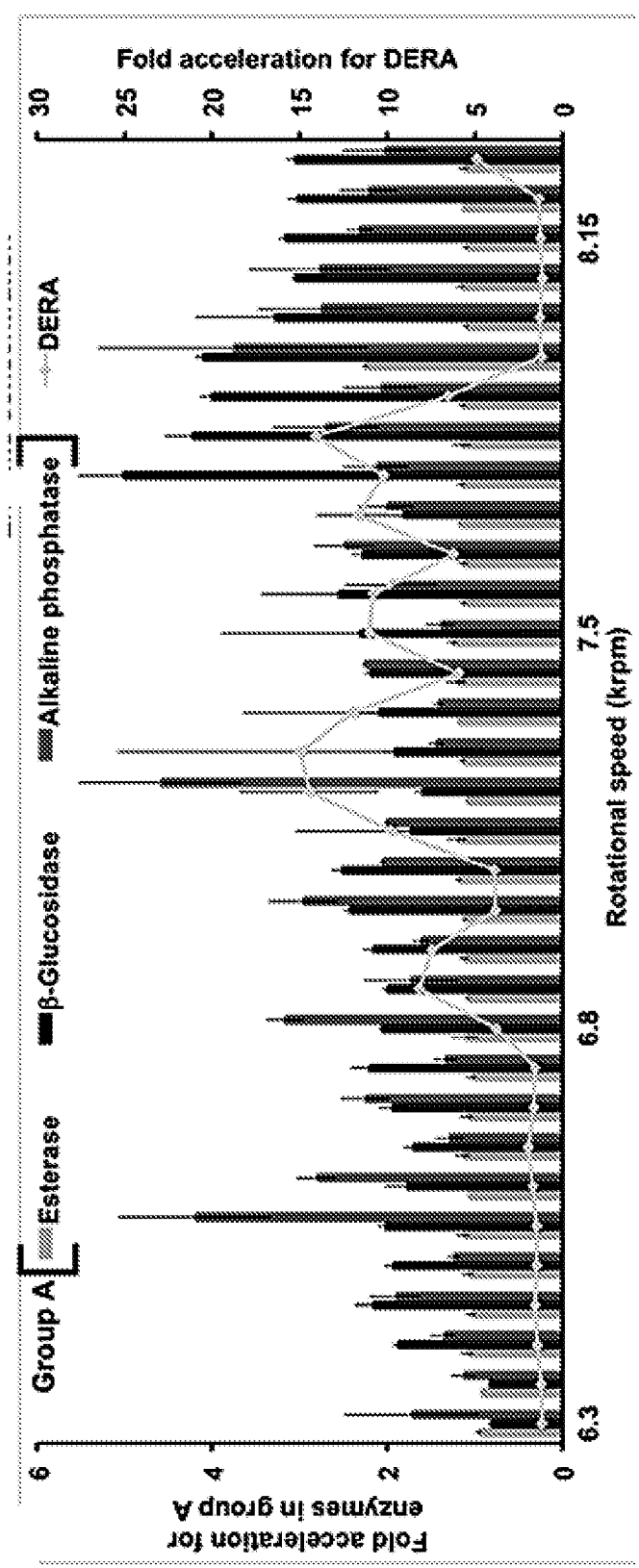
Figure 20A:
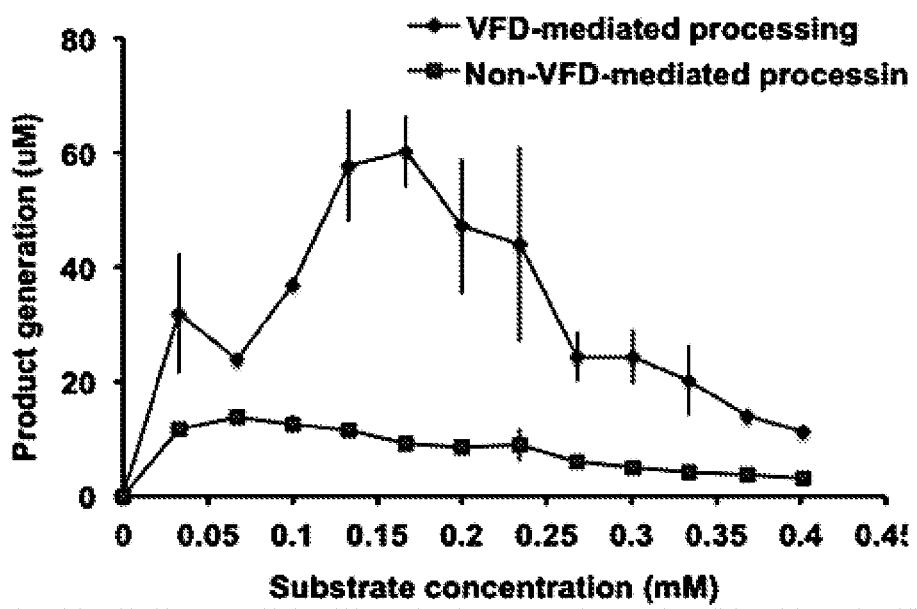
FIGS. 20A-20D. Rapid scanning of reaction space by simultaneously altering the concentrations of substrates and their respective enzymes. In this representation, the amount of product generated is plotted vs. the concentration of substrate in the solution.
Figure 20B:
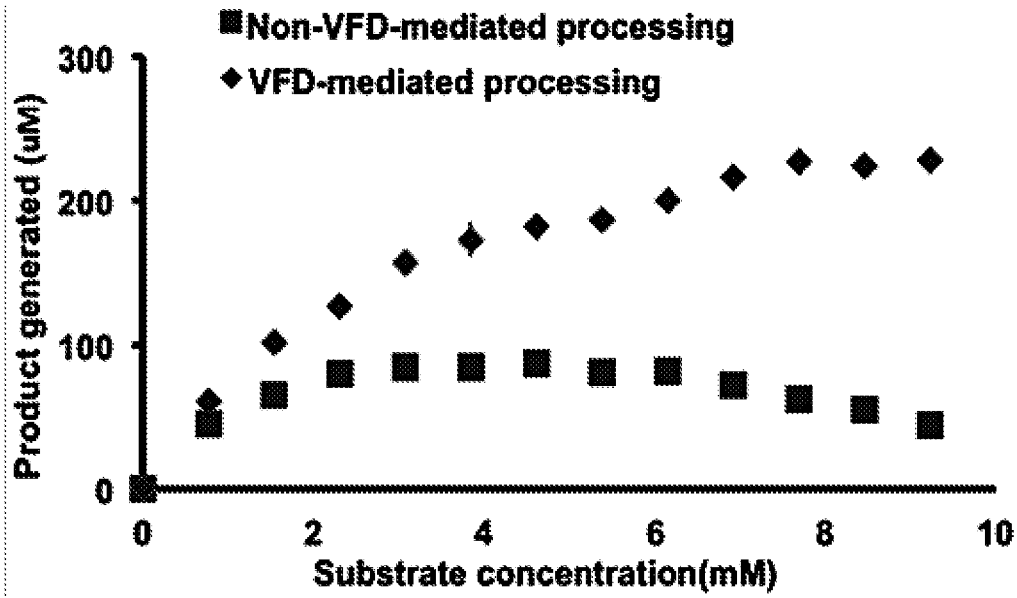
Figure 20C:
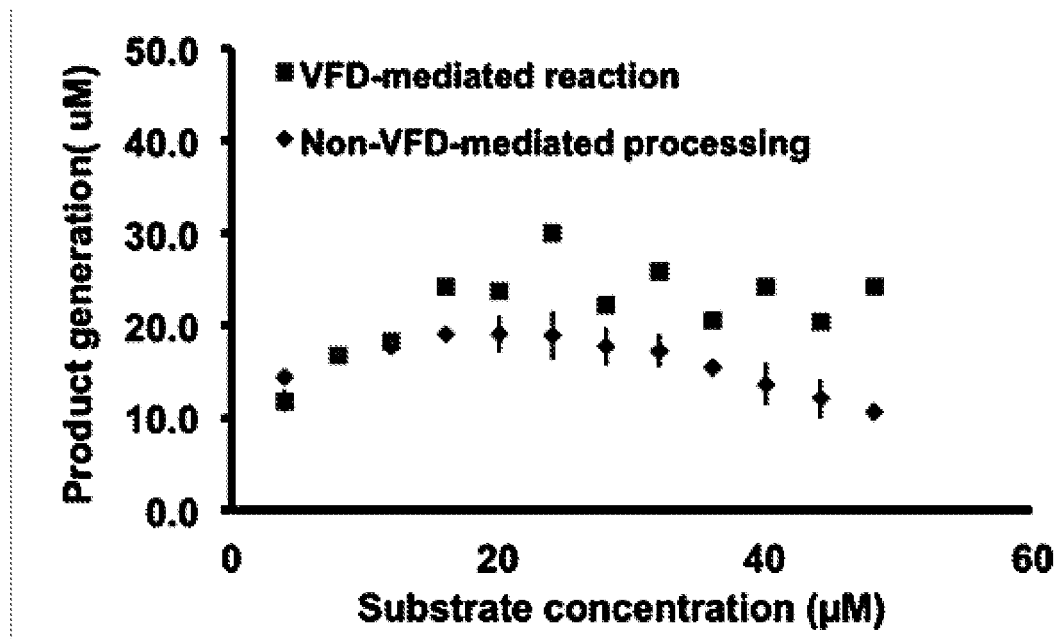
Figure 20D:
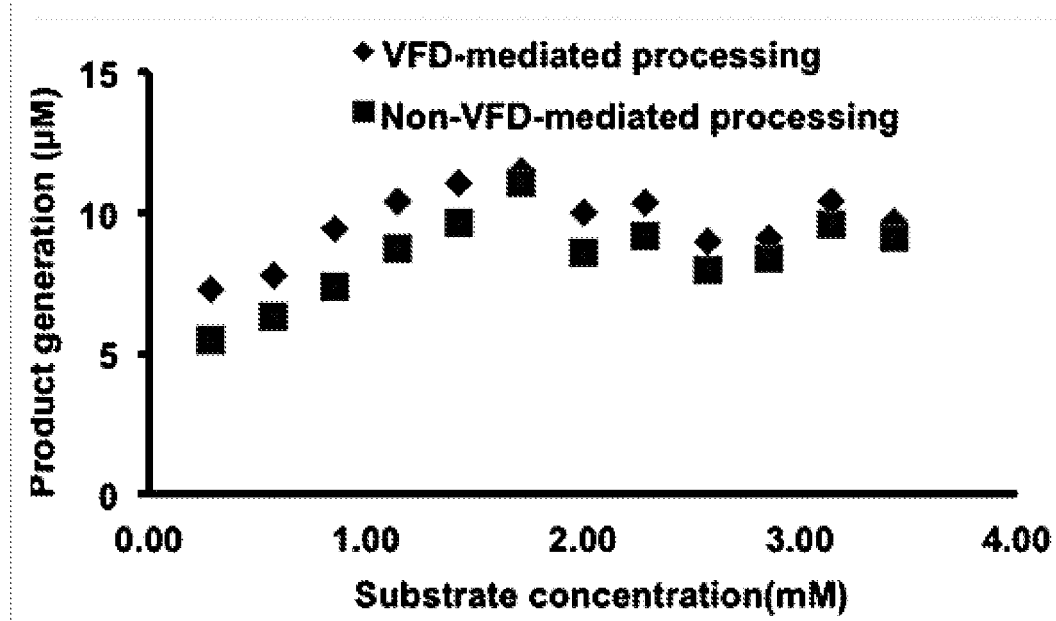
Figure 21A:
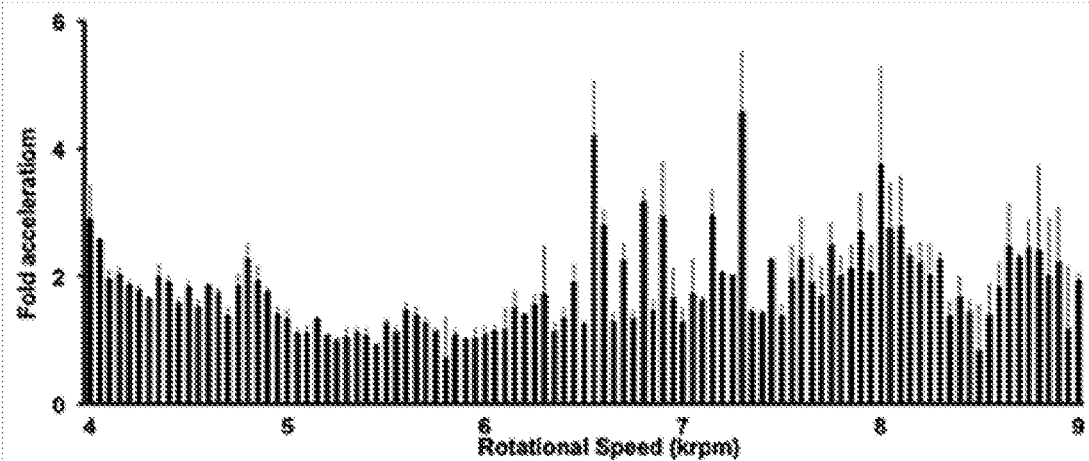
FIGS. 21A-21D. Variation in the rotational speed of the sample tube for the enzymes alkaline phosphatase (FIG. 21A), β-glucosidase (FIG. 21B), DERA (FIG. 21C), and esterase (FIG. 21D). β-glucosidase rotational speed scan was conducted at ±250 rpm around the optimal rotational speeds found for alkaline phosphatase in order to rapidly find rotational speeds that mediated VFD-based enzyme acceleration. The rotational speed dependency for VFD-mediated enzyme acceleration is fine and intricate. Though the above rotational speed landscapes are done in 50-rpm increments, the rotational speed dependency of an enzyme is sensitive to ±5 rpm, as detailed in FIG. 10. These broad rotational speed scans are performed to allow a rotational speed to be elucidated that can then be further enhanced. Error is indicated as standard deviation around the mean (n=3). The concentration of enzyme and substrate used in the above experiment are as follows: Alkaline phosphatase (6.77 nM) and its substrate p-nitrophenol phosphate (0.167 mM), β-glucosidase (19.3 nM) and its substrate 4-nitrophenyl β-D-glucopyranoside (7.5 mM), esterase (0.12 nM) and its substrate p-nitrophenol acetate (44 µM) and DERA (7.69 µM) and its fluorogenic substrate (0.52 mM). A total volume of 1.30 mL was used in these experiments.
Figure 21B:
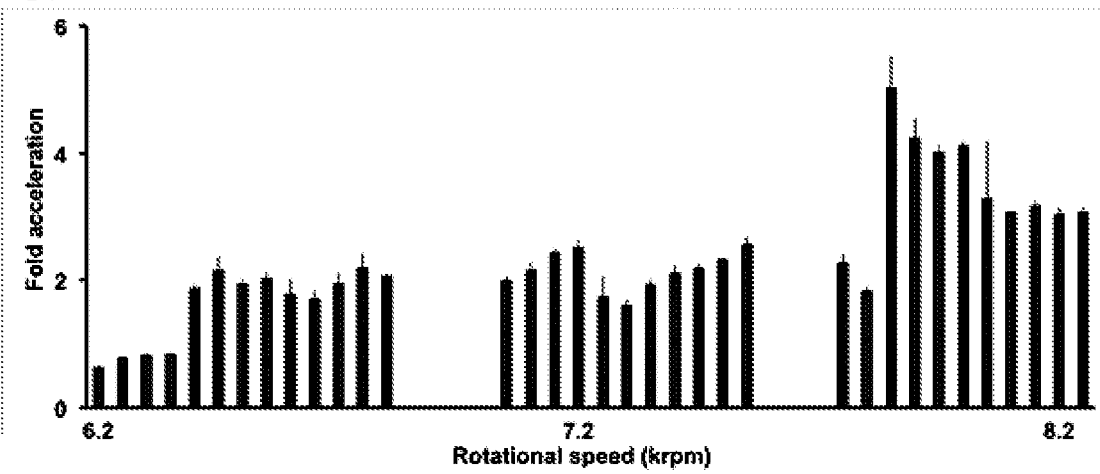
Figure 21C:
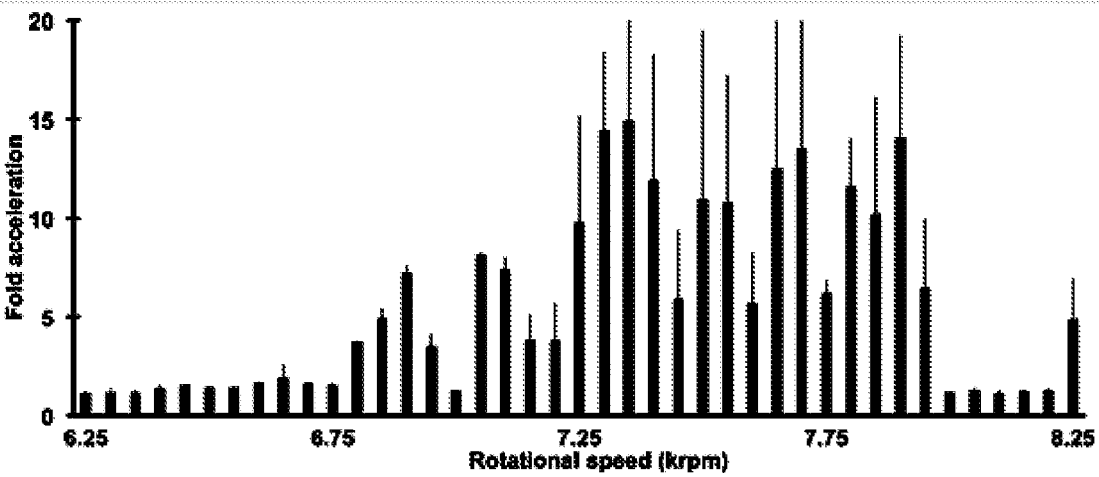
Figure 21D:
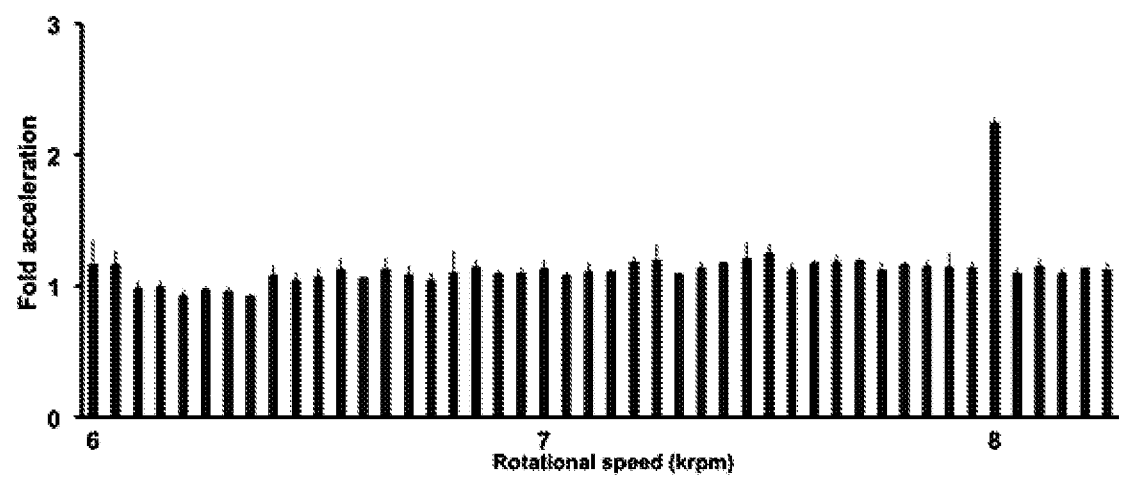

Next, substrate and enzyme concentrations were simultaneously varied for the rapid scanning of reaction space to find effective reaction conditions (FIG. 9B). This optimization unexpectedly revealed that VFD-mediated enzyme reactions are less susceptible to substrate inhibition than conventional conditions. For example, β-glucosidase without VFD processing encounters substrate inhibition at around 3.1 mM 4-nitrophenyl β-D-glucopyranoside; VFD processing delays the onset of substrate inhibition until almost a three-fold higher concentration (FIG. 20B). With the exception of DERA, the three enzymes tolerated higher concentrations of substrate without losing VFD-mediated acceleration. This decrease in substrate inhibition suggests the VFD increases enzymatic $k_{cat}$, as further demonstrated below. DERA catalyzed the retro-aldol reaction of a pro-fluorophore at 144 μmol h$^{-1}$L$^{-1}$ when processed in the VFD (7.90 krpm rotational speed), compared to 10.7 mol h$^{-1}$L$^{-1}$ under non-VFD conditions. DERA has previously been employed to synthesize high-value, complex, polyoxygenated compounds [7b]. The VFD-mediated DERA reaction achieved an average 15-fold enhancement. Conventional approaches to improving DERA have applied extensive screening [7b] and multiple rounds of error-prone PCR. For example, screening 20,000 colonies yielded a 10-fold increase in DERA activity [14]. Comparing the efforts required to achieve >10-fold acceleration by VFD in several days with conventional protein engineering, highlights the power of the approach reported here.

Figure 9D:
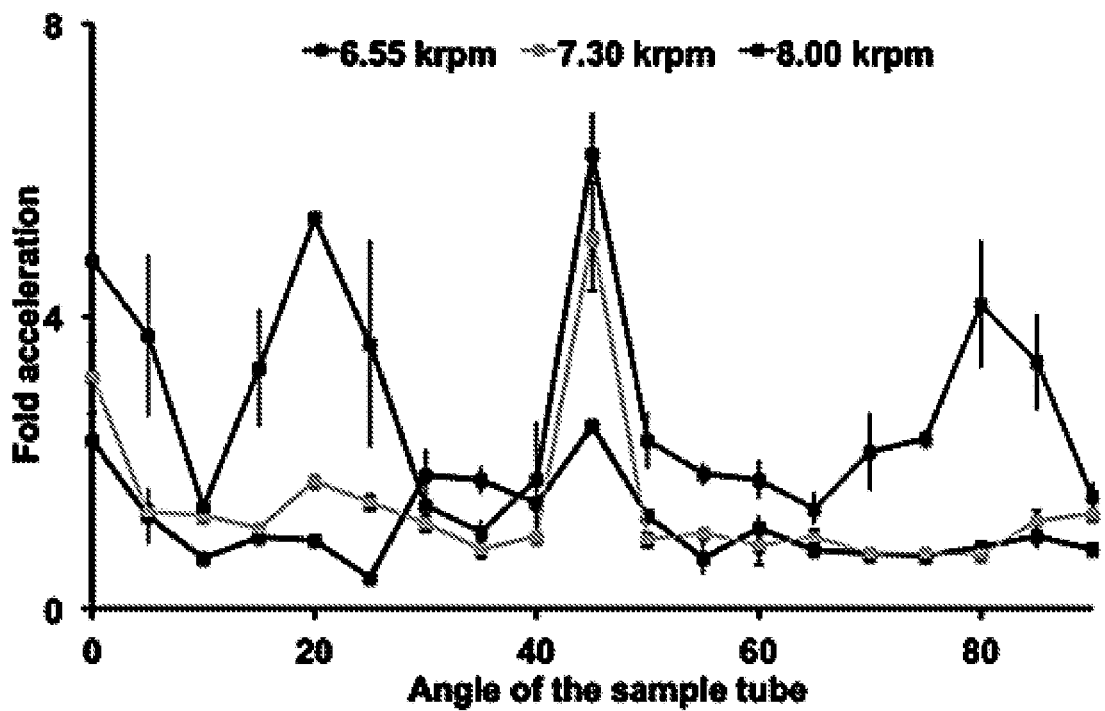
Figure 9E:
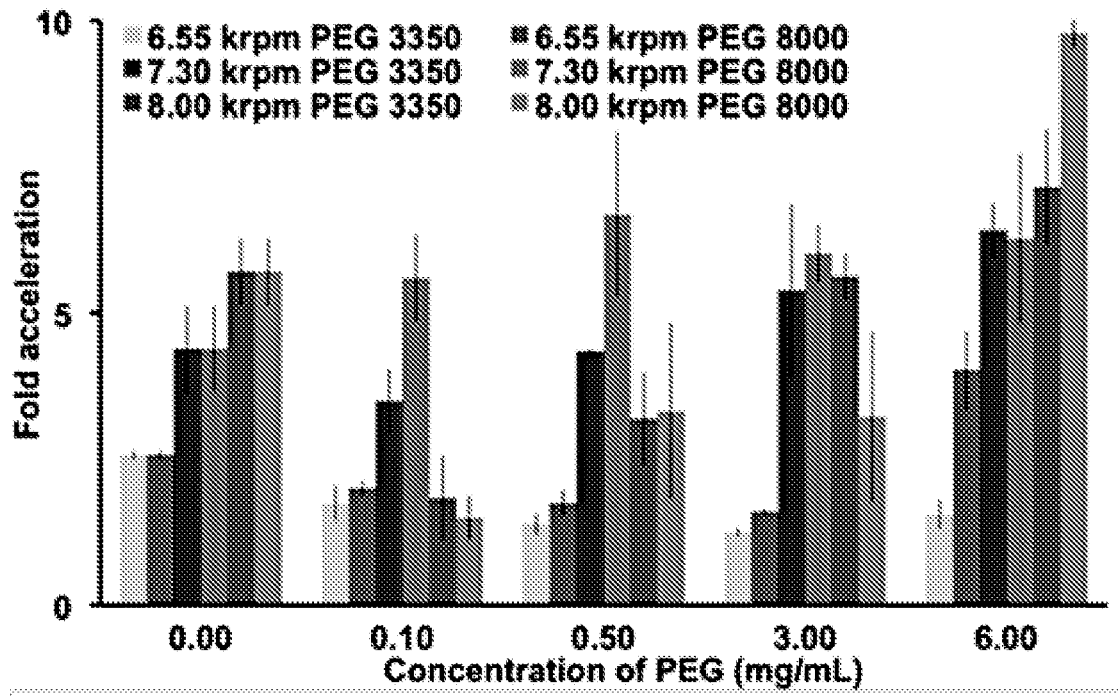

Enzyme acceleration by the VFD is sensitive to the tilt angle of the sample tube and the viscosity of the solution (FIGS. 9D-9E). A tilt angle of 45° provided the strongest response, as has been previously observed in other VFD experiments [8b]. Second, concentrations of viscous, steric crowding reagents that decrease or terminate enzymatic catalysis in the non VFD-mediated control conditions were overcome in the VFD. Biocatalytic acceleration was achieved, for example, in high concentrations of PEG 8000 (6.00 mg/ml, 0.75 M), a condition that suppresses enzymatic catalysis in non-VFD conditions. Without wishing to be bound by theory, it is believed that through rapid micro mixing or other associated phenomena, VFD-processed alkaline phosphatase tolerated high concentration of PEG 8000, resulting in ≈9-fold enhancement. The relative indifference to high concentrations of substrate and steric crowding suggests the VFD could be applied to processes requiring complex mixtures and minimal amounts of solvent.

Figure 10:
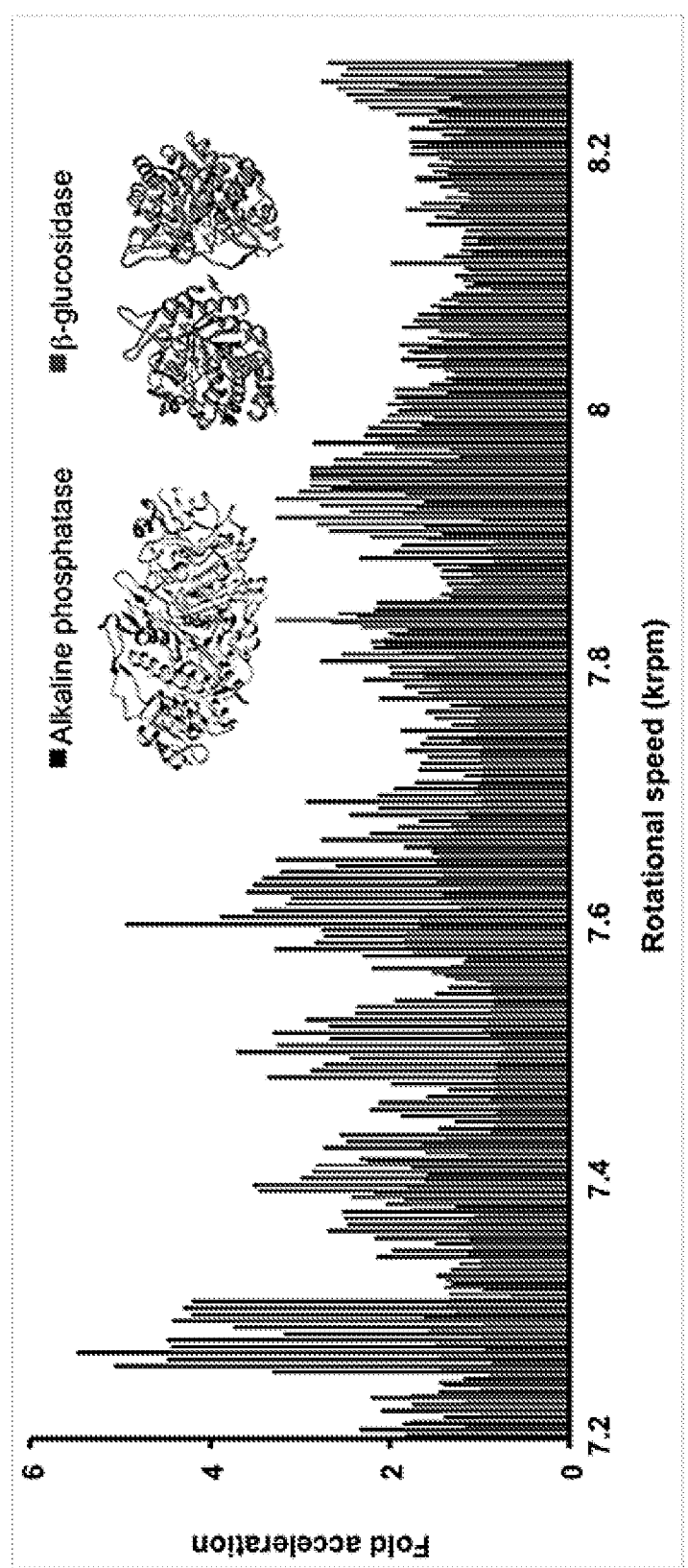
FIG. 10. The rotational landscape of β-glucosidase and alkaline phosphatase. Though the two enzymes have similar levels of response at some rotational speeds, distinctly different rotational landscapes are revealed. The results demonstrate the enzyme specificity of VFD-mediated acceleration. Each data point represents the mean (n=2) for a 10 min reaction at the indicated rotational speeds. The alkaline phosphatase enzyme-substrate solution used FAsTAP™ alkaline phosphatase (6.77 nM) and p-nitrophenol phosphate solution (0.17 mM) whilst the β-glucosidase enzyme-substrate system used β-glucosidase (19.3 nM) and 4-nitrophenyl β-D-glucopyranoside (7.5 mM).
Figure 29A:
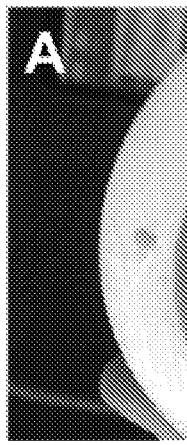
Figure 28B:
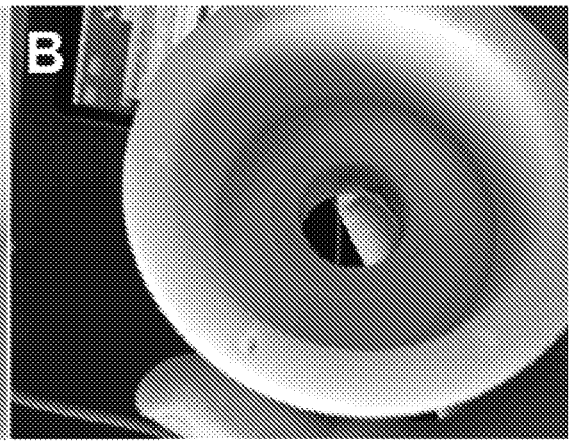

The dependence on rotational speeds was also specific to each enzyme (FIGS. 9C and 11A-11C). Such requirements can reflect differences in enzyme size, structure and dynamics. Esterase for example was highly dependent on a single rotational speed for enhanced activity. When processing esterase under VFD-mediated conditions, the only rotational speed to generate an enhancement was 8.00-krpm; at all other rotational speeds, the enzyme behaved similarly to non-VFD-mediated conditions. To map out the fine details of such resonances, a high-resolution scan of rotational speeds examined the acceleration of alkaline phosphatase and β-glucosidase (FIG. 10). The rotational landscapes are intricate with little overlap of optimal rotational speeds. Device-specific variations in rotational landscapes were also observed, believed to be due in part to differences between device bearings and components (e.g., the TEFLON™ collar, which wears due to friction from the sample tube); thus, FIG. 10 depicts two enzymes processed by a single VFD. In addressing this issue of wear, and avoiding variable vibrations, we turned to 3D printing. Fabricating the collar out of high-density ABS plastic allowed an interchangeable sleeve to be incorporated. Changing the insert upon wear insures reproducibility of the reported experiments (FIG. 29).

Michaelis-Menten-based experiments were performed with β-glucosidase, and the kinetic constants for both VFD-processed and non-VFD conditions were derived (Table 2 following). The $k_{cat}$ in the VFD-mediated reaction was around 2.5-fold faster than the non-VFD reaction (FIG. 10). A lower Michaelis-Menten constant ($K_m$) was also obtained for the VFD-processed enzyme-substrate solution; 2.50 mM compared to 3.76 mM for a non-VFD mediated reaction. The decrease in $K_m$ demonstrates the higher affinity for the β-glucosidase-substrate interaction under VFD-mediated conditions. The increase of $k_{cat}$ and the decrease in $K_m$ leads to an increase in enzyme efficiency ($k_{cat}/K_m$) of around 3.5-fold for the VFD-mediated reaction.

TABLE 2

Michaelis-Menten parameters for the VFD vs. non-VFD mediated processing of β-glucosidase.*

| Parameter | Non VFD-mediated reaction | VFD-mediated rate acceleration |
|---|---|---|
| $V_{max}$ (nM s$^{-1}$) | 128 ± 5.71 | 309 ± 52.4 |
| $K_M$ (mM) | 3.76 ± 0.15 | 2.50 ± 0.44 |
| $k_{cat}$ (s$^{-1}$) | 13.4 ± 0.59 | 32.1 ± 5.45 |
| $k_{cat}/K_M$ (mM$^{-1}$s$^{-1}$) | 3.55 ± 0.19 | 13.32 ± 4.03 |

*For this VFD-process, β-glucosidase (9.26 nM), a rotational speed of 7.60 krpm was used, as this provided the most consistent enhancement over sustained time periods. Error indicates the standard deviation around the mean (n = 3). There was no overlapping error at 95% confidence limits. The raw data was fitted to a Michaelis-Menten plot and analyzed using a least squares fitting (LSF) approach (FIGS. 27B-27C, 28B-28C).

Without wishing to be bound by theory, it is believed that enzymes are accelerated in the VFD in part from the instantaneous pressure changes generated by Faraday waves. Three possible mechanisms could harness such pressures. Firstly, transient pressurization of the active site around the substrate could occur. In this situation, a decrease in the active site volume through pressurization [15] could increase the turnover number of the enzyme; such enhancement follows from the Van't Hoff equation [16]. Secondly, pressure-induced protein conformational changes could occur at accelerated rates [17]. As enzymatic catalysis correlates with protein motion, faster protein motions could accelerate catalysis by contributing to the rate-determining process [17]. Thirdly, enzymatic catalysis requires a fine balance between protein stability and conformational flexibility [18]. Pressure-driven conformational changes may increase enzyme activity through β and α-relaxations [19]. These small changes can lead to the acquisition of protein conformations more suited for catalysis [18].

The rotational landscape can be specific for each enzyme and appears to result from enzyme-specific preferences.

Single-molecule experiments have elucidated the range of speeds and conformations required for enzymatic catalysis, which are specific for each enzyme [20]. The range of acceleration disclosed herein falls within the expected range of enzyme speeds uncovered through such experiments. Thus, the VFD-driven rate acceleration could shift the distribution of enzyme conformational states to favor catalytic events. It is believed that shaped Faraday waves with specific timing can provide further control and enhancement of biocatalysis.

To recapitulate, control reactions with alkaline phosphatase (MW 46 kDa, E.C 3.1.3.1) confirmed that enzymatic acceleration in the VFD arises from the unique attributes of the device. First, identical enzyme-substrate solutions were centrifuged at 14 krpm (17530 g) to mimic the introduction of centrifugal forces exceeding levels expected inside the VFD sample tube; no increase in enzymatic activity resulted from centrifugation (FIG. 12). Second, as a control for simple vortexing without a thin-film, the enzyme-substrate solution (1.3 mL in a 15.0 mL Eppendorf tube) was vigorously mixed by a laboratory vortexer; again, no rate enhancement resulted from this control (FIG. 13). Third, as a control for the VFD transforming the substrate without the enzyme present, the four enzymes were omitted during identical VFD processing conditions that generated a VFD-mediated response; no evidence of substrate conversion to product was observed at the substrate concentrations reported here. The possibility of in situ protein folding and generation of higher surface area particles [1] during processing were also eliminated as follows. The enzyme has the same degree of catalytic competence before and after VFD treatment, eliminating the possibility that the VFD restores correct structure (FIG. 14). Furthermore, DLS analysis shows no decrease in particle size following VFD processing (following). The values displayed in the table following compare the VFD-processed β-glucosidase solution to the non-VFD-processed enzyme solution.

TABLE 3

DLS data

| Sample | PDI | Peak 1 (d · nm) | Peak 2 (d · nm) |
|---|---|---|---|
| Non-VFD processed | 0.491 | 177.2 | 5271 |
| VFD processed | 0.431 | 176.8 | 5295 |

PDI—Polydispersity index; d · nm—mean diameter of particles (nm).

Figure 11A:
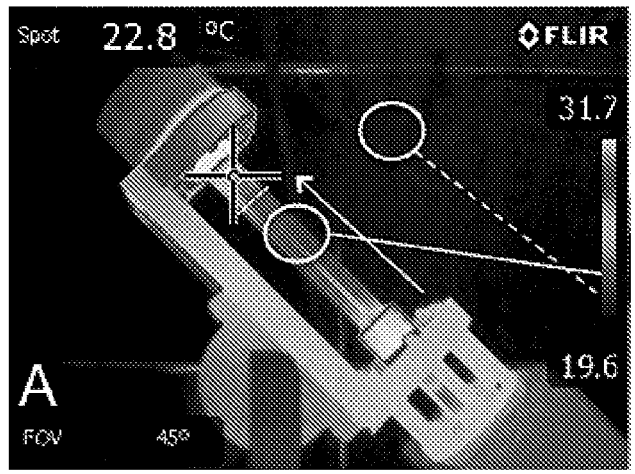
FIGS. 11A-11C. Control experiments and VFD features preventing friction-based temperature increases from impacting enzyme assays.
Figure 11B:
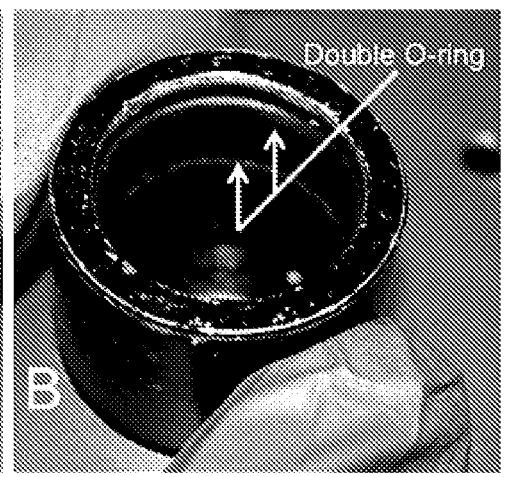
Figure 11C:

Additionally, the reported acceleration in enzymatic catalysis likely does not result from a temperature increase during VFD processing. We apply short processing times with a dual bearing device to limit temperature variation due to friction. Monitoring by thermal imaging IR camera has shown that the temperature increase for such conditions is <2° C. [2]. In the thermal image (FIG. 11A), we demonstrate that after 1 h of processing the sample tube remains at slightly above ambient temperature with any heat generation being localized to the upper bearing (FIG. 11A). Furthermore, the device has been fitted with two O-rings, both on the lower bearing that limits heat transfer from the bearing to the sample tube (FIG. 11B). Additionally, experiments were conducted on a 1.30 mL scale to prevent fluid in the sample tube from reaching same height as the upper bearing, where heat transfer into the fluid could take place (FIG. 11C). To further demonstrate the lack of significant heating by the VFD, the solution temperature was measured directly by a thermometer in 1.30 mL of $H_2O$ processed by the VFD at 8 krpm for 1 h. The temperature of the solution rose slightly from 23.0 to 25.0° C. As an additional consideration, the enzyme DERA can be accelerated on average ~15-fold compared to the non-VFD-processed control; a temperature driven acceleration of 15-fold would require a dramatic change in temperature (tens of degrees). Such a temperature increase has not been observed. Thus, the reported enzyme rate acceleration likely results from the Faraday waves produced through sample tube vibration, not increased temperature.

Centrifuge Control

The enzyme-substrate solution (alkaline phosphatase and p-nitrophenol phosphate) was subjected to centrifugation in a bench top centrifuge at the indicated rotational speeds for 10 min. A direct comparison was then made between a VFD sample and a centrifuged sample (FIG. 12).

Control Reaction in a Convention Vortexer.

The enzyme-substrate solution (1.3 mL) (β-glucosidase and 4-nitrophenyl β-D-glucopyranoside) was added to an Eppendorf tube, and vortexed for 10 min at 25° C. before quenching as described herein. No increase in enzyme rates comparable to the VFD-processed solution was observed (FIG. 13).

VFD-Processed Vs. Non-VFD-Processed Enzyme Solutions for Analysis in a Kinetic Assay.

To ensure that protein folding was not driving enzymatic acceleration, a comparative kinetic study was performed with VFD-processed and non-VFD-processed β-glucosidase and 4-nitrophenyl β-D-glucopyranoside. In this experiment, β-glucosidase (77 nM solution, 2.00 mL) was added to a sample tube and rotated at 7850 rpm for 10 min. The enzyme was collected and 0.500 mL of treated enzyme added to 0.500 mL of 0.01 M 4-nitrophenyl β-D-glucopyranoside. The solution was immediately mixed and 100 µL was added to a 96-well micro plate for kinetic analysis. As a control, non-VFD-treated enzyme was also tested under identical conditions. There was no significant difference in activities between VFD-processed and non-VFD-processed enzymes.

VFD-Processed Enzyme Vs. Non-VFD-Treated Enzyme Dynamic Light Scattering (DLS) Measurements.

To examine particle size after VFD-processing, DLS measurements were performed on VFD- and non-VFD-processed enzyme solutions. β-glucosidase (77 nM solution, 2.00 mL) was added to a sample tube and rotated at 7850 rpm for 10 min. The enzyme was collected and then centrifuged (24154 g) for 20 min. The solution was then passed through a syringe filter (0.22 µm, 30 mm diameter) into a DLS cuvette and the measurements performed. The results indicated that there are imperceptible differences between the samples (Table 3).

Materials and Methods.

Unless otherwise indicated, all commercially available reagents and solvents were used directly from the supplier without further purification. Technical grade solvents and silica gel (60-120 mesh) were used for column chromatography with visualization accomplished with UV light (254 nm) and/or a potassium permanganate solution (40 g $K_2CO_3$, 600 mL of water, 6.0 g $KMnO_4$ and 5.0 mL 2.0 M NaOH). $^1$H NMR and $^{13}$C NMR spectra were recorded at ambient temperature using $CDCl_3$ (7.27 ppm) or $D_6$-DMSO (2.50 ppm), unless otherwise indicated on a Brülker 400 MHz spectrometer. Chemical shift values are expressed as parts per million (ppm) and J-values are in Hertz (Hz). Splitting patterns are indicated as s:singlet, d:doublet, t:triplet, q:quartet, hex:hextet or combination, br.s:broad singlet or m:multiplet. The vortex fluid device (VFD) sample tubes were commercial quality borosilicate glass, with an internal diameter of 17.7 mm, and were cleaned with piranha solution (4:1, sulfuric acid: $H_2O_2$), rinsed with $diH_2O$, dried using acetone, and stored in an oven at 160° C. prior to usage. FTIR spectra were collected using Perkin Elmer at 25° C. Optical rotation was measured using a Perkin Elmer device at RT using a 1.0 dm3 glass cell. All buffered solutions were prepared with double-deionized water ($diH_2O$, >18 MΩ) from a Milli-Q water system (Millipore, Bedford, Mass.).

Composition of Non-VFD Solutions.

In a 2.0 mL Eppendorf tube, enzyme and substrate in the appropriate buffer (below) were mixed (final volume of 1.3 mL). The reaction proceeded for the indicated length of time and then quenched as described. A 100 µL aliquot of the reaction mixture was transferred to a 96-well plate (Corning, UV transparent, pathlength of 0.375 cm) and the absorption was measured at the required wavelength (MicroQuant; Biotek Instruments, Winooski, Vt.).

General VFD-Mediated Enzyme Acceleration.

The outside length of the sample tube was lubricated with Dow Corning high vacuum grease before insertion into the VFD. A solution of enzyme and substrate in buffer (1.30 mL) identical to the comparison described above was added to this tube. The sample tube was then stoppered with a B19 SUBA SEAL™ cap, and the tube rotated about its axis at the specified tilt angle for the indicated length of time Immediately after rotation, the solution was added to the quenching reagent to terminate the reaction. The tube was then rinsed with the buffer and re-used in subsequent experiments. To measure enzyme activity in this VFD-processed sample, 100 µL of the solution was added to a 96-well plate, and the absorption measured at the specified wavelength (below). A ratio of this activity to activity of the solution from the non-VFD treated sample determined the level of VFD-mediated enzyme enhancement. All enzyme measurements were performed in triplicate unless otherwise stated.

Enzymes, Buffers and Assays.

Alkaline Phosphatase.

Buffer.

The enzyme buffer, 1.0 M diethanolamine, was prepared as follows: 140 g of diethanolamine was added to 1.0 L of $H_2O$, then the pH of the solution was adjusted to pH 9.8 at 25° C. with 5 M HCl. This buffer was further diluted to 1 M diethanolamine, and 500 µL of 1 M $MgCl_2$ was added. The resulting buffer was filtered-sterilized through a 0.22 µm filter (Corning), and stored wrapped in aluminum foil at 4° C.

Assay.

FAsTAP™ thermosensitive alkaline phosphatase (1.0 µL, 0.11 mM) was added to 10 mL of the diethanolamine buffer to generate an enzyme stock solution (11.1 nM). This solution was made fresh every two hours and stored on ice. Each sample was prepared by combining 0.800 mL of the enzyme stock solution and 0.500 mL of alkaline phosphatase liquid substrate system (pNPP, Sigma-Aldrich, 0.435 mM); this solution (1.3 mL) was added to either an Eppendorf or VFD sample tube. The reaction was incubated at 25° C. for 10 min unless otherwise indicated. After this time period, 4.0 M NaOH (150 µL) was added to quench the reaction. The sample (100 µL) was then transferred to a 96-well micro plate reader, and the absorbance measured at 402 nm ($\lambda_{max}$). The molar absorption coefficient of p-nitrophenol after the quench described above was 15644 $M^{-1}cm^{-1}$.

β-Glucosidase.

Buffer.

50 mM sodium acetate, pH 5.0 buffer was prepared as follows: 4.37 g sodium acetate (anhydrous) was dissolved in 1.0 L diH2O and ~1.1 mL of glacial acetic acid to generate a buffer of pH 5.0 at 25° C. The buffer was then filtered-sterilized through a 0.22 µm filter and stored at 25° C. Assay: In a 15 mL falcon tube, 5.0 mg of lyophilized β-glucosidase enzyme (Sigma) was re-suspended in 10 mL of 50 mM sodium acetate, pH 5.0 buffer. From this solution, a 100 µL aliquot was transferred to 10 mL of 50 mM sodium acetate, pH 5.0 buffer to create a 77 nM solution. The substrate solution consisted of 0.01 M 4-nitrophenyl β-D-glucopyranoside (31.25 mg) in 10 mL of 50 mM sodium acetate, pH 5.0 buffer. Each sample was prepared by combining 0.325 mL of the enzyme stock solution and 0.975 mL of the substrate stock solution; this solution (1.30 mL total volume) was added to either an Eppendorf or VFD sample tube. The reaction was performed for 10 mM unless otherwise indicated. Then, a solution of 0.70 M glycine, NaOH, pH 10.8 buffer (200 µL) was added to quench the reaction. The sample was then transferred to a 96-well micro plate reader, and the absorbance was measured at 405 nm. The molar absorption coefficient of p-nitrophenol after the quench described above was 9413 $M^{-1}cm^{-1}$.

Esterase.

Buffer.

50 mM phosphate, pH 7.0 buffer was prepared as follows: 1.459 g of monosodium phosphate and 3.867 g of dibasic phosphate were mixed in 500 mL of $diH_2O$. The pH of the resulting solution was adjusted to pH 7.0 at 25° C. with 5.0 M HCl. The buffer was then filtered-sterilized through a 0.22 µm filter and stored at 10° C.

Assay.

In a 15 mL falcon tube, 64 mg of p-nitrophenylacetate was re-suspended in 10 mL of ACS REAGENT SELECT™ grade methanol (Sigma) to generate a stable solution that was stored at 4° C. Then, 3.0 mL of this solution was added to 100 mL of $H_2O$ with rapid mixing before further dilution with 100 mL phosphate buffer (50 nM, pH 7.0) in generating a 0.052 mM stock solution. The enzyme solution for esterase was prepared as follows. To a 15 mL falcon tube, 5.0 mg of esterase was added, and dissolved in 10 mL phosphate buffer to create a working solution of 0.806 mM. This stock solution was further diluted to produce a 0.806 nM working solution. Each reaction used 1.10 mL of substrate solution and 0.20 mL of enzyme solution (1.3 mL total volume). Unless otherwise indicated, reactions were incubated for 20 min. To quench the reaction, 1.0 mL of propan-1-ol was added. 100 µL of the sample was transferred to a 96-well reader microtiter plate, and the absorbance measured at 405 nM. The molar absorption coefficient of p-nitrophenol after the quench described above was 6423 $M^{-1} cm^{-1}$.

DERA.

Enzyme assays and also protein production of py-DERA, referred to as DERA, were adapted from previous publications [S3].

Enzyme Production.

Enzyme Assay Buffer.

100 mM bis-tris propane, pH 8.5 buffer was prepared as follows. 28.23 g bis-tris propane was dissolved into 900 mL NANOpure water. The solution was adjusted to pH 8.5 at 25° C. with ~5 mL of conc. HCl and a final volume of 1 L. The solution was filtered-sterilized through a 0.22 µm filter and stored at 25° C.

Assay.

The substrate solution was generated by re-suspending 30 mg of 7-deoxyribosyl-4-methylumbelliferone in 3.0 mL of DMSO. The volume was adjusted to 15 mL with 100 mM bis-tris propane, pH 8.5 to generate a final 6.80 mM solution in 20% DMSO. The substrate solution was wrapped in aluminum foil and stored at 25° C.

Enzyme Solution.

Figure 15:
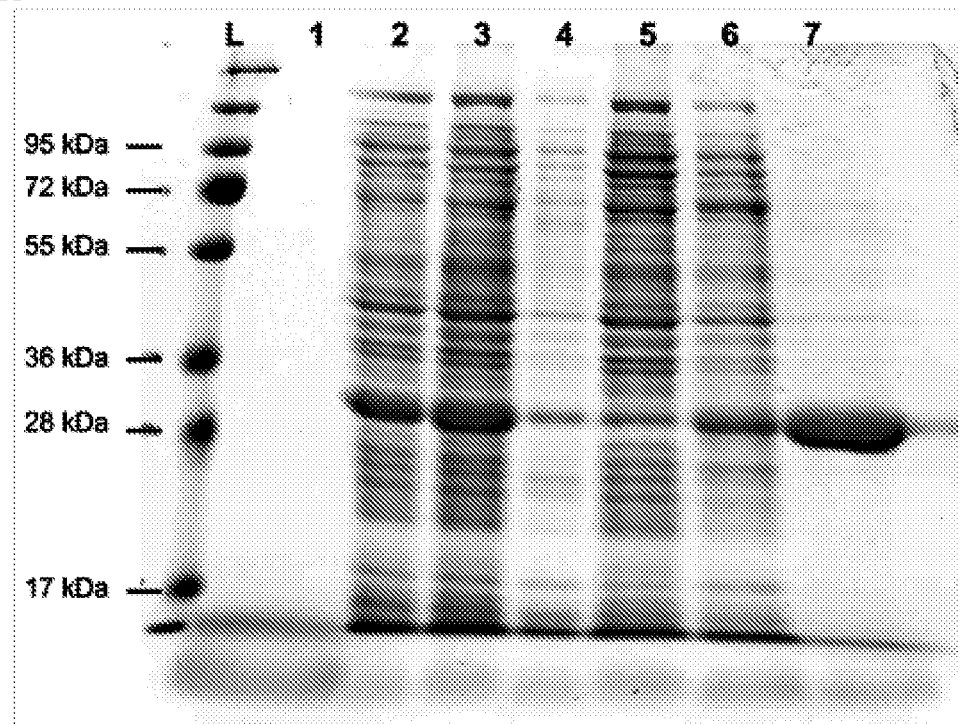
FIG. 15. Step-wise purification of DERA. In this 12% Tris-glycine SDS-PAGE, each lane was loaded with 15 µL of sample. Lane L: PageRuler Plus pre-stained protein ladder (ThermoFisher Scientific, Waltham, Mass.). Lane 1: 6×SDS loading dye used in all lanes. Lane 2: Cell lysate after centrifugation at 15 krpm for 1 h. Lane 3: Flow-through after weak anion exchange. Lane 4: Wash following anion exchange chromatography. Lane 5: Flow-through from the Ni2+ IMAC chromatography purification of the solution visualized in lane 3. Lane 6: Wash of the $Ni^{2+}$ IMAC column with buffer B. Lane 7: Eluted py-DERA from Ni2+ IMAC column with elution buffer (50 mM Hepes pH 7.5, 200 mM NaCl, 100 mM imidazole, 10 mM BME, 5% glycerol). The protein fraction visualized in this lane was dialyzed into the assay buffer before further experiments.
Figure 25:
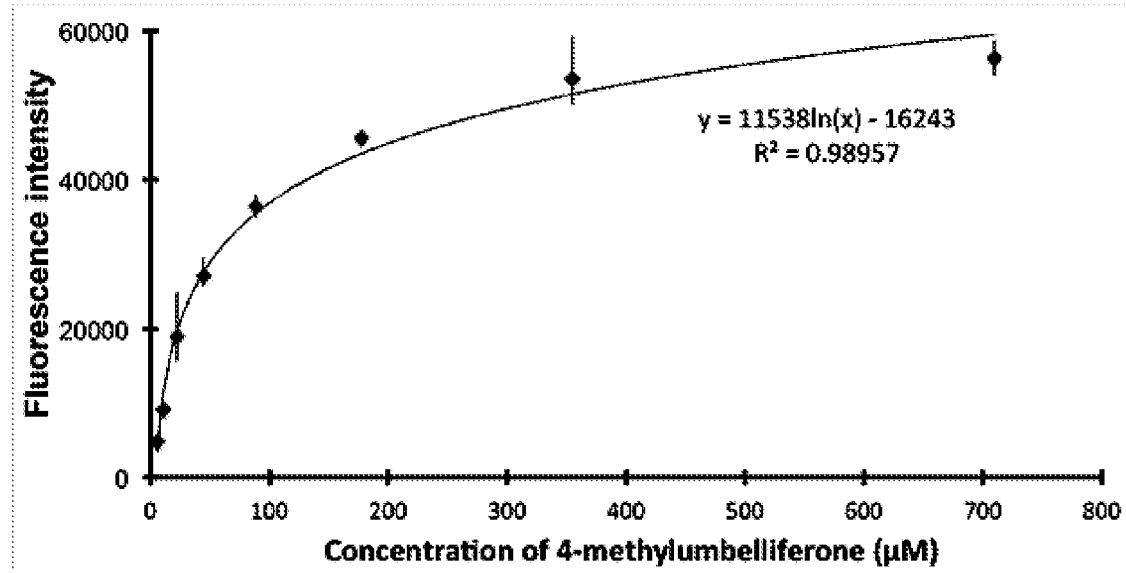
FIG. 25. A calibration curve for calculating the quantity of 4-methylumbelliferone, monitored by its fluorescence. This plot was required to determine the rate of product formation from the DERA-catalyzed decomposition pathway, detailed below, FIG. 26.

After dialyzing the recombinant py-DERA into 100 mM bis-tris propane, pH 8.5, the protein concentration was determined by $A_{280}$ using (e=16305 $M^{-1}cm^{-1}$) and a MW of 30906.5 g/mol. A working stock of 8.33 µM enzyme solution was prepared by either diluting with 100 mM bis-tris propane, pH 8.5 or through microconcentration with a 10 kDa cutoff Amicon Ultra-15 Centrifugal Filter (EMD Millipore, Billerica, Mass.). The purity of the protein was confirmed by 12% SDS-PAGE (Coomassie brilliant blue stain, FIG. 15), and the enzyme were assayed with =95% homogeneity. For each reaction, 100 µL of the fluorogenic substrate was mixed with 1.2 mL of enzyme solution (1.30 mL total volume). The enzyme reaction was incubated in the VFD or on the bench top for 2 h. To quench the reaction, 30 µL chloroacetaldehyde (~50% w/v in $H_2O$) was added. Each sample was measured in triplicate with a total volume of 200 µL in 96-well micro titer plates (96w Costar black/white bottom), and covered with an optically transparent foil (MicroAmp, Applied Biosystems, USA). A fluorescence spectrometer SpectraMax M2 (Molecular Devices, USA) quantified the release of the 4-methylumbelliferone product; the samples were measured with fluorescence excitation at 360 nm and emission at 470 nm at a constant temperature of 28° C. The concentration of 4-methylumbelliferone was determined from a calibration curve given herein (FIG. 25).

Enzymes Sources.

Alkaline phosphatase was purchased from Life Technologies (FASTAP™ thermosensitive alkaline phosphatase, 1 U/µL, 0.11 mM). β-glucosidase from almonds was purchased from Sigma and Aldrich (Lyophilized powder, 2 U/mg). Esterase from porcine liver was purchased from Sigma and Aldrich (lyophilized powder, >15 U/mg protein). These enzymes were used without further purification.

Production of Py-DERA

Since py-DERA is not commercially available, the enzyme was prepared using bacterial overexpression as follows.

The gene 2-deoxyribose-5-phosphate aldolase (DERA) from *Plasmodium* yoelii was purchased from Addgene in DH5 alpha cells (Plasmid #25577). The QIAprep Spin Miniprep Kit (Qiagen) was used as directed by the manufacturer to isolate plasmid DNA from an overnight culture of *E. coli* cells. The following PCR parameters and oligonucleotides (Eurofins MWG Operon) were used to amplify the py-DERA gene. IPRooF™ DNA Polymerase (BioRad) was used for all PCR amplification steps as directed in the manufacturer's instructions. Ten ng of plasmid #25577 was used as the template for 1 cycle at 95° C. for 1 min, 30 cycles at 95° C. for 1 min, 60° C. for 1 min, and 72° C. for 1 min, and 1 cycle at 72° C. for 5 min

```
Lig_DERA_Fwd:
                                       (SEQ ID NO: 1)
5'-GAC GAC GAC AAG ATG GCT AAT TAT ACA GAA AAA

TTC GCA GCG TGG TCA G-3';

Lig_DERA_Rev:
                                       (SEQ ID NO: 2)
5'-GAG GAG AAG CCC GGT TCA TCA CAA TGG ACA TTG

AGA AAT AAC TTT TCT CAA TTT TAT CAC TAA TGA

TGA TGA-3'.
```

DNA excised from agarose gels was purified using the QIAquick Gel Extraction Kit (QIAGEN). The purified PCR product was then used with the pET46 Ek/LIC Vector Kit (EMD Millipore Novagen, Billerica, Mass., USA) to generate the py-DERA recombinant protein expression vector. *E. coli* TOP10 cells (Invitrogen) were used to isolate the plasmid prior to transformation into other heterologous hosts. The DNA was sequencing by standard methods.

Expression and Purification of Py-DERA.

The pET46-pyDERA construct was transformed into *E. coli* ROSETTA™ (DE3) cells (Novagen). The transformed cells were transferred to an LB agar plate supplemented with 50 µg/mL kanamycin antibiotic, and incubated at 28° C. for 14-16 h. A seed culture was prepared by inoculating a single colony from the transformation plate in 50 mL of 2YT medium with 50 µg/mL kanamycin antibiotic and shaking the culture at 225 rpm for 14-16 h at 28° C. in a 250 mL baffled flask. The expression culture was then prepared by inoculating 10 mL of the seed culture in 1.0 L of TB media (12 g Tryptone, 24.0 g yeast extract, 4.0 mL glycerol, 0.17 M KH2PO4, 0.72 M K2HPO4) with 50 µg/mL kanamycin and shaking the culture at 225 rpm in 28° C. (2.0 L baffled flask). When the optical density of the culture reached $A_{600}$ 0.6, overexpression of py-DERA protein with a C-terminal 6×His-tag was induced through addition of 0.50 mM isopropyl β-D thiogalactopyranoside (IPTG), and the mixture was incubated further for 36 h at 15° C. with shaking at 225 rpm. The cells were harvested and re-suspended in buffer A (50 mM Hepes pH 7.5, 200 mM NaCl, 10 mM imidazole, 10 mM BME, 5% glycerol, 0.5% CHAPS, 250 units benzonase (Sigma), 1.0 mM PMSF, and 1.0 mM benzamidine). The cell lysate was prepared by sonication (DIGITAL SONIFIER® 450, Branson, USA; std. horn, T<8° C., 5×10 s pulses, 70% amplitude), followed by centrifugation at 33,634 g for 60 mM to remove cell debris. The supernatant was applied on to $Ni_{2+}$ NTA column pre-equilibrated with equilibration buffer (50 mM Hepes pH 7.5, 200 mM NaCl, 10 mM imidazole, 10 mM BME, 5% glycerol). The column was washed with buffer B (50 mM Hepes pH 7.5, 200 mM NaCl, 30 mM imidazole, 10 mM BME, 5% glycerol), and purified py-DERA protein was eluted using elution buffer (50 mM Hepes pH 7.5, 200 mM NaCl, 100 mM imidazole, 10 mM BME, 5% glycerol). Fractions containing purified protein identified by SDS PAGE were pooled and concentrated using microconcentration with a 10 kDa cutoff Amicon Ultra-15 Centrifugal Filter (EMD Millipore, Billerica, Mass.). The purity of the protein was confirmed using 12% SDS-PAGE (Coomassie brilliant blue stain); purification to ≥95% homogeneity was required before subsequent assays. For py-DERA assays the purified recombinant protein was dialyzed in 100 mM Bis-tris propane, pH 8.5. The protein concentrations were determined by $A_{280}$ using 16305 $M^{-1}cm^{-1}$ as the estimated molar extinction co-efficient and 30906.5 g/mol as the MW of the protein.

Assessment of Enzyme Purity.

Figure 16:
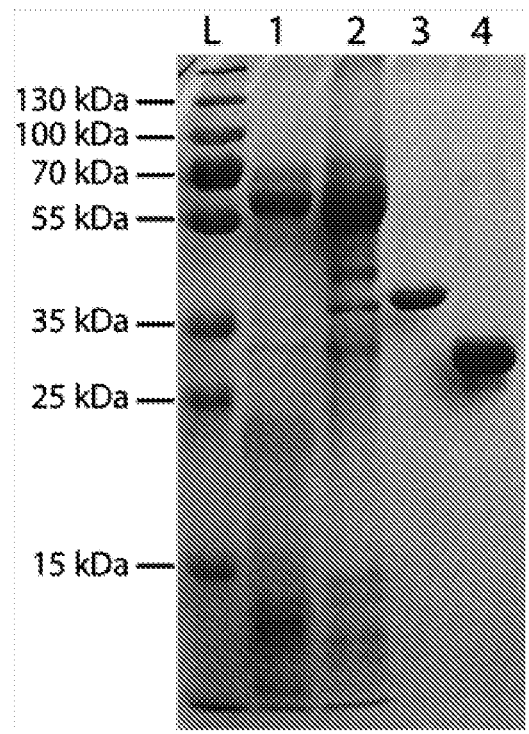
FIG. 16. An SDS-PAGE of the enzymes used in this study. In this 12% Tris-glycine SDS-PAGE, each lane was loaded with 5 µL of the indicated enzymes in 6×SDS loading dye. Lane L: PageRuler Plus pre-stained protein ladder. Lane 1: Lyophilized β-glucosidase (65 KDa) was re-suspended in phosphate buffered saline (PBS) to generate a 0.154 mM solution. Lane 2: Lyophilized esterase (62 KDa) was re-suspended in PBS to generate a 0.161 mM solution (w/v). Lane 3: Alkaline phosphatase (36 KDa) was used as purchased from the supplier. Lane 4: DERA (30 KDa) was re-suspended in its buffer (as described herein) to a final concentration 0.194 mM.

SDS-PAGE analyses of the enzymes disclosed herein are depicted in FIG. 16.

Figure 17A:
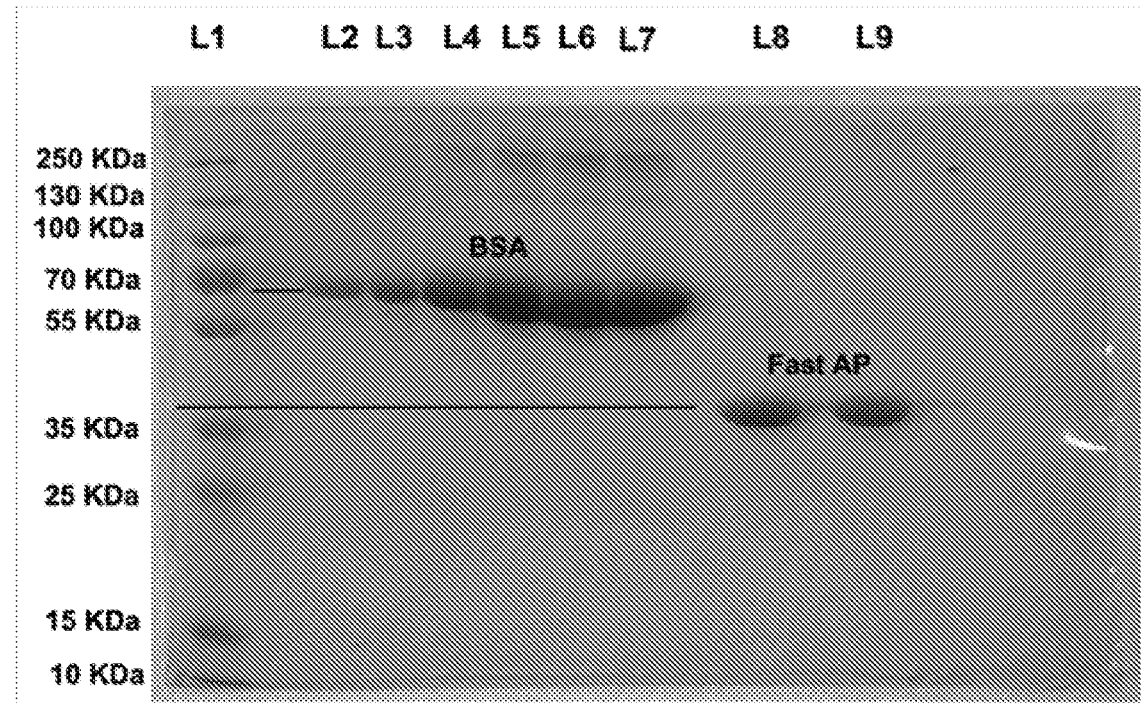
FIGS. 17A-17B.
Figure 17B:
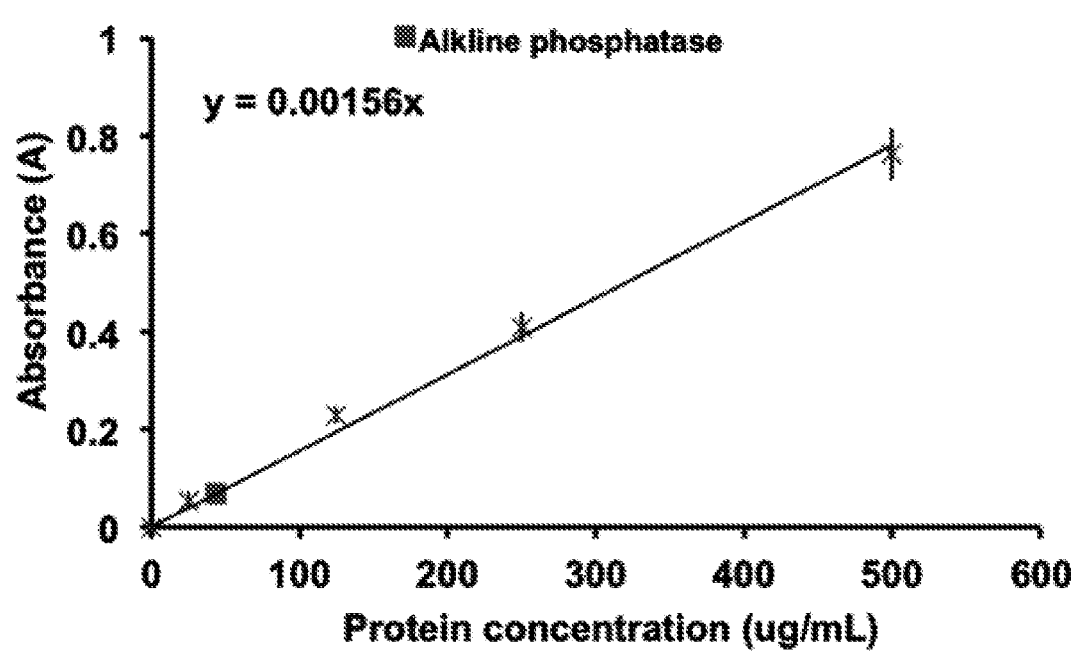
Figure 18A:
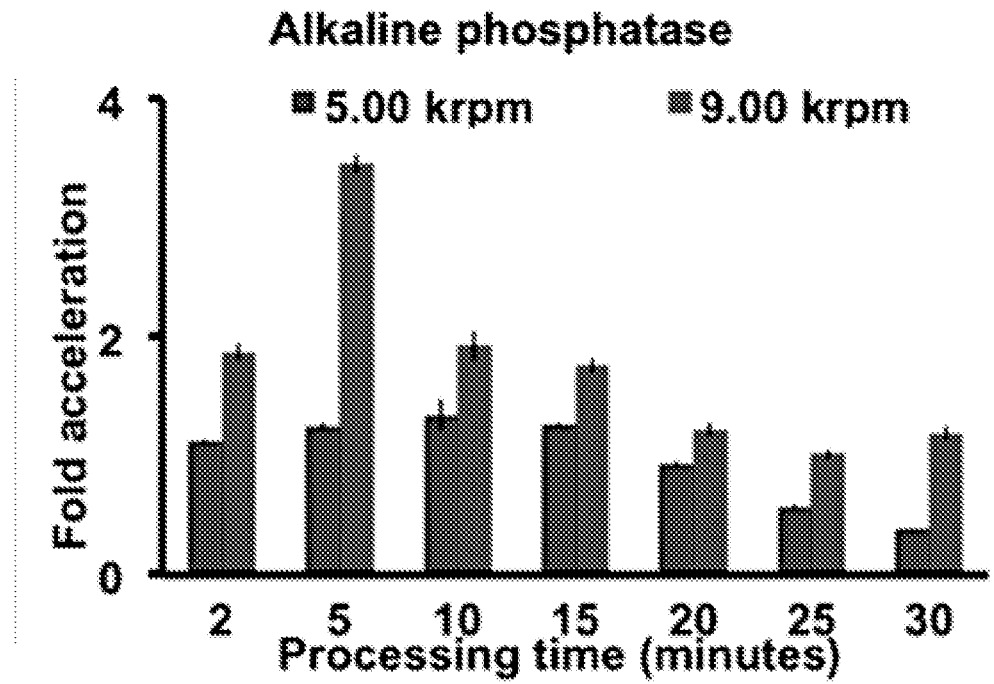
FIGS. 18A-18D. Variation in VFD-mediated reaction times at various rotational speeds for the four enzymes.
Figure 18B:
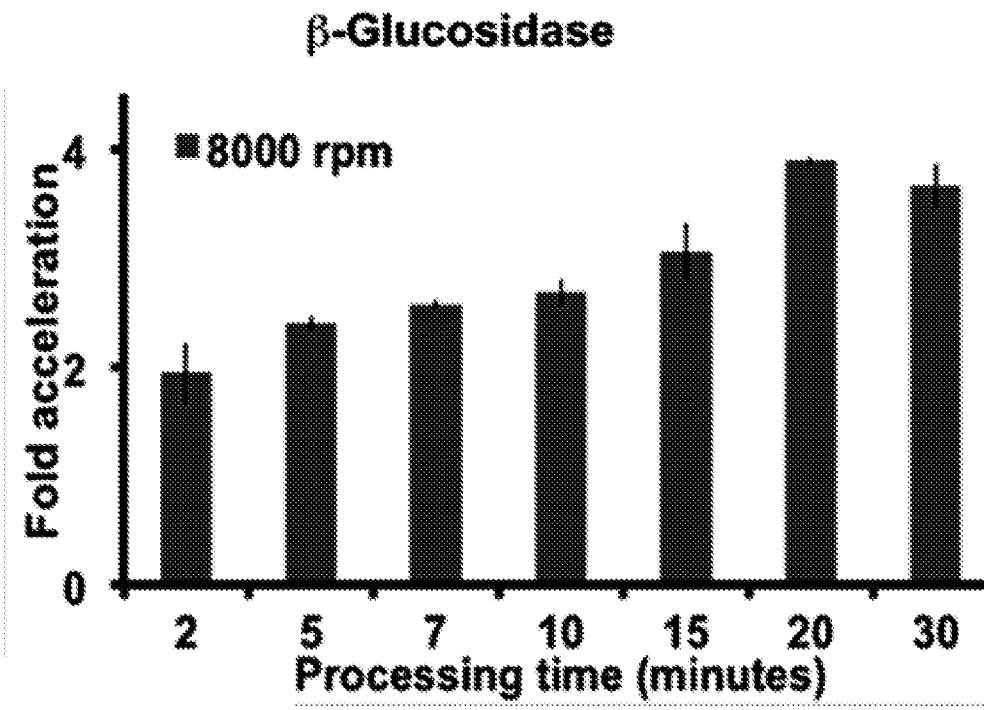
Figure 18C:
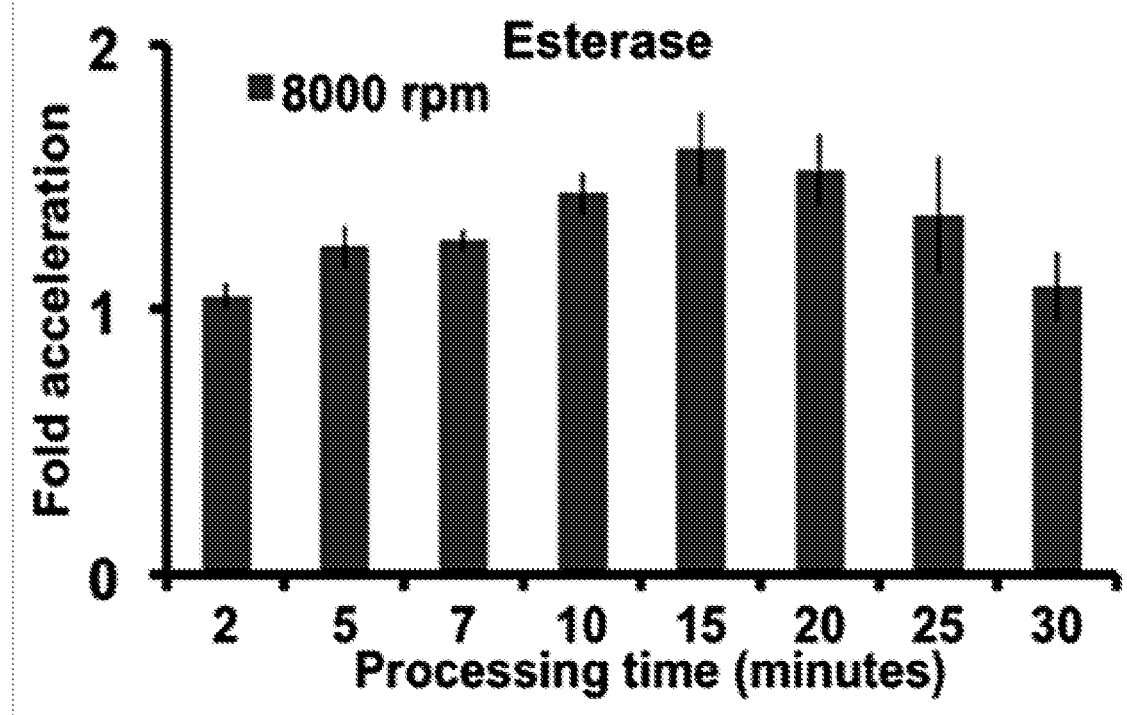
Figure 18D:
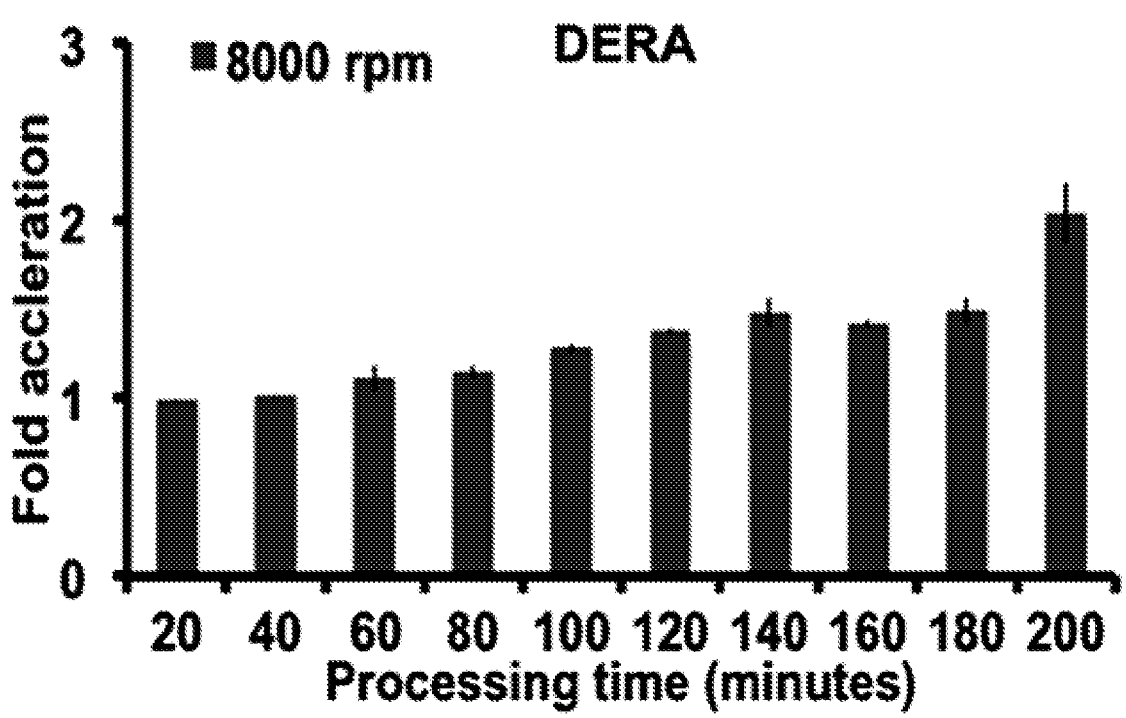

Calculation of alkaline phosphatase concentration and MW. Because it is a proprietary enzyme solution, the use of FAsTAP™ alkaline phosphatase required estimation of MW by SDS-Page chromatography (FIG. 17A) and concentration by BSA assay (FIG. 17B).

Synthesis of the Fluorophorogenic Substrate for the DERA Assay.

The synthesis of the DERA assay substrate (compound 3) was adapted from the literature [S4]. The scheme follows.

Scheme 1. Synthesis of the fluorophorogenic substrate for the DERA assay

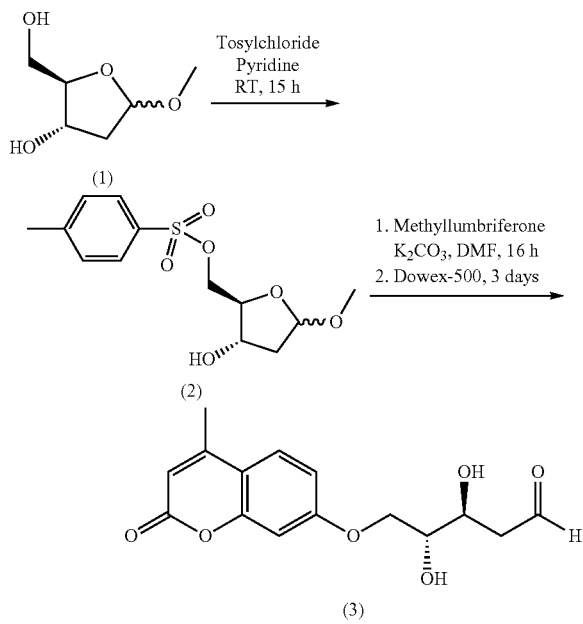

Part 1.

Toluenesulfonyl chloride (6.44 g, 33.77 mmol) was added in small portions over the course of one hour to a stirring solution of 1-O-methyl-2-deoxy-D-ribose (5.00 g, 33.77 mmol) in anhydrous pyridine (100 mL). This mixture was stirred vigorously for 15 h. Then, the solvent was removed under reduced pressure to afford a dark gum. The residue was redissolved in EtOAc (150 mL), washed with brine (1.0 M, 50 mL), saturated NaHCO$_3$ (1.0 M, 50 mL), water (50 mL) and then brine again (50 mL). The organic layer was dried over anhydrous Na$_2$SO$_4$, filtered and the solvent removed under reduced pressure to yield a yellow gum. The intermediate product was confirmed by TLC (pure EtOAc, Rf—0.75), and purified by column chromatography (neat EtOAc) to yield crude methyl 5-toluenesulfonyl-2-deoxyribose as an off-white gum, 3.32 g, 33% yield. Compound 2 had $^1$H and $^{13}$C NMR spectra identical to a previous report. [S5]

Part 2:

Crude methyl 5-toluenesulfonyl-2-deoxyriboside (2) (2.00 g, 6.62 mmol) was dissolved in anhydrous DMF (20 mL). K$_2$CO$_3$ (1.87 g, 13.24 mmol) and methylumbelliferone (1.47 g, 8.27 mmol) were added to this solution, which was then stirred at 75° C. for 15 h. Next, water (75 mL) was added, and the product extracted with EtOAc (2×50 mL). The organic layer was washed with NaOH (0.1 M, 50 mL), water (20 mL) and then dried using anhydrous MgSO$_4$. The product solution was concentrated in vacuo, and suspended in acetonitrile (5 mL) and water (15 mL). Dowex-WXD-100 (500 mg) ion exchange resin was added, and the solution stirred for 2 h. Next, the solution was briefly exposed to reduced pressure to remove any generated methanol. The remaining solution was the stirred for two days, filtered and then concentrated under vacuum. The product was purified via column chromatography with an EtOAc:acetone gradient running from 100:0 to 80:20. TLC confirmed the product purity (EtOAc, Rf—0.46). The product (3) was isolated as a thick colorless oil, which formed a white foam under vacuum, 440 mg, 24% yield. $^1$H NMR (400 MHz, DMSO-d6): δ 7.70-7.67 (m, 1H, CH-1,4-enone), 7.01-6.95 (m, 2H, CH-Aryl), 6.29 (d, J=4.00 Hz, 0.30H, CHa), 6.21 (s, 0.82H, CH), 6.17 (d, J=4.00 Hz, 0.51H, CHß), 5.43-5.39 (0.42H, CHa), 5.35-5.31 (0.46H, CHß), 5.16 (d, J=4.00 Hz, 0.69H) 4.27-3.92 (m, 4H), 2.89 (s, 0.20 Ha), 2.73 (s, 0.21Hß), 2.40 (s, 3H), 2.37-2.33 (m, 1H), 2.00-1.61 (br.m, 2H); 13 C NMR; (100.0 MHz, DMSO-d6) dc 161.6, 160.2, 154.7, 153.4 (CH-1,4-enone), 126.5 113.2, 112.4, 111.2, 101.3, 98.0, 97.0 (CH aryl), 82.9, 80.9, 70.9, 70.7, 70.5, 69.0, 42.1, 39.7, 38.9, 30.7 and 18.1; FTIR (cm$^{-1}$) 3400, 2928, 1699, 1608, 1557, 1511, 1427, 1389, 1368, 1281, 1266, 1204, 1149, 1069, 1016, 956, 845, 748, 706 and 636; [α]$^{24}$,D=+29 (c=0.0016 g/mL, CH$_3$OH). EIMS calc; 294.1 [M+Na]$^+$, found; 317.1. This compound (3) had $^1$H and $^{13}$C NMR spectra identical to the previous report.[S3].

Reaction Times for VFD-Mediated Acceleration.

Figure 19:
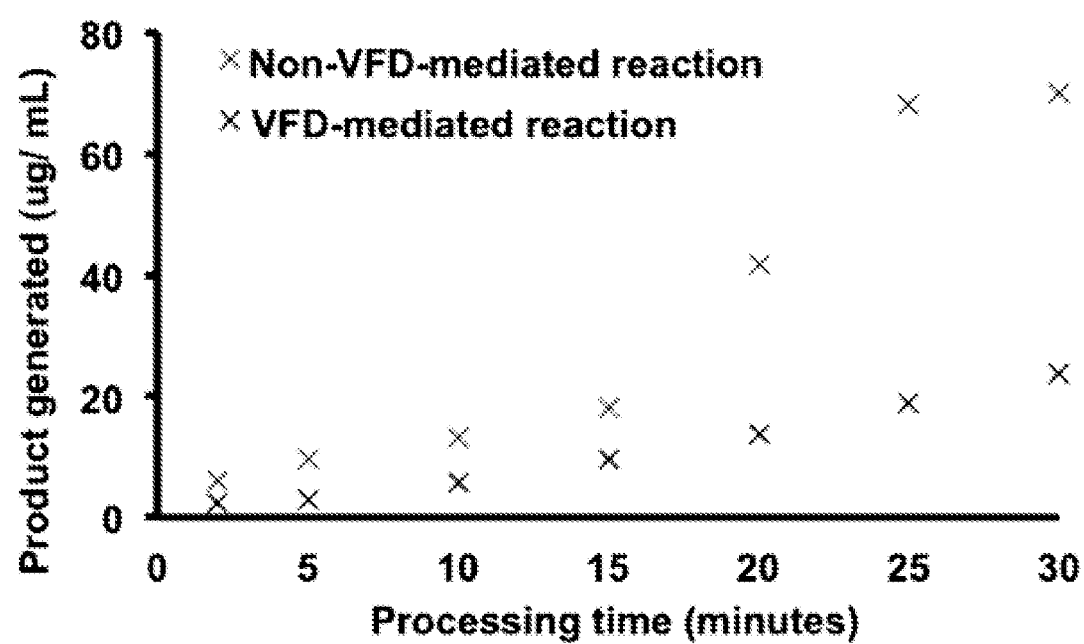
FIG. 19. Production of p-nitrophenol catalyzed by alkaline phosphatase monitored at 405 nm. Error is indicated as standard deviation around the mean (n=3). The concentrations of alkaline. X-axis: processing time (time); y-axis: product generated (µg/mL). Legend: Non-VFD-mediated reaction (generally upper crosses); VFD-mediated reaction (generally lower crosses).

Reaction times, also referred to herein as processing times, for alkaline phosphatase, β-glucosidase, esterase and DERA, are depicted in FIGS. 18A-18D. A comparison of Non-VFD-mediated and VFD-mediate reaction times are depicted in FIG. 19.

Variation of Substrate Concentration.

Comparisons of VFD-mediated and Non-VFD-mediated product generation for alkaline phosphatase, β-glucosidase, esterase and DERA are depicted in FIG. 20A-20D.

β-Glucosidase.

The 65 kDa, dimeric β-glucosidase was dissolved in the appropriate buffer (above) to 77 nM, and the substrate stock solution had a concentration of 0.010 M. For the data in FIGS. 9B and 20A, the following concentrations were used with a final volume of 1.30 mL. See table following.

TABLE 4A

Enzyme and substrate concentration for β-glucosidase and 4-nitrophenyl β-D-glucopyranoside.

| Enzyme volume (mL) | Enzyme concentration (nM) | Substrate volume (mL) | Substrate concentration (mM) |
|---|---|---|---|
| 1.20 | 71 | 0.10 | 0.8 |
| 1.10 | 65 | 0.20 | 1.5 |
| 1.00 | 59 | 0.30 | 2.3 |
| 0.90 | 53 | 0.40 | 3.1 |
| 0.80 | 47 | 0.50 | 3.8 |
| 0.70 | 41 | 0.60 | 4.6 |
| 0.60 | 35 | 0.70 | 5.4 |
| 0.50 | 29 | 0.80 | 6.2 |
| 0.40 | 23 | 0.90 | 6.9 |
| 0.30 | 17 | 1.00 | 7.7 |
| 0.20 | 11 | 1.10 | 8.5 |
| 0.10 | 0.5 | 1.20 | 9.2 |

Esterase.

This 62 kDa, trimeric esterase was dissolved in the appropriate buffer disclosed above to 0.806 nM, and the substrate stock solution had a concentration of 0.052 mM. For the data in FIGS. 9B and 20C, the following concentrations were used with a final volume of 1.30 mL. See table following.

TABLE 4B

Enzyme and substrate concentration for esterase and p-nitrophenylacetate.

| Enzyme volume (mL) | Enzyme concentration (nM) | Substrate volume (mL) | Substrate concentration (μM) |
|---|---|---|---|
| 1.20 | 0.74 | 0.10 | 4 |
| 1.10 | 0.68 | 0.20 | 8 |

TABLE 4B-continued

Enzyme and substrate concentration for esterase and p-nitrophenylacetate.

| Enzyme volume (mL) | Enzyme concentration (nM) | Substrate volume (mL) | Substrate concentration (μM) |
|---|---|---|---|
| 1.00 | 0.62 | 0.30 | 12 |
| 0.90 | 0.56 | 0.40 | 16 |
| 0.80 | 0.50 | 0.50 | 20 |
| 0.70 | 0.43 | 0.60 | 24 |
| 0.60 | 0.37 | 0.70 | 28 |
| 0.50 | 0.31 | 0.80 | 32 |
| 0.40 | 0.25 | 0.90 | 36 |
| 0.30 | 0.19 | 1.00 | 40 |
| 0.20 | 0.12 | 1.10 | 44 |
| 0.10 | 0.062 | 1.20 | 48 |

DERA.

The 30 kDa, dimeric DERA was dissolved in the appropriate buffer (above) to 8.33 μM and the substrate stock solution had a concentration of 6.80 mM. For the data in FIGS. 9B and 20D, the following concentrations were used with a final volume of 1.30 mL. See table following.

TABLE 4C

Enzyme and substrate concentration for DERA and Substrate 3/4.

| Enzyme volume (mL) | Enzyme concentration (μM) | Substrate volume (mL) | Substrate concentration (mM) |
|---|---|---|---|
| 1.20 | 7.69 | 0.10 | 0.52 |
| 1.10 | 7.05 | 0.20 | 1.05 |
| 1.00 | 6.41 | 0.30 | 1.57 |
| 0.90 | 5.77 | 0.40 | 2.09 |
| 0.80 | 5.13 | 0.50 | 2.62 |
| 0.70 | 4.49 | 0.60 | 3.14 |
| 0.60 | 3.85 | 0.70 | 3.66 |
| 0.50 | 3.21 | 0.80 | 4.18 |
| 0.40 | 2.56 | 0.90 | 4.71 |
| 0.30 | 1.92 | 1.00 | 5.23 |
| 0.20 | 1.28 | 1.10 | 5.78 |
| 0.10 | 0.64 | 1.20 | 6.28 |

Alkaline Phosphatase.

The 36 kDa, dimeric alkaline phosphatase was dissolved in the appropriate buffer (above) to 11 nM, and the substrate stock solution had a concentration of 0.435 mM. For the data in FIGS. 9B and 20A, the following concentrations were used with a final volume of 1.30 mL. See table following.

TABLE 4D

Enzyme and substrate concentrations for alkaline phosphatase and the p-nitrophenyl phosphate liquid substrate system.

| Enzyme volume (mL) | Enzyme concentration (nM) | Substrate volume (mL) | Substrate concentration (mM) |
|---|---|---|---|
| 1.20 | 10.15 | 0.10 | 0.033 |
| 1.10 | 9.31 | 0.20 | 0.067 |
| 1.00 | 8.46 | 0.30 | 0.10 |
| 0.90 | 7.61 | 0.40 | 0.13 |
| 0.80 | 6.77 | 0.50 | 0.17 |
| 0.70 | 5.92 | 0.60 | 0.20 |
| 0.60 | 5.08 | 0.70 | 0.23 |
| 0.50 | 4.23 | 0.80 | 0.27 |
| 0.40 | 3.38 | 0.90 | 0.30 |
| 0.30 | 2.53 | 1.00 | 0.33 |
| 0.20 | 1.69 | 1.10 | 0.37 |
| 0.10 | 0.84 | 1.20 | 0.40 |

The Effect of Rotation Speed on Enhancement.

The effect of rotational speed of the VFD device on the fold acceleration of enzymatic catalysis for alkaline phosphatase, b-glucosidase, DERA, and esterase are depicted in FIGS. 21A-21D, respectively.

Product Inhibition.

Product inhibition during VFD processing was examined by the following reaction conditions for alkaline phosphatase.

Phosphate Inhibition.

Figure 22A:
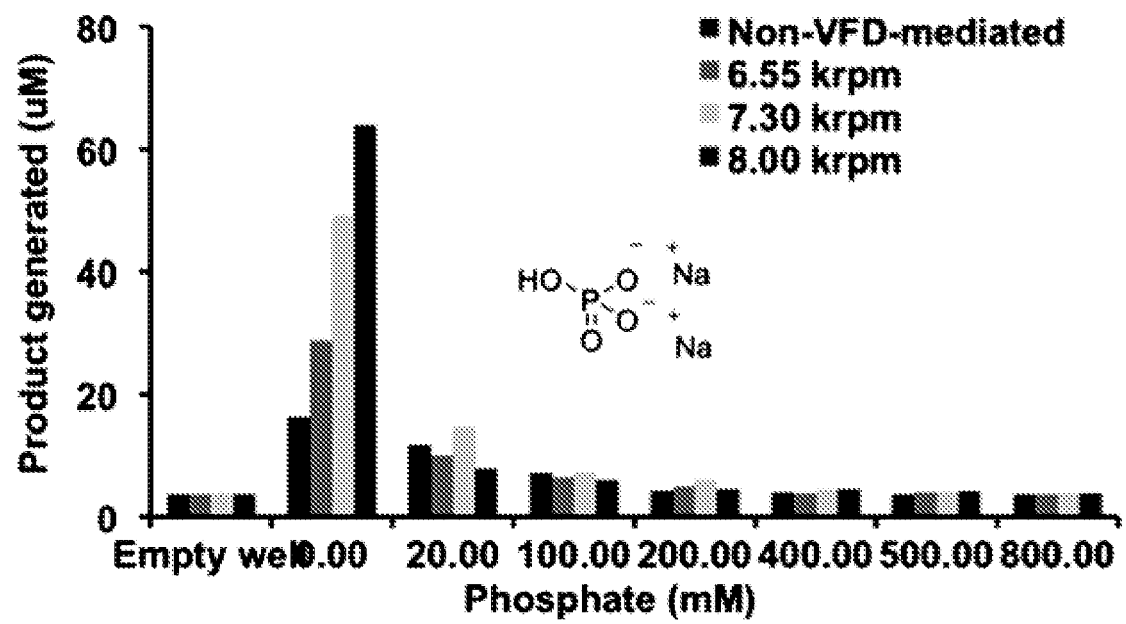
FIGS. 22A-22B. Product inhibition effects on VFD-mediated acceleration of alkaline phosphatase.
Figure 22B:
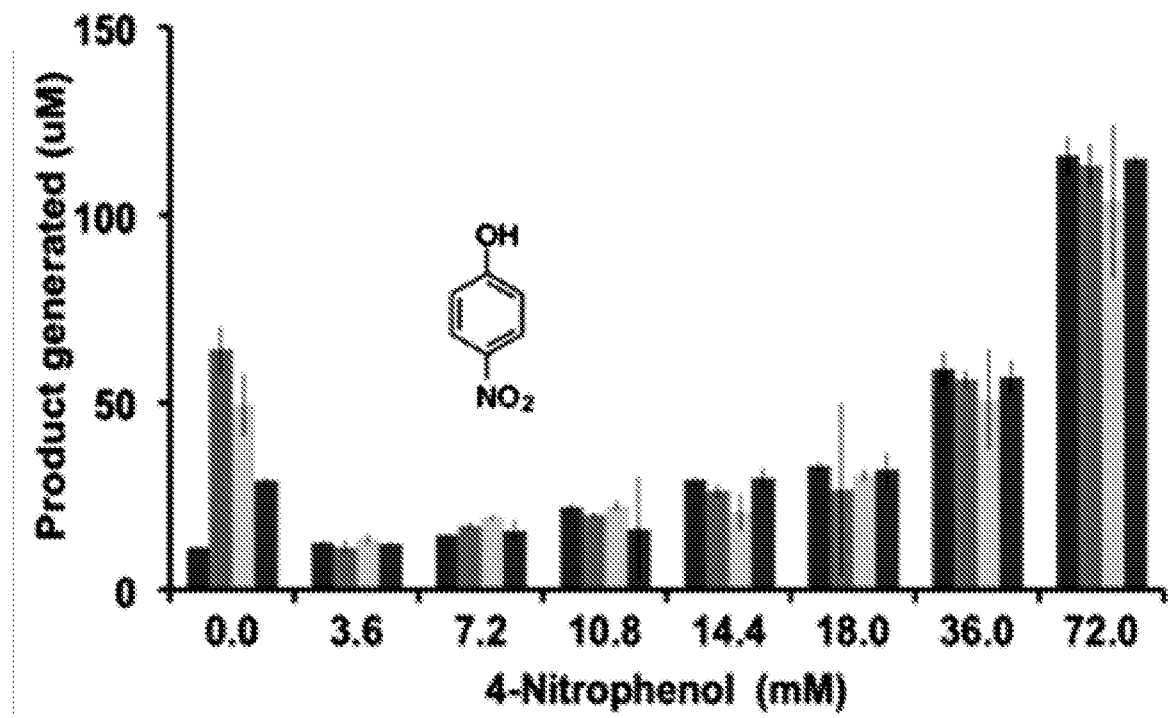

The amount of sodium phosphate, dibasic required for the indicated final concentrations was added to the enzyme buffer, and the pH adjusted to 9.8 with 5.0 M HCl. Then, alkaline phosposphatase was added to 0.80 mL of this solution before transfer to the VFD sample tube. p-Nitrophenyl phosphate liquid substrate solution (0.50 mL) was next added. The solution was rotated for 10 min at the indicated rotational speeds, and then immediately quenched with 4.0 M NaOH (0.150 mL). Analysis proceeded as described herein.

p-Nitrophenyl inhibition. The amount of p-nitrophenol required for the indicated final concentrations was added to the enzyme buffer, and the pH adjusted to 9.8 with 4.0 M NaOH. The experiment proceeded as described above. The absorbance values are higher due to the absorbance of 4-nitrophenoxide in basic solution. See FIGS. 22A-22B.

Crowding Studies.

Figure 23:
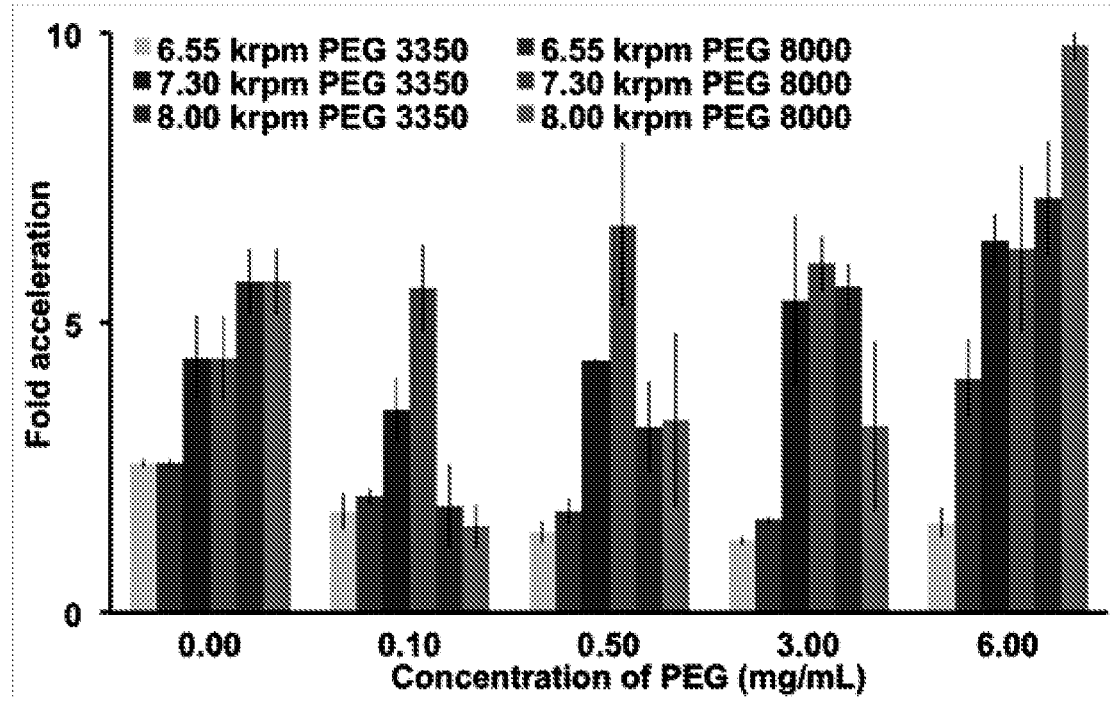
FIG. 23. Bar graph depicting that steric crowding reagents decrease activity of alkaline phosphatase in the non-VFD-processed enzyme-substrate solution. The VFD-mediated reaction, however, demonstrates effective catalysis and a high degree of enzymatic rate acceleration. Error is indicated as standard deviation around the mean (n=3). The concentration of alkaline phosphatase used was 6.77 nM, and the concentration of its substrate, p-nitrophenol phosphate, was 0.167 mM. The total volume used in this experiment was 1.30 mL. Bar graph bin order (left to right): 6.55 krpm PEG 3350; 6.55 krpm PEG 8000; 7.30 krpm PEG 3350; 7.30 krpm PEG 8000; 8.00 krpm PEG 3350; 8.00 krpm PEG 8000.
Figure 24A:
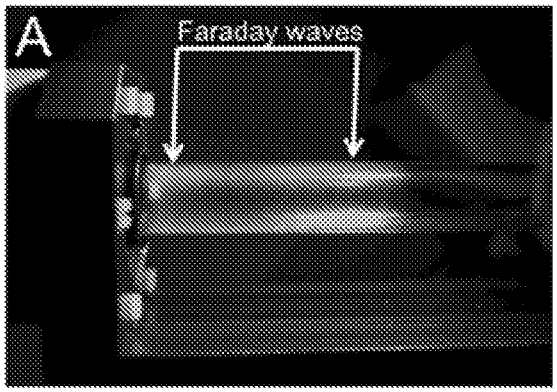
FIGS. 24A-24D. Figures provide photographs of the Faraday waves generated in the VFD at different rotational speeds.
Figure 24B:
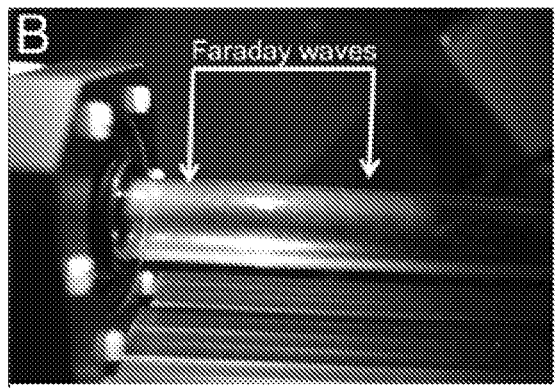
Figure 24C:
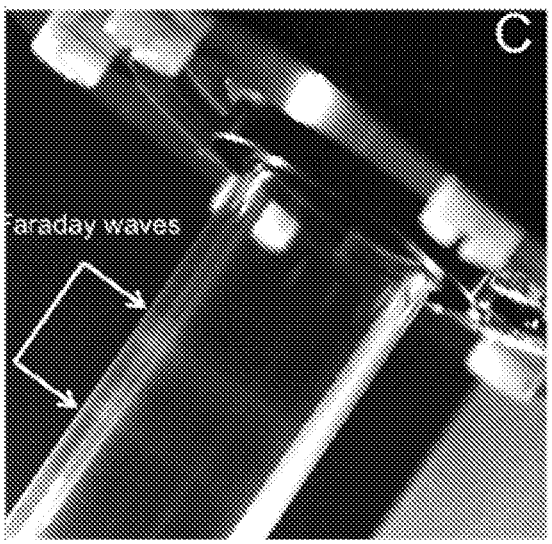
Figure 24D:
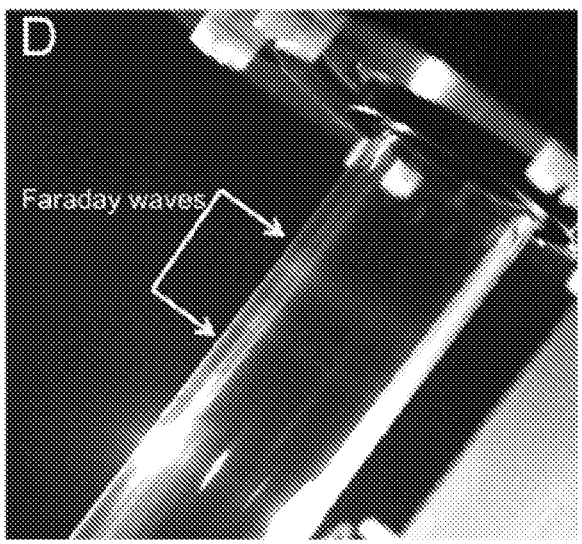

To explore the ability of VFD-mediated processing to overcome steric crowding reagents, two PEG polymers with average MW of 3350 and 8000 g/mol were added to the alkaline phosphatase-substrate solutions as follows. The appropriate quantities of PEG reagent for the indicated final concentrations were dissolved in diethanolamine buffer (total volume of 10.0 mL). Alkaline phosphatase (1.0 μL) was added, and this enzyme solution (800 μL, 11.1 nM) was added to the p-nitrophenyl phosphate liquid substrate solution (500 μL, 0.435 mM). After 10 min, the reaction was quenched through addition of 4.0 M NaOH (150 μL). The absorbance of the solution was then measured at 402 nm (FIG. 23).

Faraday Wave Studies.

The generation and observation of Faraday waves within the VFD device is depicted in FIGS. 24A-24D. It is observed that a higher rotational speeds, the Faraday waves have much shorter wavelengths.

Measuring the Rate of Product Generation with DERA Under VFD-Mediated Conditions.

Figure 26:
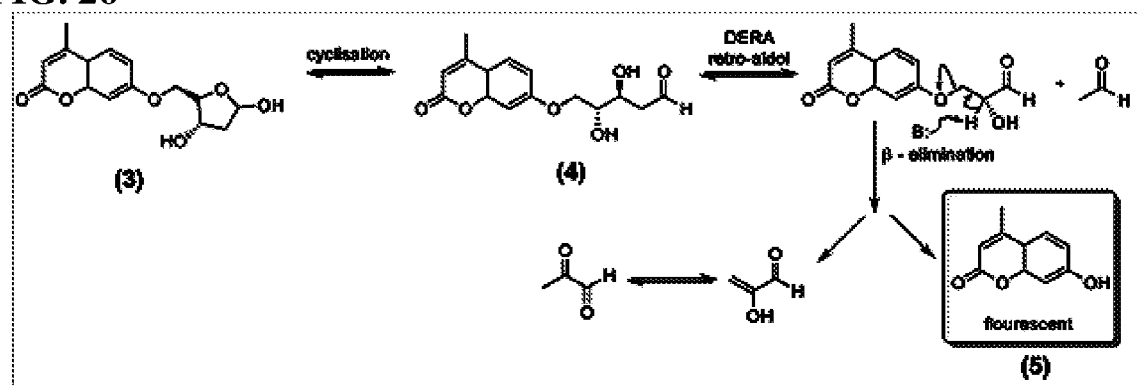
FIG. 26. Chemical scheme depicting the DERA-catalyzed formation of fluorophore (5) by a retro-aldol and subsequent β-elimination reaction.

A standard curve for quantifying concentrations of 4-methylumbelliferone was produced (FIG. 25). The indicated concentrations of 4-methylumbelliferone were dissolved in DMSO and then diluted to 100 mL of the bis-tris propane buffer described above (for a final concentration of 1.5% DMSO) in volumetric flasks. To quantify the fluorescence at each concentration, 200 μL solution was transferred to a 96-well microtiter plate, covered with an optically transparent foil, and measured as described above. A chemical scheme for synthesis of compounds 4 and 5 is disclosed in FIG. 26.

Michaelis-Menten Kinetics.

Non-VFD-Mediated Kinetics.

Figure 27A:
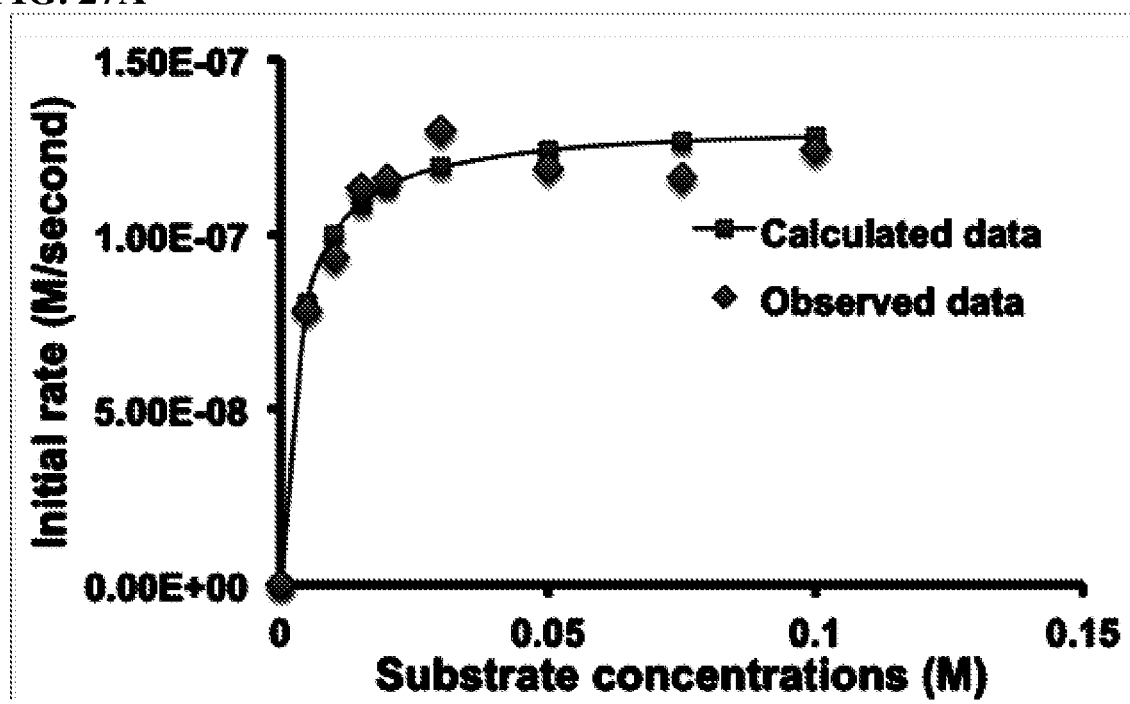
FIGS. 27A-27C. Results from a non-linear regression analysis for non-VFD-mediated Michaelis-Menten kinetics. A non-linear regression analysis was performed using an LSF approach to determine the local minima for both Km and Vmax. Results are in good agreement with the Lineweaver-Burk analysis.
Figure 27B:
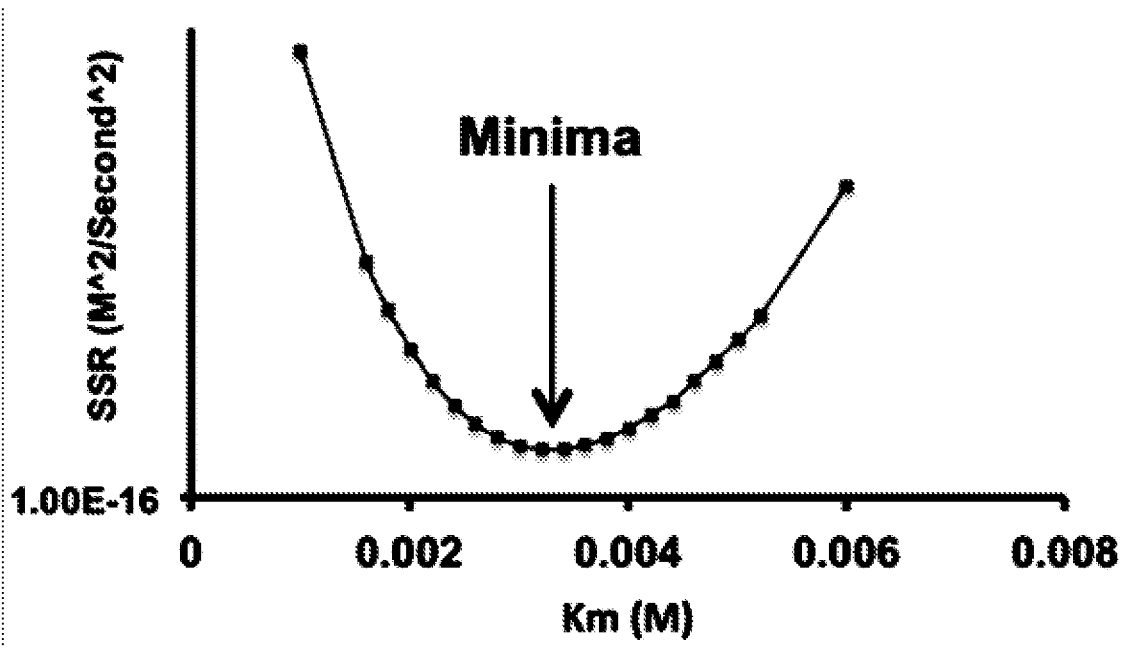
Figure 27C:
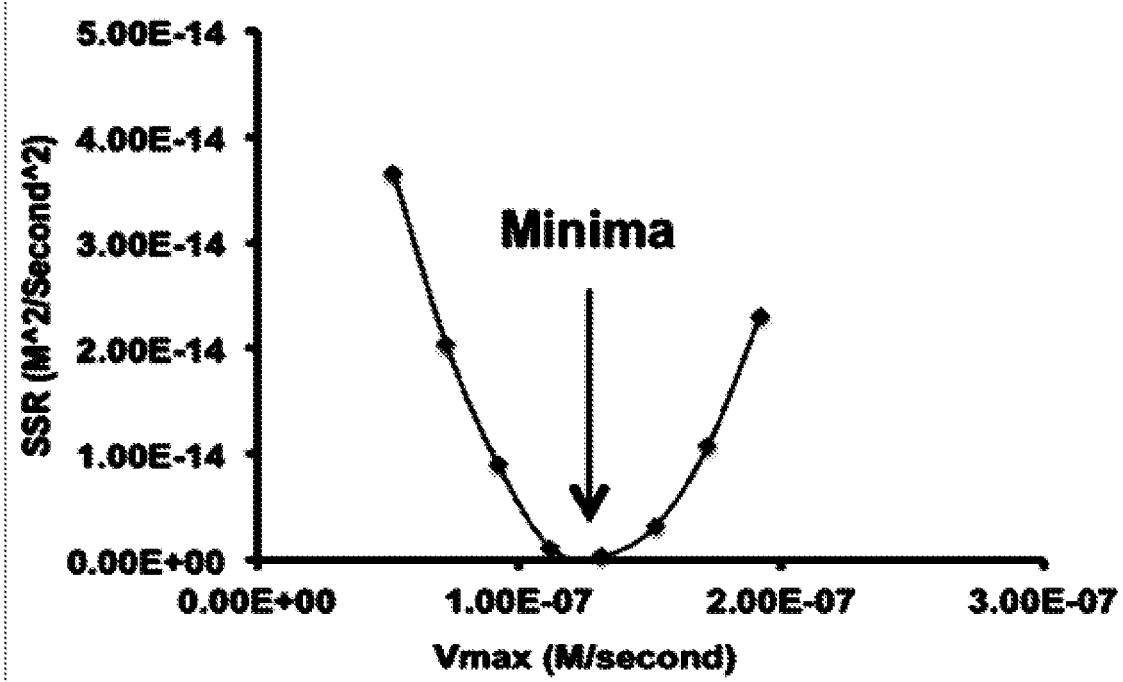

Conventional Michaelis-Menten measurements were performed as follows. The enzyme solution (β-glucosidase, 9.62 nM) and the substrate at the indicated concentration were mixed (1.30 mL total volume) and incubated for 1, 2, 3 and 4 min. Then, 200 μL of the quench solution (as described herein) was added, and the absorbance data collected as previously described. The initial rates of the reaction where calculated and fitted to the Michaelis-Menten equation. The global minimum was found for both Vmax and Km to demonstrate that these values have the lowest sum of squared fitting (SSR), whilst still maintain a good calculated fit to the data. Raw plots of initial rate as a function of substrate concentration are provided in FIG. 27A. Model fitting studies to provide the lowest value of SSR are depicted in FIGS. 27B-27C, for $K_M$ and $V_{max}$, respectively.

Figure 28A:
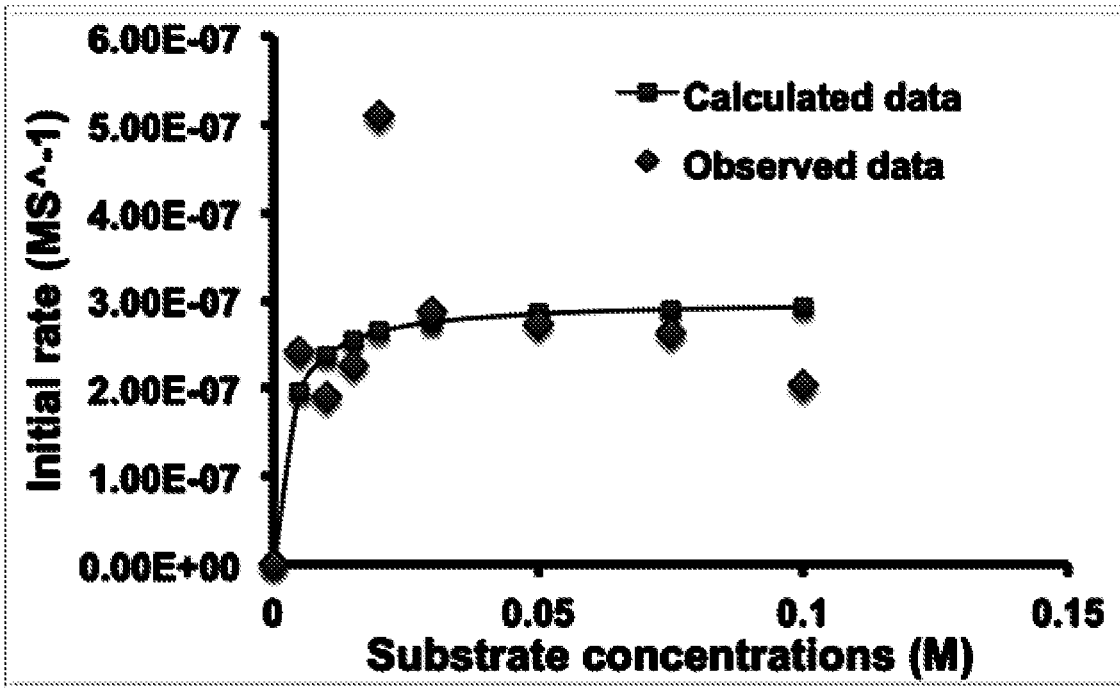
FIGS. 28A-28C. Results from a non-linear regression analysis for VFD-mediated Michaelis-Menten kinetics. A non-linear regression analysis was performed using an LSF approach to determine the local minima for both Km and Vmax. Results are in good agreement with the Lineweaver-Burk analysis.
Figure 28B:
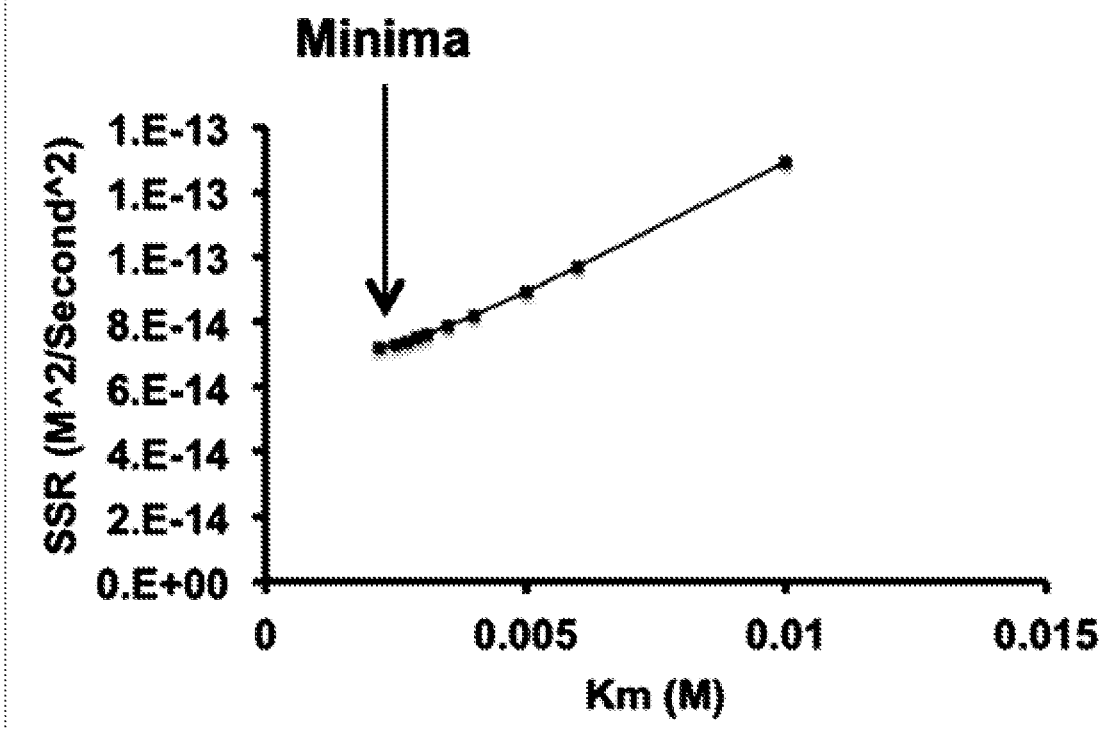
Figure 28C:
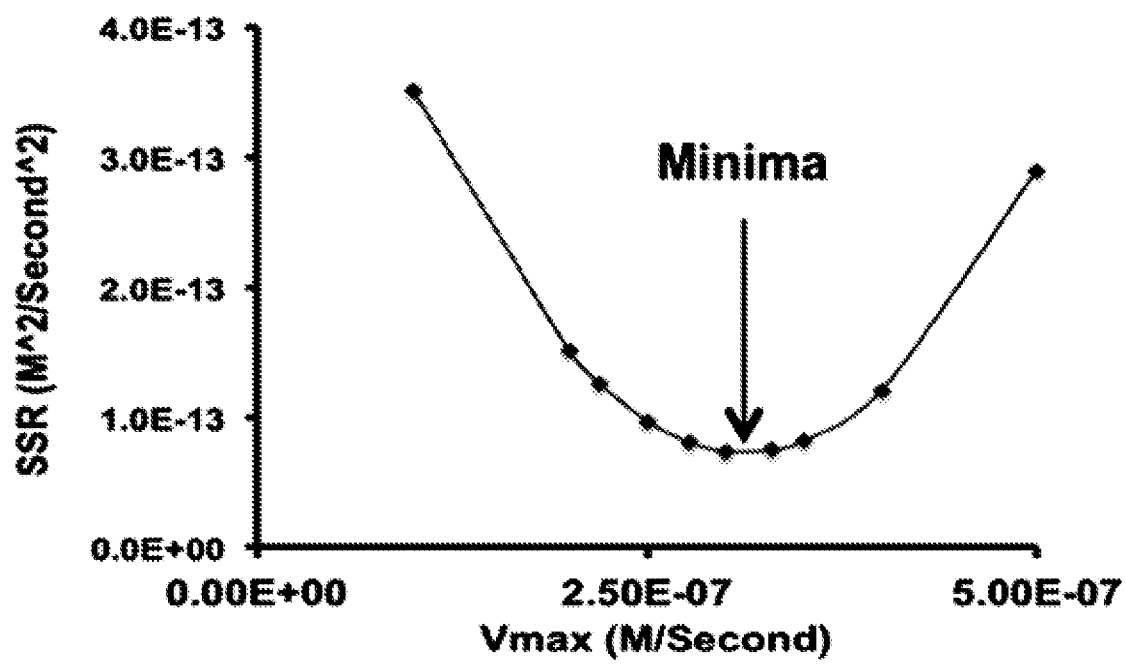

VFD-mediated kinetics. This comparable experiment applied the conditions above with the following modifications necessary for measuring enzyme kinetics in a rapidly rotating tube. The enzyme β-glucosidase, 9.62 nM) was added to the bottom of VFD sample tube, which had been inserted into the VFD. The substrate solution (775 µL) was then flowed down the side of the sample tube (1.30 mL total volume); this tube was immediately capped, and rotation began. Thus, the enzyme and substrate solutions remained apart until a fraction of a second before the VFD reached the indicated rotation speed. In order to achieve the indicated time points, the VFD motor was stopped 16 s prior to the end of the required time point; thus, each time point indicates the rotational time within 1-2 s. The quenching and measurement steps then followed the protocol described above. Raw plots of initial rate as a function of substrate concentration are provided in FIG. 28A. Model fitting studies to provide the lowest value of SSR are depicted in FIGS. 28B-28C, for $K_M$ and $V_{max}$, respectively.

A tabulation of Michaelis-Menten parameters Kmax, KM, kcat and kcat/kM for Non-VFD-mediated reaction and VFD-mediate reaction is set forth in Table 2.

3D-Printed Interchangeable Plastic Collar and Sleeve.

To maintain the vibrations generating VFD-mediated enzyme acceleration, a 3D printed plastic collar and interchangeable sleeve were created. See FIGS. 29A-29B. Thus, a relatively inexpensive consumable part can be worn and replaced to maintain enhancement. Without a collar on the upper part of the VFD, no enhancement is observed, directly linking the vibration of the sample tube within the collar to enzyme acceleration. In addressing this concern, there is provided a plastic insert that can be replaced after four hours of processing. In this experiment, an ABS-type 3D printer was used. The plastic density was set to 100% for the interchangeable sleeve and 50% plastic density for the plastic collar.

Kinetic Constants for the Enzyme-Substrate Systems Disclosed Herein.

Kinetic constants for the enzyme-substrate system disclosed herein are set forth in Table 5 following.

References

Example 4

[1] a) W. Aehle, Enzymes in Industry, WILEY-VCH, Weinheim, 2004; b) B. M. Nestl, B. A. Nebel, B. Hauer, Curr. Opin. Chem. Biol. 2011, 15, 187-193; c) R. DiCosimo, J. McAuliffe, A. J. Poulose, G. Bohlmann, Chem. Soc. Rev. 2013, 42, 6437-6474; d) D. J. Pollard, J. M. Woodley, Trends Biotechnol. 2007, 25, 66-73; e) J.-M. Choi, S.-S. Han, H.-S. Kim, Biotechnol. Adv. 2015, 33, 1443-1454; [2] a) H. Renata, Z. J. Wang, F. H. Arnold, Angew. Chem. Int. Edit. 2015, 54, 3351-3367; b) Z. J. Wang, H. Renata, N. E. Peck, C. C. Farwell, P. S. Coelho, F. H. Arnold, Angew. Chem. Int. Edit. 2014, 126, 6928-6931; c) J. B. Siegel, A. L. Smith, S. Poust, A. J. Wargacki, A. Bar-Even, C. Louw, B. W. Shen, C. B. Eiben, H. M. Tran, E. Noor, J. L. Gallaher, J. Bale, Y. Yoshikuni, M. H. Gelb, J. D. Keasling, B. L. Stoddard, M. E. Lidstrom, D. Baker, P. Natl. Acad. Sci. USA 2015, 112, 3704-3709; d) S. Wallace, E. P. Balskus, Angew. Chem. Int. Edit. 2015, 54, 7106-7109; e) P. Srivastava, H. Yang, K. Ellis-Guardiola, J. C. Lewis, Nat. Commun. 2015, 6; [3] a) A. S. Bommarius, B. R. Riebel, Biocatalysis, Wiley-VCH, Weinheim, 2004; b) K. M. Koeller, C.-H. Wong, Nature 2001, 409, 232-240; c) V. L. Schramm, Annu. Rev. Biochem. 1998, 67, 693-720; [4] M. E. Stroppolo, M. Falconi, A. M. Caccuri, A. Desideri, CMLS, Cell. Mol. Life Sci. 2001, 58, 1451-1460; [5] D. L. Nelson, M. M. Cox, Lehninger Principles of Biochemistry, 5th ed., W. H. Freeman, New York, 2008; [6] R. Wolfenden, M. J. Snider, Accounts Chem. Res. 2001, 34, 938-945; [7] a) F. Subrizi, M. Crucianelli, V. Grossi, M. Passacantando, G. Botta, R. Antiochia, R. Saladino, ACS Catalysis 2014, 4, 3059-3068; b) W. A. Greenberg, A. Varvak, S. R. Hanson, K. Wong, H. Huang, P. Chen, M. J. Burk, P. Natl. Acad. Sci. USA 2004, 101, 5788-5793; [8] a) J. Britton, S. B. Dalziel, C. L. Raston, Green Chem. 2016, 18, 2193-2200; b) J. Britton, S. B. Dalziel, C. L. Raston, RSC Adv. 2015, 5, 1655-1660; [9] T. Z. Yuan, C. F. G. Ormonde, S. T. Kudlacek, S. Kunche, J. N. Smith, W. A. Brown, K. M. Pugliese, T. J. Olsen, M. Iftikhar, C. L. Raston, G. A. Weiss, ChemBioChem 2015, 16, 393-396; [10] J. Britton, J. M. Chalker, C. L. Raston, Chem. Eur. J. 2015, 21, 10660-10665; [11] a) L. Yasmin, X. Chen, K. A. Stubbs, C. L. Raston, Sci. Rep. 2013, 3; b) J. Britton, C. L. Raston, RSC Adv. 2014, 4, 49850-49854; c) J. Britton, C. L. Raston, RSC Adv. 2015, 5, 2276-2280; [12] F. M. Menger,

TABLE 5

Kinetic constants for the enzyme-substrate systems

| Enzyme and Substrate | Kinetic constants | Kinetic measurement conditions |
|---|---|---|
| FASTAP™ alkaline phosphatase and p-nitrophenylphosphate | Unknown | Unknown |
| β-glucosidase and 4-nitrophenyl β-Dglucopyranoside | $K_M$ - Literature - 2.50 mM This work - 3.76 mM $k_{cat}$ -This work - 804 min$^{-1}$ $k_{cat}/K_M$ - Literature - 3.2 × 10$^6$M$^{-1}$min$^{-1}$ This work - 2.1 × 10$^6$M$^{-1}$min$^{-1}$ | Literature - 27° C., pH 5.6, 10 mM piperazine, 20 mM sodium acetate, 0.1 mM EDTA [S6]. This work - 25° C., pH 5.0, 50 mM sodium acetate |
| DERA and substrate 3 | Unknown | Unknown |
| Esterase and p-nitrophenylacetate | $K_M$ - Literature - 0.52 mM kcat - Literature - 1209 min$^{-1}$ $k_{cat}/K_M$ - Literature - 2320 mM$^{-1}$min$^{-1}$ | pH 7.4, 37° C., 10 mM KH$_2$PO$_4$ [S7] |

M. Ladika, J. Am. Chem. Soc. 1987, 109, 3145-3146; [13] K. Zhu, H. Liu, P. Han, P. Wei, Frontiers of Chemical Engineering in China 2010, 4, 367-371; [14] S. Jennewein, M. Schürmann, M. Wolberg, I. Hilker, R. Luiten, M. Wubbolts, D. Mink, Biotechnology Journal 2006, 1, 537-548; [15] N. Hillson, J. N. Onuchic, A. E. García, P. Natl. Acad. Sci. USA 1999, 96, 14848-14853; [16] C. J. T. Kuster, H. W. Scheeren, In High Pressure Chemistry, Wiley-VCH, Weinheim, 2007; [17] S. Hay, N. S. Scrutton, Nat. Chem. 2012, 4, 161-168; [18] K. A. Henzler-Wildman, M. Lei, V. Thai, S. J. Kerns, M. Karplus, D. Kern, Nature 2007, 450, 913-916; [19] U. R. Shrestha, D. Bhowmik, J. R. D. Copley, M. Tyagi, J. B. Leão, X.-q. Chu, P. Natl. Acad. Sci. USA 2015, 112, 13886-13891; [20] a) P. C. Sims, I. S. Moody, Y. Choi, C. Dong, M. Iftikhar, B. L. Corso, O. T. Gul, P. G. Collins, G. A. Weiss, J. Am. Chem. Soc. 2013, 135, 7861-7868; b) S. Xie, Single Mol. 2001, 2, 229-236; [S1] a) L. A. Lerin, R. A. Loss, D. Remonatto, M. C. Zenevicz, M. Balen, V. O. Netto, J. L. Ninow, C. M. Trentin, J. V. Oliveira, D. Oliveira, Bioproc. Biosyst. Eng. 2014, 37, 2381-2394; b) F. I. Braginskaya, E. A. Zaitzeva, O. M. Zorina, O. M. Poltorak, E. S. Chukrai, F. Dunn, Radiat. Environ. Bioph. 29, 47-56; [S2] J. Britton, S. B. Dalziel, C. L. Raston, Green Chem. 2016, 18, 2193-2200; [S3] M. Vedadi, J. Lew, J. Artz, M. *Amani*, Y. Zhao, A. Dong, G. A. Wasney, M. Gao, T. Hills, S. Brokx, W. Qiu, S. Sharma, A. Diassiti, Z. Alam, M. Melone, A. Mulichak, A. Wernimont, J. Bray, P. Loppnau, O. Plotnikova, K. Newberry, E. Sundararajan, S. Houston, J. Walker, W. Tempel, A. Bochkarev, I. Kozieradzki, A. Edwards, C. Arrowsmith, D. Roos, K. Kain, R. Hui, Mol. Biochem. Parasit. 2007, 151, 100-110; [S4] W. A. Greenberg, A. Varvak, S. R. Hanson, K. Wong, H. Huang, P. Chen, M. J. Burk, P. Natl. Acad. Sci. USA 2004, 101, 5788-5793; [S5] D. Wang, W. A. Nugent, J. Org. Chem 2007, 72, 7307-7312; [S6] M. P. Dale, H. E. Ensley, K. Kern, K. A. R. Sastry, L. D. Byers, Biochemistry-US 1985, 24, 3530-3539; [S7] C. P. Landowski, P. L. Lorenzi, X. Song, G. L. Amidon, J. Pharm. Exp. Thera. 2006, 316, 572-580.

Example 5—Ten-Minute Protein Purification and Assembly Line Creation for Continuous Flow Biocatalysis Abstract.

Nature applies enzyme-driven assembly lines for the synthesis of bioactive compounds. Inspired by nature's capabilities for complex organic synthesis, we report a facile method for spatially segregating attached enzymes in a continuous flow system. Using $His_n$-tag epitope complexation makes this strategy broadly applicable and telescopes protein immobilization and consequent purification. Six different proteins from complex cell lysates required only ten minutes processing for purification to >85% homogeneity. Furthermore, this "reaction-ready" system demonstrated excellent stability during five days of continuous flow processing. Towards multistep transformations in continuous flow, proteins were arrayed as ordered zones (up to 28) on the reactor surface allowing segregation of reaction conditions and catalysts. Choosing enzymes and ordering them into zones could open new opportunities for continuous flow biosynthesis.

Introduction.

Over millions of years, organisms have evolved highly efficient biosynthetic pathways to construct complex molecules through enzymatic assembly lines [1]. Polyketide biosynthesis, for example, uses multiple proteins, including some with multiple domains, to perform iterative synthetic transformations acting upon intermediate compounds. During these pathways, mobile scaffolds carry intermediates between enzyme active sites, termed substrate channeling [1f,2]. Such pathways can generate an enormous range of bioactive secondary metabolites, and substrate channeling can enhance reaction efficiency and yields [3]. Inspired by these biosynthetic pathways, multistep continuous flow offers an analogous approach in vitro.

Elegant multistep continuous flow systems have provided access to numerous APIs [4] including artemisinin [4h], rufinamide [5] and efavirenz [6]. Though relatively unexplored, multistep biosynthesis in continuous flow could provide two major benefits to API synthesis. First, starting materials, reagents and enzymatic catalysts from nature can reduce the environmental impacts associated with syntheses. Second, all natural products are synthesized through cassettes of enzymes linked in biosynthetic pathways analogous to continuous flow systems; such examples could provide a roadmap for in vitro implementation of nature's powerful synthetic technology.

Recently, we have applied a vortex fluidic device (VFD) to drive formation of thin films for continuous flow syntheses and process improvements, including single [7] and multistep transformations [8], protein folding [9], and biocatalysis [10]. The VFD confines reagents to a thin film (with ≈250 μM thickness) through rapid rotation of an angled reactor. VFD-mediated processing has several advantages over conventional processing including micro-mixing and vibrational effects [7c,7d] that can accelerate covalent and non-covalent bond formation.

Results and Discussion.

We report a simple, efficient, and rapid approach to immobilize and purify proteins in a VFD reactor. Our initial approach to immobilize proteins for continuous flow biocatalysis applied non-specific glutaraldehyde attachments to the reactor surface.[11] Although this generated a highly efficient continuous flow system for individual proteins, the method proved unworkable for creating the distinct enzyme zones necessary for enzymatic assembly lines. Specifically, the relatively slow kinetics of this attachment method prevented confinement of each enzyme to a specific zone of the reactor. Yields of attached enzymes were around 1%, which is too low for applications requiring enzymes with low catalytic rates. Here, this problem is solved using the rapid kinetics of polyhistidine attachment to IMAC resin, allowing formation of distinct enzymatic zones for multistep biocatalysis with nearly quantitative yields of attached enzymes. Furthermore, all proteins fused to a polyhistidine tag are amenable to ten-minute purification from cell lysates and then direct use for biocatalysis in continuous flow.

Telescoping protein immobilization, purification, and subsequent catalysis in a single reactor removes time consuming steps associated with biocatalysis. First, this approach does not require isolation of the pure protein before immobilization. Operating in non-clogging thin films allows the cell lysate to be applied directly to the sidewall of the reactor without centrifugation or other processing, which saves hours of time. An identical slurry of cell lysate immediately blocked conventional protein purification apparatus (FPLC) with cell debris (data not shown). Using centrifuged and non-centrifuged cell lysate provided consistently high levels of protein immobilization and protein purity of ~96% and >76%, respectively, demonstrating that this system is not only rapid, but also efficient (FIGS. 30C, 38A-38F and 39). Lastly, VFD-mediated purification avoids lengthy dialysis into a reaction buffer as the same reactor is used for protein immobilization, purification, buffer exchange, and then directly for catalysis; since the enzyme is attached to the reactor, the buffer can be rapidly exchanged.

Figure 30A:
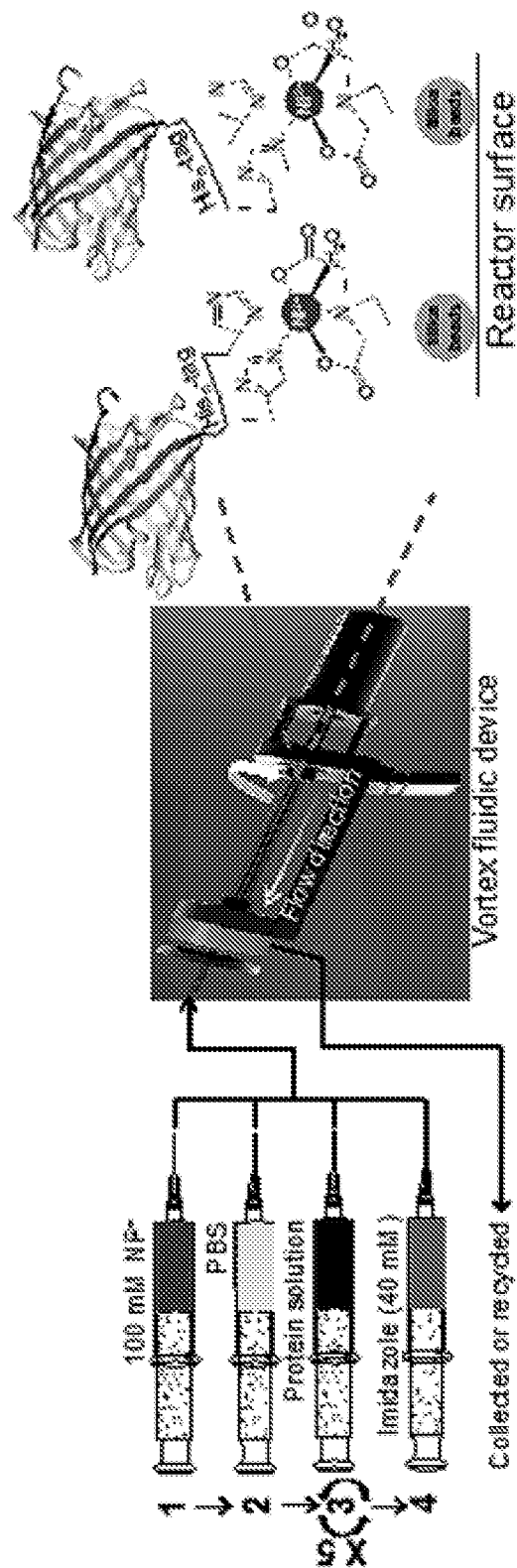
FIGS. 30A-30E. Continuous flow protein purification and immobilization.

The model proteins mCherry and enhanced green fluorescent protein (eGFP) allowed optimization of protein immobilization and their consequent purification. These fluorescent proteins allowed rapid quantification of several reaction parameters including optimal binding, purification conditions and protein stability in the reactor. Using 60 mg/cm$^2$ of silica-based IMAC resin (100 cm$^2$ reactor surface) resulted in high immobilization efficiencies for a wide range of protein concentrations (5-50 µM, FIG. 30D). Furthermore, all stages of immobilization and purification are performed in continuous flow to reduce the effort required and to increase reproducibility and throughput (FIG. 30A). The resultant protein coating appears uniform most likely through re-equilibration of protein concentration during the continuous flow coating process.

Optimization allows reactor construction in only ten minutes with each reactor providing multiple days of reactivity (FIGS. 30A and 31A-31C). Painting IMAC resin onto the inner surface of the reactor is rapid and straightforward. Pipetting a homogenous solution of IMAC resin (6 mL of commercially available suspension in 20% aq. ethanol) into the rapidly rotating reactor forms a clay-like solid that adheres to the sidewall of the reactor, and remains bound for weeks after removal of the solvent. Presumably hydrophilic interactions stabilize this interaction, as IMAC resin fails to adhere to a silanized reactor (treated with a solution of trichloro(octyl)silane in toluene as previously described[7d]). Next, a solution of Ni$^{2+}$ is flowed through the reactor to charge the resin (100 mM, 10 mL, 13.3 mL min$^{-1}$, 45 s). To avoid interference with protein immobilization, the residual Ni$^{2+}$ is removed from the resin by washing the reactor with PBS (10 mL, 13.3 mL min$^{-1}$, 45 s). Bacterial cell lysate from overexpression of polyhistidine-fused proteins is then flowed and re-cycled four times through the reactor (20 mL, 13.3 mL min$^{-1}$, 450 s, FIG. 30A). Finally, a low concentration of imidazole (40 mM, 13.3 mL, 13.3 mL min$^{-1}$, 60 s) removes non-specific binding. After protein purification by this continuous flow process, the protein can be eluted, and the IMAC resin reused.

Figure 43:
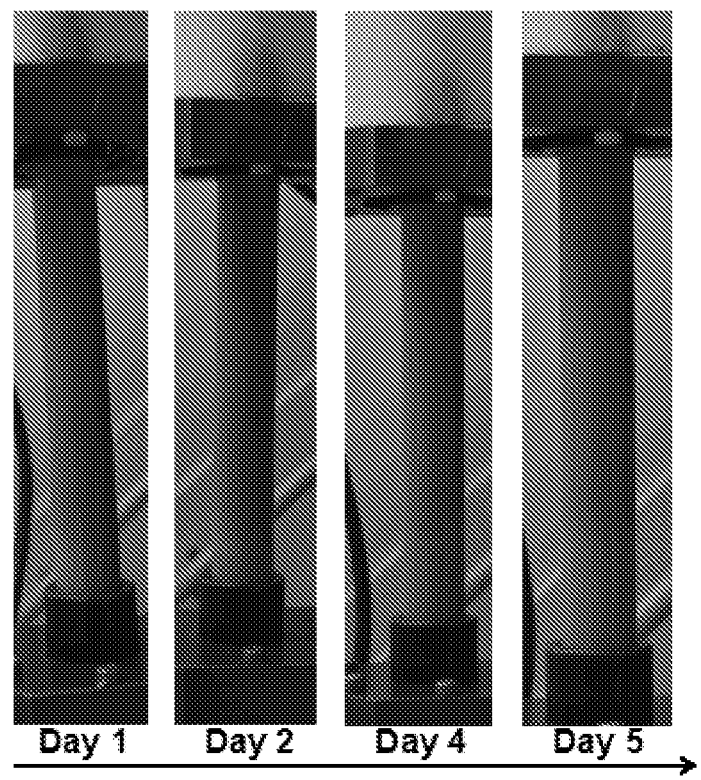
FIG. 43. The figure depicts photographs showing visual stability of mCherry on the reactor surface over continuous flow processing at days 1, 2, 4 and 5.
Figure 44A:
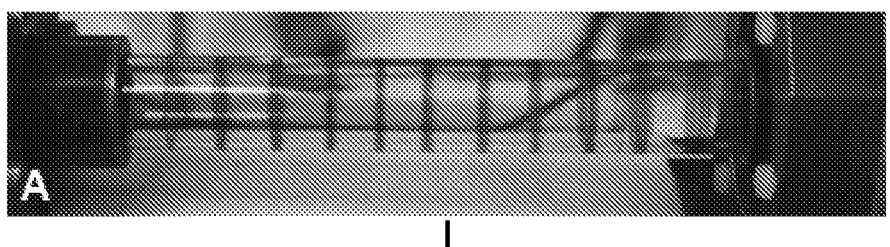
FIGS. 44A-44C. Photographs depicting creating enzymatic zones on the reactor surface.
Figure 44B:
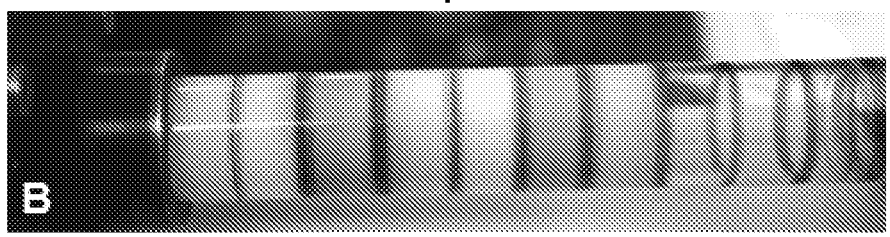
Figure 44C:
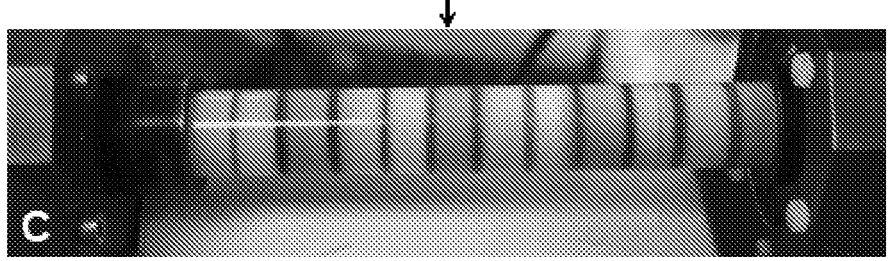

The protein bound to the reactor through the IMAC-polyhistidine complex exhibits remarkable stability. After five days of continuous flow processing with a 1.0 mL min$^{-1}$ flow rate, only 0.34% of the protein bound to the surface of the reactor was leached away from the reactor. This percentage was determined through analysis of both the flow-through and the quantities of protein retained on the reactor (FIG. 43). Depending on the stability of the protein, the reactor can be stored and reused multiple times with little loss of surface bound protein, as shown for the mCherry-modified reactor.

To demonstrate the generalizability of this approach, six proteins being used in our laboratory were purified and attached to VFD reactors. These proteins include esterase, phosphodiesterase, alkaline phosphatase, eGFP, mCherry and tobacco epi-aristolochene synthase (TEAS, a terpene cyclase).[12] Biosynthetic pathways often rely on enzymes with less than ideal properties for in vitro biochemical assays; TEAS, for example, is a poorly expressed and troublesome protein with questionable stability. The rapid and straightforward purification of TEAS demonstrates the generalizability of this approach. The expedience of a 10 min purification process is invaluable for balky proteins like TEAS, which readily aggregate and precipitate out of solution.

Well-defined stripes containing different immobilized proteins can be applied to the reactor surface (FIGS. 30B and 44A-44C). Although cell lysate can be directly added to an IMAC-treated reactor by pipette, it is more convenient to first pre-bind the protein from centrifuged cell lysates to the IMAC resin, then add this slurry to the reactor. Careful pipetting of the IMAC-protein slurry onto the rotating reactor surface allows fine control over enzyme zone length; the concentration of protein within the zone can also be controlled by this method. The approach offers exceptional versatility and potential for future applications, including for multistep biocatalysis.

Figure 30B:
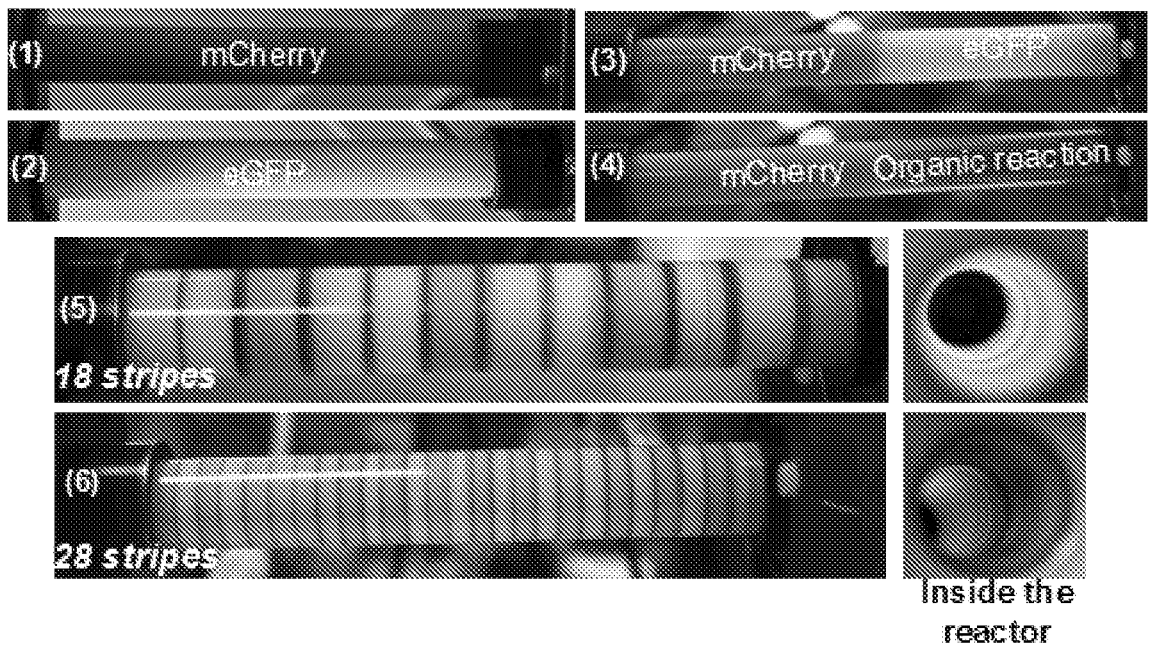
Figure 30C:
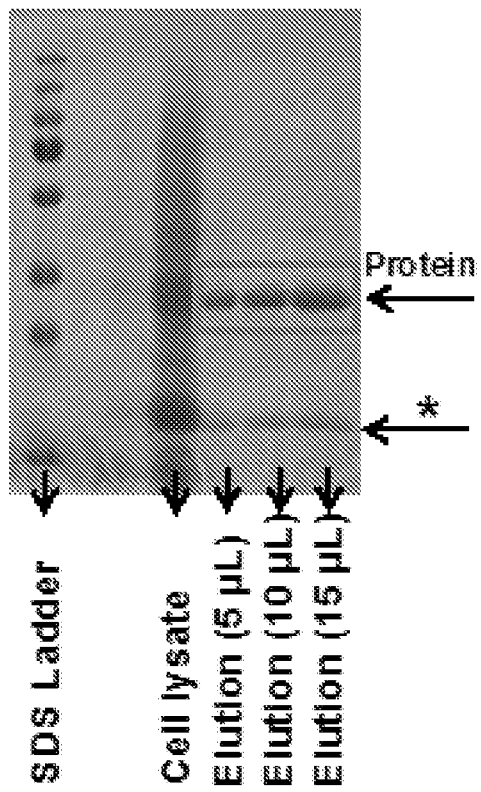
Figure 30D:
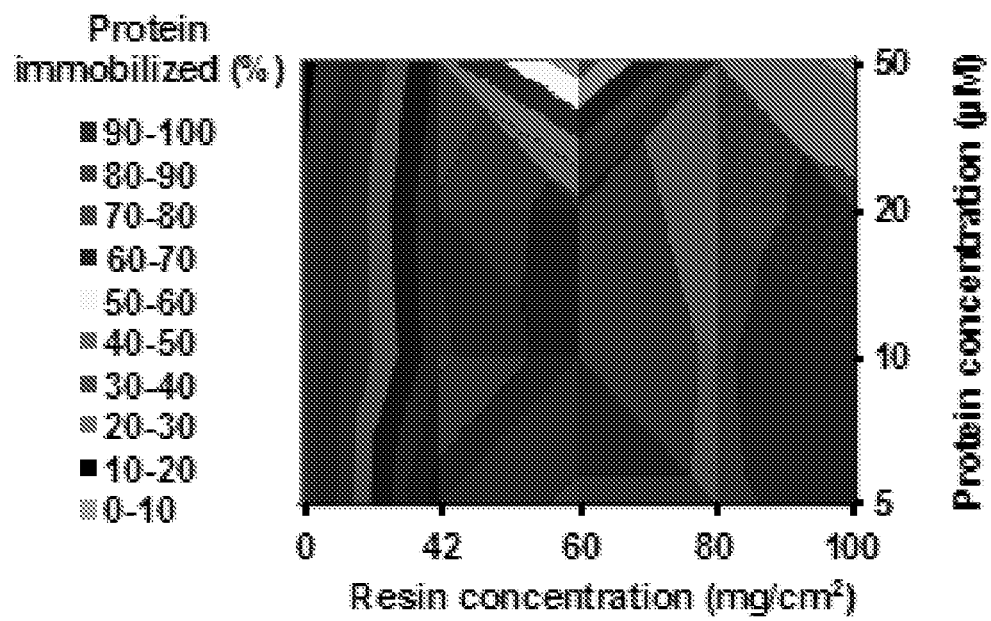
Figure 30E:
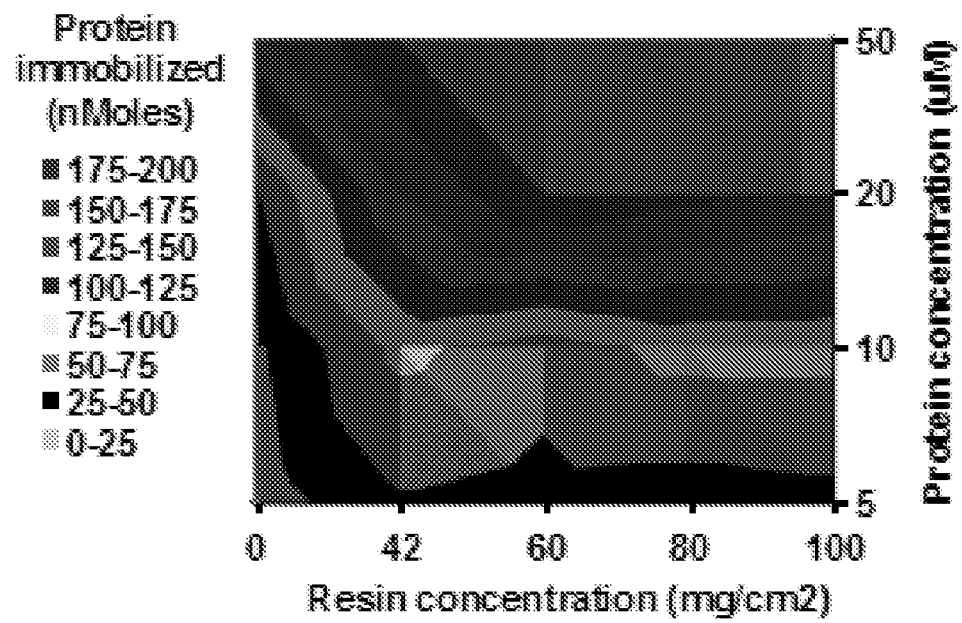

Here, we report reactors immobilized with two different proteins coating either equal or unequal zone lengths (FIG. 30B (1) and (2)). This approach allowed us to model multistep biocatalytic reactivity in continuous flow, and the effects of enzyme zones on reaction performance (vide infra). Furthermore, reactors can have a dedicated enzyme-catalyzed transformation zone as well as a zone for conventional synthetic transformations, aiding chemoenzymatic synthesis (FIG. 30B (4)). For example, stripes of different IMAC resins could create arbitrary numbers of zones on the reactor surface, including the 18 or 28 stripes shown here (FIG. 30B (5) and (6)). The large number of possible zones suggests multistep transformations requiring numerous proteins could be translated directly from cell lysate to this continuous flow system.

Figure 31A:
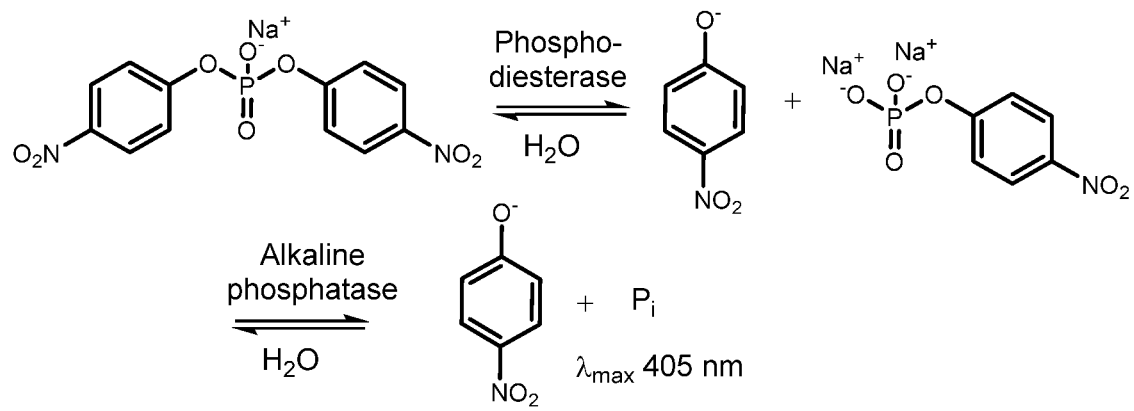
FIGS. 31A-31C. Enzyme zones and their effects on multistep continuous flow biocatalysis.
Figure 31B:
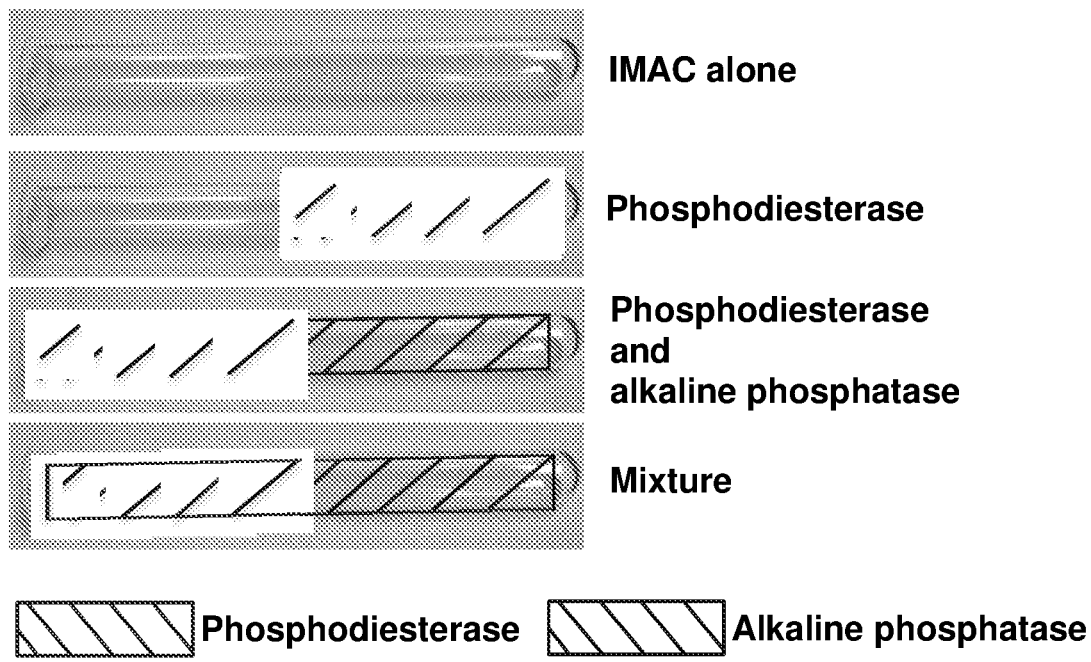
Figure 31C:
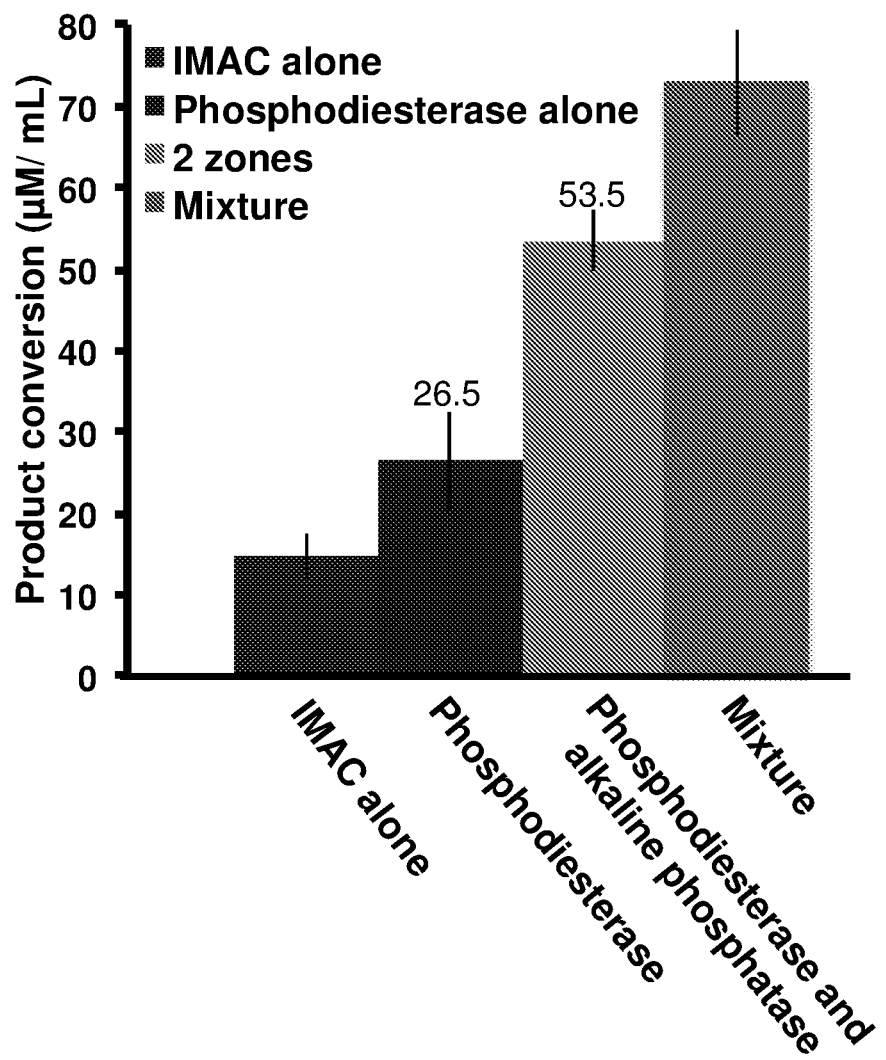

To illustrate the advantages of spatially segregated reaction zones, a multistep biosynthetic synthesis were developed that produced colorimetric responses at each step (FIGS. 31A-31C). In this reaction, both alkaline phosphatase and phosphodiesterase were recombinantly expressed and purified in continuous flow by VFD-mediated purification. Before demonstrating multistep reactivity in continuous flow, both enzymes were studied under conventional conditions to obtain Michaelis-Menten values and preferred reaction conditions (FIGS. 45-53, 54A-54B). Directly relating $k_{cat}/k_M$ values for each enzyme in the pathway provided the concentrations needed for both enzyme zones to operate at the same catalytic rate; in this example, alkaline phosphatase required a 1450 times higher concentration than phosphodiesterase to achieve a similar $k_{cat}/k_M$. As expected under these ideal conditions, applying both enzymes to the reactor surface in separate zones generated roughly twice as much p-nitrophenol product, compared to phosphodiesterase alone (26.5 vs. 53.5 µM ml$^{-1}$). Thus, we have established a method for rapidly imprinting biocatalytic pathways onto a reactor surface, and adjusting relative enzyme concentrations to maximize product formation.

The approach reported here opens possibilities for rapid implementation of biosynthetic catalysis in continuous flow. Retrosynthetic analysis of a target compound could suggest appropriate enzymes and their sequential configuration into reaction zones as illustrated here. Spatial segregation and the specific ordering of enzyme zones could facilitate such syntheses. Then, each enzyme could be synthesized in cells after transformation with the appropriate synthetic DNA before ordered coating onto the reactor surface as cell lysates.

Our laboratory has now demonstrated two key fundamental concepts for in vitro, continuous flow multistep biocatalysis. First, the VFD can accelerate enzymatic activity via an increase in $k_{cat}/k_M$.[11] Second, we here demonstrate near quantitative immobilization from complex cell lysate in ten minutes using continuous flow. Combining these advancements now allows us to explore biocatalytic assembly lines for generation of vital compounds such as polyketides in continuous flow. Such complex multi-domain enzymes are often sluggish in vitro. Combining high levels of immobilization and VFD-mediated acceleration could promote optimal reactivity. We foresee that this methodology could create efficient continuous flow systems for on-demand compound generation harnessing the power of nature. Ultimately, multi-day continuous flow could produce diverse compounds for customized therapeutics or research applications.

Materials and Methods and Supplemental Data

Unless otherwise indicated, all commercially available reagents and solvents were used directly from the supplier without further purification. The vortex fluid device (VFD) sample tubes were commercial quality borosilicate glass, with an internal diameter of 17.7 mm Prior to use, each sample tube was cleaned with piranha solution (4:1, sulfuric acid: $H_2O_2$), rinsed with $diH_2O$, dried using acetone, and stored in an oven at 160° C. All buffered solutions were prepared with double-deionized water ($diH_2O$, >18 MΩ) from a Milli-Q water system (Millipore, Bedford, Mass.).

Enzymes, Buffers and Assays mCherry

Buffer:

50 mM $H_2NaPO_4$ and 150 mM NaCl was prepared as follows: $H_2NaPO_4$ (5.999 g) and NaCl (8.766 g) were added to 1.0 L of deionized $H_2O$ and the pH of the solution adjusted to 8.0 at 25° C. with HCl. The buffer was filter-sterilized through a 0.22 µm filter (Corning), and stored at 25° C.

Protein Solution:

After dialyzing recombinant mCherry into the buffer described above, the protein concentration was determined by measuring its $A_{280}$ using extinction of 34380 $M^{-1}cm^{-1}$ and a MW of 29257 g $mol^{-1}$. Protein concentration was adjusted either by diluting with buffer or through concentrating with a 10 kDa cutoff concentrator (Sartorius). The purity of the protein was confirmed by 12% SDS-PAGE (FIG. 32), and the enzyme was assayed with ≥90% homogeneity.

eGFP

Buffer:

50 mM $Na_2PO_4$, 300 mM NaCl and 10 mM β-mercaptoethanol was prepared as follows: $H_2NaPO_4$ (3.000 g), NaCl (8.766 g) and 350 µL of β-mercaptoethanol were added to 500 mL of deionized $H_2O$ and the pH of the solution adjusted to pH 8.0 at 25° C. with HCl. The buffer was filter-sterilized through a 0.22 µm filter and stored at 25° C.

Protein Solution:

After dialyzing recombinant eGFP into the buffer described above, protein concentration was determined by $A_{280}$ using extinction of 20000 $M^{-1}$ $cm^{-1}$ and a MW of 30152.8 g $mol^-$. Protein concentration was adjusted either by diluting with buffer or through concentrating with a 10 kDa cutoff concentrator. The purity of the protein was confirmed by 12% SDS-PAGE (FIG. 33), and the enzyme was assayed with ≥90% homogeneity.

Alkaline Phosphatase

Reaction Buffer:

50 mM diethanolamine, 40 mM NaCl, 1 mM $MgCl_2.6H_2O$, 1 mM $NiCl_2.6H_2O$, at pH 9.8 buffer was prepared as follows: NaCl (2.324 g), $MgCl_2.6H_2O$ (203 mg) and $NiCl_2.6H_2O$ (237 mg) were dissolved in 800 mL of $diH_2O$. Diethanolamine (5.257 g) was added to this solution, and the pH adjusted to 9.8 with 1 M NaOH at 25° C. The buffer was then filtered-sterilized through a 0.22 µm filter and stored at 4° C.

Dialysis Buffer:

300 mM Tris-HCl, pH 8.0 buffer was prepared as follows: Tris-HCl (47.28 g) was dissolved in 1.0 L of $diH_2O$. The pH of the solution was adjusted to 8.0 with 6 M NaOH at 25° C. The buffer was stored at 25° C.

Assay:

1 mL of activity buffer containing 0.70 mM bis(p-nitrophenyl) phosphate sodium salt was added to glass LCMS vial. The solution was warmed to the required temperature for the specific reaction (25° C.-70° C.) in a heating block for two min. After this time, 50 µL of 6.15 µM alkaline phosphatase was added to the solution. The reactions were typically performed for five min. unless otherwise indicated. After the reaction had subsided, 200 µL of 4 M NaOH was added to quench the reaction and 200 µL of this solution was then transferred to a 96-well polystyrene plate (Costar) to measure its absorbance at 405 nm. The molar absorption coefficient of p-nitrophenol after the quench described above was 4242 $M^{-1}$ $cm^{-1}$.

Enzyme Solution:

After dialyzing recombinant alkaline phosphatase, the protein concentration was determined by $A_{280}$ using extinction of 32890 $M^{-1}$ $cm^{-1}$ and a MW of 50212.3 g $mol^{-1}$. Enzyme concentration was altered either by diluting with buffer or through concentration with a 10 kDa cutoff concentrator. The purity of the protein was confirmed by 12% SDS-PAGE (FIG. 34), and the assayed enzyme had ≥90% homogeneity.

Phosphodiesterase

Reaction Buffer:

50 mM diethanolamine, 40 mM NaCl, 1 mM $MgCl_2.6H_2O$, 1 mM $NiCl_2.6H_2O$, at pH 9.8 buffer was prepared as follows: NaCl (2.324 g), $MgCl_2.6H_2O$ (203 mg) and $NiCl_2.6H_2O$ (237 mg) were dissolved in 800 mL of $diH_2O$. Diethanolamine (5.257 g) was added to this solution, and the pH adjusted to 9.8 with 1 M NaOH at 25° C. The buffer was then filtered-sterilized through a 0.22 µm filter and stored at 4° C.

Dialysis Buffer:

Phosphate-buffered saline (PBS, 137 mM NaCl, 2.7 mM KCl, 10 mM $Na_2HPO_4$, 1.8 mM $KH_2PO_4$, pH 7.2) buffer was prepared as follows: NaCl (8.00 g), KCl (0.20 g), Na2HPO4 (1.15 g) and $KH_2PO_4$ (0.20 g) were dissolved in 800 mL of $diH_2O$. The pH of the solution was adjusted to 7.2 with 1 M HCl at 25° C. The volume of the buffer was then adjusted to 1.0 L and then filtered-sterilized through a 0.22 µm filter and stored at 25° C.

Assay:

To a 2 mL Eppendorf tube was added 1 mL of the buffer containing 0.01 M bis(p-nitrophenyl) phosphate sodium salt. The solution was warmed to the required temperature for the specific reaction (25° C.-70° C.) in a heating block for three min. After this time, 0.1 µL of the dialyzed phosphodiesterase was added to the solution and the reaction assayed for the indicated times. After the reaction time had subsided, 300 µL of 4 M NaOH was added to terminate the reaction. 100 µL of this sample was then transferred to a 96-well micro plate reader, and the solution's absorbance was measured at 405 nm. The molar absorption coefficient of p-nitrophenol after the quench described above was 4242 $M^{-1}$ $cm^{-1}$. Enzyme solution: After dialyzing the recombinant phosphodiesterase into the buffer described above, the protein concentration was determined by Bradford assay. A working solution of 2 mg $mL^{-1}$ enzyme was prepared by diluting the enzyme with buffer or through concentration with a 10 kDa concentrator. The purity of the protein was confirmed by 12% SDS-PAGE (FIG. 35), and the assayed enzyme had ≥90% homogeneity.

Esterase

Reaction Buffer:

50 mM $HPO_4^{3-}$ at pH 7.0 was prepared as follows: $H_2NaPO_4$ (1.459 g) and of $HNa_2PO_4$ (3.867 g) were dissolved in 500 mL of $diH_2O$. The pH of the resulting solution was adjusted to 7.0 at 25° C. with 5.0 M HCl. The buffer was then filtered-sterilized through a 0.22 μm filter and stored at 10° C.

Dialysis Buffer:

PBS (137 mM NaCl, 2.7 mM KCl, 10 mM $Na_2HPO_4$, 1.8 mM $KH_2PO_4$, pH 7.2) buffer was prepared as follows: NaCl (8.00 g), KCl (0.20 g), $Na_2HPO_4$ (1.15 g) and $KH_2PO_4$ (0.20 g) were dissolved in 800 mL of $diH_2O$. The pH of the solution was adjusted to pH 7.2 with 1 M HCl at 25° C. The volume of the buffer was then adjusted to 1.0 L and then filtered-sterilized through a 0.22 μm filter Immediately before dialysis, 10% v/v glycerol was added into the solution to maintain protein solubility.

Assay:

In a 15 mL falcon tube, 64 mg of p-nitrophenylacetate was re-suspended in 10 mL of ACS REAGENT SELECT™ grade methanol (Sigma) to generate a stable solution that was stored at 4° C. Then, 3.0 mL of this solution was added to 100 mL of $H_2O$ with rapid mixing before further dilution with 100 mL phosphate buffer (50 nM, pH 7.0) in generating a 0.052 mM stock solution. Esterase (1 μL, 0.038 mM) was diluted into 10 mL of phosphate buffer for testing the enzymatic activity at different temperatures using a heat block. The working enzyme stock (200 μL) was added to the substrate solution (1.10 mL), and the reaction was performed for five min. The reaction was quenched by addition of 1.00 mL of propanol, and 100 μL of the sample was transferred to a 96-well plate before measuring its absorbance at 405 nm. The molar absorption coefficient of p-nitrophenol in the solution described above was 6423 $M^{-1}$ $CM^{-1}$.

Enzyme Solution:

After dialyzing the recombinant esterase into PBS at pH 8.0, the protein concentration was determined by measuring its $A_{280}$ using extinction 38390 $M^{-1}$ $cm^{-1}$ and a MW of 38293.2 g $mol^{-1}$. A working stock of 8.33 μM enzyme solution was prepared by either diluting with buffer or through concentration with a 10 kDa concentrator. The purity of the protein was confirmed by 12% SDS-PAGE (FIG. 36), and the assayed enzyme had ≥95% homogeneity.

Tobacco Epi-Aristolochene Synthase (TEAS)

Buffer:

PBS (137 mM NaCl, 2.7 mM KCl, 10 mM $Na_2HPO_4$, 1.8 mM $KH_2PO_4$, 10 mM β-mercaptoethanol, pH 7.2) buffer was prepared as follows: NaCl (8.00 g), KCl (0.20 g), $Na_2HPO_4$ (1.15 g) and $KH_2PO_4$ (0.20 g) were dissolved in 800 mL of $diH_2O$. The pH of the solution was adjusted to pH 7.2 with 1 M HCl at 25° C. The volume of the buffer was then adjusted to 1.0 L and then filtered-sterilized through a 0.22 μm filter Immediately before dialysis, 7.5% v/v glycerol and β-mercaptoethanol (2.805 mL) were added to the solution to maintain protein solubility and stability.

Enzymes

Production of mCherry

Since mCherry containing a polyhistidine tag is not commercially available, the enzyme was prepared using bacterial overexpression as follows:

The gene mCherry from *Discosoma* sp. was purchased from Addgene (Plasmid #27705). The following PCR parameters and oligonucleotides (Integrated DNA Technologies) were used to amplify the mCherry gene. Iproof DNA Polymerase (BioRad) was used for all PCR amplification steps as directed in the manufacturer's instructions. Ten ng of plasmid #27705 was used as the template for one cycle at 95° C. for five min, 29 cycles at 95° C. for one min, 60° C. for one min, and 72° C. for one min, and one cycle at 72° C. for five min mCherryfwd:
(SEQ ID NO: 3)
5'-GAC GAC GAC AAG GTA GTA GTA GTA GTA GTA ATG
GTG AGC AAG GGC GAG GAG GAC AAC ATG GCC ATC-3'.

mCherryrev:
(SEQ ID NO: 4)
5'-GAG GAG AAG CCC GGT TCA CTT GTA CAG CTC GTC
CAT GCC GCC GGT GGA GTG GCG GCC CTC-3'.

The DNA was then extracted from a 1% agarose gel using a Zymoclean Gel DNA Recovery Kit. This DNA was then used with the pET46 Ek/LIC Vector Kit (EMD Mollipore Novagen, Billerica, Mass., USA) to generate the mCherry protein expression vector. To isolate the plasmid, *E. coli* NovaBlue cells were used (EMD Millipore, PureLink Quick Plasmid Miniprep Kit) prior to transforming into other heterologous hosts.

Expression and Purification of mCherry

Figure 32:
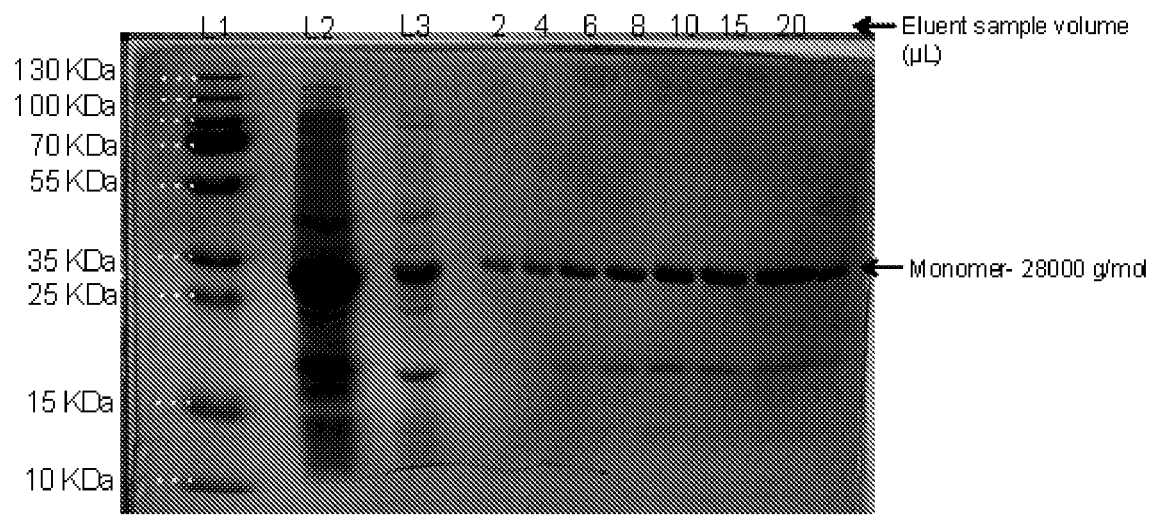
FIG. 32. VFD-mediated purification of mCherry. In this 12% tris-glycine SDS-PAGE, each lane was loaded with 10 µL of sample unless otherwise indicated. Lane 1: PageRuler Plus pre-stained protein ladder (ThermoFisher Scientific, Waltham, Mass.). Lane 2: Cell lysate. Lane 3: Flow-through after ten cycles through the VFD. The other lanes shown in this gel show the volume of elution fraction from the VFD after immobilization and purification (Elution buffer—250 mM imidazole, 50 mM NaH$_2$PO$_4$, 300 mM NaCl, 10 mM 2-mercaptoethanol at pH 8.0).

The pET46-mCherry construct was transformed via heat shock into *E. coli* BL21 Mar (DE3) cells. The transformed cells were transferred to an LB agar plate supplemented with 50 μg/mL carbenicillin antibiotic, and incubated at 37° C. for 14-16 h. A seed culture was prepared by inoculating a single colony from the plate into 5 mL of LB medium with 50 μg/mL carbenicillin antibiotic before shaking at 220 rpm for 6-7 h at 37° C. in a 13 mL culture tube. The expression culture was then prepared by inoculating 5 mL of the seed culture per 1.0 L of LB media with 50 μg/mL carbenicillin and then shaking at 220 rpm at 37° C. When the optical density of the culture reached $A_{600}$-0.6, overexpression of mCherry protein with an N-terminal $His_{12}$ tag was induced through the addition of 0.1 mM IPTG. The induced expression culture was incubated at 20° C. for 18-20 h shaking at 220 rpm. The cells were harvested and resuspended in buffer (50 mM $NaH_2PO_4$, 100 mM NaCl pH 8.0, and 100 μL of Halt Protease Inhibitor Cocktail ((100×) from ThermoFisher (cat #78430, AEBSF (1 mM), aprotinin (800 nM), betastatin (50 uM), E64 (15 uM), leupeptin (20 uM), pepstatin A (10 uM)). The cell lysate was prepared by sonication (Digital Sonifier 450, Branson, USA; std. horn, T<8° C., 4×60 s pulses (1 s on, 2 off), 50% amplitude), and the supernatant purified by VFD-mediated purification as described below. Fractions containing purified protein identified by SDS-PAGE were pooled and concentrated in a 10 kDa concentrator. The purity of the protein was confirmed using 12% SDS-PAGE (FIG. 32).

Production, Expression and Purification of eGFP

Figure 33:
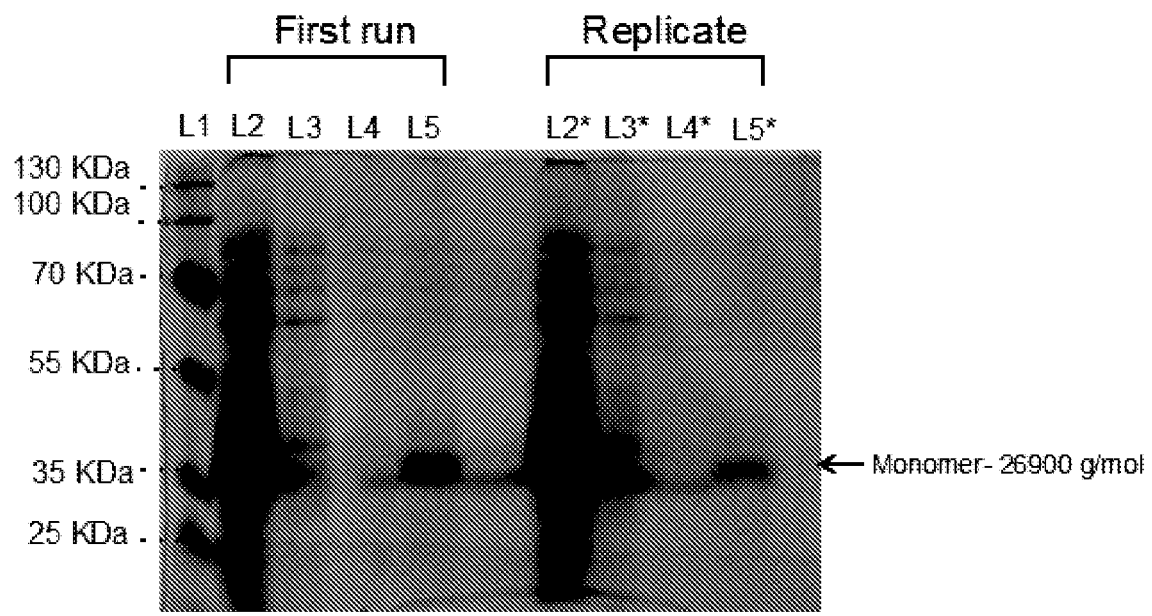
FIG. 33. VFD-mediated purification of eGFP. In this 12% tris-glycine SDS-PAGE, each lane was loaded with 10 µL of sample. Lane 1: PageRuler Plus pre-stained protein ladder. Lane 2: Cell lysate. Lane 3: Flow-through after ten cycles through the VFD. Lane 4: The eluent from the wash step (Wash buffer—10 mM imidazole, 50 mM NaH$_2$PO$_4$, 300 mM NaCl, 10 mM 2-mercaptoethanol, pH 8.0). The other lanes shown in this gel show the volume of elution fraction from the VFD after immobilization and purification (Elution buffer—250 mM imidazole, 50 mM NaH$_2$PO$_4$, 300 mM NaCl, 10 mM β-mercaptoethanol, pH 8.0).

The eGFP gene was sub-cloned into a pET-28 vector using NdeI and EcoRI restriction enzymes for bacterial protein expression. The vector was first transformed via heat shock into *E. coli* BL21 Mar (DE3) cells. The transformed cells were transferred to an LB agar plate supplemented with 50 μg/mL kanamycin antibiotic, and incubated at 37° C. for 10-12 h. A seed culture was prepared by inoculating a single colony from the transformation plate into 5 mL of LB supplemented with 50 μg/mL kanamycin antibiotic, then shaking at 220 rpm for 6-7 h at 37° C. in a 15 mL culture tube. The expression culture was then prepared by inoculating 5 mL of the seed culture per 1.0 L of LB supplemented with 50 μg/mL kanamycin, then shaking at 220 rpm at 37° C. When the optical density of the culture reached $A_{600}$-0.7, overexpression of eGFP protein with an N-terminal $His_6$ tag was induced through the addition of 0.5 mM IPTG. The induced expression culture was incubated at 37° C. for 3 h shaking at 170 rpm. The cells were harvested and resuspended in buffer (50 mM $NaH_2PO_4$, 100 mM NaCl pH 8.0, 100 μL of Halt Protease Inhibitor Cocktail). The cell lysate was prepared by sonication (Digital Sonifier 450, Branson, USA; std. horn, T<8° C., 4×60 s pulses (1-sec on, 2-sec off), 50% amplitude), and the supernatant was purified by VFD-mediated purification as described below. Fractions containing purified protein identified by SDS PAGE were pooled and concentrated with a 5 kDa concentrator. The purity of the protein was confirmed using 12% SDS-PAGE (FIG. 33).

Production of Alkaline Phosphatase

Since alkaline phosphatase containing a polyhistidine tag is not commercially available, the enzyme was prepared using bacterial overexpression as follows.

The alkaline phosphatase gene was extracted from the genomic DNA of BL21 Mar (DE3) *Escherichia coli* as follows: 3.0 mL of BL21 Mar (DE3) cells were cultured overnight in LB at 37° C. with shaking at 220 rpm, and were then centrifuged at 14,000 rpm for two min. The supernatant was discarded and the resulting pellet resuspended in 600 μL of lysis buffer (4.67 mL TE buffer, 300 μL 10% SDS, 0.011 g proteinase K, and 10 μL RNAase), and incubated at 37° C. for one h. Following this, 300 μL of phenol and 300 μL of chloroform were added, and the sample was mixed via inversion until homogeneous. The mixture was then centrifuged for five min at 14 krpm, and the upper aqueous phase was extracted. Another 250 μL portion of both phenol and chloroform were added to the sample before mixing and centrifuging as before. After removing the aqueous phase, three volumes of −20° C. molecular biology grade ethanol were added to the sample. The sample was stored at −20° C. for 45 min, and then spun down at 14 krpm for ten min. Once the supernatant was discarded, 1 mL of 70% ethanol was added and the sample was spun at 14 krpm for two min. The supernatant was again discarded, and the DNA allowed to air dry before final resuspension in TE buffer (100 μL).

The following PCR parameters and oligonucleotides were used to extract the alkaline phosphatase gene from the genomic DNA and subsequently clone it into a Novagen pET46 vector. Herculase ii Fusion DNA polymerase (Agilent Technologies) was used for all PCR amplification steps as directed in the manufacturer's instructions. Touchdown cycling was performed to carry out PCR amplification: one cycle at 98° C. for 30 s, 33 cycles at 98° C. for 10 s, 79.8° C. for 30 s (with a decrease of 0.5° C. every cycle), 72° C. for 30 s, 19 cycles at 98° C. for 10 s, 55.8° C. for 30 s, 72° C. for 3 min 30 s, one cycle at 72° C. for 5.5 min.

```
EcoliAPForward:
                                        (SEQ ID NO: 5)
5'-GAC GAC GAC AAG ATG GTG AAA CAA AGC ACT ATT

GCA CTG GCA CTC TTA CCG-3'.
```

-continued

```
EcoliAP6HReverse:
                                        (SEQ ID NO: 6)
5'-GAG GAG AAG CCC GGT TCA TCA GTG GTG GTG GTG

GTG GTG TTT CAG CCC CAG GGC-3'.
```

The PCR amplification product was extracted from a 1% agarose gel and purified with the Zymoclean Gel DNA Recovery Kit. The gel-extracted DNA was then used with the pET46 Ek/LIC Vector Kit to generate the AP protein expression vector. *E. coli* NovaBlue cells were used to isolate the plasmid with the PureLink Quick Plasmid Miniprep Kit prior to transformation into other heterologous hosts.

Expression and Purification of Alkaline Phosphatase

Figure 34:
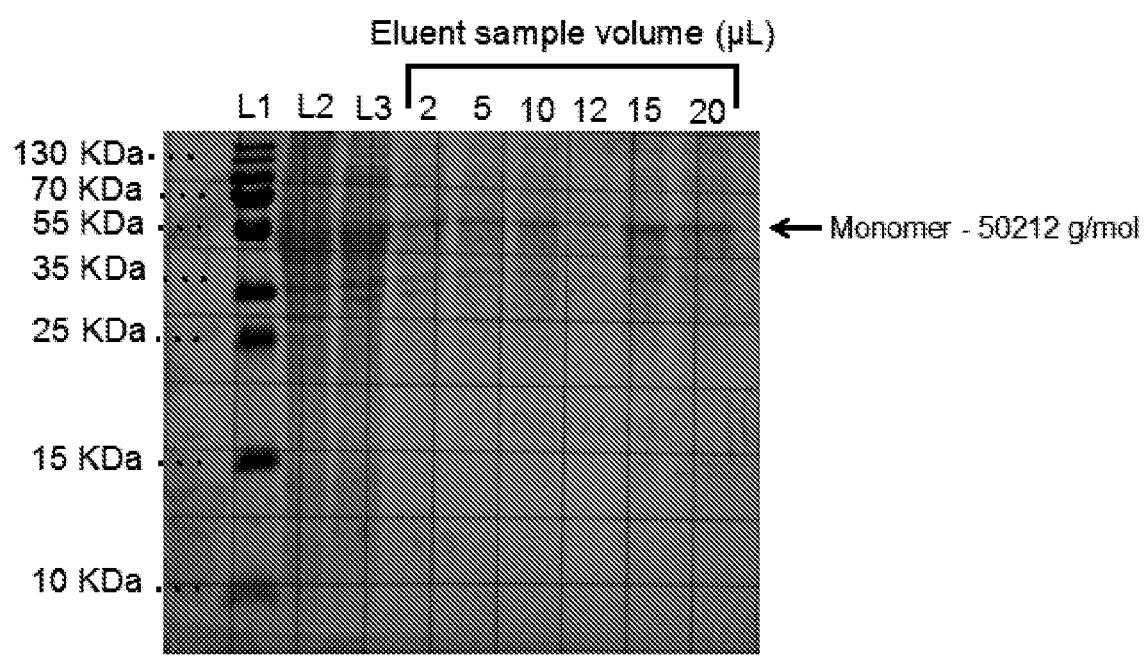
FIG. 34. VFD-mediated purification of alkaline phosphatase. In this 12% Tris-glycine SDS-PAGE, each lane was loaded with 10 µL of sample unless otherwise indicated. Lane 1: PageRuler Plus pre-stained protein ladder. Lane 2: Cell lysate. Lane 3: Flow-through after ten cycles through the VFD. Other lanes show the elution fraction from the VFD after immobilization and purification. The protein fraction visualized in this lane was dialyzed into the assay buffer before further experiments.

The pET46-AP construct was transformed via heat shock into *E. coli* BL21 Mar (DE3) cells. The transformed cells were transferred to an LB agar plate supplemented with 50 μg/mL carbenicillin antibiotic, and incubated at 37° C. for 14-16 h. A seed culture was prepared by inoculating a single colony from the transformation plate into 5 mL of LB medium with 50 μg/mL carbenicillin antibiotic, then shaking at 220 rpm for 6-7 h at 37° C. in a 15 mL culture tube. The expression culture was then prepared by inoculating 5 mL of the seed culture per 1.0 L of LB media with 50 μg/mL carbenicillin, then shaking at 220 rpm at 37° C. When the optical density of the culture reached $A_{600}$ 0.6-0.7, overexpression of AP protein with a C-terminal $His_6$ tag was induced through the addition of 0.5 mM IPTG. The induced expression culture was incubated at 30° C. for 18-20 h shaking at 220 rpm. The cells were harvested and resuspended in buffer (300 mM Tris-HCl, pH 8.0, 20% w/v sucrose, 0.1 mg/mL lysozyme and 100 μL protease inhibitor cocktail) and allowed to shake at 150 rpm at 4° C. for one h. The cell lysate was prepared by sonication as previously described, and the supernatant then purified by VFD-mediated purification as described below. Fractions containing purified protein identified by SDS PAGE were pooled and concentrated using a 10 kDa concentrator. The purity of the protein was confirmed using 12% SDS-PAGE (FIG. 34). Purification to ≥95% homogeneity was required before subsequent assays. For activity assays the purified recombinant protein was dialyzed into 300 mM Tris, pH 8.0.

Production of Phosphodiesterase

Since phosphodiesterase fused to a polyhistidine tag is not commercially available, the enzyme was prepared using bacterial overexpression and purification as follows.

The open reading frame encoding phosphodiesterase from *M. Jannashchii* was amplified as follows from a plasmid purchased from Addgene in DH5α cells (Plasmid #11538).

The QIAprep Spin Miniprep Kit was used as directed by the manufacturer to isolate plasmid DNA from an overnight culture of *E. coli* cells. The following PCR parameters and oligonucleotides were used to amplify the gene encoding phosphodiesterase. I-proof DNA polymerase was used for all PCR amplification steps as directed in the manufacturer's instructions. Here, plasmid (0.25 μL, #11538), 25 mM DNTP's (0.25 μL), 10×PFU buffer (2.50 μL), forward and reverse primers (0.25 μL), I proof enzyme (0.50 μL) and $diH_2O$ (21.0 μL) were subjected to the PCR conditions: one cycle at 98° C. for five min, 25 cycles at 98° C. for one min, 65° C. for one min, and 72° C. for one min, and one cycle at 72° C. for five min.

Lig_Phosphodiesterase_Forward:
(SEQ ID NO: 7)
5'-GAC-GAC-GAC-AAG-ATG-AAA-ATT-GGG-ATA-ATG-AGC-GAT-ACC-CAT-GAC-3'.

Lig_Phosphodiesterase_Reverse:
(SEQ ID NO: 8)
5'-GAG-GAG-AAG-CCC-GGT-TCA-TCA-TAA-CAC-TAT-CTC-CCT-ATA-CTC-CTT-3'..

The resultant DNA fragment (≈498 base pairs) was excised from a 1% agarose gel and purified using the QIAquick Gel Extraction Kit. The purified PCR product was then used with the pET46 Ek/LIC Vector Kit to generate the phosphodiesterase recombinant protein expression vector. *E. coli* Nova blue cells were used to isolate the plasmid prior to transformation into other heterologous hosts.

Expression and Purification of Phosphodiesterase

Figure 35:
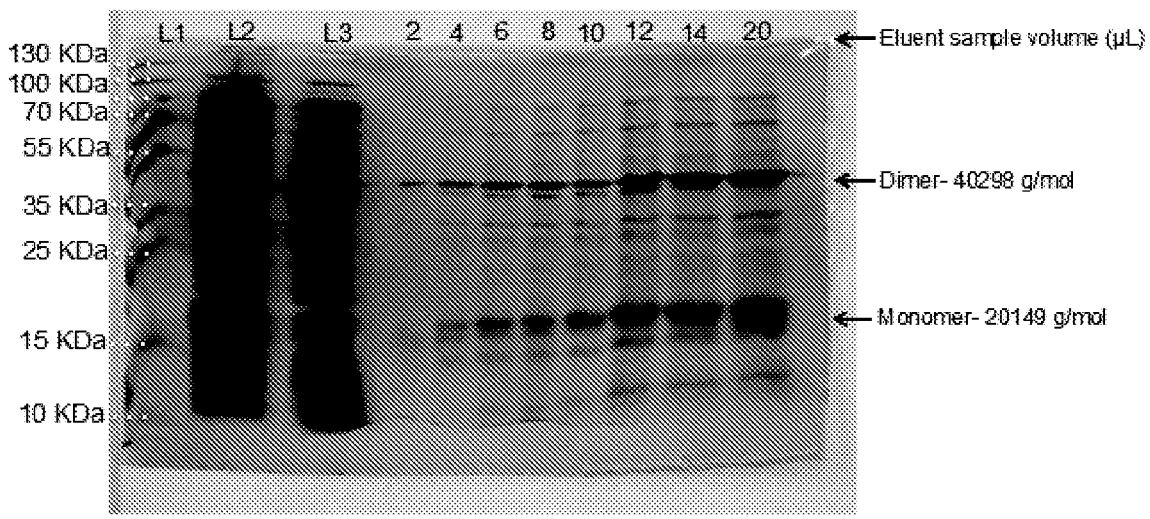
FIG. 35. VFD-mediated purification of phosphodiesterase. In this 12% Tris-glycine SDS-PAGE, each lane was loaded with 10 µL of sample unless otherwise indicated. Lane 1: PageRuler Plus pre-stained protein ladder. Lane 2: Cell lysate. Lane 3: Flow-through after ten cycles through the VFD. Other lanes show the volume of elution fraction from the VFD after immobilization and purification. The purified protein fraction visualized was dialyzed into the assay buffer before further experiments.

The pET46-phosphodieserse construct was transformed via heat shock into *E. coli* BL21 (DE3) cells. The transformed cells were transferred to an LB agar plate supplemented with 50 μg/mL carbenicillin antibiotic, and incubated at 28° C. for nine h. A seed culture was prepared by inoculating a single colony from the transformation plate into 90 mL of LB medium with 50 μg/mL carbenicillin antibiotic and shaking the culture at 225 rpm for 14-16 h at 37° C. in a 250 mL baffled flask. The expression culture was then prepared by inoculating 10 mL of the seed culture into 1.0 L of LB media with 50 μg/mL carbenicillin and shaking the culture at 225 rpm in 37° C. (2.0 L baffled flask). When the culture reached an $A_{600}$ of 0.6, overexpression of phosphodiesterase protein with a C-terminal $His_6$ tag was induced through addition of 0.50 mM IPTG and the mixture was incubated further for three h at 37° C. with shaking at 225 rpm. The cells were harvested and re-suspended in buffer A (50 mM $NaH_2PO_4$, pH 8.0, 300 mM NaCl, 10 mM β-mercaptoethanol, 100 μL protease inhibitor cocktail). The cell lysate was prepared by sonication as previously described, and the supernatant was purified by VFD-mediated purification as described below. Fractions containing purified protein identified by SDS-PAGE were pooled and concentrated using a 3 kDa concentrator. The purity of the protein was confirmed using 12% SDS-PAGE (FIG. 35). Purification to ≥85% homogeneity was required before subsequent assays. For activity assays the purified recombinant protein was dialyzed into PBS, pH 7.2.

Production of Esterase

Since an esterase containing a polyhistidine tag is not commercially available, the enzyme was prepared using bacterial overexpression as follows.

The genomic DNA of *Lactobacillus plantarum* was purchased from ATCC (#8014D-5). The following PCR parameters and oligonucleotides (IIDT) were used to amplify the esterase gene from the genomic DNA by touch down PCR. Touchdown cycling: one cycle at 98° C. for 30 s, 33 cycles at 98° C. for 10 s, 79.8° C. for 30 s (decreases 0.5° C. every cycle), 72° C. for 30 s, 19 cycles at 98° C. for 10 s, 55.8° C. for 30 s, 72° C. for three min. 30 s, one cycle at 72° C. for five min 30 s. Herculase ii Fusion DNA polymerase (Agilent Technologies) was used for the PCR amplification steps.

EstLICNew_Forward:
(SEQ ID NO: 9)
5'-GAC GAC GAC AAG ATG CCA ACA ATT AAT TCG ATT CAA ACA ACC GTC-3'.

EstLICNew_Reverse:
(SEQ ID NO: 10)
5'-GAG GAG AAG CCC GGT TCA TCA CTA ATT AAA CGC GGC CGC CAT CAC-3'.

DNA excised from a 1% agarose gel and purified using the Zymo Gel DNA Extraction Kit. The purified PCR product was then used with the pET46 Ek/LIC Vector Kit to generate the esterase recombinant protein expression vector. *E. coli* TOP10 cells were used to isolate the plasmid prior to transformation into other heterologous hosts.

Expression and Purification of Esterase

Figure 36:
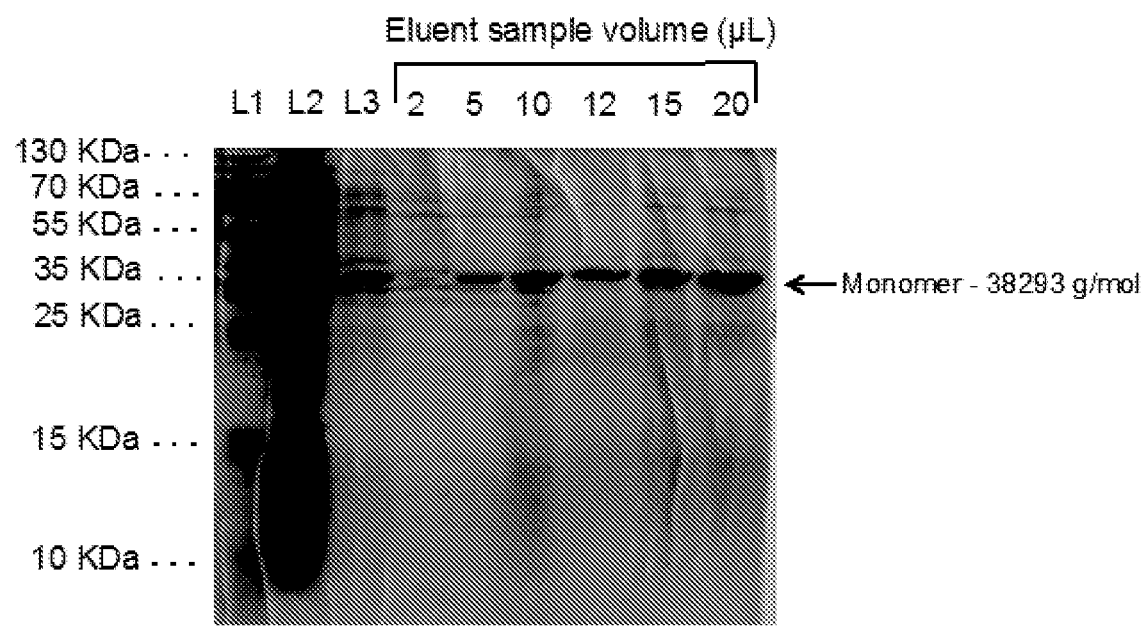
FIG. 36. VFD-mediated purification of esterase. In this 12% Tris-glycine SDS-PAGE, each lane was loaded with 10 µL of sample unless otherwise indicated. Lane 1: PageRuler Plus pre-stained protein ladder. Lane 2: Cell lysate. Lane 3: Flow-through after ten cycles through the VFD. Other lanes show the volume of elution fraction from the VFD after immobilization and purification. The purified protein fraction visualized was dialyzed into the assay buffer before further experiments unless used directly after purification.

The pET46-esterase construct was transformed via heat shock into *E. coli* BL21 (DE3) cells. The transformed cells were transferred to an LB agar plate supplemented with 50 μg/mL carbenicillin antibiotic, and incubated at 37° C. for 10-12 h. A seed culture was prepared by inoculating a single colony from the transformation plate in 25 mL of LB medium with 50 carbenicillin antibiotic and shaking the culture at 225 rpm for seven h at 37° C. in a 250 mL baffled flask. The expression culture was then prepared by inoculating 10 mL of the seed culture in 1.0 L of LB media with 50 μg/mL carbenicillin and shaking the culture at 225 rpm in 37° C. (3 L baffled flask). When the optical density of the culture reached $A_{600}$ 0.6, overexpression of esterase protein with a N-terminal $His_6$ tag was induced through addition of 0.50 mM IPTG, and the culture was incubated further for 16 h at 18° C. with shaking at 170 rpm. The cells were harvested and re-suspended in buffer A (50 mM $NaH_2PO_4$, pH 8.0, 300 mM NaCl, 10 mM β-mercaptoethanol, 100 μL protease inhibitor cocktail). The cell lysate was prepared by sonication as previously described, and the supernatant was purified by VFD-mediated purification as described below. Fractions containing purified protein identified by SDS-PAGE were pooled and concentrated with a 3 kDa concentrator. The purity of the protein was confirmed using 12% SDS-PAGE (FIG. 36). Purification to ≥90% homogeneity was required before subsequent assays. For activity assays the purified recombinant protein was dialyzed into PBS, pH 7.2.

Expression and Purification of TEAS

Figure 37:
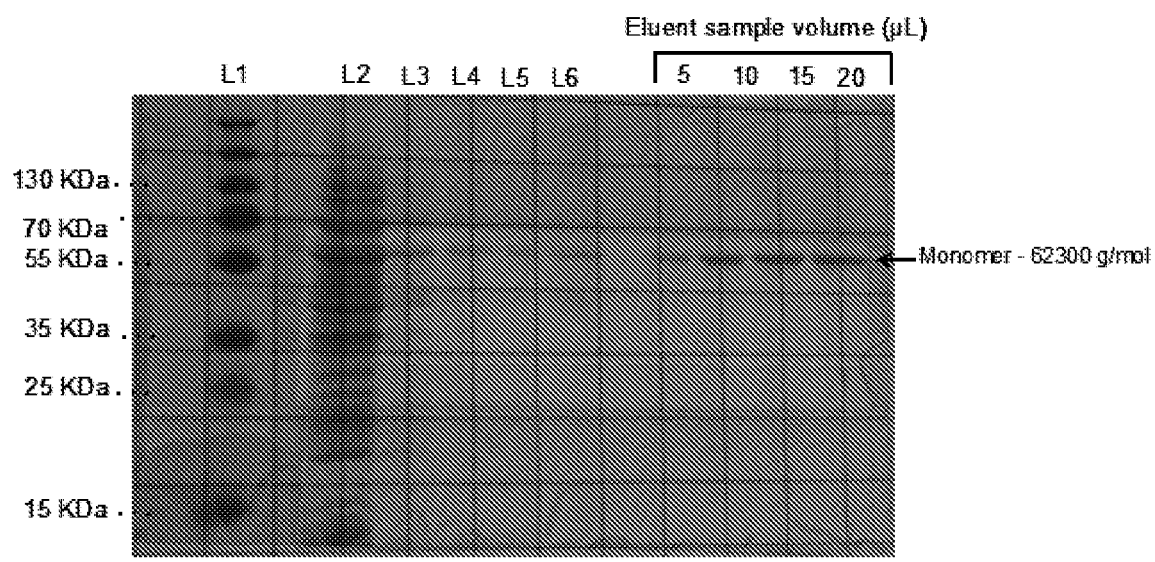
FIG. 37. VFD-mediated purification of TEAS. In this 12% tris-glycine SDS-PAGE, each lane was loaded with 10 µL of sample unless otherwise indicated. Lane 1. PageRuler Plus pre-stained protein ladder. Lane 2: Cell lysate. Lane 3: 10 mM imidazole wash. Lane 4: 20 mM imidazole wash. Lane 5: 30 mM imidazole wash. Lane 6: 40 mM imidazole wash. Other shown in this gel show the volume of elution fraction from the VFD after immobilization and purification.
Figure 38A:
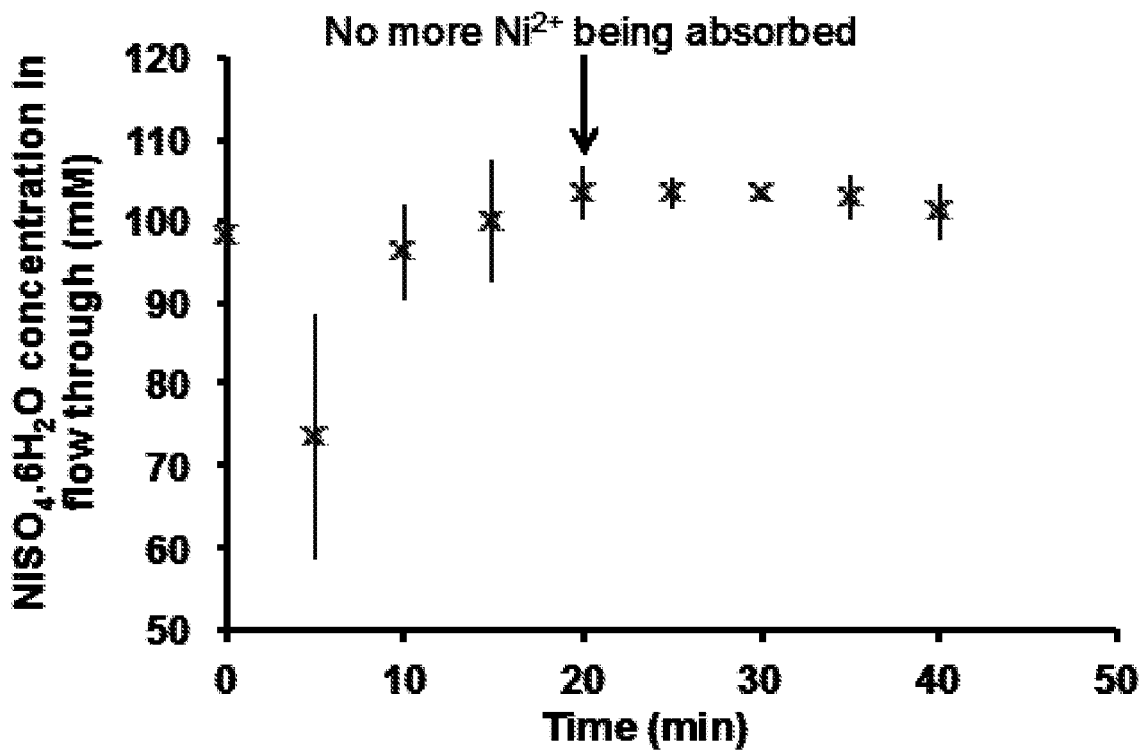
FIGS. 38A-38F. Optimization experiments for protein immobilization onto the reactor surface. For these experiments, 6.00 mL of homogeneous of IMAC resin (4.196 g solid IMAC resin) was added to the inner surface of the sample tube and the ethanol then removed for 30 min
Figure 38B:
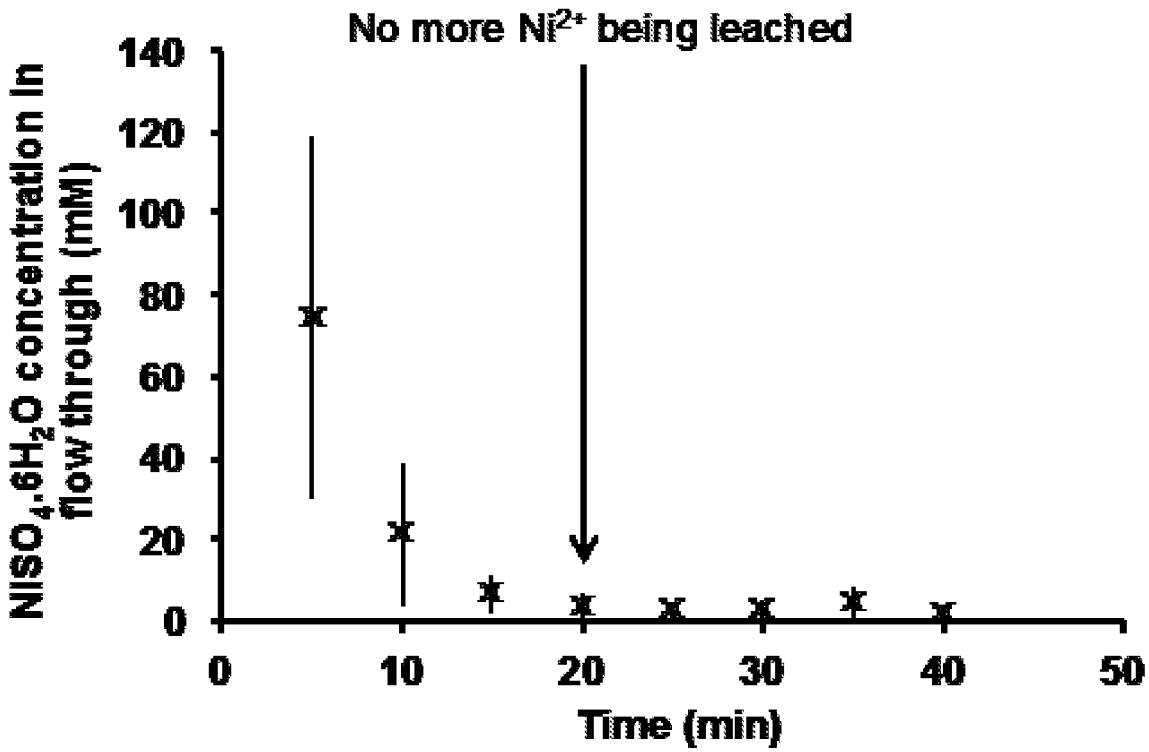
Figure 38C:
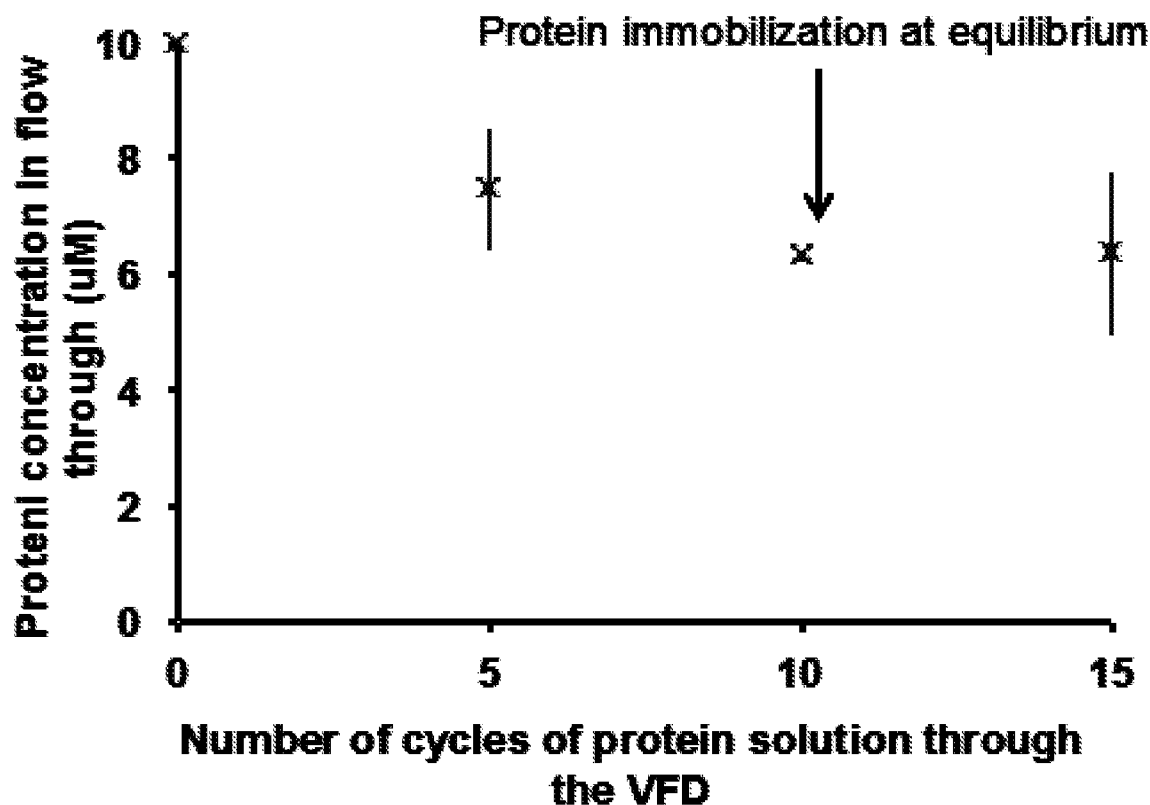
Figure 38D:
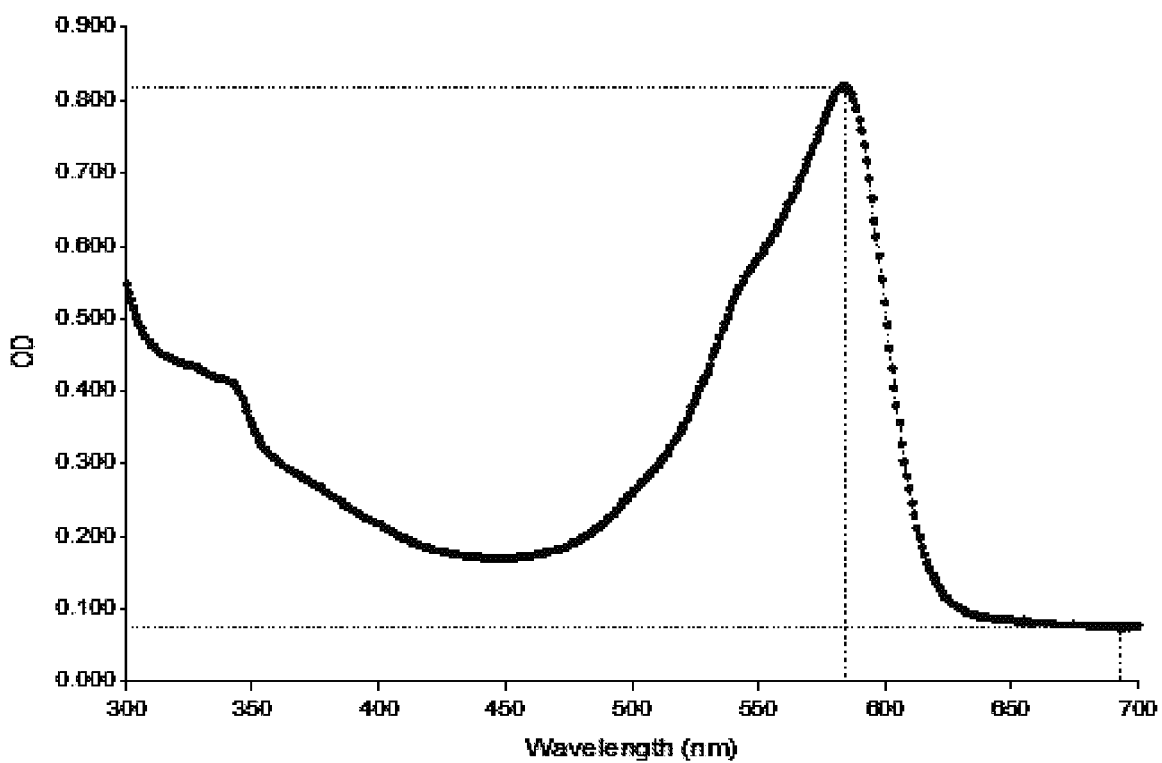
Figure 38E:
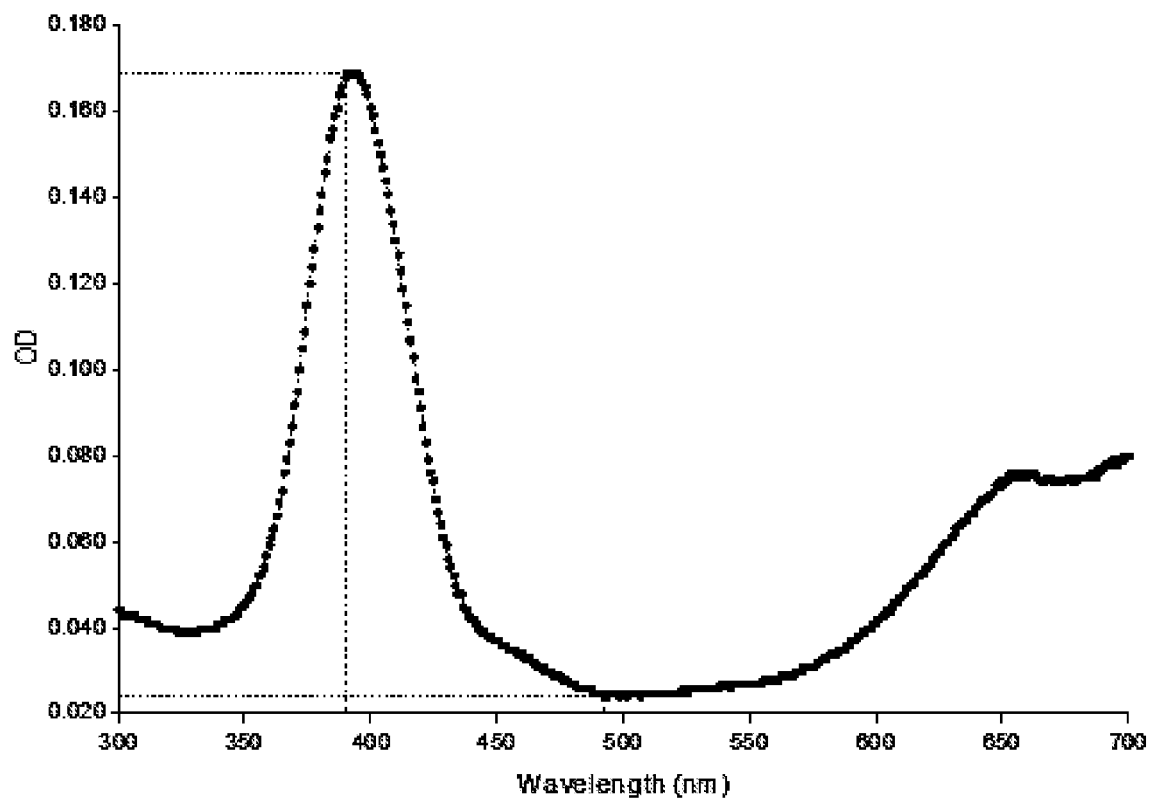
Figure 38F:
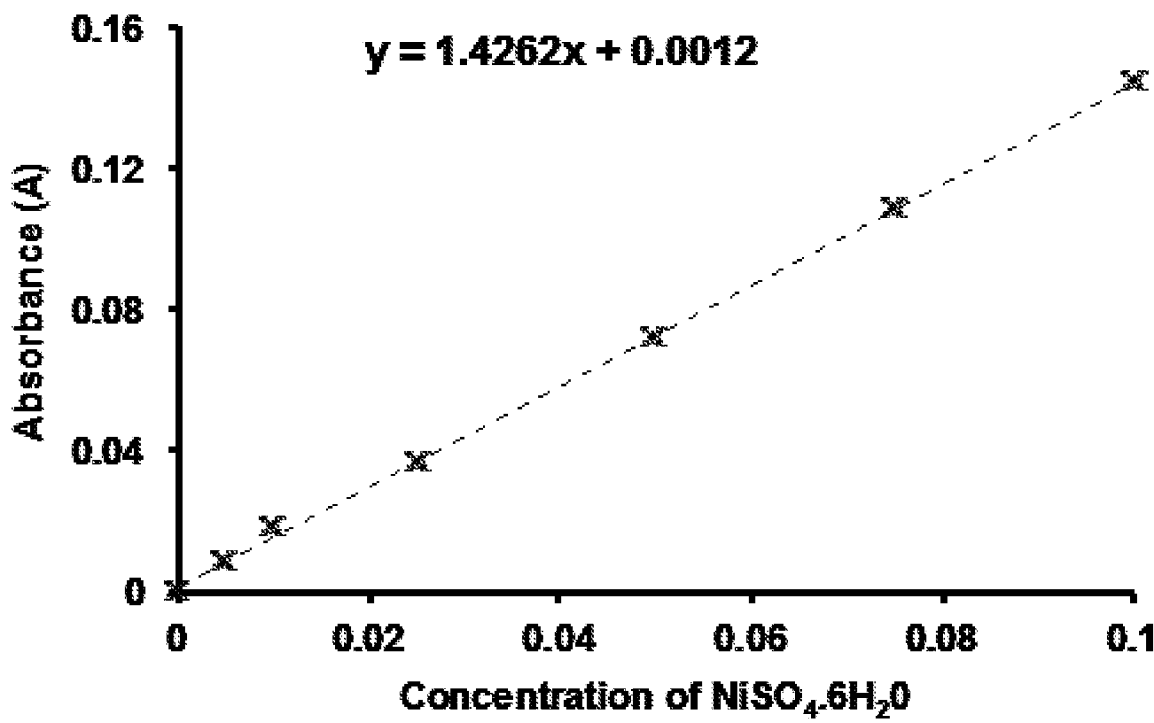
Figure 39:
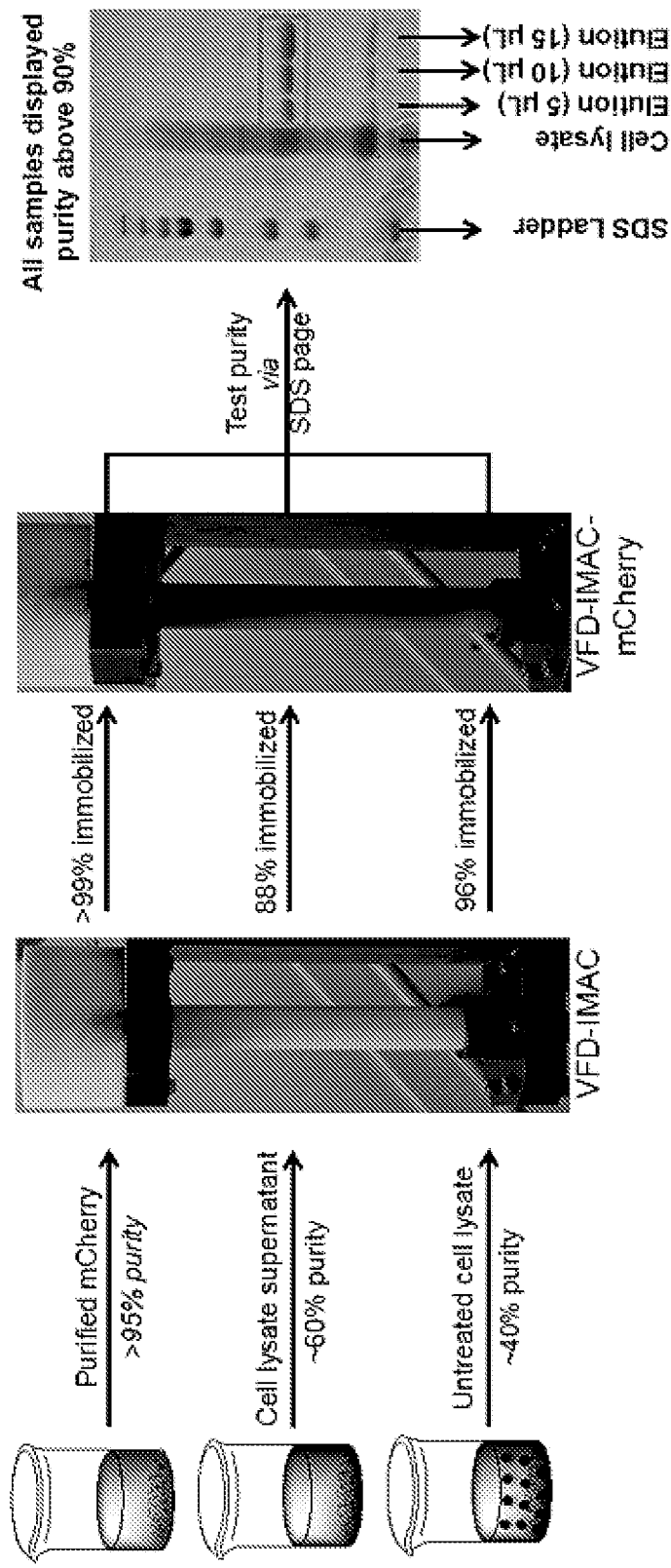
FIG. 39. Depiction of optimization experiments for protein immobilization from treated and non-treated cell lysate. This figure schematically demonstrates the protein immobilization yields for purified mCherry and then centrifuged and non-centrifuged cell lysate. After coating the VFD reactor with IMAC resin, the protein solution is then flowed through the reactor so that the protein of interest is abstracted from the solution, and then subsequently purified.
Figure 40A:
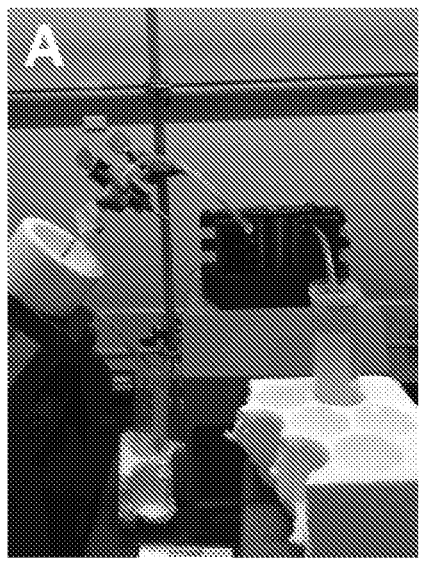
FIGS. 40A-40E. Photographs depicting reactor set up for VFD-mediated protein purification and immobilization.
Figure 40B:
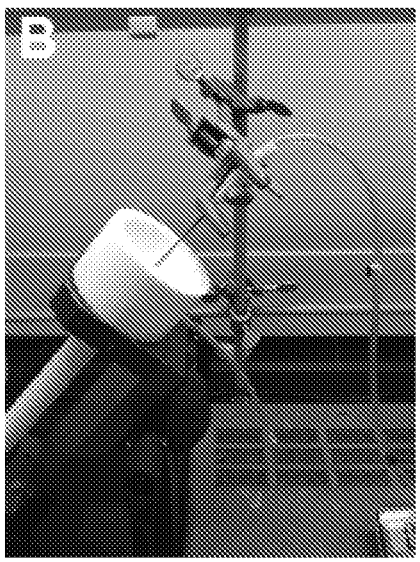
Figure 40C:
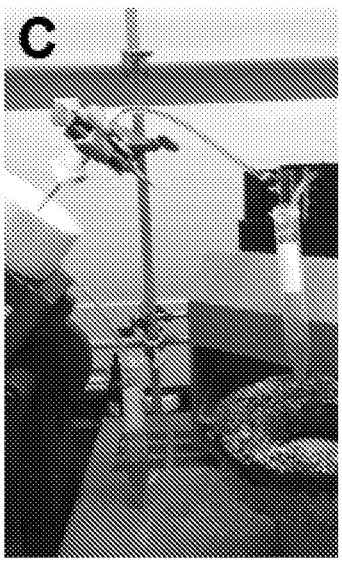
Figure 40D:
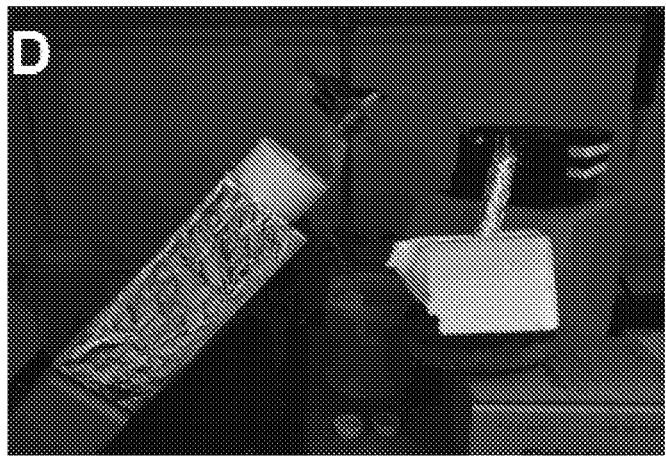
Figure 40E:
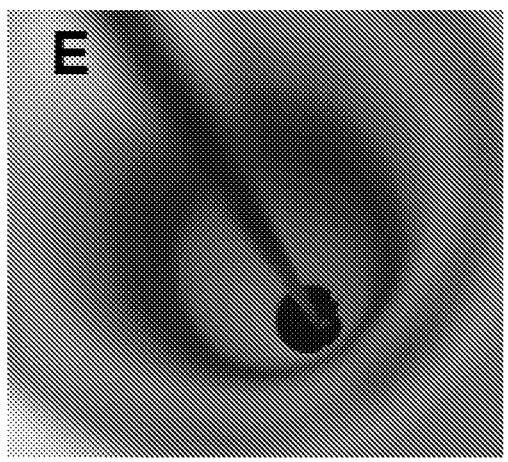

Our laboratory has previously published the plasmid containing the gene for TEAS, thus please refer to this publication for further details [S1]. The pET28-TEAS construct was transformed into *E. coli* BL21 Mar (DE3) cells. The transformed cells were transferred to an LB agar plate supplemented with 50 kanamycin antibiotic, and incubated at 37° C. for 14-16 h. A seed culture was prepared by inoculating a single colony from the plate into 5 mL of LB medium with 50 μg/mL carbenicillin antibiotic before shaking at 225 rpm for 6-7 h at 37° C. in a 15 mL culture tube. The expression culture was then prepared by inoculating 5 mL of the seed culture per 1.0 L of LB media with 50 kanamycin, then shaking at 220 rpm at 37° C. When the optical density of the culture reached $A_{600}$-0.5, the cultures were transferred to an incubator set at 18° C. Once the cultures had reached $A_{600}$-0.65 overexpression of TEAS protein with an N-terminal $His_6$ tag was induced through the addition of 0.5 mM IPTG. The induced expression culture was incubated at 18° C. for 18-20 h shaking at 220 rpm. The cells were harvested and resuspended in buffer (50 mM NaH$_2$PO$_4$, 100 mM NaCl pH 8.0, and 100 µL of Halt Protease Inhibitor Cocktail. The cell lysate was prepared by sonication as previously described, and the supernatant was purified by VFD-mediated purification as described below. Fractions containing purified protein identified by SDS-PAGE were pooled and concentrated with a 3 kDa concentrator. The purity of the protein was confirmed using 12% SDS-PAGE (FIG. 37). Purification to ≥90% homogeneity was desired before subsequent assays.

VFD Reactor Set-Up

The vortex fluidic device (VFD) was set to a tilt angle of 45° relative to the horizontal, with the inclined sample tube rotating at 8 krpm. Below are the methods for continuous flow protein purification, immobilization and elution of the purified protein.

Initial Optimization Studies for Protein Immobilization in Continuous Flow.

For the immobilization process, a series of optimization steps were first performed to allow rapid and efficient protein immobilization. The figures herein detail each optimization step and the outcome.

Initial Studies Protein Purification in Continuous Flow

The VFD was fitted with a 17.7 mm internal diameter sample tube and rotated at 8 krpm at a 45° tilt angle. To the rotating tube was added 6.00 mL of homogenous IMAC-resin to create a thin layer evenly covering the sample tube. The sample tube is then rotated at 25° C. for ten min. At this point, the sample tube rotation is halted, and a jet feed is inserted down the center of the sample tube. The sample tube rotation is then started, and maintained at 8 krpm. The whole process is now performed in continuous flow by passing reagents through a peristaltic or syringe pump and down the jet feed. Once transported down the jet feed, the fluid enters the hemisphere of the sample tube, and then climbs the wall of the sample tube as more fluid is added. Once the fluid exits the sample tube, it is then channeled into a collection flask, or is recycled back into the device.

First, a NiSO$_4$.6H$_2$O solution is flowed through the VFD (20 mL, 100 mM, 1 mL min$^{-1}$) to charge the IMAC resin by creation of the nickel complex as depicted in FIG. 30A. Following this, PBS (20 mL, pH 7.2, 1 mL min$^{-1}$) is added to remove any residual nickel not bound to the IMAC resin. This fraction is collected and disposed in the correct manner Next, the protein solution (purified, a centrifuged cell lysate, or non-centrifuged cell lysate) is passed through the VFD for ten cycles at a flow rate of 1 mL min$^{-1}$. At the end of this process, the protein containing the polyhistidine tag is now bound to the reactor, and the collected supernatant contains unwanted protein. Now, imidazole washes are performed to increase the purity of the protein on the reactor. Gradient washes of 10, 20, 30 and 40 mM imidazole are used (20 mL of each wash, 1 mL min$^{-1}$) and the fractions collected and disposed of. The reactor now contained purified protein. At this stage, if the protein is to be harvested and used for non-VFD reactions it can be eluted with imidazole (250 mM, 30 mL, 1 mLmin$^{-1}$) This fraction is then collected and then dialyzed into the reaction buffer of choice.

If the reactor is to be used directly for biocatalysis in continuous flow, the reaction buffer is simply flowed through (30 mL, 1 mL min$^{-1}$) in equilibrating the reactor for the transformation. The substrate can then be flowed through the reactor at a flow rate and concentration of choice. At the end of the experiment the protein can be eluted and stored as described above. After protein elution from the reactor, the IMAC can be purified in continuous flow ready for the next reaction. For this, a series of reagents are flowed through the reactor:

1. (6 M GuHCl, 0.2 M acetic acid, 20 mL)
2. H$_2$O (20 mL)
3. SDS (2%, 20 mL)
4. Ethanol (20 mL, 25%)
5. Ethanol (20 mL, 75%)
6. Ethanol (20 mL, 100%)
7. Ethanol (20 mL, 25%)
8. H$_2$O (20 mL)
9. EDTA (20 mL, 100 mM, pH 8.0)
10. H$_2$O (20 mL)

At this point, the column can be recharged with the NiSO$_4$.6H$_2$O solution as previously described.

Rapid Protein Purification in Continuous Flow.

Figure 41A:
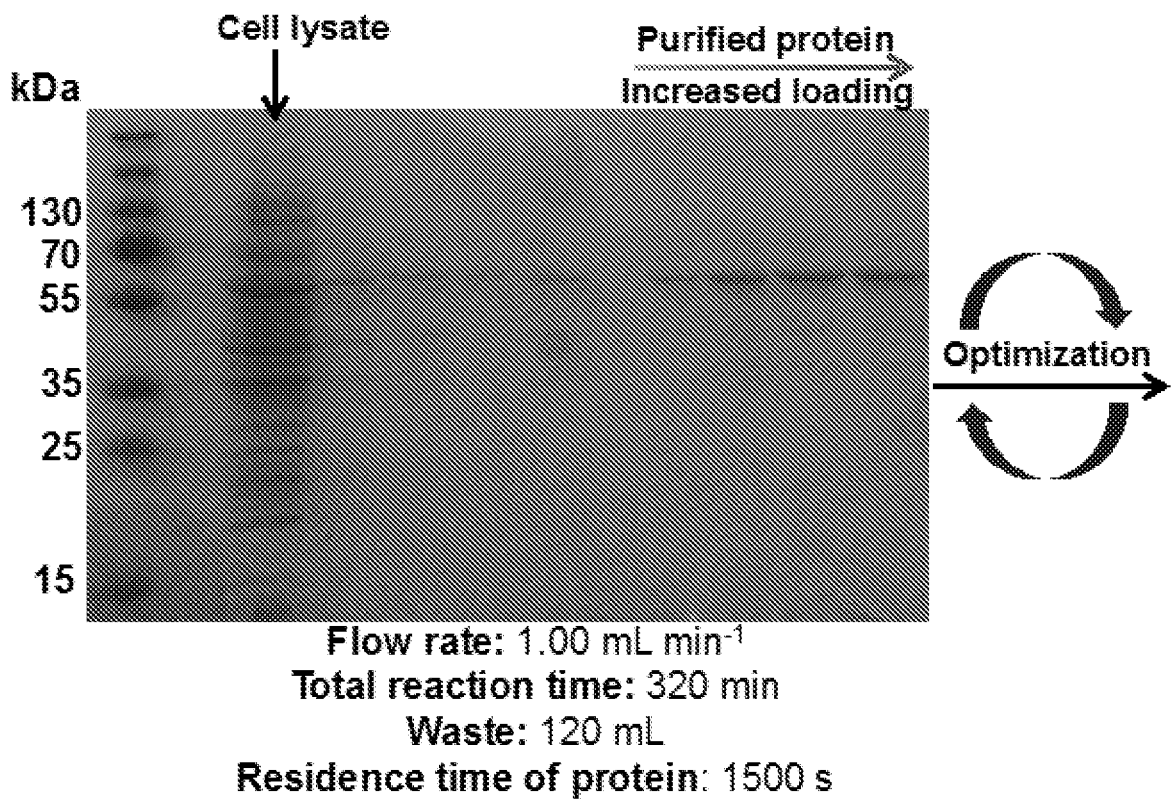
FIGS. 41A-41B. Generating rapid purification for TEAS.
Figure 41B:
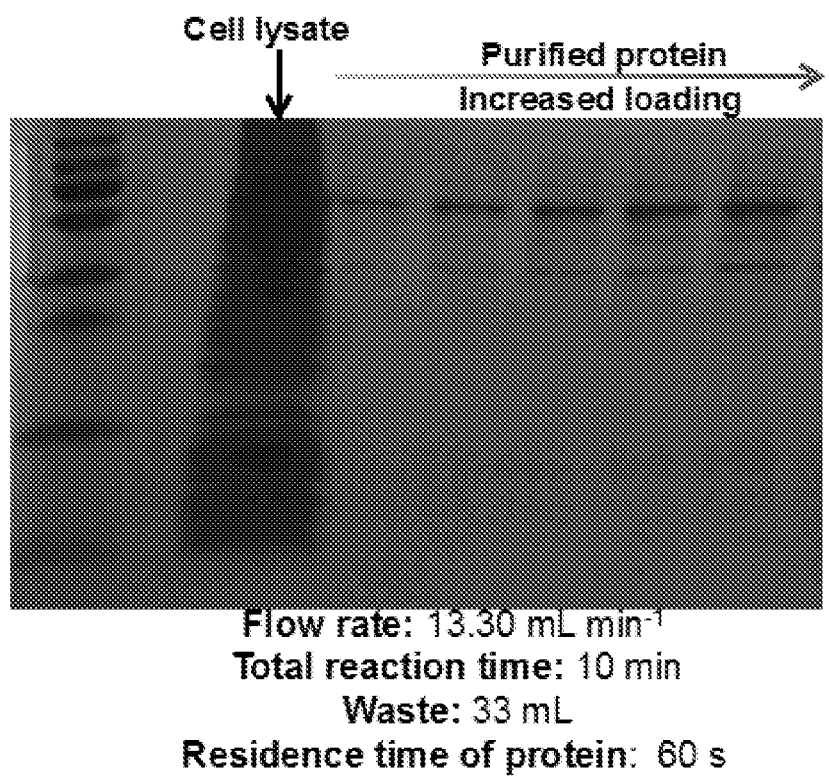
Figure 42:
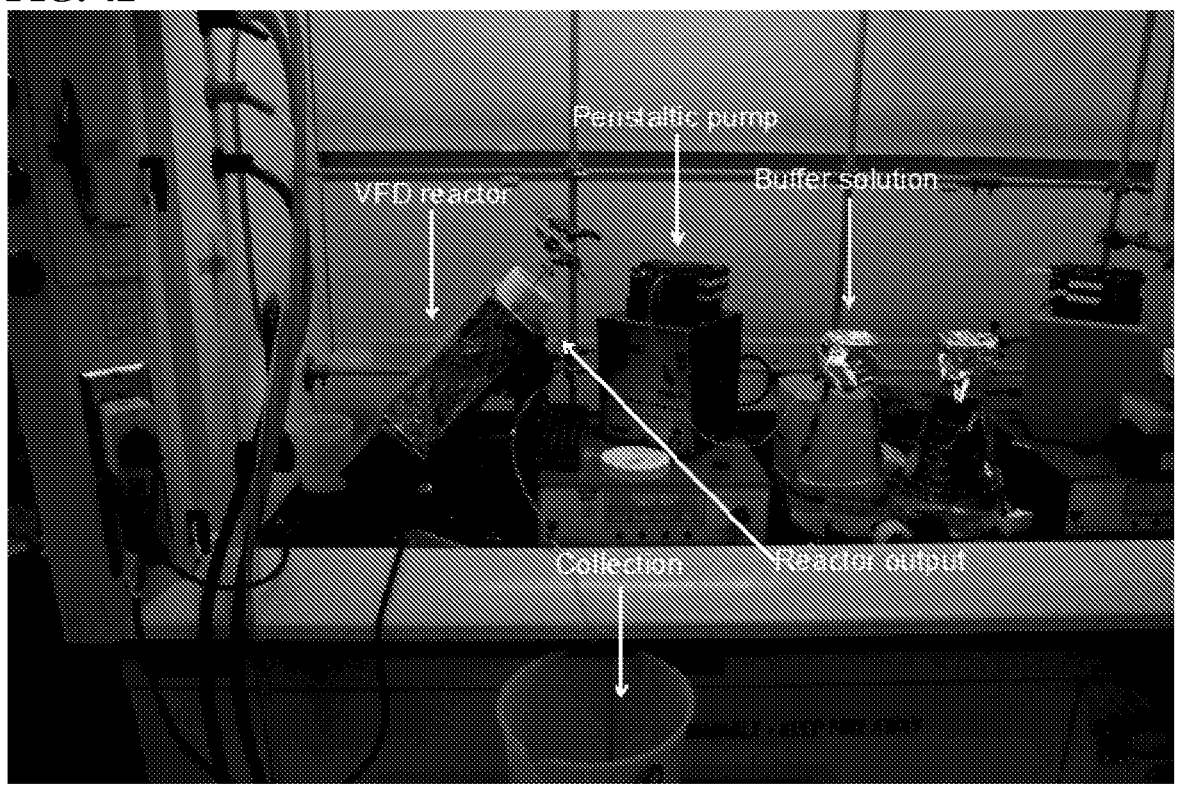
FIG. 42. Photograph of reactor set up for VFD-mediated continuous flow experimentation, showing the main components for the continuous flow experiment described herein: VFD reactor, peristatic pump, buffer solution reservoir, reader output, and collection.

Following purification of all the six proteins described above, the flow rate and quantity of reagents needed were optimized to afford a more rapid and efficient system requiring only ten min. For this optimization, TEAS protein was used, as it was most unstable protein. First to be explored was the flow rate of reagents through the VFD. Using the maximum flow rate of the peristaltic pump (13.30 mL min$^{-1}$) allowed for rapid purification with no visual decrease in the purity of the protein. Furthermore, the quantity of NiSO$_4$.6H$_2$O flowed through the system was reduced to 10 mL, as previous optimization studies reveled that this quantity is sufficient to reach Ni$^{2+}$ saturation on the reactor surface. Furthermore, the quantity of PBS flowed through after the NiSO$_4$.6H$_2$O solution was also reduced to 10 mL. As demonstrated in FIGS. 38A-38F, after five cycles of protein solution through the reactor it seems to reach a state of equilibrium. Thus five cycles of protein solution through the device at 13.30 mL/min still afforded purified protein. The last step in the optimized protocol reduced the volume of imidazole wash solution used. Here, only 10 mL of 40 mM imidazole was flowed through to remove any non-specific binding. Through this process, the total residence time of the protein through the reactor is only 60 s, and the total reaction time was reduced from 320 to only ten min. Importantly, the waste was also reduced from 120 to 33 mL per 20 mL of protein solution (FIGS. 41A-41B).

Continuous Flow Reactions for Testing Immobilization Longevity

To test the longevity of the immobilized protein, a non-centrifuged cell lysate of mCherry was coated to the reactor surface as detailed above. A solution of PBS was then flowed through the reactor for five days, and the quantity of mCherry in the flow through solution quantified using UV visible spectroscopy as detailed above. To determining the percentage of mCherry lost from the surface of the reactor, the protein was eluted from the reactor after five days, and the concentration determined. A differences calculation between the amount of protein leached and the overall protein concentration determined the percentage of protein leached. The experiment was conducted for five days with only 0.34% loss of protein from the surface of the reactor, demonstrating that this approach to protein immobilization has the potential to be run for significantly longer reaction times.

Creating Enzymatic Zones on the Reactor Surface.

To create enzymatic zones on the surface of the reactor surface the following protocol is followed. IMAC solution (3.00 mL per half a reactor) and PBS (3.00 mL, pH 8.0) are added to a 15 mL tube. The tube is shaken vigorously for one min, and then centrifuge at 1 krpm for five min. The supernatant is discarded and NiSO$_4$.6H$_2$O solution is added (10 mL, 100 mM). The tube was then placed on a rotating bed at 4° C. for two h to charge the IMAC resin. After this time, the tube was then centrifuged at 1 krpm for five min. The supernatant was discarded and PBS (3.00 mL, pH 8.0) added. The tube was vigorously shaken for one min. and then centrifuged for five min. at 8 krpm. 95% of the supernatant was removed from the tube and the protein solution (4.00 mL, pH 8.0) added. For kinetic experiments using stripes, purified protein was used to gain accurate kinetic data. The solution is then mixed with a spatula, and then incubated at 4° C. on a rotating bed for two h. After this time, the tube is centrifuged at 1 krpm for five min and then 85% of the supernatant is then discarded.

A sample tube is then inserted into the VFD and rotated at 8 krpm. The protein-bound IMAC was then added to the sample tube by a Pasteur pipette. The IMAC solution is added drop-by-drop to the required zone creating stripes down to a minimum of ~1 cm in width. For every 1 cm zone width, around 250 mg of enzyme bound IMAC is used, as this creates sharp, distinguishable zones. However, for other patterns, a total of 6.00 g of IMAC coats a single sample tube. Once the stripes have been added to the surface of the reactor, the IMAC is left to set for around ten min. After this point, the rotation is stopped for the sample tube, and the jet feed is added down the center of the sample tube as detailed previously. The reactor is now ready for continuous flow biocatalysis.

Phosphodiesterase Reactivity Data.

To optimize reactivity for recombinant expressed phosphodiesterase, enzyme-substrate solutions were subjected to variable reaction conditions including: enzyme concentration, reaction temperature and solvent compatibility. Below each experimental set-up is detailed and the result highlighted.

Phosphodiesterase Concentration Effects.

Figure 45:
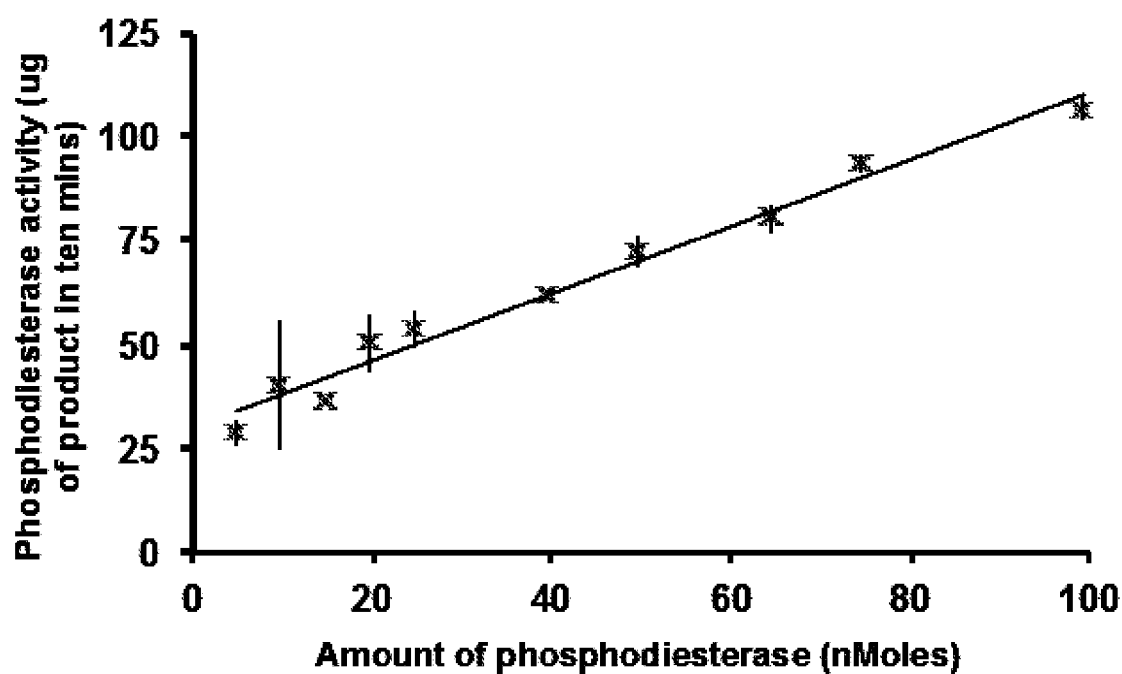
FIG. 45. Monitoring the effect of phosphodiesterase quantity on the liberation of p-nitrophenol. In this experiment, 1000 µL of substrate solution (0.7 mM bis(p-nitrophenyl) phosphate sodium salt) was added to a 2.00 mL sinter vial and the solution was heated to 70° C. over five min. Once temperature had been reached, the required amount of phosphodiesterase was added and the reaction proceeded for ten min. After ten min, the reaction was quenched with 300

Recombinant expressed phosphodiesterase (2.00 mg mL$^{-1}$) was used to explore the enzymes activity (FIG. 45). For this experiment, the buffer was the same as described above, but with no acetonitrile component, and using only a single metal source (1 mM NiCl$_2$.6H$_2$O).

Phosphodiesterase Reaction Temperature Effects.

Recombinant expressed phosphodiesterase (4.96 nMoles) was used to explore the enzymes activity at various temperatures (FIG. 46). For this experiment, the buffer was the same as described above, but with no acetonitrile component, and using only a single metal source (1 mM NiCl$_2$.6H$_2$O).

Phosphodiesterase Solvent Compatibility.

Recombinant expressed phosphodiesterase (4.96 nMoles) was exposed to a range of organic solvents and the enzymes activity monitored (FIG. 47). For this experiment, the buffer was the same as described above, but contained 5% (v:v) of the organic solvent to be tested, and using only a single metal source (1 mM NiCl$_2$.6H$_2$O).

Phosphodiesterase Activity in Varying Levels of Acetonitrile.

Recombinant expressed phosphodiesterase (4.96 nMoles) was used to explore the enzymes compatibility with a range of acetonitrile concentrations (FIG. 48). For this experiment the buffer was exactly the same as described above, but with varying compositions of acetonitrile. Once again, only a singular metal source (1 mM NiCl$_2$.6H$_2$O) was used in this experiment.

Phosphodiesterase Reactivity Profiles in Varying Levels of Acetonitrile.

Recombinant expressed phosphodiesterase (4.96 nMoles) was used to explore the enzymes reactivity profile with higher concentrations of acetonitrile (FIG. 49). For this experiment the buffer was exactly the same as described above, but with various amounts of acetonitrile. Once again, only a singular metal source (1 mM NiCl$_2$.6H$_2$O) was used in this experiment. Longer reaction times were needed for effective conversion.

Alkaline Phosphatase Reactivity Data.

To optimize reactivity for recombinant expressed alkaline phosphatase, enzyme-substrate solutions were subjected to variable reaction conditions including: enzyme concentration, reaction temperature and metal salt preference. Below each experimental set-up is detailed and the result highlighted.

Alkaline Phosphatase and Phosphodiesterase Comparative Data.

In achieving efficient multistep reactivity, reaction temperature and metal dependency of the two enzymes were taken into consideration. Below are graphical representations describing the effects of variable temperature and the effects of different metal ions on the activity of both alkaline phosphatase and phosphodiesterase.

Michaelis-Menten Kinetics.

To achieve effective multistep reactivity in continuous flow, both alkaline phosphatase and phosphodiesterase must be operating at the same rate. First, the catalytic perfection of each protein ($k_{cat}/k_M$) under theoretical limiting conditions was derived (FIGS. 54A-54B). The alkaline phosphatase reaction mixture contained one equivalent of p-nitrophenol, as this is the theoretical maximum of p-nitrophenol present in the system during the multistep reaction. After deriving the $k_{cat}/k_M$ values for both proteins, these values are compared, and the concentration of both enzymes adjusted to ensure that both enzyme zones operate at the same catalytic rate. This was experimentally reflected, as there was exactly a two-fold increase in the amount of p-nitrophenol liberated.

Multistep Synthesis with Alkaline Phosphatase and Phosphodiesterase.

To achieve the multistep reactivity as demonstrated herein, e.g., FIGS. 31A-31C, enzymatic-IMAC zones containing phosphodiesterase and alkaline phosphatase are applied on the surface of the reactor. In this experiment, the required concentration of alkaline phosphatase and phosphodiesterase is first bound to 3.00 mL of homogenous IMAC, and then subsequently added to the reactor surface.

First, homogenous IMAC resin (3.00 mL) was added to a 15 mL falcon tube. After centrifugation at 1 krpm for five min, the supernatant was removed and NiSO$_4$.6H$_2$O solution (3.00 mL, 100 mM) added. This tube was subjected to gentle agitation for two h at 4° C. at which point the tube was once again centrifuged at 1 krpm for five min. The supernatant was discarded and PBS was added (3.00 mL). The tube was inverted several times and then centrifuged. The supernatant was then removed and this process and was repeated three times per tube. After the last volume of PBS had been removed, this silica is now charged and ready to bind the protein of interest.

To a smaller tube (5 mL) was added either phosphodiesterse (5 μL of a 635 μg/mL protein solution) and enzyme buffer (3.95 mL) to afford a 4.00 mL solution with a final concentration of 0.793 μg/mL, or alkaline phosphatase (2.80 mL of a 1638 μg/mL protein solution) and reaction buffer (1.20 mL) to afford a 4.00 mL solution with a final concentration of 1150 μg/mL. These concentrations were determined by the Michaelis-Menten kinetics as described above. The protein solution (4.00 mL) was added to the falcon tube containing the charged IMAC resin and then were subjected to gentle agitation for two h at 4° C. After this time, the falcon tubes were centrifuged at 1 krpm for five min, and 85% of the supernatant was discarded and the remaining slurry was stirred until homogenous. Depending upon how many zones were required for each enzyme (2, 4, 6 or 8), the reactor was split up into zones of equal length. The protein-IMAC solution was then applied to these zones as described above in FIG. 39. In order to use always the same concentration, the 3.00 mL of IMAC-Enzyme solution is evenly shared between the zones.

To test the efficiency of the enzyme zones, bis(PNNP) (2.0 mM) was flowed through the reactor at a flow rate of 0.50 mL min$^{-1}$ at a reactor temperature of 65° C. The first 6.8 mL exiting the reactor were discarded as the system is reaching a point of equilibrium. After this point, small aliquots (1.30 mL) are taken and quenched with the NaOH quench (300 μL). Ten aliquots are taken in total and analyzed as described above. Error is reported as standard deviation around the means (n=10)

References

Example 5

[1] a) J. Staunton, K. J. Weissman, Nat. Prod. Rep. 2001, 18, 380-416; b) S. C. Wenzel, R. Muller, Nat. Prod. Rep. 2007, 24, 1211-1224; c) J. L. Meier, M. D. Burkart, Chem. Soc. Rev 2009, 38, 2012-2045; d) M. A. Fischbach, C. T. Walsh, Chem. Rev. 2006, 106, 3468-3496; e) C. C. Ladner, G. J. Williams, J Ind. Microbiol. Biot 2016, 43, 371-387; f) C. T. Walsh, Accounts Chem. Res 2008, 41, 4-10; [2] K. J. Weissman, Nat. Prod. Rep. 2015, 32, 436-453; [3] a) I. Wheeldon, S. D. Minteer, S. Banta, S. C. Barton, P. Atanassov, M. Sigman, Nat. Chem. 2016, 8, 299-309; b) R. N. Perham, Annu. Rev. Biochem. 2000, 69, 961-1004; c) J. Fu, Y. R. Yang, A. Johnson-Buck, M. Liu, Y. Liu, N. G. Walter, N. W. Woodbury, H. Yan, Nat. Nano. 2014, 9, 531-536; [4] a) A. Adamo, R. L. Beingessner, M. Behnam, J. Chen, T. F. Jamison, K. F. Jensen, J.-C. M. Monbaliu, A. S. Myerson, E. M. Revalor, D. R. Snead, T. Stelzer, N. Weeranoppanant, S. Y. Wong, P. Zhang, Science 2016, 352, 61-67; b) P. L. Heider, S. C. Born, S. Basak, B. Benyahia, R. Lakerveld, H. Zhang, R. Hogan, L. Buchbinder, A. Wolfe, S. Mascia, J. M. B. Evans, T. F. Jamison, K. F. Jensen, Org. Process Res. Dev. 2014, 18, 402-409; c) S. Newton, C. F. Carter, C. M. Pearson, L. de C. Alves, H. Lange, P. Thansandote, S. V. Ley, Angew. Chem. Int. Edit. 2014, 53, 4915-4920; d) A. R. Bogdan, S. L. Poe, D. C. Kubis, S. J. Broadwater, D. T. McQuade, Angew. Chem. Int. Edit. 2009, 48, 8547-8550; e) D. T. McQuade, P. H. Seeberger, J. Org. Chem 2013, 78, 6384-6389; f) T. Tsubogo, H. Oyamada, S. Kobayashi, Nature 2015, 520, 329-332; g) B. Gutmann, D. Cantillo, C. O. Kappe, Angew. Chem. Int. Edit. 2015, 54, 6688-6728; h) F. Levesque, P. H. Seeberger, Angew. Chem. Int. Edit. 2012, 51, 1706-1709; [5] P. Zhang, M. G. Russell, T. F. Jamison, Org. Process Res. Dev. 2014, 18, 1567-1570; [6] C. A. Correia, K. Gilmore, D. T. McQuade, P. H. Seeberger, Angew. Chem. Int. Edit. 2015, 54, 4945-4948; [7] a) L. Yasmin, X. Chen, K. A. Stubbs, C. L. Raston, Sci. Rep. 2013, 3, 2282; b) L. Yasmin, T. Coyle, K. A. Stubbs, C. L. Raston, Chem. Commun. 2013, 49, 10932-10934; c) J. Britton, S. B. Dalziel, C. L. Raston, Green Chem. 2016, 18, 2193-2200; d) J. Britton, S. B. Dalziel, C. L. Raston, RSC Adv. 2015, 5, 1655-1660; [8] a) J. Britton, J. M. Chalker, C. L. Raston, Chem. Eur. J. 2015, 21, 10660-10665; b) J. Britton, J. W. Castle, G. A. Weiss, C. Raston, Chem. Eur. J. 2016, DOI: 10.1002/chem.201602373; [9] T. Z. Yuan, C. F. G. Ormonde, S. T. Kudlacek, S. Kunche, J. N. Smith, W. A. Brown, K. M. Pugliese, T. J. Olsen, M. Iftikhar, C. L. Raston, G. A. Weiss, ChemBioChem 2015, 16, 393-396; [10] J. Britton, L. M. Meneghini, C. L. Raston, G. A. Weiss, Angew. Chem. Int. Edit. 2016; [11] J. Britton, C. L. Raston, G. A. Weiss, Chem. Commun. 2016, 52, 10159-10162; [12] J. E. Diaz, C.-S. Lin, K. Kunishiro, B. K. Feld, S. K. Avrantinis, J. Bronson, J. Greaves, J. G. Saven, G. A. Weiss, Protein Sci. 2011, 20, 1597-1606; [S1] J. E. Diaz, C.-S. Lin, K. Kunishiro, B. K. Feld, S. K. Avrantinis, J. Bronson, J. Greaves, J. G. Saven, G. A. Weiss, Protein Science 2011, 20, 1597-1606.

Example 6—Rapid Protein Immobilization for Thin Film Continuous Flow Biocatalysis Abstract.

A versatile enzyme immobilization strategy for thin film continuous flow processing is disclosed. Here, non-covalent and glutaraldehyde bioconjugation are used to immobilize enzymes on the surfaces of borosilicate reactors. This approach requires only ng of protein per reactor tube, with the stock protein solution readily recycled to sequentially coat >10 reactors. Confining reagents to thin films during immobilization reduced the amount of protein, piranha-cleaning solution, and other reagents by ~96%. Through this technique, there was no loss of catalytic activity over 10 h processing. The results reported here combines the benefits of thin film flow processing with the mild conditions of biocatalysis.

Introduction.

Nature builds diverse and complex natural products through assembly line biosynthesis. Polyketide synthases for example, are multi-domain proteins that perform iterative processes to synthesize a large range of secondary metabolites [1,2]. Continuous flow has emerged as an analogous, in vitro process, for synthesizing compounds through multistep processes.

Enzymes can perform a wide range of transformations including reductions [3,4], oxidations [5,6], cyclization [7,8], aziridinations[9] and nitration reactions [10]. Improving the performance of these enzymes typically relies on directed evolution [11,12] and computational design [13, 14]. These widely used techniques can improve reaction rates and enzyme promiscuity to accept non-natural substrates. Although such approaches can increase the utility and adoption of biocatalyzed transformations, scaling up enzyme-catalyzed reactions can be challenging.

Translating reactions into continuous flow can increase reaction yields and safety [15,16], aid multistep transformations [17,18], and decrease human effort and waste [19,20]. Furthermore, enzymes in synthetic pathways can improve sustainability metrics by avoiding hazardous solvents and toxic metals. Combining the benefits of continuous flow and biocatalysis offers numerous advantages such as processing with immobilized enzymes and rapid scale-up. Continuous flow biocatalysis has thus increasingly become a focus of many laboratories, as shown in a few examples [21,24].

Immobilizing enzymes can increase their industrial viability by creating reusable biocatalysts with potentially improved reactivity, purity, specificity, selectivity, thermal stability and pH tolerance [25-30]. Given this importance, many immobilization strategies have been described, including attachment to magnetic nanoparticles and nanomaterials [31,32], supports through antibody-specific epitopes and crosslinking [33], and also entrapment within a polymer network [34]. Glutaraldehyde crosslinking was chosen here due to its simplicity, commercial availability, and success in previous immobilization studies [35,36].

Results and Discussion.

Recently, we have focused on utilizing thin films to mediate protein folding [37], biocatalysis [38] and molecular assembly line processes [39]. This involves processing in a vortex fluidic device (VFD) which confines reagents to a ≈250 µM thin film. Here, micro-mixing, shear stress and mechanical vibrations [40,41] can operate upon reagents to increase reaction yields and efficiencies. Processing in a single VFD with a 20 mm external diameter reactor can achieve flow rates up to 20 mL min$^{-1}$. Larger scale processing is possible by applying multiple VFDs. In pursuing new multistep transformations, we have recently embarked on exploring thin film continuous flow biocatalysis. In future experiments, using enzymes alone, or in conjunction with organic reagents will require immobilization of minute quantities of protein for efficient continuous flow reactors.

Unlike other continuous flow systems, the VFD reactor is made from borosilicate glass. This material can simplify bioconjugation, as explored systematically here. APTES (3-aminopropyl triethoxysilane) was coupled to the reactor surface to create a layer of nucleophilic amines (FIG. 56, Step a). This APTES modified reactor was then used for rapid covalent and non-covalent immobilization. Non-covalent immobilization can be achieved though surface-exposed functionalities on the protein interacting with the APTES layer through salt bridges and hydrogen bonds (FIG. 56, Step b). In contrast, covalent immobilizations used surface-exposed lysine sidechains (also thiols, phenols and imidazoles [36]) on the protein to form imine and amine bonds with a glutaraldehyde-modified APTES linker (FIG. 56, Steps c and d). The structure of the glutaraldehyde linker and resultant cross-link has been simplified in FIG. 56; in aqueous solution, for example, many different forms of glutaraldehyde can exist [35,36].

Coating the reactor with APTES required optimizing a three-step process. First, treatment with piranha solution exposes high concentrations of silinols on the reactor surface. Although the reactor can be filled with piranha solution (50 mL), confining 3 mL to a thin film for one min. offers the same cleaning efficiency, whilst reducing the volume of this highly hazardous fluid by 94%. After washing and drying, the reactor surface is then derivatized with a dilute APTES solution (79.5 mM, 60 µL in 3 mL MeOH). Again, confining reagents to a thin film reduced the quantities of MeOH and APTES required by 94%. Lastly, the APTES-modified surface is heated to 160° C. to drive the condensation reaction to completion (FIG. 56, Step a).

Figure 57A:
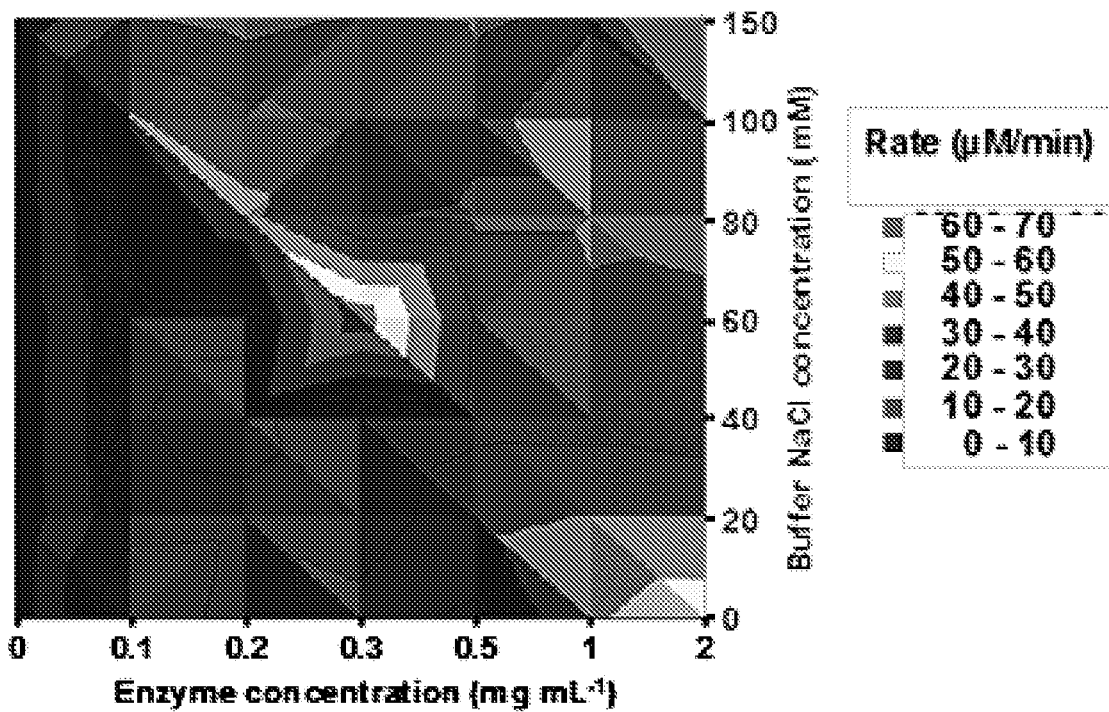
Figure 57B:
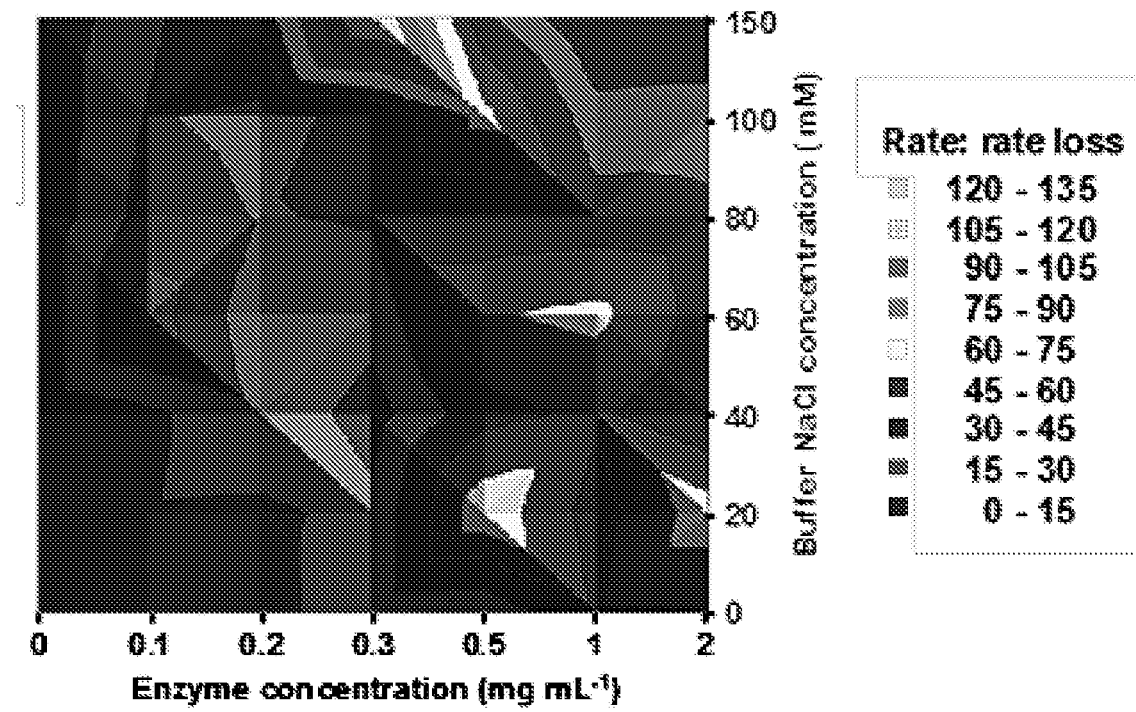
Figure 57C:
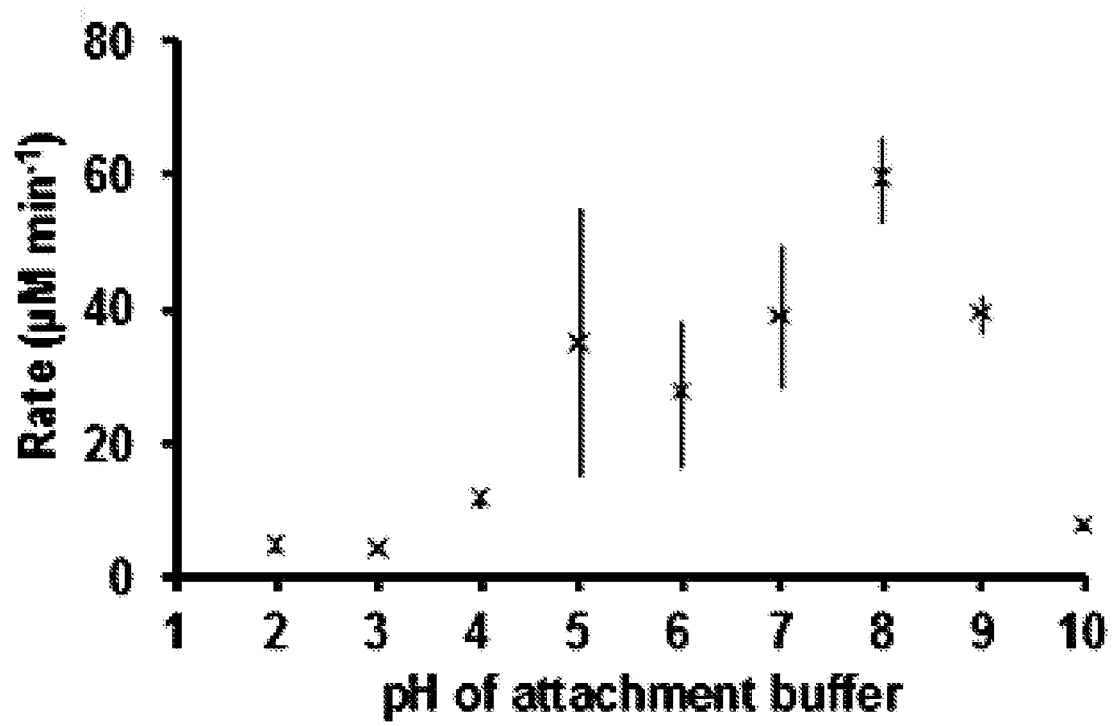
Figure 57D:
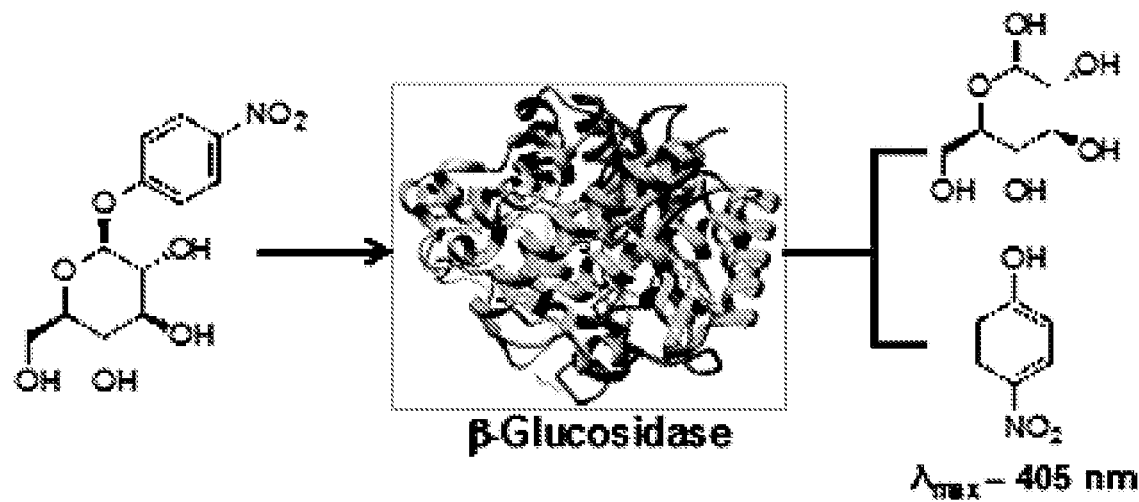

Non-covalent immobilization is sometimes preferred to covalent immobilization as introducing random covalent bonds can distort enzymes' structures [28]. For testing a large number of non-covalent immobilization variables, a colorimetric enzyme-substrate assay was used, β-glucosidase and 4-nitrophenyl β-D-glucopyranoside, respectively. This assay offers high throughput conditions (5 min per reaction), an effective quench solution, and stability to vortexing conditions (FIG. 57D) [38].

β-Glucosidase and buffer salt concentrations play an integral role in non-covalent immobilization efficiency and activity. Varying both of these variables simultaneously generated a contour plot (FIG. 57A). A β-glucosidase concentration of 0.3 mg mL$^{-1}$ was optimal, with variation either side of this concentration decreasing immobilization efficiency. Furthermore, confining the protein solution to a thin film for immobilization reduced the volume of protein solution used from 50 to 3 mL, i.e., a reduction of 94% (15 mg to 0.9 mg). Additionally, 60 mM NaCl in PBS was found to be optimal, but taking into account rate loss over time revealed that 150 mM NaCl in PBS is superior, with no decrease in substrate transformation rate over 30 min (FIG. 57B). The higher salt concentration during adsorption could increase the strength of the enzyme-APTES interaction [42].

Next we examined the conditions required for covalent immobilization. Covalent immobilization can increase enzyme stability greatly through the addition of short spacers off the reactor surface [27]. Reacting glutaraldehyde with the APTES-coated reactor, followed by the sequential addition of β-glucosidase solution afforded an imine linker for immobilization (FIG. 56, Step c). Furthermore, this imine can be reduced to the amine with NaBH$_3$CN solution (FIG. 56, Step d) [43,44]. Notably, lysine residues in the active site are typically uninvolved in catalysis, and this immobilization strategy is therefore unlikely to perturb enzyme function [36]. Once again, these steps were performed in the thin film, resulting in a 96% reduction in quantity of buffer and reagents required.

Figure 58A:
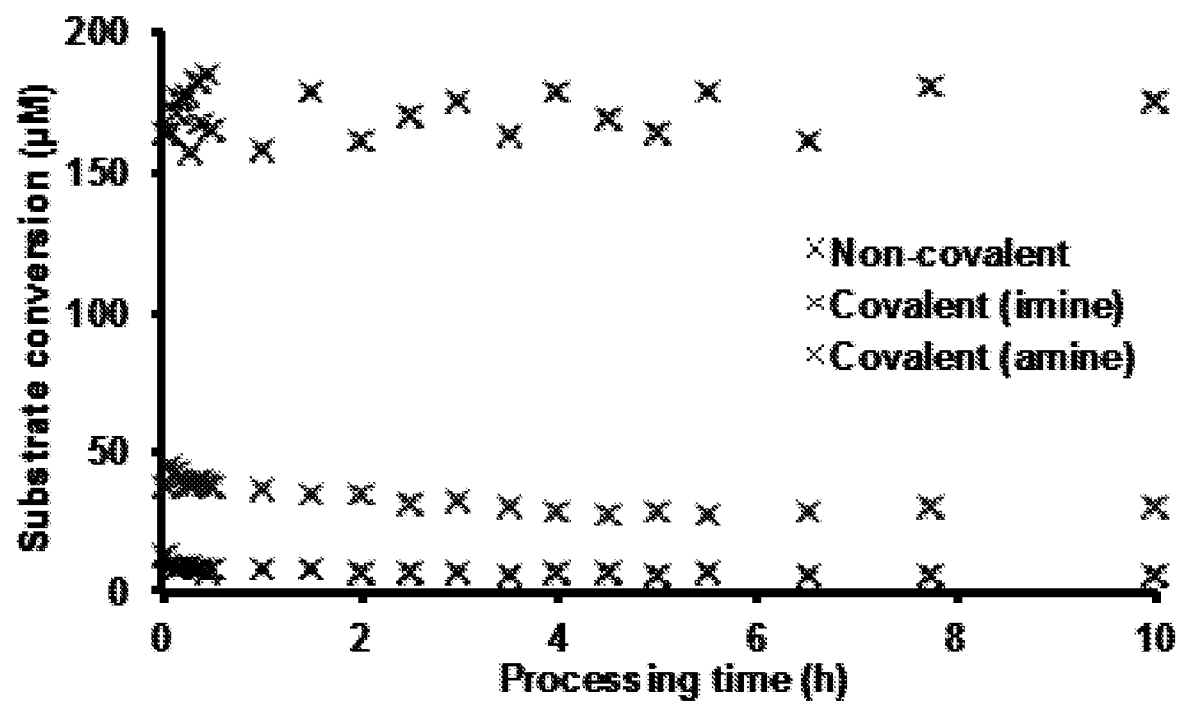
Figure 58B:
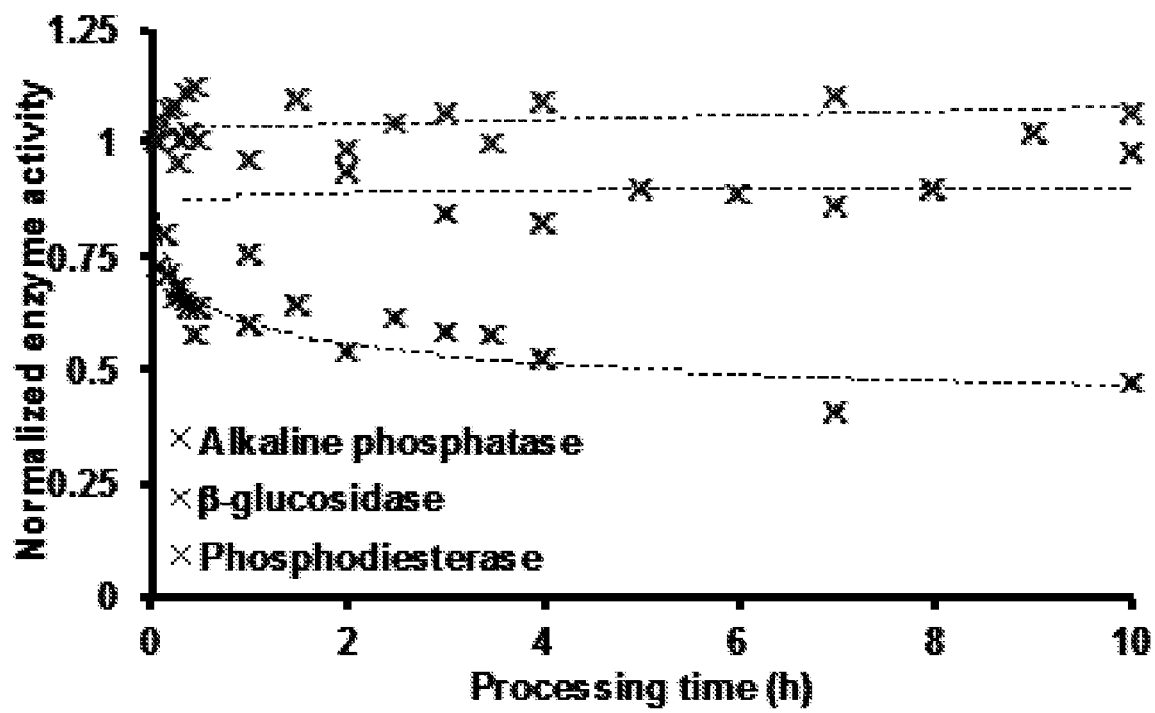
Figure 58C:
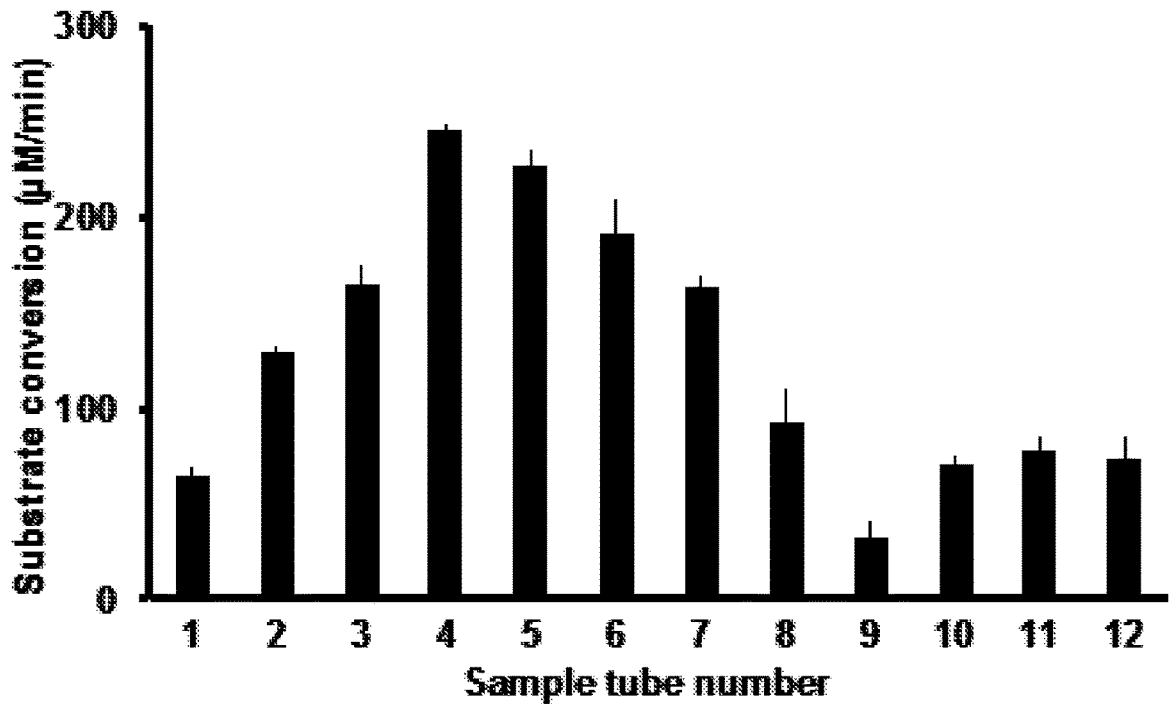

Switching to covalent immobilization increased the yields of conjugated enzyme with a concomitant increase in the rates of substrate conversion. Although a slight increase in enzyme immobilization efficiency and reaction rate results from switching to covalent immobilization, the reduction of imine to amine provides a dramatic improvement. This reduction prevents hydrolysis of the imine, thus increasing the concentration of protein on the surface of the reactor tube (FIG. 58A). To test the stability of these immobilization strategies, each immobilized enzyme was subjected to a continuous flow reaction at 1.0 mL min$^{-1}$; all immobilizations demonstrated excellent stability, with no loss of activity after 10 h of processing recorded with the amine linker (FIG. 58A).

Our second requirement for this immobilization strategy was to make it general. Given that proteins have a hydrophilic surface, most enzymes have a surface-exposed lysine residue for immobilization. As small quantities of protein are used in this immobilization strategy (0.9 mg), we were able to explore phosphodiesterase, a poorly overexpressing recombinant protein. Immobilizing phosphodiesterase and a commercially available alkaline phosphatase via amine-glutaraldehyde immobilization (FIG. 56, Step c) resulted in stable levels of substrate conversion for 10 h in continuous flow (1 mL min$^{-1}$, FIG. 58B).

The final criterion for this immobilization method was to increase immobilization efficiency. This process already uses a low quantity of protein, but, to address efficiency further, it would be useful to know how much of protein is on the surface of the reactor. Two complimentary experiments revealed that 15.4 to 69.8 ng of β-glucosidase are present on the surface of the reactor after covalent immobilization (FIGS. 59-60). This surprising result opened up the possibility to recycle the protein stock solution (0.3 mg mL$^{-1}$). Indeed, recycling the stock solution of β-glucosidase allowed the coating of 12 reactor tubes with no observable decrease in substrate conversion between the first tube and the last (FIG. 3c). We were unable to identify why recycling the enzyme solution increased substrate conversion levels for sample tubes 2-8. This trend subsides with additional sample tubes, and we believe that it is an experimental artifact.

Figure 58D:
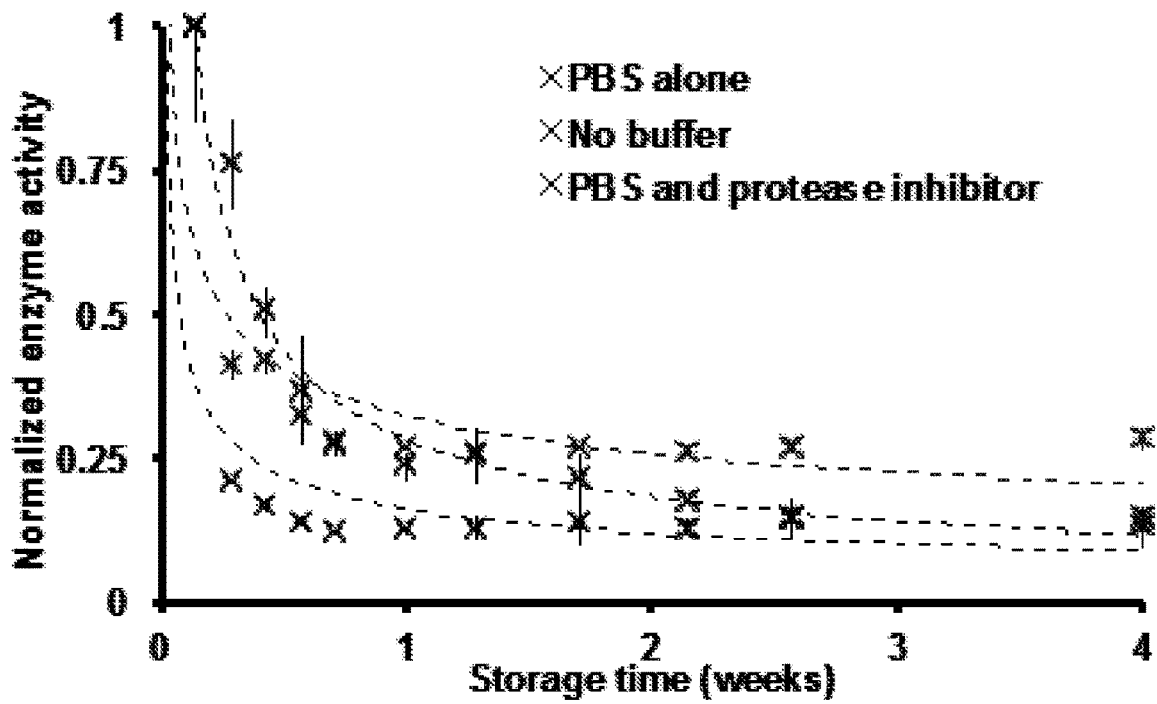

Lastly, sample tube storage was investigated, which was deemed important given that sample tubes are often transported to other laboratories. Surprisingly, a dry sample tube bearing surface bound β-glucosidase provided reasonable substrate conversion after one month of storage (4° C.

storage, 19 μM min$^{-1}$ conversion, FIG. 58D). It is believed that the decrease in substrate conversion can result from a combination of protein leaching and unfolding.

In conclusion, a rapid and general technique for protein immobilization onto a thin film continuous flow reactor has been developed. Importantly, using thin films for reagent confinement reduced the volume of protein solution, piranha solution, APTES, MeOH, glutaraldehyde, NaBH$_3$CN and a range of buffers by an average of 95%. The ability to use a small amount of protein (900 μg) to coat >10 sample tubes provides a general strategy to increase the efficiency of enzyme-mediated transformations in continuous flow. Incorporating biocatalysts into multistep processes offers the potential to create complex molecules using nature's machinery. The findings reported here will facilitate biocatalysts by allowing low expressing proteins to be used in complex substrate transformations such as natural products and pharmaceutical ingredients.

Supplemental Experimental

Example 6

All immobilizations and substrate transformations experiments were performed at 8 krpm rotational speed with a tilt angle of 45° relative to the horizontal position. To test the immobilization efficiency, the confined mode of operation was used with β-glucosidase as the model enzyme. For immobilization efficiency experiments, the following analysis was performed: first, β-D-glucopyranoside (1.50 mL, 0.01 M) was added to the sample tube by pipette, the sample tube was then capped and rotated for 5 min. Thereafter, the substrate solution was removed and added to an Eppendorf tube (2 mL) containing a quenching solution (NaOH-glycine buffer, 0.7 M glycine, pH 10.8, 200 μL). To analyze substrate conversion levels, 100 μL of this solution was then transferred to a UV transparent, 96-well microtiter plate (Costar), and the absorption at 405 nm recorded. Each sample tube was tested six consecutive times, with each set of reaction conditions tested on two individual sample tubes. The error reported indicates the standard deviation around the mean (n=12).

Preparation of the APTES Coated Sample Tube.

FIG. 61 depicts preparation of the APTES coated sample tube. A 20 mm external diameter sample tube was loaded into the VFD and then fresh piranha solution (3 mL) was added. The sample tube was capped by a B19 Suba Seal and then rotated at 8 krpm for 1 min. Note: the piranha solution is highly dangerous and corrosive. This step should only be performed by an experienced, well-trained technician expert in appropriate safety measures. After rotation, the sample tube was emptied before washing with diH$_2$O (10×10 mL) and then oven-dried for 2 h at 160° C. Next, the sample tube was removed from the oven and immediately capped. After cooling to ambient temperature, MeOH (3 mL) was added to the sample tube along with APTES (60 μL). The sample tube was then capped, loaded into the VFD, and rotated at 8 krpm for 30 min. Next, the sample tube was rinsed with MeOH (6×5 mL), and heated (1 h, 160° C.) in an oven. The sample tube was then cooled to ambient temperature before usage. The reaction shown above is a simplified representation of the APTES-treated surface [S1,S2].

Non-covalent immobilization. FIG. 62 depicts non-covalent immobilization of proteins on APTES coated sample tube. The enzyme to be immobilized was solubilized (3 mL, 0.30 mg/mL in PBS (150 mM NaCl, 2.7 mM KCl, 10 mM Na$_2$PO$_4$, 1.8 mM KH$_2$PO$_4$,) pH 8.0) and then added to a freshly prepared APTES-coated sample tube. The sample tube was then capped, loaded into the VFD, and rotated at 8 krpm for 30 min. Next, the sample tube is removed from the VFD and washed with PBS (5×5 mL, pH 8.0) and then sodium acetate (50 mM, pH 5.0) to create a non-covalent immobilized enzyme reactor. The sample tube surface must not be allowed to dry completely (especially in vacuo) as such conditions could denature the protein Immediate usage of the enzyme immobilized sample tubes is recommended, as storage decreases activity, as described in FIG. 58D.

Imine-Glutaraldehyde Cross-Linker Immobilization.

FIG. 63 depicts imine-glutaraldehyde cross-linker immobilization. Glutaraldehyde solution (90 μL in 3.00 mL PBS) was added to a freshly coated APTES sample tube. The sample tube was then capped, and inserted into a VFD. The sample tube was rotated at 8 krpm for 30 min to introduce the APTES-glutaraldehyde cross-linker. After rotation, the sample tube is then rinsed with PBS (6×5 mL) and inverted to remove the majority of the buffer solution. After 10 min, enzyme immobilization was carried out as described above for the non-covalent immobilization. We suggest immediate usage of the enzyme-immobilized, sample tubes as storage decreases activity as described in FIG. 58D.

Amine-Glutaraldehyde Cross-Linker Immobilization.

FIG. 64 depicts amine-glutaraldehyde cross-linker immobilization. Glutaraldehyde solution (90 μL in 3.00 mL PBS) was added to a freshly coated sample tube. The sample tube was then capped, and inserted into a VFD. The sample tube was rotated at 8 krpm for 30 min to create the APTES-glutaraldehyde cross linker. After rotation, the sample tube was then rinsed with PBS (6×5 mL) and inverted to remove the majority of the buffer solution. The enzyme immobilization step was then carried out as described above. Following this, the sample tube was removed from the VFD and washed with PBS (5×5 mL, pH 8.0), and inverted to remove the majority of the buffer solution. The sample tube was then loaded back into the VFD before addition of NaBH$_3$CN (18.8 mg) in sodium acetate buffer (50 mM, pH 5.0, 3.00 mL). The sample tube was then capped and rotated at 8 krpm for 30 min. Next, the sample tube was rinsed with sodium acetate buffer (2×5 mL) and then inverted for 10 min to remove excess buffer, and to afford the amine-glutaraldehyde cross linker Immediate usage of the enzyme immobilized sample tubes is recommended as storage decreases activity as described in FIG. 58D.

Enzymes, Buffers and Assays

Enzymes.

Alkaline phosphatase was purchased from Life Technologies (Fast thermosensitive alkaline phosphatase, 1 U/μL, 0.11 mM, 4.4 mg/mL). β-glucosidase was purchased from Sigma and Aldrich (Lyophilized powder, 2 U/mg). These enzymes were used without further purification. Phosphodiesterase (2 mg/mL) was prepared using bacteria expression as previously described [S3] and purified using immobilized metal affinity chromatography to 95% purity. Quantitates and concentrations for the enzymes and substrates used in the continuous flow experiments as detailed herein. The flow rate used for this experiment was 1.0 mL/min with the continuous flow set up detailed previously [S4].

Alkaline Phosphatase Conditions.

The reaction is depicted following.

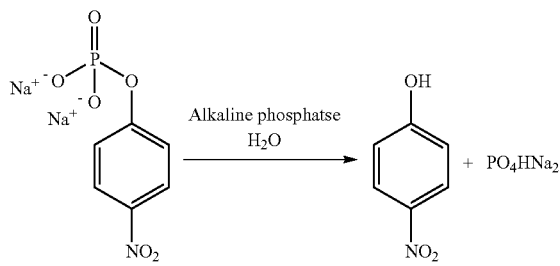

The p-nitrophenol phosphate substrate solution (0.01 M in 1.0 M diethanolamine) was prepared as follows: 140 g of diethanolamine was added to 1.0 L of $H_2O$, then the pH of the solution was adjusted to pH 9.8 using 5 M HCl. This buffer was further diluted to 1 M diethanolamine, and then 500 µL of 1 M $MgCl_2$ was added. The resulting buffer was filtered-sterilized through a 0.22 µm filter (Corning), and stored wrapped in aluminum foil at 4° C. In creating the active substrate solution, p-nitrophenol phosphate (3.714 g, 0.01 M) was added to this buffer and this solution was then immediately used. The enzyme solution (0.25 mg/mL) was formulated by adding alkaline phosphatase (170 µL) to PBS (3.00 mL, pH 8.0) and then used immediately for immobilization. Sampling occurred at the times indicated in FIG. 58B. For this sampling method, a 1.6 mL aliquot was collected from the continuous flow exit, and was immediately quenched with a NaOH solution (4.0 M, 150 µL). The aliquot was then analyzed via absorption spectroscopy as described above. The molar absorption coefficient of p-nitrophenol after the quench described above was 15644 $M^{-1}$ $cm^{-1}$.

β-Glucosidase Conditions.

The reaction is depicted following.

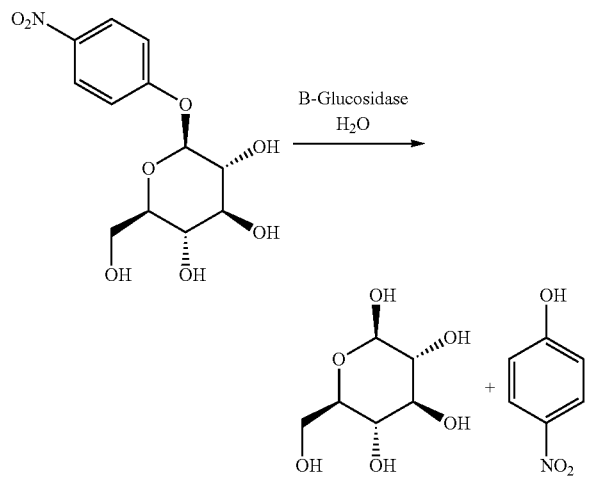

The 4-nitrophenyl β-D-glucopyranoside substrate solution (0.01 M in 50 mM sodium acetate) was prepared as follows: 4.37 g sodium acetate was dissolved in 1.0 L $diH_2O$ and ≈1.1 mL of glacial acetic acid to generate a buffer of pH 5.0. The buffer was then filtered-sterilized through a 0.22 µm filter and stored at 23±2° C. To formulate the active substrate solution, 4-nitrophenyl β-D-glucopyranoside (3.125 g, 0.01 M) was added to this buffer, and was used immediately. The enzyme solution (0.30 mg/mL) composed of β-glucosidase (3 mg) added to 10 mL of PBS (3.00 mL) was immediately used for immobilization. Sampling occurred at the times indicated in FIG. 58B. For this sampling method, a 1.6 mL aliquot was collected from the continuous flow exit and was immediately quenched with glycine-NaOH solution (0.7 M glycine, pH 10.8, 200 µL). The aliquot was then analyzed via absorption spectroscopy as described above. The molar absorption coefficient of p-nitrophenol after the quench described above was 9413 $M^{-1}$ $cm^{-1}$.

Phosphodiesterase Conditions.

The reaction is depicted following.

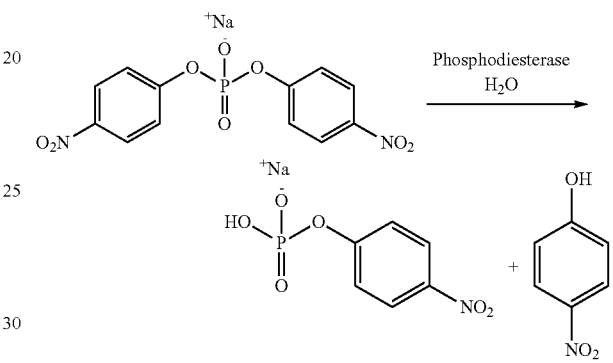

The bis(p-nitrophenyl)phosphate substrate solution (0.7 mM in 50 mM diethanolamine) was prepared as follows: diethanolamine (5.257 g, 50 mM) and NaCl (2.320 g, 40 mM) were added to 1.0 L of $H_2O$. The pH of the solution was adjusted to pH 9.8 with 5 M HCl. Following this, $NiCl_2 \cdot 6H_2O$ (237 mg, 1.0 mM) was added to the solution and the resulting buffer was then filtered-sterilized through a 0.22 µm filter (Corning), and stored wrapped in aluminum foil at 4° C. To create the active substrate solution, sodium bis(p-nitrophenyl)phosphate (237 mg, 0.7 mM) was added to this buffer, and the solution was used immediately. The enzyme solution (0.30 mg/mL) was formulated by adding phosphodiesterase (450 µL) to PBS (3.00 mL), and the solution used immediately for immobilization. Sampling occurred at the times indicated in FIG. 58B as follows. A 1.6 mL aliquot was collected from the continuous flow exit and was immediately quenched with a NaOH (4.0 M, 300 µL). The aliquot was then analyzed via absorption spectroscopy as described above. The molar absorption coefficient of p-nitrophenol after the quench described above was 4242 $M^{-1}$ $cm^{-1}$.

Determination of the Amount of β-Glucosidase Attached to the Reactor Surface.

To determine the quantity of β-glucosidase on the surface of the reactor, two complimentary methods were used. The first method quantified the enzyme removed during the wash steps; thus, estimation of quantities of β-glucosidase adhering to the surface was simply the difference between enzyme levels in the initial and the wash solutions. The second method determines the amount of β-glucosidase present by monitoring substrate conversion rates for the modified surface. A calibration plot with substrate conversion rates allowed determination of quantities of enzyme. Both methods provided similar and complementary results.

Method 1: Comparing Initial and Wash Solutions of Enzyme Concentrations.

This method quantifies the amount of β-glucosidase washed out of the tube after immobilization with a simple difference calculation used to determine enzyme immobilization on the reactor surface. This method assumes that no enzyme is lost to unfolding during the half hour for this experiment.

The calibration curve required enzyme solutions at three different concentrations, which were prepared as follows. β-glucosidase at the indicated quantities (0.90, 0.60 or 0.3 mg) was added to PBS (3 mL, pH 8.0). Each solution was then added to a separate 500 mL volumetric flask. The 500 mL volumetric flasks were then filled with PBS (50 mL, pH 8.0) and then sodium acetate buffer (447 mL, 50 mM, pH 5.0).

The amount of β-glucosidase washed out of the tube after immobilization by non-covalent and imine-glutaraldehyde cross-linking was determined with the following procedure. First, the sample tube was rinsed with PBS (50 mL, pH 8.0) and the wash solutions added to a 500 mL volumetric flask. The contents of the volumetric flask were then diluted to 500 mL with sodium acetate buffer (50 mM, pH 5.0). The pH for the wash steps can maximize enzyme immobilization during this processing (pH 8.0), and switching to pH 5.0 allows the enzyme catalysis assay to proceed at its optimal pH.

The following protocol quantified enzyme activities and therefore enzyme concentration. Each enzyme solution (500 μL) was added to 4-nitrophenyl β-D-glucopyranoside solution (500 μL, 0.01 M). The reactions were incubated at RT for 10 min. Thereafter, NaOH-glycine quenching solution (200 μL) as described above was added to halt the reaction. The solutions were then analyzed using absorption spectroscopy as detailed above. The error is reported as standard deviation around the mean (n=3, FIG. 59).

Method 2. Determination of β-Glucosidase Quantity by Enzyme Activity.

This method looks at the amount of β-glucosidase present on the VFD reactor surface by direct monitoring of the catalytic rates for enzyme attached to the VFD reactor. Such rates were compared to identical control solutions with specified amounts of enzyme, and not subjected to VFD processing. This method assumes that the enzyme rate remains unchanged by attachment to the VFD reactor.

For this experiment, the protocol above was used with the following changes. The concentration of enzyme was varied as indicated in FIG. 60. The reaction time was five minutes.

References

Example 6

[1] M. A. Fischbach and C. T. Walsh, Chem. Rev., 2006, 106, 3468-3496; [2] A. T. Keatinge-Clay, Nat. Prod. Rep., 2016, 33, 141-149; [3] H. Sato, W. Hummel and H. Gröger, Angew. Chem. Int. Edit., 2015, 54, 4488-4492; [4] N. G. Turrini, M. Hall and K. Faber, Adv. Synth. Catal., 2015, 357, 1861-1871; [5] A. Ilie, R. Agudo, G.-D. Roiban and M. T. Reetz, Tetrahedron, 2015, 71, 470-475; [6] S. Sirajuddin and A. C. Rosenzweig, Biochemistry-US, 2015, 54, 2283-2294; [7] G. K. T. Nguyen, A. Kam, S. Loo, A. E. Jansson, L. X. Pan and J. P. Tam, J. Am. Chem. Soc., 2015, 137, 15398-15401; [8] E. Oueis, M. Jaspars, N. J. Westwood and J. H. Naismith, Angew. Chem. Int. Edit., 2016, 128, 5936-5939; [9] C. C. Farwell, R. K. Zhang, J. A. McIntosh, T. K. Hyster and F. H. Arnold, ACS Central Sci., 2015, 1, 89-93; [10] S. C. Dodani, G. Kiss, J. K. B. Cahn, Y. Su, V. S. Pande and F. H. Arnold, Nat. Chem., 2016, 8, 419-425; [11] P. A. Romero and F. H. Arnold, Nat. Rev. Mol. Cell. Biol., 2009, 10, 866-876; [12] N. J. Turner, Nat. Chem. Biol., 2009, 5, 567-573; [13] C. E. Tinberg, S. D. Khare, J. Dou, L. Doyle, J. W. Nelson, A. Schena, W. Jankowski, C. G. Kalodimos, K. Johnsson, B. L. Stoddard and D. Baker, Nature, 2013, 501, 212-216; [14] J. B. Siegel, A. L. Smith, S. Poust, A. J. Wargacki, A. Bar-Even, C. Louw, B. W. Shen, C. B. Eiben, H. M. Tran, E. Noor, J. L. Gallaher, J. Bale, Y. Yoshikuni, M. H. Gelb, J. D. Keasling, B. L. Stoddard, M. E. Lidstrom and D. Baker, P. Natl. Acad. Sci. USA, 2015, 112, 3704-3709; [15] A. Herath, R. Dahl and N. D. P. Cosford, Org. Lett., 2010, 12, 412-415; [16] D. Obermayer, T. N. Glasnov and C. O. Kappe, J. Org. Chem., 2011, 76, 6657-6669; [17] A. Adamo, R. L. Beingessner, M. Behnam, J. Chen, T. F. Jamison, K. F. Jensen, J.-C. M. Monbaliu, A. S. Myerson, E. M. Revalor, D. R. Snead, T. Stelzer, N. Weeranoppanant, S. Y. Wong and P. Zhang, Science, 2016, 352, 61-67; [18] A. R. Bogdan, S. L. Poe, D. C. Kubis, S. J. Broadwater and D. T. McQuade, Angew. Chem. Int. Edit., 2009, 48, 8547-8550; [19] S. Newton, C. F. Carter, C. M. Pearson, L. de C. Alves, H. Lange, P. Thansandote and S. V. Ley, Angew. Chem. Int. Edit., 2014, 53, 4915-4920; [20] S. V. Ley, D. E. Fitzpatrick, R. J. Ingham and R. M. Myers, Angew. Chem. Int. Edit., 2015, 54, 3449-3464; [21] L. H. Andrade, W. Kroutil and T. F. Jamison, Org. Lett., 2014, 16, 6092-6095; [22] J.-M. Choi, S.-S. Han and H.-S. Kim, Biotechnol. Adv., 2015, 33, 1443-1454; [23] R. Porcar, V. Sans, N. Ríos-Lombardía, V. Gotor-Fernández, V. Gotor, M. I. Burguete, E. García-Verdugo and S. V. Luis, ACS Catal., 2012, 2, 1976-1983; [24] D. Zhao and K. Ding, ACS Catal., 2013, 3, 928-944; [25] C. Garcia-Galan, Á. Berenguer-Murcia, R. Fernandez-Lafuente and R. C. Rodrigues, Adv. Synth. Catal., 2011, 353, 2885-2904; [26] U. Guzik, K. Hupert-Kocurek and D. Wojcieszyńska, Molecules, 2014, 19, 8995; [27] C. Mateo, J. M. Palomo, G. Fernandez-Lorente, J. M. Guisan and R. Fernandez-Lafuente, Enzyme Microb. Tech., 2007, 40, 1451-1463; [28] R. C. Rodrigues, C. Ortiz, A. Berenguer-Murcia, R. Torres and R. Fernandez-Lafuente, Chem. Soc. Rev, 2013, 42, 6290-6307; [29] F. Secundo, Chem. Soc. Rev., 2013, 42, 6250-6261; [30] V. Stepankova, S. Bidmanova, T. Koudelakova, Z. Prokop, R. Chaloupkova and J. Damborsky, ACS Catal., 2013, 3, 2823-2836; [31] H. Vaghari, H. Jafarizadeh-Malmiri, M. Mohammadlou, A. Berenjian, N. Anarjan, N. Jafari and S. Nasiri, Biotechnol. Lett., 2016, 38, 223-233; [32] K. Min and Y. J. Yoo, Biotechnol. Bioproc. E., 2014, 19, 553-567; [33] O. Barbosa, C. Ortiz, Á. Berenguer-Murcia, R. Torres, R. C. Rodrigues and R. Fernandez-Lafuente, Biotechnol. Adv., 2015, 33, 435-456; [34] R. A. Sheldon and S. van Pelt, Chem. Soc. Rev., 2013, 42, 6223-6235; [35] O. Barbosa, C. Ortiz, A. Berenguer-Murcia, R. Torres, R. C. Rodrigues and R. Fernandez-Lafuente, RSC Adv., 2014, 4, 1583-1600; [36] I. Migneault, C. Dartiguenave, M. J. Bertrand and K. C. Waldron, BioTechniques, 2004, 37, 790-802; [37] T. Z. Yuan, C. F. G. Ormonde, S. T. Kudlacek, S. Kunche, J. N. Smith, W. A. Brown, K. M. Pugliese, T. J. Olsen, M. Iftikhar, C. L. Raston and G. A. Weiss, ChemBioChem, 2015, 16, 393-396; [38] J. Britton, L. M. Meneghini, C. L. Raston and G. A. Weiss, Angew. Chem. Int. Edit., 2016, In Press; [39] J. Britton, J. M. Chalker and C. L. Raston, Chem. Eur. J., 2015, 21, 10660-10665; [40] J. Britton, S. B. Dalziel and C. L. Raston, RSC Adv., 2015, 5, 1655-1660; [41] J. Britton, S. B. Dalziel and C. L. Raston, Green Chem., 2016, 18, 2193-2200; [42] B. C. C. Pessela, M. Fuentes, C. Mateo, R. Munilla, A. V. Carrascosa, R. Fernandez-Lafuente and J. M. Guisan, Enzyme Microb. Tech., 2006, 39, 909-915; [43] A.

W. Miller and J. F. Robyt, Biotechnol. Bioeng., 1983, 25, 2795-2800; [44] F. Rusmini, Z. Zhong and J. Feijen, Biomacromolecules, 2007, 8, 1775-1789; [S1] H.-S. Jung, D.-S. Moon and J.-K. Lee, J. Nanomaterials, 2012, 2012, 8; [S2] C. J. Stanford, M. Dagenaid, J.-H. Park and P. Deshong, Curr. Anal. Chem., 2008, 4, 356-361; [S3] S. Chen, A. F. Yakunin, E. Kuznetsova, D. Busso, R. Pufan, M. Proudfoot, R. Kim and S.-H. Kim, J. Bio. Chem., 2004, 279, 31854-31862; [S4] J. Britton, S. B. Dalziel and C. L. Raston, Green Chem., 2016, 18, 2193-2200.

EMBODIMENTS

Embodiments disclosed herein include embodiments P1 to P13 following.

Embodiment P1

A method for reacting an enzyme and a substrate, the method including contacting an enzyme with a substrate of the enzyme in a solution in a vortex fluid device (VFD) under conditions suitable to enhance reaction of the substrate with the enzyme relative to a reaction not conducted in a VFD.

Embodiment P2

The method of embodiment P1, wherein the VFD includes a thin film tube reactor, the reactor including a tube having a longitudinal axis, an inner cylindrical surface, a close and an open end, wherein the tube is rotatable about the longitudinal axis, and wherein the angle of the longitudinal axis relative to the horizontal is variable between about 0 degrees and about 90 degrees.

Embodiment P3

The method of embodiment P2, wherein the thin film tube reactor is substantially cylindrical or includes at least a portion that is tapered.

Embodiment P4

The method of embodiment P2, wherein the thin film tube includes a lip adjacent to the open end.

Embodiment P5

The method of embodiment P2, wherein the speed of rotation of the thin film tube about the longitudinal axis is variable.

Embodiment P6

The method of embodiment P1, wherein the VFD is operated at constant volume of solution.

Embodiment P7

The method of embodiment P1, wherein the VFD is operated for continuous flow of substrate contacting the enzyme.

Embodiment P8

The method of embodiment P2, wherein the enzyme is uniformly disposed along the longitudinal axis of the thin film tube reactor.

Embodiment P9

The method of embodiment P2, wherein the enzyme is disposed along the longitudinal axis of the thin film tube reactor in regions, the regions not contiguous.

Embodiment P10

The method of embodiment P1, wherein the enzyme includes a plurality of enzymes.

Embodiment P11

The method of embodiment P1, wherein said substrate comprises a plurality of substrates.

Embodiment P12

The method of embodiment P1, wherein said method is conducted at room temperature.

Embodiment P13

The method of embodiment P1, wherein said method is conducted at atmospheric pressure.

Further embodiments disclosed herein include embodiments 1 to 55 following.

Embodiment 1

A method for reacting an enzyme and a substrate, the method including: a. combining an enzyme and a substrate of the enzyme to form an enzyme-substrate mixture; b. mechanically mixing the enzyme mixture; and c. applying a vibrational energy to the enzyme-substrate mixture, thereby reacting the enzyme and said substrate.

Embodiment 2

The method of embodiment 1, wherein the enzyme-substrate mixture is a liquid enzyme-substrate mixture.

Embodiment 3

The method of any one of embodiments 1-2, wherein the mechanically mixing said enzyme mixture forms an enzyme-substrate mixture thin film and wherein the vibrational energy is sufficient to produce a vibrational response within the enzyme-substrate mixture thin film.

Embodiment 4

The method of any one of embodiments 1-3, wherein the vibrational response is a Faraday wave.

Embodiment 5

The method of any one of embodiments 1-4, wherein the vibrational energy is sufficient to reduce reaction time of the enzyme at least 2 fold relative to reaction time of the enzyme in the absence of the vibrational energy.

Embodiment 6

The method of any one of embodiments 1-5, wherein the vibrational energy produces a harmonic vibrational frequency.

Embodiment 7

The method of any one of embodiments 1-6, wherein the mechanically mixing is rotationally mixing.

Embodiment 8

The method of any one of embodiments 1-7, wherein the rotational speed is about 3 krpm to about 10 krpm.

Embodiment 9

The method of any one of embodiments 1-8, wherein the enzyme-substrate mixture is within a glass container.

Embodiment 10

The method of any one of embodiments 1-9, wherein the glass container has a tilt angle of about 20 degree to about 90 degree.

Embodiment 11

The method of any one of embodiments 1-10, wherein the enzyme is a water soluble enzyme.

Embodiment 12

The method of any one of embodiments 1-11, wherein the water soluble enzyme is an esterase, a lipase, deoxyribose-5-phosphate aldolase (DERA), β-glucosidase, or an alkaline phosphatase.

Embodiment 13

A method for purifying a protein, said method comprising: a. contacting a protein mixture comprising said protein with a protein binding film, wherein said protein binding film is immobilized to a solid support, thereby forming a protein binding film complex; and b. separating said protein from said protein binding film complex, thereby obtaining a purified protein.

Embodiment 14

The method of embodiment 13, wherein said contacting comprises mechanically mixing.

Embodiment 15

The method of any one of embodiments 13-14, wherein said protein mixture is within a cell lysate.

Embodiment 16

The method of any one of embodiments 13-15, wherein said protein binding film is covalently immobilized to said solid support.

Embodiment 17

The method of any one of embodiments 13-16, wherein said protein binding film is non-covalently immobilized to said solid support.

Embodiment 18

The method of any one of embodiments 13-17, wherein said protein is covalently bound to said protein binding film.

Embodiment 19

The method of any one of embodiments 13-18, wherein said protein is non-covalently bound to said protein binding film.

Embodiment 20

The method of any one of embodiments 13-19, wherein said protein comprises a binding moiety.

Embodiment 21

The method of any one of embodiments 13-20, wherein said binding moiety is an expression tag.

Embodiment 22

The method of any one of embodiments 13-21, wherein said expression tag is a His-tag.

Embodiment 23

The method of any one of embodiments 13-22, wherein said protein binding film comprises a binding partner of said binding moiety.

Embodiment 24

The method of any one of embodiments 13-23, wherein said binding partner is nickel, cobalt or copper.

Embodiment 25

The method of any one of embodiments 13-24, wherein said solid support is an inner surface of a reactor.

Embodiment 26

The method of any one of embodiments 13-25, wherein said reactor comprises a closed end and an open end.

Embodiment 27

The method of any one of embodiments 13-26, wherein said reactor is cylindrical.

Embodiment 28

The method of any one of embodiments 13-27, wherein said reactor is a glass reactor.

Embodiment 29

The method of any one of embodiments 13-28, wherein said protein mixture is contacted with said protein binding film by continuous flow.

Embodiment 30

The method of any one of embodiments 13-29, wherein said mechanically mixing is rotationally mixing.

Embodiment 31

The method of any one of embodiments 13-30, wherein said rotationally mixing has a rotational speed of about 3 krpm to 10 krpm.

Embodiment 32

An enzyme reactor comprising a first enzyme, a protein binding film and a solid support, wherein said first enzymes is immobilized to said protein binding film in a first zone, and wherein said protein binding film is immobilized to said solid support.

Embodiment 33

The enzyme reactor of embodiment 32, wherein said enzyme reactor comprises one or more additional enzymes.

Embodiment 34

The enzyme reactor of any one of embodiments 32-33, wherein said one or more additional enzymes are immobilized to said protein binding film in said first zone.

Embodiment 35

The enzyme reactor of any one of embodiments 32-34, wherein at least one of said one or more additional enzymes are immobilized to said protein binding film in one or more zones that are different from said first zone.

Embodiment 36

The enzyme reactor of any one of embodiments 32-35, wherein said enzyme reactor comprises one or more additional zones.

Embodiment 37

The enzyme reactor of any one of embodiments 32-36, wherein said protein binding film is covalently immobilized to said solid support.

Embodiment 38

The enzyme reactor of any one of embodiments 32-37, wherein said protein binding film is non-covalently immobilized to said solid support.

Embodiment 39

The enzyme reactor of any one of embodiments 32-38, wherein said first enzyme or said one or more additional enzymes are covalently bound to said protein binding film.

Embodiment 40

The enzyme reactor of any one of embodiments 32-39, wherein said first enzyme or said one or more additional enzymes are non-covalently bound to said protein binding film.

Embodiment 41

The enzyme reactor of any one of embodiments 32-40, wherein said first enzyme or said one or more additional enzymes comprise a binding moiety.

Embodiment 42

The enzyme reactor of any one of embodiments 32-41, wherein said binding moiety is an expression tag.

Embodiment 43

The enzyme reactor of any one of embodiments 32-42, wherein said expression tag is a His-tag.

Embodiment 44

The enzyme reactor of any one of embodiments 32-43, wherein said protein binding film comprises a binding partner of said binding moiety.

Embodiment 45

The enzyme reactor of any one of embodiments 32-44, wherein said binding partner is nickel, cobalt or copper.

Embodiment 46

The enzyme reactor of any one of embodiments 32-45, wherein said protein binding film comprises an amine group.

Embodiment 47

The enzyme reactor of any one of embodiments 32-46, wherein said solid support is an inner surface of a reactor.

Embodiment 48

The enzyme reactor of any one of embodiments 32-47, wherein said reactor comprises a closed end and an open end.

Embodiment 49

The enzyme reactor of any one of embodiments 32-48, wherein said reactor is cylindrical.

Embodiment 50

The enzyme reactor of any one of embodiments 32-49, wherein said reactor is a glass reactor.

Embodiment 51

The enzyme reactor of any one of embodiments 32-50, wherein said first and said one or more additional zones are along the longitude axis of said solid support.

Embodiment 52

A method for reacting an enzyme and a substrate, said method comprising: a. contacting said protein binding film of said enzyme reactor of embodiment 32 with a substrate of said first enzyme; and b. allowing said substrate to react with said first enzyme.

Embodiment 53

The method of embodiment 52, wherein said substrate is contacted with said protein binding film by continuous flow.

Embodiment 54

The method of any one of embodiments 52-53, further comprising applying a vibrational energy to said enzyme reactor.

Embodiment 55

The method of any one of embodiments 52-54, wherein said substrate is a plurality of substrates.

---

What is claimed is:

1. A method for reacting an enzyme and a substrate in a solution, the method comprising:
   (i) combining the enzyme and the substrate of the enzyme in a solution in a tube reactor of a vortex fluid device to form a solution comprising an enzyme-substrate mixture;
   (ii) rotationally mixing the solution comprising the enzyme-substrate mixture at a speed from 4,000 rpm to 15,000 rpm in the tube reactor of the vortex fluid device; and
   (iii) applying a mechanical vibrational energy to the solution comprising the enzyme-substrate mixture in the tube reactor of the vortex fluid device, thereby reacting the enzyme and the substrate;
   wherein the tube reactor comprises a longitudinal axis and an inner cylindrical surface; wherein the tube reactor is rotatable about the longitudinal axis; wherein the tube reactor is held between an upper bearing and a lower bearing; and wherein the tube reactor has a tilt angle from 20 degrees to 90 degrees.

2. The method of claim 1, comprising rotationally mixing the solution comprising the enzyme-substrate mixture at a speed from 6,500 rpm to 9,000 rpm.

3. The method of claim 1, comprising rotationally mixing the solution comprising the enzyme-substrate mixture at a speed from 6,000 rpm to 10,000 rpm.

4. The method of claim 1, wherein rotationally mixing the solution comprising the enzyme-substrate mixture forms an enzyme-substrate mixture thin film, and wherein the mechanical vibrational energy produces a vibrational response within the enzyme-substrate mixture thin film.

5. The method of claim 4, wherein the vibrational response is a Faraday wave.

6. The method of claim 1, wherein the mechanical vibrational energy produces a harmonic vibrational frequency.

7. The method of claim 1, wherein the solution comprising the enzyme-substrate mixture further comprises at least one steric crowding agent.

8. The method of claim 1, wherein the enzyme is a water-soluble enzyme.

9. The method of claim 8, wherein the water-soluble enzyme is an esterase, a lipase, deoxyribose-5-phosphate aldolase, β-glucosidase, or an alkaline phosphatase.

10. The method of claim 1, wherein the method is conducted at atmospheric pressure and at room temperature.

11. The method of claim 1, wherein the tube reactor has a tilt angle of 45 degrees.

\* \* \* \* \*